(12) United States Patent
Schneider et al.

(10) Patent No.: US 11,590,169 B1
(45) Date of Patent: Feb. 28, 2023

(54) COMPOSITIONS AND METHODS FOR TREATING CANCER WITH ANTI-CD123 IMMUNOTHERAPY

(71) Applicant: Lentigen Technology, Inc., Gaithersburg, MD (US)

(72) Inventors: Dina Schneider, Potomac, MD (US); Zhongyu Zhu, Frederick, MD (US); Florian Tomszak, Bergisch Gladbach (DE); Rafijul Bari, Rockville, MD (US)

(73) Assignee: LENTIGEN TECHNOLOGY, INC., Gaithersburg, MD (US)

( * ) Notice: Subject to any disclaimer, the term of this patent is extended or adjusted under 35 U.S.C. 154(b) by 0 days.

(21) Appl. No.: 17/685,132

(22) Filed: Mar. 2, 2022

(51) Int. Cl.
| | |
|---|---|
| *A61K 35/17* | (2015.01) |
| *C12N 5/0783* | (2010.01) |
| *C07K 14/705* | (2006.01) |
| *A61P 35/00* | (2006.01) |
| *C07K 14/725* | (2006.01) |

(52) U.S. Cl.
CPC ............. *A61K 35/17* (2013.01); *A61P 35/00* (2018.01); *C07K 14/7051* (2013.01); *C07K 14/70578* (2013.01); *C12N 5/0636* (2013.01)

(58) Field of Classification Search
CPC .................................................... A61K 35/17
See application file for complete search history.

(56) References Cited

U.S. PATENT DOCUMENTS

| | | |
|---|---|---|
| 3,060,165 A | 10/1962 | Craig et al. |
| 3,896,111 A | 7/1975 | Kupchan et al. |
| 4,137,230 A | 1/1979 | Hashimoto et al. |
| 4,151,042 A | 4/1979 | Higashide et al. |
| 4,235,871 A | 11/1980 | Papahadjopoulos et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isely et al. |
| 4,486,414 A | 12/1984 | Pettit |
| 4,501,728 A | 2/1985 | Geho et al. |
| 4,689,401 A | 8/1987 | Ferris |
| 4,816,444 A | 3/1989 | Pettit et al. |
| 4,837,028 A | 6/1989 | Allen et al. |
| 4,879,278 A | 11/1989 | Pettit et al. |
| 4,880,935 A | 11/1989 | Thorpe |
| 4,902,505 A | 2/1990 | Pardridge et al. |
| 4,957,735 A | 9/1990 | Huang et al. |
| 4,978,744 A | 12/1990 | Pettit et al. |
| 4,986,988 A | 1/1991 | Pettit et al. |
| 5,019,369 A | 5/1991 | Presant et al. |
| 5,055,303 A | 10/1991 | Riley, Jr. |
| 5,076,973 A | 12/1991 | Pettit et al. |
| 5,079,163 A | 1/1992 | Piatak et al. |
| 5,122,368 A | 6/1992 | Greenfield et al. |
| 5,138,036 A | 8/1992 | Pettit et al. |
| 5,188,837 A | 2/1993 | Domb |
| 5,208,020 A | 5/1993 | Chari et al. |
| 5,208,021 A | 5/1993 | Johnson et al. |
| 5,254,342 A | 10/1993 | Shen et al. |
| 5,271,961 A | 12/1993 | Mathiowitz et al. |
| 5,410,024 A | 4/1995 | Pettit et al. |
| 5,416,064 A | 5/1995 | Chari et al. |
| 5,449,752 A | 9/1995 | Fujii et al. |
| 5,506,206 A | 4/1996 | Kozarich et al. |
| 5,514,670 A | 5/1996 | Friedman et al. |
| 5,521,284 A | 5/1996 | Pettit et al. |
| 5,530,097 A | 6/1996 | Pettit et al. |

(Continued)

FOREIGN PATENT DOCUMENTS

| | | |
|---|---|---|
| EP | 0425235 B1 | 9/1996 |
| WO | WO 2004/010957 | 2/2004 |

(Continued)

OTHER PUBLICATIONS

Ahmad et al., "scFv antibody: principles and clinical application," Clinical and Developmental Immunology, Oct. 2012, vol. 2012, 15 pages.

Al-Lazikani et al., "Standard conformations for the canonical structures of immunoglobulins," Journal of Molecular Biology, Nov. 7, 1997, 273(4):927-48.

Bari et al., "A distinct subset of highly proliferative and lentiviral vector (LV)-transducible NK cells define a readily engineered subset for adoptive cellular therapy," Frontiers in Immunology, Aug. 22, 2019, 10:2001, 12 pages.

Barry et al., "A natural killer—dendritic cell axis defines checkpoint therapy—responsive tumor microenvironments," Nature Medicine, Aug. 2018, 24(8):1178-91.

(Continued)

*Primary Examiner* — Scott Long
(74) *Attorney, Agent, or Firm* — Serge Sira, Esq.; Gregory J. Hwa, Esq.; Fish & Richardson P.C.

(57) ABSTRACT

Chimeric antigen receptors containing CD123 antigen binding domains are disclosed. Nucleic acids, recombinant expression vectors, host cells, antigen binding fragments, and pharmaceutical compositions, relating to the chimeric antigen receptors are also disclosed. Methods of treating or preventing cancer in a subject, and methods of making chimeric antigen receptor T cells are also disclosed.

20 Claims, 18 Drawing Sheets

Specification includes a Sequence Listing.

(56) References Cited

U.S. PATENT DOCUMENTS

| | | | |
|---|---|---|---|
| 5,534,496 | A | 7/1996 | Lee et al. |
| 5,554,725 | A | 9/1996 | Pettit |
| 5,599,902 | A | 2/1997 | Pettit et al. |
| 5,622,929 | A | 4/1997 | Willner et al. |
| 5,635,483 | A | 6/1997 | Pettit et al. |
| 5,663,149 | A | 9/1997 | Pettit et al. |
| 5,665,860 | A | 9/1997 | Pettit et al. |
| 5,780,588 | A | 7/1998 | Pettit et al. |
| 5,792,458 | A | 8/1998 | Johnson et al. |
| 5,824,805 | A | 10/1998 | King et al. |
| 6,034,065 | A | 3/2000 | Pettit et al. |
| 6,214,345 | B1 | 4/2001 | Firestone et al. |
| 6,239,104 | B1 | 5/2001 | Pettit et al. |
| 6,323,315 | B1 | 11/2001 | Pettit et al. |
| 6,441,163 | B1 | 8/2002 | Chari et al. |
| 6,884,869 | B2 | 4/2005 | Senter et al. |
| 7,338,929 | B2 | 3/2008 | Debinski et al. |
| 7,498,298 | B2 | 3/2009 | Doronina et al. |
| 7,964,566 | B2 | 6/2011 | Doronina et al. |
| 10,844,128 | B2 | 11/2020 | Orentas et al. |
| 2002/0197266 | A1 | 12/2002 | Debinski |
| 2005/0238649 | A1 | 10/2005 | Doronina et al. |
| 2006/0024317 | A1 | 2/2006 | Boyd et al. |
| 2006/0074008 | A1 | 4/2006 | Senter et al. |
| 2011/0070248 | A1 | 3/2011 | Ichikawa et al. |
| 2011/0212088 | A1 | 9/2011 | Sabbadini et al. |
| 2016/0046724 | A1 | 2/2016 | Brogdon |
| 2016/0208018 | A1 | 7/2016 | Chen |
| 2020/0010555 | A1 | 1/2020 | Orentas et al. |
| 2021/0130479 | A1 | 5/2021 | Orentas et al. |

FOREIGN PATENT DOCUMENTS

| | | |
|---|---|---|
| WO | WO 2015/140268 | 5/2017 |
| WO | WO 2017/075147 | 5/2017 |

OTHER PUBLICATIONS

Bird et al., "Single-chain antigen-binding proteins," Science, Oct. 21, 1988, 242(4877):423-6.

Bottcher et al., "NK cells stimulate recruitment of cDC1 into the tumor microenvironment promoting cancer immune control," Cell, Feb. 22, 2018, 172(5):1022, 31 pages.

Brenner et al., "Overview of gene therapy clinical progress including cancer treatment with gene-modified T cells," Hematology Am. Soc. Hematol. Educ. Program, 2009, pp. 675-681.

Brown et al., "Stem-like tumor-initiating cells isolated from IL13Rα2 expressing gliomas are targeted and killed by IL13-zetakine—redirected T cells," Clinical Cancer Research, Apr. 15, 2012, 18(8):2199-209.

Capecchi, "High efficiency transformation by direct microinjection of DNA into cultured mammalian cells," Cell, Nov. 1, 1980, 22(2):479-88.

Clay et al., "Efficient transfer of a tumor antigen-reactive TCR to human peripheral blood lymphocytes confers anti-tumor reactivity," The Journal of Immunology, Jul. 1, 1999, 163(1):507-13.

D'Aloia et al., "CAR-T cells: the long and winding road to solid tumors," Cell Death and Disease, 2018, 9(282), 12 pages.

Di Stasi et al., "Inducible apoptosis as a safety switch for adoptive cell therapy," New England Journal of Medicine, Nov. 3, 2011, 365:1673-83.

Dubowchik et al., "Receptor-mediated and enzyme-dependent targeting of cytotoxic anticancer drugs," Pharmacology & Therapeutics, Aug. 1, 1999, 83(2):67-123.

Felgner et al., "Lipofection: a highly efficient, lipid-mediated DNA-transfection procedure," Proceedings of the National Academy of Sciences, Nov. 1987, 84(21):7413-7.

Foster et al., "Antitumor activity of EBV-specific T lymphocytes transduced with a dominant negative TGF-β receptor," Journal of Immunotherapy, Jun. 2008, 31(5):500-5.

Fumoto et al., "Targeted Gene Delivery: Importance of Administration Routes," Intech, 2013, 30 pages.

Funatsu et al., "The complete amino acid sequence of the A-chain of abrin-a, a toxic protein from the seeds of Abrus precatorius," Agricultural and Biological Chemistry, Apr. 1, 1988, 52(4):1095-7.

GenBank Accession No. AAA35664.1, "T lymphocyte surface glycoprotein (CD8-beta) precursor," Apr. 27, 1993, retrieved Jul. 20, 2022 from URL <https://www.ncbi.nlm.nih.gov/protein/AAA35664.1/>, 2 pages.

Gillespie et al., "Phase I open study of the effects of ascending doses of the cytotoxic immunoconjugate CMB-401 (hCTM01-calicheamicin) in patients with epithelial ovarian cancer," Annals of Oncology, Jun. 1, 2000, 11(6):735-41.

Girard-Gagnepain et al., "Baboon envelope pseudotyped LVs outperform VSV-G-LVs for gene transfer into early-cytokine-stimulated and resting HSCs," Blood, The Journal of the American Society of Hematology, Aug. 21, 2014, 124(8):1221-31.

Goyal et al., "Inclusion of a furin-sensitive spacer enhances the cytotoxicity of ribotoxin restrictocin containing recombinant single-chain immunotoxins," Biochemical Journal, Jan. 15, 2000, 345(2):247-54.

Graham et al.,, "A new technique for the assay of infectivity of human adenovirus 5 DNA," Virology, Apr. 1, 1973, 52(2):456-67.

Granzin et al.. "Highly efficient IL-21 and feeder cell-driven ex vivo expansion of human NK cells with therapeutic activity in a xenograft mouse model of melanoma," Oncoimmunology, Sep. 1, 2016, 5(9):e1219007, 37 pages.

Hamers-Casterman et al., "Naturally occurring antibodies devoid of light chains," Nature, Jun. 1993, 363(6428):446-8.

Haso et al., "Anti-CD22—chimeric antigen receptors targeting B-cell precursor acute lymphoblastic leukemia," Blood, The Journal of the American Society of Hematology, Feb. 14, 2013, 121(7):1165-74.

Holliger et al., "Diabodies: small bivalent and bispecific antibody fragments," Proceedings of the National Academy of Sciences, Jul. 15, 1993, 90(14):6444-8.

Huse et al., "Generation of a large combinatorial library of the immunoglobulin repertoire in phage lambda," Science, Dec. 8, 1989, 246(4935):1275-81.

Huston et al., "Protein engineering of antibody binding sites: recovery of specific activity in an anti-digoxin single-chain Fv analogue produced in *Escherichia coli*," Proceedings of the National Academy of Sciences, Aug. 1988, 85(16):5879-83.

Ijntema et al., "Hydroxyapatite microcarriers for biocontrolled release of protein drugs," International Journal of Pharmaceutics, Dec. 5, 1994, 112(3):215-24.

Imai et al., "Genetic modification of primary natural killer cells overcomes inhibitory signals and induces specific killing of leukemic cells," Blood, Jul. 1, 2005, 106(1):376-83.

Imamura et al., "Autonomous growth and increased cytotoxicity of natural killer cells expressing membrane-bound interleukin-15," Blood, The Journal of the American Society of Hematology, Aug. 14, 2014, 124(7):1081-8.

Johnston et al., "Sustained delivery of interleukin-2 from a poloxamer 407 gel matrix following intraperitoneal injection in mice," Pharmaceutical Research, Mar. 1992, 9(3):425-34.

Kamble et al., "Leukemia burden and outcome of allogeneic transplant in acute myelogenous leukemia," Biology of Blood and Marrow Transplantation, Jun. 1, 2006, 12(6):691-2.

Kindt et al., "Antibodies: Structure and Function," Kuby Immunology (6th ed.), Aug. 15, 2006, p. 91.

Klein et al., "High-velocity microprojectiles for delivering nucleic acids into living cells," Nature, May 1987, 327(6117):70-3.

Knorr et al., "Clinical-scale derivation of natural killer cells from human pluripotent stem cells for cancer therapy," Stem Cells Translational Medicine, Apr. 2013, 2(4):274-83.

Kochenderfer et al., "B-cell depletion and remissions of malignancy along with cytokine-associated toxicity in a clinical trial of anti-CD19 chimeric-antigen-receptor—transduced T cells," Blood, The Journal of the American Society of Hematology, Mar. 22, 2012, 119(12):2709-20.

(56) References Cited

OTHER PUBLICATIONS

Kueberuwa et al., "CD19 CAR T Cells Expressing IL-12 Eradicate Lymphoma in Fully Lymphoreplete Mice through Induction of Host Immunity," Mol. Ther., Oncolytics, 2018, 19(8):41-51.
Kuroda et al., "Simplified lentivirus vector production in protein-free media using polyethylenimine-mediated transfection," Journal of Virological Methods, May 1, 2009, 157(2):113-21.
Langer, "Polymer-controlled drug delivery systems," Accounts of Chemical Research, Oct. 1, 1993, 26(10):537-42.
Lau et al., "Conjugation of doxorubicin to monoclonal anti-carcinoembryonic antigen antibody via novel thiol-directed cross-linking reagents," Bioorganic & Medicinal Chemistry, Oct. 1, 1995, 3(10):1299-304.
Lau et al., "Novel doxorubicin-monoclonal anti-carcinoembryonic antigen antibody immunoconjugate activity in vitro," Bioorganic & Medicinal Chemistry, Oct. 1, 1995, 3(10):1305-12.
Lee et al., "Anti-CD19 chimeric antigen receptor (CAR) T cells produce complete responses with acceptable toxicity but without chronic B-cell aplasia in children with relapsed or refractory acute lymphoblastic leukemia (ALL) even after all allogeneic hematopoietic stem cell transplantation (HSCT)," Blood, Nov. 15, 2013, 122(21):68, 2 pages (abstract only).
Lee et al., "Calicheamicins, a novel family of antitumor antibiotics. III: Isolation, purification and characterization of calicheamicins B1Br, γ1Br, α2I, α3I, β1I, γ1I and δ1I," The Journal of Antibiotics, Jul. 25, 1989, 42(7):1070-87.
Lefranc et al., "IMGT unique numbering for immunoglobulin and T cell receptor variable domains and Ig superfamily V-like domains," Developmental & Comparative Immunology, Jan. 1, 2003, 27(1):55-77.
Lehner et al., "Redirecting T cells to Ewing's sarcoma family of tumors by a chimeric NKG2D receptor expressed by lentiviral transduction or mRNA transfection," PloS one, Feb. 15, 2012, 7(2):e31210, 12 pages.
Li et al., "Human iPSC-derived natural killer cells engineered with chimeric antigen receptors enhance anti-tumor activity," Cell Stem Cell. Aug. 2, 2018, 23(2):181-92.
Lonberg, "Fully human antibodies from transgenic mouse and phage display platforms," Current Opinion in Immunology, Aug. 1, 2008, 20(4):450-9.
Lonberg, "Human antibodies from transgenic animals," Nature Biotechnology, Sep. 2005, 23(9):1117-25.
Long et al., "Lessons learned from a highly-active CD22-specific chimeric antigen receptor," Oncoimmunology, Apr. 1, 2013, 2(4):e23621, 3 pages.
Mabry et al., "Therapeutic bispecific antibodies: The selection of stable single-chain fragments to overcome engineering obstacles," IDrugs: The Investigational Drugs Journal, Aug. 1, 2010, 13(8):543-9.
Miller et al., "Successful adoptive transfer and in vivo expansion of human haploidentical NK cells in patients with cancer," Blood, Apr. 15, 2005, 105(8):3051-7.
Milone, "Chimeric receptors containing CD137 signal transduction domains mediate enhanced survival of T cells and increased antileukemic efficacy in vivo," Molecular Therapy, Aug. 1, 2009, 17(8):1453-64.
NCBI RefSeq: NP_000064.1, "T-cell surface glycoprotein CD3 gamma chain precursor [Homo sapiens]," dated Mar. 15, 2015, 3 pages.
NCBI RefSeq: NP_000130.1, "High affinity immunoglobulin epsilon receptor subunit beta isoform 1 [Homo sapiens]," dated Mar. 15, 2015, 3 pages.
NCBI RefSeq: NP_000607.1, "T-cell surface glycoprotein CD4 isoform 1 precursor [Homo sapiens]," dated Mar. 15, 2015, 3 pages.
NCBI RefSeq: NP_000617.1, "B-cell antigen receptor complex-associated protein beta chain isoform 1 precursor [Homo sapiens]," dated Mar. 15, 2015, 3 pages.
NCBI RefSeq: NP_000723.1, "T-cell surface glycoprotein CD3 delta chain isoform A precursor [Homo sapiens]," dated Mar. 15, 2015, 3 pages.
NCBI RefSeq: NP_000724.1, "T-cell surface glycoprotein CD3 epsilon chain precursor [Homo sapiens]," dated Mar. 15, 2015, 3 pages.
NCBI RefSeq: NP_001552.2, "Tumor necrosis factor receptor superfamily member 9 precursor [Homo sapiens]," dated Mar. 15, 2015, 3 pages.
NCBI RefSeq: NP_001758.2, "T-cell surface antigen CD2 precursor [Homo sapiens]," dated Mar. 15, 2015, 3 pages.
NCBI RefSeq: NP_001759.3, "T-cell surface glycoprotein CD8 alpha chain isoform 1 precursor [Homo sapiens]," dated Mar. 15, 2015, 3 pages.
NCBI RefSeq: NP_001762.2, "B-cell receptor CD22 isoform 1 precursor [Homo sapiens]," dated Mar. 15, 2015, 3 pages.
NCBI RefSeq: NP_001774.1, "B-cell antigen receptor complex-associated protein alpha chain isoform 1 precursor [Homo sapiens]," dated Mar. 15, 2015, 3 pages.
NCBI RefSeq: NP_001806.2, "Carcinoembryonic antigen-related cell adhesion molecule 3 isoform 1 precursor [Homo sapiens]," dated Mar. 15, 2015, 3 pages.
NCBI RefSeq: NP_003318.1, "Tumor necrosis factor receptor superfamily member 4 precursor [Homo sapiens]," dated Mar. 15, 2015, 3 pages.
NCBI RefSeq: NP_004097.1, "High affinity immunoglobulin epsilon receptor subunit gamma precursor [Homo sapiens]," dated Mar. 15, 2015, 3 pages.
NCBI RefSeq: NP_006130.1, "T-cell-specific surface glycoprotein CD28 isoform 1 precursor [Homo sapiens]," dated Mar. 15, 2015, 3 pages.
NCBI RefSeq: NP_036224.1, "Inducible T-cell costimulator precursor [Homo sapiens]," dated Mar. 15, 2015, 3 pages.
NCBI RefSeq: NP_055022.2, "T-cell surface glycoprotein CD5 precursor [Homo sapiens]," dated Mar. 15, 2015, 3 pages.
NCBI RefSeq: NP_932170.1, "T-cell surface glycoprotein CD3 zeta chain isoform 1 precursor [Homo sapiens]," dated Mar. 15, 2015, 3 pages.
Neville et al., "Enhancement of immunotoxin efficacy by acid-cleavable cross-linking agents utilizing diphtheria toxin and toxin mutants," Journal of Biological Chemistry, Sep. 5, 1989, 264(25):14653-61.
Ni et al., "Sustained effector function of IL-Dec. 15, 2018—preactivated NK cells against established tumors," Journal of Experimental Medicine, Dec. 17, 2012, 209(13):2351-65.
Nicolson et al., "The interaction of Ricinus communis agglutinin with normal and tumor cell surfaces," Biochimica et Biophysica Acta (BBA)-Biomembranes, May 9, 1972, 266(2):543-7.
Olsnes et al., "Mechanism of action of the toxic lectins abrin and ricin," Nature, Jun. 1974, 249(5458):627-31.
Olsnes, "Ricin and ricinus agglutinin, toxic lectins from castor bean," Methods in Enzymology, Jan. 1, 1978, 50:330-5.
PCT International Preliminary Report on Patentability in International Appln. No. PCT/US2019/052226, dated Mar. 23, 2021, 10 pages.
PCT International Search Report and Written Opinion in International Appln. No, PCT/US2019/052226, dated Jan. 28, 2020, 16 pages.
Phillips et al., "Targeting HER2-positive breast cancer with trastuzumab-DM1, an anti body-cytotoxic drug conjugate," Cancer Research, Nov. 15, 2008, 68(22):9280-90.
Poljak, "Production and structure of diabodies," Structure, Dec. 1, 1994, 2(12):1121-3.
Porter et al., "Chimeric antigen receptor-modified T cells in chronic lymphoid leukemia," New England Journal of Medicine, Aug. 25, 2011, 365:725-33.
Rathore et al., "Overproduction of fungal ribotoxin α-sarcin in Escherichia coli: generation of an active immunotoxin," Gene, Jan. 1, 1997, 190(1):31-5.
Romee et al., "Cytokine-induced memory-like natural killer cells exhibit enhanced responses against myeloid leukemia," Science Translational Medicine, Sep. 21, 2016, 8(357):357ra123, 18 pages.
Rubnitz et al., "NKAML: a pilot study to determine the safety and feasibility of haploidentical natural killer cell transplantation in childhood acute myeloid leukemia," Journal of Clinical Oncology, Feb. 2, 2010, 28(6):955-9.

(56) References Cited

OTHER PUBLICATIONS

Schneider et al., "A unique human immunoglobulin heavy chain variable domain-only CD33 CAR for the treatment of acute myeloid leukemia," Frontiers in Oncology, Nov. 22, 2018, 8:539, 16 pages.
Sheriff et al., "Redefining the minimal antigen-binding fragment," Nature Structural Biology, Sep. 1996, 3(9):733-6.
Shimasaki et al., "NK cells for cancer immunotherapy," Nature Reviews Drug Discovery, Mar. 2020, 19(3):200-18.
Spanholtz et al., "Clinical-grade generation of active NK cells from cord blood hematopoietic progenitor cells for immunotherapy using a closed-system culture process," PloS one, Jun. 16, 2011, 6(6):e20740, 11 pages.
Sridhar et al., "Regional Delivery of Chimeric Antigen Receptor (CAR) T-Cells for Cancer Therapy," Cancers (Basel), 2017, 9:92, 10 pages.
Stirpe et al., "Ribosome-inactivating proteins from plants: Present status and future prospects," Bio/Technology, Apr. 1992, 10(4):405-12.
Suzuki et al., "Engineering receptor-mediated cytotoxicity into human ribonucleases by steric blockade of inhibitor interaction," Nature Biotechnology, Mar. 1999, 17(3):265-70.
Thorpe et al., "New coupling agents for the synthesis of immunotoxins containing a hindered disulfide bond with improved stability in vivo," Cancer Research, Nov. 15, 1987, 47(22):5924-31.
Tian et al., "Impact of pre-transplant disease burden on the outcome of allogeneic hematopoietic stem cell transplant in refractory and relapsed acute myeloid leukemia: a single-center study," Leukemia & Lymphoma, May 4, 2015, 56(5):1353-61.
UniProt ID: P01861, "Immunoglobulin heavy constant gamma 4," Feb. 23, 2022, retrieved Jul. 20, 2022 from URL <https://rest.uniprot.org/unisave/P01861?format=txt&versions=174>, 6 pages.
Ward et al., "Binding activities of a repertoire of single immunoglobulin variable domains secreted from *Escherichia coli*," Nature, Oct. 1989, 341(6242):544-6.
Winter et al., "Antibody-based therapy," Humanized Antibodies, Immunology Today, May 1993, 14(6):243-6.
Yu et al., "The biosynthetic gene cluster of the maytansinoid antitumor agent ansamitocin from Actinosynnema pretiosum," Proceedings of the National Academy of Sciences, Jun. 11, 2002, 99(12):7968-73.
Yvon et al., "Immunotherapy of metastatic melanoma using genetically engineered GD2-specific T cells," Clinical Cancer Research, Sep. 15, 2009, 15(18):5852-60.
Zhao et al., "A herceptin-based chimeric antigen receptor with modified signaling domains leads to enhanced survival of transduced T lymphocytes and antitumor activity," The Journal of Immunology, Nov. 1, 2009, 183(9):5563-74.
Zhao et al., "Primary human lymphocytes transduced with NY-ESO-1 antigen-specific TCR genes recognize and kill diverse human tumor cell lines," The Journal of Immunology, Apr. 1, 2005, 174(7):4415-23.

COMPOSITIONS AND METHODS FOR TREATING CANCER WITH ANTI-CD123 IMMUNOTHERAPY

SEQUENCE LISTING

The instant application contains a Sequence Listing which has been submitted electronically in ASCII format and is hereby incorporated by reference in its entirety. Said ASCII copy, created on Mar. 1, 2022, is named Sequence_Listing.txt and is 128 kilobytes in size.

FIELD OF THE DISCLOSURE

This application relates to the field of cancer, particularly to CD123 antigen binding domains and chimeric antigen receptors (CARs) containing such CD123 antigen binding domains and methods of use thereof.

BACKGROUND

Cancer is one of the most deadly threats to human health. In the U.S. alone, cancer affects nearly 1.3 million new patients each year, and is the second leading cause of death after cardiovascular disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making treatment extremely difficult.

AML is a devastating disease with overall survival rate of only 26%. While young patients tend to have a better prognosis for treatment in AML, the five year survival in older patients may be as low as only 5%. First line treatment of AML involves multiple rounds of chemotherapy, (i.e. induction, consolidation) which bear high risk of toxicity. If hematopoietic stem cell transplant is performed after the 1st remission, the 5 year disease-free survival rate is only 30-50% (http://www.cancer.ca/en/cancer-information/cancer-type/leukemia-acute-myelogenous-aml/prognosis-and-survival/survival-statistics/?region=on). In addition, AML patients with high disease burden may not be candidates for bone marrow transplant, and minimal residual disease pre-transplant correlates with AML relapse. The present 1st line induction/consolidation therapy often fails to achieve MDR-negative remission to sufficiently reduce tumor burden, thus the risk of AML relapse after 1st line therapy with or without BMT remains high (1) Biol Blood Marrow Transplant. 2006 June; 12(6):691-2, Leukemia burden and outcome of allogeneic transplant in acute myelogenous leukemia, Kamble R T, Hjortsvang E, Selby G B; (2) Leuk Lymphoma. 2015 May; 56(5):1353-61. Impact of pre-transplant disease burden on the outcome of allogeneic hematopoietic stem cell transplant in refractory and relapsed acute myeloid leukemia: a single-center study. Tian H et al.). PBDCN is a rare myeloid neoplasm that is classified as a subtype of AML and is sometimes treated as AML with induction and consolidation chemotherapy, and sometimes as ALL. BMT is often administered at 1st remission. However, there are currently no ongoing clinical trials for PBDCN, and no approved 1st line treatment. (Leukemia Lymphoma Society, https://www.lls.org/leukemia/blastic-plasmacytoid-dendritic-cell-neoplasm). Therefore, better therapeutic modalities are urgently needed for CD123+ malignancies.

CAR approaches targeting CD123 are superior to chemotherapy because they may achieve better efficacy in eliminating CD123+ tumor cells and tumor stem cells, and because they avoid the toxicities associated with chemotherapy. Importantly, CAR T cells are expected to be more efficient than chemotherapy in eliminating minimal residual disease, resulting in better long-term treatment prognosis. Furthermore, CAR123 may be used for tumor debulking as a bridge to transplant, as may help patient with high tumor burden become eligible for BMT.

CAR123 represents an improvement over prior art because unique human ScFv (hereinafter "hScFv") sequences are used in the CAR design, as opposed to murine-derived ScFvs employed in CAR designs elsewhere. Mouse-derived sequences carry the risk of immunogenicity, and may induce allergic or anaphylactic responses in patients, leading to CAR T elimination, or life-threatening anaphylaxis.

Chimeric Antigen Receptors (CARs) are hybrid molecules comprising three essential units: (1) an extracellular antigen-binding motif, (2) linking/transmembrane motifs, and (3) intracellular T-cell signaling motifs (Long A H, Haso W M, Orentas R J. Lessons learned from a highly-active CD22-specific chimeric antigen receptor. Oncoimmunology. 2013; 2 (4):e23621). The antigen-binding motif of a CAR is commonly fashioned after a single chain Fragment variable (ScFv), the minimal binding domain of an immunoglobulin (Ig) molecule. Alternate antigen-binding motifs, such as receptor ligands (i.e., IL-13 has been engineered to bind tumor expressed IL-13 receptor), intact immune receptors, library-derived peptides, and innate immune system effector molecules (such as NKG2D) also have been engineered. Alternate cell targets for CAR expression (such as NK or gamma-delta T cells) are also under development (Brown C E et al. Clin Cancer Res. 2012; 18(8):2199-209; Lehner M et al. PLoS One. 2012; 7 (2):e31210). There remains significant work with regard to defining the most active T-cell population to transduce with CAR vectors, determining the optimal culture and expansion techniques, and defining the molecular details of the CAR protein structure itself.

The linking motifs of a CAR can be a relatively stable structural domain, such as the constant domain of IgG, or designed to be an extended flexible linker. Structural motifs, such as those derived from IgG constant domains, can be used to extend the ScFv binding domain away from the T-cell plasma membrane surface. This may be important for some tumor targets where the binding domain is particularly close to the tumor cell surface membrane (such as for the disialoganglioside GD2; Orentas et al., unpublished observations). To date, the signaling motifs used in CARs always include the CD3-ζ chain because this core motif is the key signal for T cell activation. The first reported second-generation CARs featured CD28 signaling domains and the CD28 transmembrane sequence. This motif was used in third-generation CARs containing CD137 (4-1BB) signaling motifs as well (Zhao Y et al. J Immunol. 2009; 183 (9): 5563-74). With the advent of new technology, the activation of T cells with beads linked to anti-CD3 and anti-CD28 antibody, and the presence of the canonical "signal 2" from CD28 was no longer required to be encoded by the CAR itself. Using bead activation, third-generation vectors were found to be not superior to second-generation vectors in in vitro assays, and they provided no clear benefit over second-generation vectors in mouse models of leukemia (Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. Anti-CD22- chimeric antigen receptors targeting B cell precursor acute lymphoblastic leukemia, Blood. 2013; 121 (7):1165-74; Kochenderfer J N et al. Blood. 2012; 119 (12):2709-20). This is borne out by the clinical success of CD19-specific CARs that are in a second generation CD28/CD3-ζ (Lee D W et al. American Society of Hematology Annual Meeting. New Orleans, La.; Dec. 7-10, 2013) and a CD137/CD3-ζ signaling format (Porter D L et al. N Engl J Med. 2011; 365 (8): 725-33). In addition to CD137, other tumor necrosis factor receptor superfamily members such as OX40 also are able to provide important persistence signals in CAR-transduced T cells (Yvon E et al. Clin Cancer Res. 2009; 15(18):5852-60). Equally important are the culture conditions under which the CAR T-cell populations were cultured.

T-cell-based immunotherapy has become a new frontier in synthetic biology; multiple promoters and gene products are envisioned to steer these highly potent cells to the tumor microenvironment, where T cells can both evade negative regulatory signals and mediate effective tumor killing. The elimination of unwanted T cells through the drug-induced dimerization of inducible caspase 9 constructs with AP1903 demonstrates one way in which a powerful switch that can control T-cell populations can be initiated pharmacologically (Di Stasi A et al. N Engl J Med. 2011; 365(18):1673-83). The creation of effector T-cell populations that are immune to the negative regulatory effects of transforming growth factor-β by the expression of a decoy receptor further demonstrates that degree to which effector T cells can be engineered for optimal antitumor activity (Foster A E et al. J Immunother. 2008; 31(5):500-5). Thus, while it appears that CARs can trigger T-cell activation in a manner similar to an endogenous T-cell receptor, a major impediment to the clinical application of this technology to date has been limited in vivo expansion of CAR+ T cells, rapid disappearance of the cells after infusion, and disappointing clinical activity. Accordingly, there is an urgent and long felt need in the art for discovering novel compositions and methods for treatment of AML using an approach that can exhibit specific and efficacious anti-tumor effect without the aforementioned shortcomings (i.e. high toxicity, insufficient efficacy).

In addition, natural killer (NK) cell-based cancer immunotherapy has been gaining momentum in the past years (Shimasaki, N., Jain, A. & Campana, D. NK cells for cancer immunotherapy. Nat Rev Drug Discov 19, 200-218 (2020)). Human haploidentical NK cells were shown to be amenable to adoptive transfer and expansion in pediatric and adult cancer patients. (Miller, J. S. et al, Blood 105, 3051-3057 (2005); Rubnitz, J. E. et al. J. Clin. Oncol. 28, 955-959 (2010)). Moreover, second-generation CD19-CAR NK cells generated ex-vivo were effective in killing B Cell ALL (Imai, C., Iwamoto, S. & Campana, D. Blood 106, 376-383 (2005). NK cells activity in vivo may be further enhanced by expression of IL-15, IL-12, IL-18, or other cytokine variants stimulating autonomous growth, cytotoxicity, and prolonged effector function (Imamura, M. et al. *Blood* 124, 1081-1088 (2014)); Ni, J., Miller, M., Stojanovic, A., Garbi, N. & Cerwenka, A. J. Exp. Med. 209, 2351-2365 (2012). By secreting chemoattractants such as CCL5, XCL1 and FLT3L, NK cells are capable of attracting dendritic cells to tumor sites, and thus promote tumor microenvironment favorable for tumor control by the immune system (Bottcher, J. P. et al. Cell 172, 1022-1037 (2018); Barry, K. C. et al, A natural killer-dendritic cell axis defines checkpoint therapy-responsive tumor microenvironments. Nat. Med. 24, 1178-1191 (2018)). In addition, NK cells may be rendered more effective against tumors by manipulation of culture conditions. For example, NK cell activation with cytokines IL-12, IL-15 and IL-18 enhanced NK cell anti-AML responses (Romee, R. et al. Sci. Transi. Med. 8, 357ra123 (2016)).

Clinical generation of NK cells from cord blood hematopoietic progenitors is feasible (Spanholtz, J. et al. PLOS ONE 6, e20740 (2011); Knorr, D. A. et al. Stem Cell Transl. Med. 2, 274-283 (2013)) Similarly, CAR NK cells may be derived by differentiation form iPSCs expressing CAR (Li, Y., Hermanson, D. L., Moriarity, B. S. & Kaufman, D. S. Cell Stem Cell 23, 181-192 (2018). While methods for generating highly effective NK cells and CAR NK cells for cancer therapy are continuing to evolve, significant strides have been made in this field in the past years (Granzin, M. et al. Oncoimmunology 5, e1219007 (2016)). Taken together, these findings demonstrate the emerging potential of CAR NK cells in cancer immunotherapy.

The present invention addresses these needs by providing CAR compositions and therapeutic methods that can be used to treat cancers and other diseases and/or conditions. In particular, the present invention, as disclosed and described herein, provides CARS that may be used in the treatment of diseases, disorders or conditions associated with dysregulated expression of CD123 and which CARs contain CD123 antigen binding domains that exhibit a high surface expression on transduced T cells and NK cells, exhibit a high degree of cytolysis, and transduced T cell in vivo expansion and persistence.

SUMMARY

Novel anti-CD123 antibodies or antigen binding domains thereof and chimeric antigen receptors (CARs) that contain such CD123 antigen binding domains are provided herein, as well as host cells (e.g., T cells) expressing the receptors, and nucleic acid molecules encoding the receptors. CAR may consist either of a single molecule expressed on the effector cell surface, or a CAR comprised of an effector cell-expressed signaling module and a soluble targeting module, such as when the soluble targeting module binds to the cell-expressed signaling module, a complete functional CAR is formed. The CARs exhibit a high surface expression on transduced T cells, with a high degree of cytolysis and transduced T cell expansion and persistence in vivo. Methods of using the disclosed CARs, host cells, and nucleic acid molecules are also provided, for example, to treat a cancer in a subject.

Thus, in one aspect, an isolated polynucleotide encoding a human anti-CD123 antibody or a fragment thereof is provided comprising a nucleic acid sequence selected from the group consisting of SEQ ID NOs: 1, 3, 5, 7, 9, 11, 15, 17, 19, 21, 23, 25, 69, 71, 77, and 87.

In one embodiment, an isolated polynucleotide encoding a fully human anti-CD123 antibody or a fragment thereof is provided, wherein the antibody or a fragment thereof comprises a fragment selected from the group consisting of an Fab fragment, an F(ab')$_2$ fragment, an Fv fragment, and a single chain Fv (ScFv).

In one embodiment, an isolated polynucleotide encoding a fully human anti-CD123 antibody or a fragment thereof is provided, wherein the antibody or a fragment thereof comprises an amino acid sequence selected from the group consisting of SEQ ID NOs: 2, 4, 6, 8, 10, 12, 16, 18, 20, 22, 24, 26, 70, 72, 78, and 88.

In one aspect, an isolated nucleic acid molecule encoding a chimeric antigen receptor (CAR) is provided comprising, from N-terminus to C-terminus, at least one CD123 antigen binding domain encoded by a nucleotide sequence comprising a nucleic acid sequence selected from the group consisting of SEQ ID NOs: 1, 3, 5, 7, 9, 11, 15, 17, 19, 21, 23, 25, 69, 71, 77, and 87, at least one transmembrane domain, and at least one intracellular signaling domain.

In one embodiment, an isolated nucleic acid molecule encoding the CAR is provided wherein the encoded extracellular CD123 antigen binding domain comprises at least one single chain variable fragment of an antibody that binds to CD123.

In another embodiment, an isolated nucleic acid molecule encoding the CAR is provided wherein the encoded extracellular CD123 antigen binding domain comprises at least one heavy chain variable region of an antibody that binds to CD123.

In one embodiment, the targeting domain of the CAR is expressed separately in the form of monoclonal antibody, ScFv Fab, Fab'2 and is containing an antigen-targeting domain comprising a nucleic acid sequence selected from the group consisting of SEQ ID NOs: 1, 3, 5, 7, 9, 11, 15, 17, 19, 21, 23, 25, 69, 71, 77, and 87, coupled to an additional binding tag or epitope, whereas the effector-cell expressed component of the CAR contains a binding domain specifically directed to bind the tag or epitope expressed on the soluble CAR module, such as specific binding on the soluble component of the CAR to the cell bound component of the CAR forms the full functional CAR structure.

In another embodiment, the targeting domain of the CAR is expressed separately in the form of a monoclonal antibody, ScFv Fab, Fab'2 and contains an antigen-targeting domain comprising a nucleic acid sequence selected from the group consisting of SEQ ID NOs: 1, 3, 5, 7, 9, 11, 15, 17, 19, 21, 23, 25, 69, 71, 77, and 87, and an additional ScFv, whereas the effector-cell expressed component of the CAR contains a tag or epitope specifically reactive with the additional ScFv expressed on the soluble CAR module, such as specific binding on the soluble component of the CAR to the cell bound component of the CAR forms the full functional CAR structure.

In yet another embodiment, an isolated nucleic acid molecule encoding the CAR is provided wherein the encoded CAR extracellular CD123 antigen binding domain further comprises at least one lipocalin-based antigen binding antigen (anticalins) that binds to CD123.

In one embodiment, an isolated nucleic acid molecule is provided wherein the encoded extracellular CD123 antigen binding domain is connected to the transmembrane domain by a linker domain.

In another embodiment, an isolated nucleic acid molecule encoding the CAR is provided wherein the encoded CD123 extracellular antigen binding domain is preceded by a sequence encoding a leader or signal peptide.

In yet another embodiment, an isolated nucleic acid molecule encoding the CAR is provided comprising at least one CD123 antigen binding domain encoded by a nucleotide sequence comprising a nucleic acid sequence selected from the group consisting of SEQ ID NOs: 1, 3, 5, 7, 9, 11, 15, 17, 19, 21, 23, 25, 69, 71, 77, and 87, and wherein the CAR additionally encodes an extracellular antigen binding domain targets an antigen that includes, but is not limited to, CD19, CD20, CD22, ROR1, mesothelin, CD33, CD38, CD138, BCMA (CD269), GPC2, GPC3, FGFR4, c-Met, PSMA, Glycolipid F77, EGFRvIII, GD-2, NY-ESO-1 TCR, MAGE A3 TCR, or any combination thereof.

In certain embodiments, an isolated nucleic acid molecule encoding the CAR is provided wherein the additionally encoded extracellular antigen binding domain comprises an anti-CD19 ScFv antigen binding domain, an anti-CD20 ScFv antigen binding domain, an anti-CD22 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESo-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In one aspect, the CARs provided herein further comprise a linker or spacer domain.

In one embodiment, an isolated nucleic acid molecule encoding the CAR is provided wherein the extracellular CD123 antigen binding domain, the intracellular signaling domain, or both are connected to the transmembrane domain by a linker or spacer domain.

In one embodiment, an isolated nucleic acid molecule encoding the CAR is provided wherein the encoded linker domain is derived from the extracellular domain of CD8 or CD28, and is linked to a transmembrane domain.

In another embodiment, an isolated nucleic acid molecule encoding the CAR is provided wherein the encoded CAR further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In yet another embodiment, an isolated nucleic acid molecule encoding the CAR is provided wherein the encoded intracellular signaling domain further comprises a CD3 zeta intracellular domain.

In one embodiment, an isolated nucleic acid molecule encoding the CAR is provided wherein the encoded intracellular signaling domain is arranged on a C-terminal side relative to the CD3 zeta intracellular domain.

In another embodiment, an isolated nucleic acid molecule encoding the CAR is provided wherein the encoded at least one intracellular signaling domain comprises a costimulatory domain, a primary signaling domain, or a combination thereof.

In further embodiments, an isolated nucleic acid molecule encoding the CAR is provided wherein the encoded at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, an isolated nucleic acid molecule encoding the CAR is provided that further contains a leader sequence or signal peptide wherein the leader or signal peptide nucleotide sequence comprises the nucleotide sequence of SEQ ID NO: 13, SEQ ID NO: 39, SEQ ID NO: 41, or SEQ ID NO: 43.

In yet another embodiment, an isolated nucleic acid molecule encoding the CAR is provided wherein the encoded leader sequence comprises the amino acid sequence of SEQ ID NO: 14 SEQ ID NO: 40, SEQ ID NO: 42, or SEQ ID NO: 44.

In one aspect, a chimeric antigen receptor (CAR) is provided herein comprising, from N-terminus to C-terminus, at least one CD123 antigen binding domain, at least one transmembrane domain, and at least one intracellular signaling domain.

In one embodiment, a CAR is provided wherein the extracellular CD123 antigen binding domain comprises at least one single chain variable fragment of an antibody that binds to the antigen, or at least one heavy chain variable region of an antibody that binds to the antigen, or a combination thereof.

In another embodiment, a CAR is provided wherein the at least one transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In some embodiments, the CAR is provided wherein CAR additionally encodes an extracellular antigen binding domain comprising CD19, CD20, CD22, ROR1, mesothelin, CD33, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, or an amino acid sequence with 85%, 90%, 95%, 96%, 97%, 98% or 99% identity thereof, or any combination thereof.

In one embodiment, the CAR is provided wherein the extracellular antigen binding domain comprises an anti-CD19 ScFv antigen binding domain, an anti-CD20 ScFv antigen binding domain, an anti-CD22 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESo-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In another embodiment, the CAR is provided wherein the extracellular antigen binding domain comprises an immunoglobulin variable heavy chain only (VH) anti-CD19 antigen binding domain, an anti-CD20 VH antigen binding domain, an anti-CD22 VH antigen binding domain, an anti-ROR1 VH antigen binding domain, an anti-mesothelin VH antigen binding domain, an anti-CD33 VH antigen binding domain, an anti-CD38 VH antigen binding domain, an anti-CD123 (IL3RA) VH antigen binding domain, an anti-CD138 VH antigen binding domain, an anti-BCMA (CD269) VH antigen binding domain, an anti-GPC2 VH antigen binding domain, an anti-GPC3 VH antigen binding domain, an anti-FGFR4 VH antigen binding domain, an anti-c-Met VH antigen binding domain, an anti-PMSA VH antigen binding domain, an anti-glycolipid F77 VH antigen binding domain, an anti-EGFRvIII VH antigen binding domain, an anti-GD-2 VH antigen binding domain, an anti-NY-ESO-1 TCR VH antigen binding domain, an anti-MAGE A3 TCR VH antigen binding domain, or an amino acid sequence with 85%, 90%, 95%, 96%, 97%, 98% or 99% identity thereof, or any combination thereof.

In another embodiment, the CAR is provided wherein the extracellular antigen binding domain comprises a protein or a peptide (P) sequence capable of specifically binding target antigen, which may be derived from a natural or a synthetic sequence comprising anti-CD19 P antigen binding domain, an anti-CD20 P antigen binding domain, an anti-CD22 P antigen binding domain, an anti-ROR1 P antigen binding domain, an anti-mesothelin P antigen binding domain, an anti-CD33 P antigen binding domain, an anti-CD38 P antigen binding domain, an anti-CD123 (IL3RA) P antigen binding domain, an anti-CD138 P antigen binding domain, an anti-BCMA (CD269) P antigen binding domain, an anti-GPC2 P antigen binding domain, an anti-GPC3 P antigen binding domain, an anti-FGFR4 P antigen binding domain, an anti-c-Met P antigen binding domain, an anti-PMSA P antigen binding domain, an anti-glycolipid F77 P antigen binding domain, an anti-EGFRvIII P antigen binding domain, an anti-GD-2 P antigen binding domain, an anti-NY-ESO-1 TCR P antigen binding domain, an anti-MAGE A3 TCR P antigen binding domain, or an amino acid sequence with 85%, 90%, 95%, 96%, 97%, 98% or 99% identity thereof, or any combination thereof. In another embodiment, a CAR is provided wherein the at least one intracellular signaling domain comprises a costimulatory domain and a primary signaling domain.

In yet another embodiment, a CAR is provided wherein the at least one intracellular signaling domain comprises a costimulatory domain comprising a functional signaling domain of a protein selected from the group consisting of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, the nucleic acid sequence encoding a CAR comprises the nucleic acid sequence of SEQ ID NO: 1. In one embodiment, the nucleic acid sequence encodes a CAR comprising the amino acid sequence of SEQ ID NO: 2.

In another embodiment, the nucleic acid sequence encoding a CAR comprises the nucleic acid sequence of SEQ ID NO: 3. In one embodiment, the nucleic acid sequence encodes a CAR comprising the amino acid sequence of SEQ ID NO: 4.

In another embodiment, the nucleic acid sequence encoding a CAR comprises the nucleic acid sequence of SEQ ID NO: 5. In one embodiment, the nucleic acid sequence encodes a CAR comprising the amino acid sequence of SEQ ID NO: 6.

In another embodiment, the nucleic acid sequence encoding a CAR comprises the nucleic acid sequence of SEQ ID NO: 7. In one embodiment, the nucleic acid sequence encodes a CAR comprising the amino acid sequence of SEQ ID NO: 8.

In another embodiment, the nucleic acid sequence encoding a CAR comprises the nucleic acid sequence of SEQ ID NO: 9. In one embodiment, the nucleic acid sequence encodes a CAR comprising the amino acid sequence of SEQ ID NO: 10.

In another embodiment, the nucleic acid sequence encoding a CAR comprises the nucleic acid sequence of SEQ ID NO: 11. In one embodiment, the nucleic acid sequence encodes a CAR comprising the amino acid sequence of SEQ ID NO: 12.

In another embodiment, the nucleic acid sequence encoding a CAR comprises the nucleic acid sequence of SEQ ID NO: 15. In one embodiment, the nucleic acid sequence encodes a CAR comprising the amino acid sequence of SEQ ID NO: 16.

In another embodiment, the nucleic acid sequence encoding a CAR comprises the nucleic acid sequence of SEQ ID NO: 17. In one embodiment, the nucleic acid sequence encodes a CAR comprising the amino acid sequence of SEQ ID NO: 18.

In another embodiment, the nucleic acid sequence encoding a CAR comprises the nucleic acid sequence of SEQ ID NO: 19. In one embodiment, the nucleic acid sequence encodes a CAR comprising the amino acid sequence of SEQ ID NO: 20.

In another embodiment, the nucleic acid sequence encoding a CAR comprises the nucleic acid sequence of SEQ ID NO: 21. In one embodiment, the nucleic acid sequence encodes a CAR comprising the amino acid sequence of SEQ ID NO: 22.

In another embodiment, the nucleic acid sequence encoding a CAR comprises the nucleic acid sequence of SEQ ID NO: 23. In one embodiment, the nucleic acid sequence encodes a CAR comprising the amino acid sequence of SEQ ID NO: 24.

In another embodiment, the nucleic acid sequence encoding a CAR comprises the nucleic acid sequence of SEQ ID NO: 25. In one embodiment, the nucleic acid sequence encodes a CAR comprising the amino acid sequence of SEQ ID NO: 26.

In another embodiment, the nucleic acid sequence encoding a CAR comprises the nucleic acid sequence of SEQ ID NO: 69. In one embodiment, the nucleic acid sequence encodes a CAR comprising the amino acid sequence of SEQ ID NO: 70.

In another embodiment, the nucleic acid sequence encoding a CAR comprises the nucleic acid sequence of SEQ ID NO: 71. In one embodiment, the nucleic acid sequence encodes a CAR comprising the amino acid sequence of SEQ ID NO: 72.

In another embodiment, the nucleic acid sequence encoding a CAR comprises the nucleic acid sequence of SEQ ID NO: 77. In one embodiment, the nucleic acid sequence encodes a CAR comprising the amino acid sequence of SEQ ID NO: 78.

In another embodiment, the nucleic acid sequence encoding a CAR comprises the nucleic acid sequence of SEQ ID NO: 87. In one embodiment, the nucleic acid sequence encodes a CAR comprising the amino acid sequence of SEQ ID NO: 88.

In one aspect, the CARs disclosed herein are modified to express or contain a detectable marker for use in diagnosis, monitoring, and/or predicting the treatment outcome such as progression free survival of cancer patients or for monitoring the progress of such treatment.

In one embodiment, the nucleic acid molecule encoding the disclosed CARs can be contained in a vector, such as a viral vector. The vector is a DNA vector, an RNA vector, a plasmid vector, a cosmid vector, a herpes virus vector, a measles virus vector, a lentivirus vector, adenoviral vector, adeno-associated viral vector, baculovirus vector, foamy virus vector, or a retrovirus vector, or a combination thereof.

In certain embodiments, the lentiviral vectors encoding one or more of the CARs disclosed herein may be used to produce the genomic material packaged into pseudotyped lentiviral particles. In one embodiment, the pseudotyped lentiviral particles comprise Vesicular Stomatitis Virus-Envelope Glycoprotein (VSV-G) pseudotyped lentiviral vector particles. In another embodiment, the pseudotyped lentiviral particles comprise Baboon Envelope Glycoprotein Pseudotyped Vector (BaEV-G) pseudotyped lentiviral vector particles. In yet another embodiment, the pseudotyped lentiviral particles comprise Feline Endogenous Retrovirus Envelop Glycoprotein RD114 (RD114-G).

In certain embodiments, the vector further comprises a promoter wherein the promoter is an inducible promoter, a tissue specific promoter, a constitutive promoter, a suicide promoter or any combination thereof.

In yet another embodiment, the vector expressing the CAR can be further modified to include one or more operative elements to control the expression of CAR T cells, or to eliminate CAR-T cells by virtue of a suicide switch. The suicide switch can include, for example, an apoptosis inducing signaling cascade or a drug that induces cell death. In a preferred embodiment, the vector expressing the CAR can be further modified to express an enzyme such as thymidine kinase (TK) or cytosine deaminase (CD).

In another aspect, host cells including the nucleic acid molecule encoding the CAR are also provided. In some embodiments, the host cell is a T cell, such as a primary T cell obtained from a subject. In one embodiment, the host cell is a CD8$^+$ T cell.

In yet another aspect, a pharmaceutical composition is provided comprising an anti-tumor effective amount of a population of human T cells, wherein the T cells comprise a nucleic acid sequence that encodes a chimeric antigen receptor (CAR), wherein the CAR comprises at least one extracellular antigen binding domain comprising a CD123 antigen binding domain comprising the amino acid sequence selected from the group consisting of SEQ ID NOs: 70, 72, 78, and 88; at least one linker domain; at least one transmembrane domain; and at least one intracellular signaling domain, wherein the T cells are T cells of a human having a cancer. The cancer includes, inter alia, a hematological cancer such as leukemia (e.g., chronic lymphocytic leukemia (CLL), acute lymphocytic leukemia (ALL), or chronic myelogenous leukemia (CML), lymphoma (e.g., mantle cell lymphoma, non-Hodgkin's lymphoma or Hodgkin's lymphoma)) or multiple myeloma, or a combination thereof.

In one embodiment, a pharmaceutical composition is provided wherein the at least one transmembrane domain of the CAR contains a transmembrane domain of a protein selected from the group consisting of the alpha, beta or zeta chain of the T-cell receptor, CD28, CD3 epsilon, CD45, CD4, CD5, CD8, CD9, CD16, CD22, Mesothelin, CD33, CD37, CD64, CD80, CD86, CD134, CD137 and CD154, or a combination thereof.

In another embodiment, a pharmaceutical composition is provided wherein the human cancer includes an adult carcinoma comprising oral and pharynx cancer (tongue, mouth, pharynx, head and neck), digestive system cancers (esophagus, stomach, small intestine, colon, rectum, anus, liver, interhepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, the genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

In yet another embodiment, a pharmaceutical composition is provided comprising an anti-tumor effective amount of a population of human T cells of a human having a cancer wherein the cancer is a refractory cancer non-responsive to one or more chemotherapeutic agents. The cancer includes hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (Chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma lung cancer, breast cancer, ovarian cancer, prostate cancer, colon cancer, melanoma or other hematological cancer and solid tumors, or any combination thereof.

In another aspect, methods of making CAR-containing T cells (hereinafter "CAR-T cells") are provided. The methods include transducing a T cell with a vector or nucleic acid molecule encoding a disclosed CAR that specifically binds CD123, thereby making the CAR-T cell.

In yet another aspect, a method of generating a population of RNA-engineered cells is provided that comprises introducing an in vitro transcribed RNA or synthetic RNA of a nucleic acid molecule encoding a disclosed CAR into a cell of a subject, thereby generating a CAR cell.

In yet another aspect, a method for diagnosing a disease, disorder or condition associated with the expression of CD123 on a cell, is provided comprising a) contacting the cell with a human anti-CD123 antibody or fragment thereof, wherein the antibody or a fragment thereof comprises an amino acid sequence selected from the group consisting of SEQ ID NOs: 70, 72, 78, and 88; and b) detecting the presence of CD123 wherein the presence of CD123 diagnoses for the disease, disorder or condition associated with the expression of CD123.

In one embodiment, the disease, disorder or condition associated with the expression of CD123 is cancer including hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma lung cancer, breast cancer, ovarian cancer, prostate cancer, colon cancer, melanoma or other hematological cancer and solid tumors, or any combination thereof.

In another embodiment, a method of diagnosing, prognosing, or determining risk of a CD123-related disease in a mammal, is provided comprising detecting the expression of CD123 in a sample derived from the mammal comprising: a) contacting the sample with a human anti-CD123 antibody or fragment thereof, wherein the antibody or a fragment thereof comprises an amino acid sequence selected from the group consisting of SEQ ID NOs: 70, 72, 78, and 88; and b) detecting the presence of CD123 wherein the presence of CD123 diagnoses for a CD123-related disease in the mammal.

In another embodiment, a method of inhibiting CD123-dependent T cell inhibition, is provided comprising contacting a cell with a human anti-CD123 antibody or fragment thereof, wherein the antibody or a fragment thereof comprises an amino acid sequence selected from the group consisting of SEQ ID NOs: 70, 72, 78, and 88. In one embodiment, the cell is selected from the group consisting of a CD123-expressing tumor cell, a tumor-associated macrophage, and any combination thereof.

In another embodiment, a method of blocking T-cell inhibition mediated by a CD123-expressing cell and altering the tumor microenvironment to inhibit tumor growth in a mammal, is provided comprising administering to the mammal an effective amount of a composition comprising an isolated anti-CD123 antibody or fragment thereof, wherein the antibody or a fragment thereof comprises an amino acid sequence selected from the group consisting of SEQ ID NOs: 70, 72, 78, and 88. In one embodiment, the cell is selected from the group consisting of a CD123-expressing tumor cell, a tumor-associated macrophage, and any combination thereof.

In another embodiment, a method of inhibiting, suppressing or preventing immunosuppression of an anti-tumor or anti-cancer immune response in a mammal, is provided comprising administering to the mammal an effective amount of a composition comprising an isolated anti-CD123 antibody or fragment thereof, wherein the antibody or a fragment thereof comprises an amino acid sequence selected from the group consisting of SEQ ID NOs: 70, 72, 78, and 88. In one embodiment, the antibody or fragment thereof inhibits the interaction between a first cell with a T cell, wherein the first cell is selected from the group consisting of a CD123-expressing tumor cell, a tumor-associated macrophage, and any combination thereof.

In another aspect, a method is provided for inducing an anti-tumor immunity in a mammal comprising administering to the mammal a therapeutically effective amount of a T cell transduced with vector or nucleic acid molecule encoding a disclosed CAR.

In another embodiment, a method of treating or preventing cancer in a mammal is provided comprising administering to the mammal one or more of the disclosed CARs, in an amount effective to treat or prevent cancer in the mammal. The method includes administering to the subject a therapeutically effective amount of host cells expressing a disclosed CAR that specifically binds CD123 and/or one or more of the aforementioned antigens, under conditions sufficient to form an immune complex of the antigen binding domain on the CAR and the extracellular domain of CD123 and/or one or more of the aforementioned antigens in the subject.

In yet another embodiment, a method is provided for treating a mammal having a disease, disorder or condition associated with an elevated expression of a tumor antigen, the method comprising administering to the subject a pharmaceutical composition comprising an anti-tumor effective amount of a population of T cells, wherein the T cells comprise a nucleic acid sequence that encodes a chimeric antigen receptor (CAR), wherein the CAR includes at least one extracellular CD123 antigen binding domain comprising the amino acid sequence of SEQ ID NOs: 70, 72, 78, or 88, or any combination thereof, at least one linker or spacer domain, at least one transmembrane domain, at least one intracellular signaling domain, and wherein the T cells are T cells of the subject having cancer.

In yet another embodiment, a method is provided for treating cancer in a subject in need thereof comprising administering to the subject a pharmaceutical composition comprising an anti-tumor effective amount of a population of T cells, wherein the T cells comprise a nucleic acid sequence that encodes a chimeric antigen receptor (CAR), wherein the CAR comprises at least one CD123 antigen binding domain comprising the amino acid sequence of SEQ ID NOs: 70, 72, 78, or 88, or any combination thereof, at least one linker or spacer domain, at least one transmembrane domain, at least one intracellular signaling domain, wherein the T cells are T cells of the subject having cancer. In some embodiments of the aforementioned methods, the at least one transmembrane domain comprises a transmembrane the alpha, beta or zeta chain of the T-cell receptor, CD28, CD3 epsilon, CD45, CD4, CD5, CD8, CD9, CD16, CD22, Mesothelin, CD33, CD37, CD64, CD80, CD86, CD134, CD137 and CD154, or a combination thereof.

In yet another embodiment, a method is provided for generating a persisting population of genetically engineered T cells in a human diagnosed with cancer. In one embodiment, the method comprises administering to a human a T cell genetically engineered to express a CAR wherein the CAR comprises at least one CD123 antigen binding domain comprising the amino acid sequence of SEQ ID NOs: 70, 72, 78, or 88, or any combination thereof, at least one transmembrane domain; and at least one intracellular signaling domain wherein the persisting population of genetically engineered T cells, or the population of progeny of the T cells, persists in the human for at least one month, two months, three months, four months, five months, six months, seven months, eight months, nine months, ten months, eleven months, twelve months, two years, or three years after administration.

In one embodiment, the progeny T cells in the human comprise a memory T cell. In another embodiment, the T cell is an autologous T cell.

In all of the aspects and embodiments of methods described herein, any of the aforementioned cancers, diseases, disorders or conditions associated with an elevated expression of a tumor antigen that may be treated or prevented or ameliorated using one or more of the CARs disclosed herein.

In yet another aspect, a kit is provided for making a chimeric antigen receptor T-cell as described supra or for preventing, treating, or ameliorating any of the cancers, diseases, disorders or conditions associated with an elevated expression of a tumor antigen in a subject as described supra, comprising a container comprising any one of the nucleic acid molecules, vectors, host cells, or compositions disclosed supra or any combination thereof, and instructions for using the kit.

It will be understood that the CARs, host cells, nucleic acids, and methods are useful beyond the specific aspects and embodiments that are described in detail herein. The foregoing features and advantages of the disclosure will become more apparent from the following detailed description, which proceeds with reference to the accompanying figures.

BRIEF DESCRIPTION OF THE FIGURES

(FIG. 1A) Anti-CD123 CAR constructs were generated by linking the single chain fragment variable sequence (scFv) targeting CD123 in frame to CD8 hinge (H) and transmembrane domain (TM), the 4-1BB (CD137) co-stimulatory domain and the CD3 zeta activation domain. (FIG. 1B) T cells were activated with TransAct CD3/CD28 reagent in the presence of IL-2, and transduced with lentiviral vectors encoding CAR123 constructs. On culture day 7, viable transduced T cells (7-AAD negative) were assayed for CAR surface expression using CD123 Fc followed by anti-Fc-AF647. Percentage of CAR T-positive populations in relation to non-transduced T cell control. (FIG. 1C) CAR T cell viability was measured by trypan blue exclusion (Vi-Cell) at culture day 3 and day 7. The CD33 CAR construct (1906) was included as control.

(FIG. 5A) CD123 CAR candidate D0126 and control CAR 33 LTG1906 were included in the first animal study, (FIG. 5B) CD123 CAR candidate D0131 was added to D0126 and LTG1906 in the second animal study Tumor alone (TA) and untransduced T cells (UTD) groups were included as controls in both studies.

(FIG. 6A) Representative time course bioluminescent images of tumor burden in mice. (FIG. 6B) Time course of tumor growth based on mouse whole body bioluminescence (radiance) were quantified and individually plotted as shown, n=6, (FIG. 6C) Percentage change in body weight was recorded every other day, n=6, mean±SEM. (FIG. 6D) Survival curves of mice following CAR T treatment and controls.

FIG. 8A shows representative time course bioluminescent images of the tumor burden in each group. (FIG. 8B) Time course plot of tumor growth based on mouse whole body bioluminescence (radiance), n=6, mean±SEM. (FIG. 8C) Percentage of body weight change was recorded every other day, n=6, mean±SEM. FIG. 8D Survival curve of CAR T and control groups overtime is shown.

(FIG. 10A) Isolation and purity of NK cells. (FIG. 10B) Target cells were generated by overexpressing CD123 on the RS4-11 cell line. CD123 transduced RS4-11 were sorted, and limited dilution was performed to generate homogenous CD123 expressing RS4-11 cells.

(FIG. 12A) NK cells were transduced with a lentiviral vector containing CD123-CAR constructs D0126 and Z32. CD123-CAR expressions were determined on Day 8 after transduction. (FIG. 12B) Cytotoxicity of CD123-CAR-NK cells was determined using RS411-CD123 target cells. Results represented 3 independent experiments.

(FIG. 13A) NK cells were transduced with different volumes of the lentiviral vectors containing CD123-CAR. CD123-CAR expressions were detected on Day 8 after transduction. (FIG. 13B) Cytotoxicity of CD123-CAR-NK cells was determined using RS411-CD123 target cells. The effector and target ratio used for the cytotoxicity experiments was 1:1.

(FIG. 14A) NK cells were transduced with CD123-CAR constructs D0126 and Z32 and expanded parallel with untransduced NK cells. (FIG. 14B) NK cells viability were determined at the different time point in culture after transduced with CD123-CAR. D1, D3, D5, D8, and D11 indicate one day, three days, five days, eight days and eleven days after transduction. UTD indicates untransduced NK cells; Z32 indicates CD123 binder Z32; D0126 indicates CD123 binder D0126.

DETAILED DESCRIPTION

Definitions

Figure 1A:
FIGS. 1A-1C depict CD123 CAR structure, surface expression and cell viability in human primary T cells.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements. The phrase "and/or" means "and" or "or." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

The term "about" when referring to a measurable value such as an amount, a temporal duration, and the like, is meant to encompass variations of .+-0.20% or in some instances .+-0.10%, or in some instances .+-0.5%, or in some instances .+-0.1%, or in some instances .+-0.0.1% from the specified value, as such variations are appropriate to perform the disclosed methods.

Unless otherwise noted, the technical terms herein are used according to conventional usage. Definitions of common terms in molecular biology can be found in Benjamin Lewin, Genes VII, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

The present disclosure provides for CD123 antibodies or fragments thereof as well as chimeric antigen receptors (CARs) having such CD123 antigen binding domains. The enhancement of the functional activity of the CAR directly relates to the enhancement of functional activity of the CAR-expressing T cell. As a result of one or more of these modifications, the CARs exhibit both a high degree of cytokine-induced cytolysis and cell surface expression on transduced T cells, along with an increased level of in vivo T cell expansion and persistence of the transduced CAR-expressing T cell.

The unique ability to combine functional moieties derived from different protein domains has been a key innovative feature of Chimeric Antigen Receptors (CARs). The choice of each of these protein domains is a key design feature, as is the way in which they are specifically combined. Each design domain is an essential component that can be used across different CAR platforms to engineer the function of lymphocytes. For example, the choice of the extracellular binding domain can make an otherwise ineffective CAR be effective.

The invariable framework components of the immunoglobulin-derived protein sequences used to create the extracellular antigen binding domain of a CAR can either be entirely neutral, or they can self-associate and drive the T cell to a state of metabolic exhaustion, thus making the therapeutic T cell expressing that CAR far less effective. This occurs independently of the antigen binding function of this CAR domain. Furthermore, the choice of the intracellular signaling domain(s) also can govern the activity and the durability of the therapeutic lymphocyte population used for immunotherapy. While the ability to bind target antigen and the ability to transmit an activation signal to the T cell through these extracellular and intracellular domains, respectively, are important CAR design aspects, what has also become apparent is that the choice of the source of the extracellular antigen binding fragments can have a significant effect on the efficacy of the CAR and thereby have a defining role for the function and clinical utility of the CAR.

Surprisingly and unexpectedly it has now been discovered that use of an entirely human antigen binding domain in a CAR, rather than using mouse-derived antigen binding fragments which are prone to induce anti-mouse immune response and CAR T elimination in a host (c.f., the UPenn-sponsored clinical trial using mouse derived SS1 ScFv sequence, NCT02159716), may also determine the functional activity of a CAR-expressing T cell.

The CARs disclosed herein are expressed at a high level in a cell. A cell expressing the CAR has a high in vivo proliferation rate, produces large amounts of cytokines, and has a high cytotoxic activity against a cell having, on its surface, a CD123 antigen to which a CAR binds. The use of a human extracellular CD123 antigen binding domain results in generation of a CAR that functions better in vivo, while avoiding the induction of anti-CAR immunity in the host immune response and the killing of the CAR T cell population. The CARs expressing the entirely human extracellular CD123 ScFv antigen binding domain exhibit superior activities/properties including i) prevention of poor CAR T persistence and function as seen with mouse-derived binding sequences; ii) lack of regional (i.e. intrapleural) delivery of the CAR to be efficacious; and iii) ability to generate CAR T cell designs based both on binders with high and low affinity to CD123. This latter property allows investigators to better tune efficacy vs toxicity, and/or tissue specificity of the CAR T product, since lower-affinity binders may have higher specificity to tumors vs normal tissues due to higher expression of CD123 on tumors than normal tissue, which may prevent on-target off tumor toxicity and bystander cell killing.

What follows is a detailed description of the inventive CARs including a description of their extracellular CD123 antigen binding domain, the transmembrane domain and the intracellular domain, along with additional description of the CARs, antibodies and antigen binding fragments thereof, conjugates, nucleotides, expression, vectors, and host cells, methods of treatment, compositions, and kits employing the disclosed CARs.

A. Chimeric Antigen Receptors (CARs)

The CARs disclosed herein comprise at least one CD123 antigen binding domain capable of binding to CD123, at least one transmembrane domain, and at least one intracellular domain.

A chimeric antigen receptor (CAR) is an artificially constructed hybrid protein or polypeptide containing the antigen binding domains of an antibody (e.g., single chain variable fragment (ScFv)) linked to T-cell signaling domains via the transmembrane domain. Characteristics of CARs include their ability to redirect T-cell specificity and reactivity toward a selected target in a non-MHC-restricted manner, and exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

As disclosed herein, the intracellular T cell signaling domains of the CARs can include, for example, a T cell receptor signaling domain, a T cell costimulatory signaling domain, or both. The T cell receptor signaling domain refers to a portion of the CAR comprising the intracellular domain of a T cell receptor, such as, for example, and not by way of limitation, the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen.

1. Extracellular Domain

In one embodiment, the CAR comprises a target-specific binding element otherwise referred to as an antigen binding domain or moiety. The choice of domain depends upon the type and number of ligands that define the surface of a target cell. For example, the antigen binding domain may be chosen to recognize a ligand that acts as a cell surface marker on target cells associated with a particular disease state. Thus, examples of cell surface markers that may act as ligands for the antigen binding domain in the CAR include those associated with viral, bacterial and parasitic infections, autoimmune disease and cancer cells.

In one embodiment, the CAR can be engineered to target a tumor antigen of interest by way of engineering a desired antigen binding domain that specifically binds to an antigen on a tumor cell. Tumor antigens are proteins that are produced by tumor cells that elicit an immune response, particularly T-cell mediated immune responses. The selection of the antigen binding domain will depend on the particular type of cancer to be treated. Tumor antigens include, for example, a glioma-associated antigen, carcinoembryonic antigen (CEA), .beta.-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and CD123. The tumor antigens disclosed herein are merely included by way of example. The list is not intended to be exclusive and further examples will be readily apparent to those of skill in the art.

In one embodiment, the tumor antigen comprises one or more antigenic cancer epitopes associated with a malignant tumor. Malignant tumors express a number of proteins that can serve as target antigens for an immune attack. These molecules include, but are not limited to, tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

In one preferred embodiment, the tumor antigen is CD123 and the tumors associated with expression of CD123 comprise lung mesothelioma, ovarian, and pancreatic cancers that express high levels of the extracellular protein CD123, or any combination thereof.

The type of tumor antigen may also be a tumor-specific antigen (TSA) or a tumor-associated antigen (TAA). A TSA is unique to tumor cells and does not occur on other cells in the body. A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSAs or TAAs include the following: Differentiation antigens such as MART-1/MelanA (MART-I), gp100 (Pmel 17), tyrosinase, TRP-1, TRP-2 and tumor-specific multi-lineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alphafetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90Mac-2 binding protein\cyclophilin C-associated protein, TAAL6, TAG72, TLP, and TPS.

In one embodiment, the antigen binding domain portion of the CAR targets an antigen that includes but is not limited to CD19, CD20, CD22, ROR1, CD123, CD33, c-Met, PSMA, Glycolipid F77, EGFRvIII, GD-2, MY-ESO-1 TCR, MAGE A3 TCR, and the like.

In a preferred embodiment, the antigen binding domain portion of the CAR targets the extracellular CD123 antigen.

In one preferred embodiment, the isolated nucleic acid molecule encoding the extracellular CD123 MT-16 antigen binding domain comprises a nucleotide sequence of SEQ ID NO: 69, or a sequence with 85%, 90%, 95%, 96%, 97%, 98% or 99% identity thereof. In one embodiment, an isolated nucleic acid molecule is provided wherein the encoded extracellular CD123 MT-16 antigen binding domain comprises an amino acid sequence of SEQ ID NO: 70, or an amino acid sequence with 85%, 90%, 95%, 96%, 97%, 98% or 99% identity to an amino acid sequence of SEQ ID NO: 70.

In one preferred embodiment, the isolated nucleic acid molecule encoding the extracellular CD123 MT-32 antigen binding domain comprises a nucleotide sequence of SEQ ID NO: 71, or a sequence with 85%, 90%, 95%, 96%, 97%, 98% or 99% identity thereof. In one embodiment, an isolated nucleic acid molecule is provided wherein the encoded extracellular CD123 MT-32 antigen binding domain comprises an amino acid sequence of SEQ ID NO: 72, or an amino acid sequence with 85%, 90%, 95%, 96%, 97%, 98% or 99% identity to an amino acid sequence of SEQ ID NO: 72.

In one preferred embodiment, the isolated nucleic acid molecule encoding the extracellular CD123 Z16 antigen binding domain comprises a nucleotide sequence of SEQ ID NO: 77, or a sequence with 85%, 90%, 95%, 96%, 97%, 98% or 99% identity thereof. In one embodiment, an isolated nucleic acid molecule is provided wherein the encoded extracellular CD123 Z16 antigen binding domain comprises an amino acid sequence of SEQ ID NO: 78, or an amino acid sequence with 85%, 90%, 95%, 96%, 97%, 98% or 99% identity to an amino acid sequence of SEQ ID NO: 78.

In one preferred embodiment, the isolated nucleic acid molecule encoding the extracellular CD123 Z32 antigen binding domain comprises a nucleotide sequence of SEQ ID NO: 87, or a sequence with 85%, 90%, 95%, 96%, 97%, 98% or 99% identity thereof. In one embodiment, an isolated nucleic acid molecule is provided wherein the encoded extracellular CD123 Z32 antigen binding domain comprises an amino acid sequence of SEQ ID NO: 88, or an amino acid sequence with 85%, 90%, 95%, 96%, 97%, 98% or 99% identity to an amino acid sequence of SEQ ID NO: 88.

The generation and binding characteristics of the specific CD123 variable heavy chain only and ScFv antigen binding fragments or antigen binders described herein is shown in Example 1.

Figure 1B:
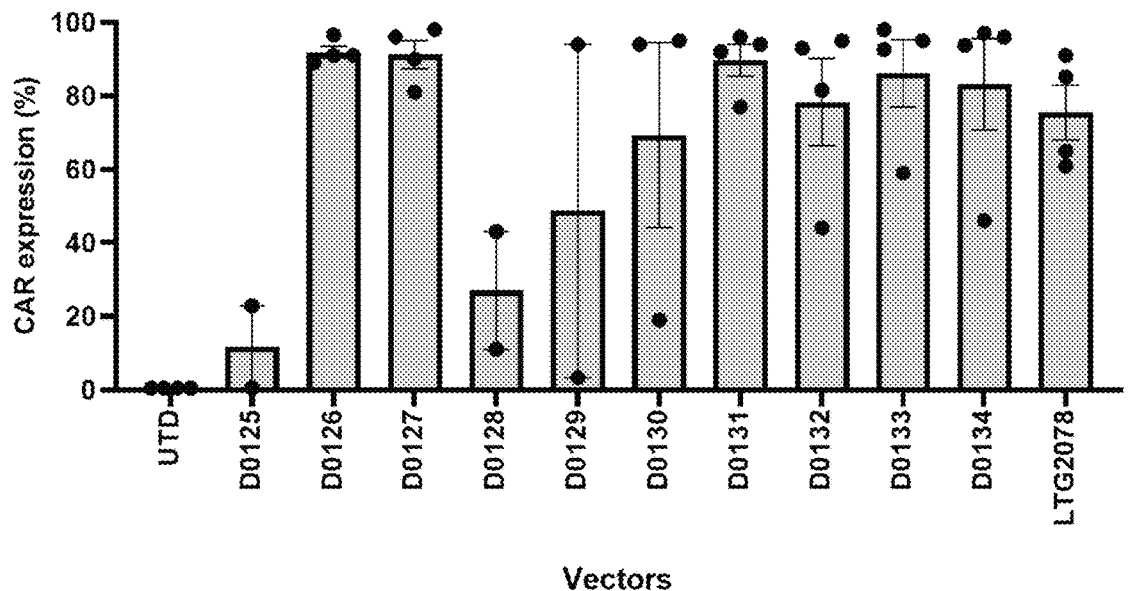
Figure 1C:
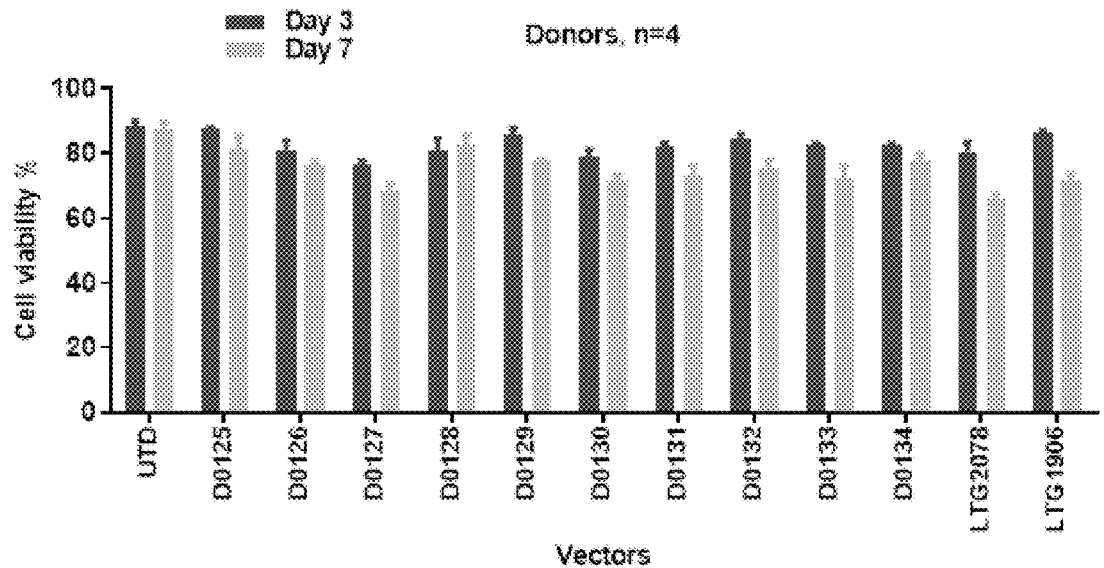

In the various embodiments of the CD123-specific CARs disclosed herein, the general scheme is set forth in FIGS. 1A-1C and includes, from the N-terminus to the C-terminus, a signal or leader peptide, anti-CD123 ScFv, extracellular linker, CD8 transmembrane, 4-1BB, CD3 zeta, wherein the bolded text represents the cloning sites for linking domains.

In one embodiment, the nucleic acid sequence encoding a CAR comprises the nucleic acid sequence of SEQ ID NO: 1, and encodes the CAR comprising the amino acid sequence as set forth in SEQ ID NO: 2.

In one embodiment, the nucleic acid sequence encoding a CAR comprises the nucleic acid sequence of SEQ ID NO: 3, or a sequence with 85%, 90%, 95%, 96%, 97%, 98% or 99% identity thereof, and encodes the CAR comprising the amino acid sequence as set forth in SEQ ID NO: 4 or a sequence with 85%, 90%, 95%, 96%, 97%, 98% or 99% identity thereof.

In another embodiment, the nucleic acid sequence encoding a CAR comprises the nucleic acid sequence of SEQ ID NO: 5, and encodes the CAR comprising the amino acid sequence as set forth in SEQ ID NO: 6.

In another embodiment, the nucleic acid sequence encoding a CAR comprises the nucleic acid sequence of SEQ ID NO: 7 or a sequence with 85%, 90%, 95%, 96%, 97%, 98% or 99% identity thereof, and encodes the CAR comprising the amino acid sequence as set forth in SEQ ID NO: 8 or a sequence with 85%, 90%, 95%, 96%, 97%, 98% or 99% identity thereof.

In another embodiment, the nucleic acid sequence encoding a CAR comprises the nucleic acid sequence of SEQ ID NO: 9, and encodes the CAR comprising the amino acid sequence as set forth in SEQ ID NO: 10.

In another embodiment, the nucleic acid sequence encoding a CAR comprises the nucleic acid sequence of SEQ ID NO: 11 or a sequence with 85%, 90%, 95%, 96%, 97%, 98% or 99% identity thereof, and encodes the CAR comprising the amino acid sequence as set forth in SEQ ID NO: 12 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 15, and encodes the CAR comprising the amino acid sequence as set forth in SEQ ID NO: 16.

In yet another embodiment, the nucleic acid sequence encoding a CAR comprises the nucleic acid sequence of SEQ ID NO: 17 or a sequence with 85%, 90%, 95%, 96%, 97%, 98% or 99% identity thereof, and encodes the CAR comprising the amino acid sequence as set forth in SEQ ID NO: 18 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 19, and encodes the CAR comprising the amino acid sequence as set forth in SEQ ID NO: 20.

In yet another embodiment, the nucleic acid sequence encoding a CAR comprises the nucleic acid sequence of SEQ ID NO: 21 or a sequence with 85%, 90%, 95%, 96%, 97%, 98% or 99% identity thereof, and encodes the CAR comprising the amino acid sequence as set forth in SEQ ID NO: 22 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 23, and encodes the CAR comprising the amino acid sequence as set forth in SEQ ID NO: 24.

In yet another embodiment, the nucleic acid sequence encoding a CAR comprises the nucleic acid sequence of SEQ ID NO: 25 or a sequence with 85%, 90%, 95%, 96%, 97%, 98% or 99% identity thereof, and encodes the CAR comprising the amino acid sequence as set forth in SEQ ID NO: 26 or a sequence with 85%, 90%, 95%, 96%, 97%, 98% or 99% identity thereof.

The development of anti-CD123 CAR T cells incorporating single chain fragment variable (ScFv) sequences reactive with CD123 antigen, is described in Examples 3 and 4 infra, and the generation of NK cells expressing CD123 CAR constructs is shown in Example 5 infra.

Example 3 describes the generation and in vitro evaluation of CAR T cells targeting the CD123 antigen for the treatment of AML.

Lentiviral vectors encoding the CD123 CAR constructs were used for CAR transduction into human primary T cells at multiplicity of infection (MOI) of 40. Different CD123 CAR construct exhibited different level of expression ranging from 0-80% (n=4 donors), FIG. 1B. CAR D0126, D0127, D0131, D0132, D0133 and D0134 exhibited similar or higher surface expression than positive CAR 123 control LTG2078; while CAR D0130 had slightly lower surface expression, followed by D0129 and D0128, while D0125 had lowest expression in multiple donors. Cell viability was examined at day 3 and day 7 after T cell activation, as showed in FIG. 1C. All the CD123 CAR T cells showed improved or equivalent viability compared with control CAR LTG2078.

Figure 3A:
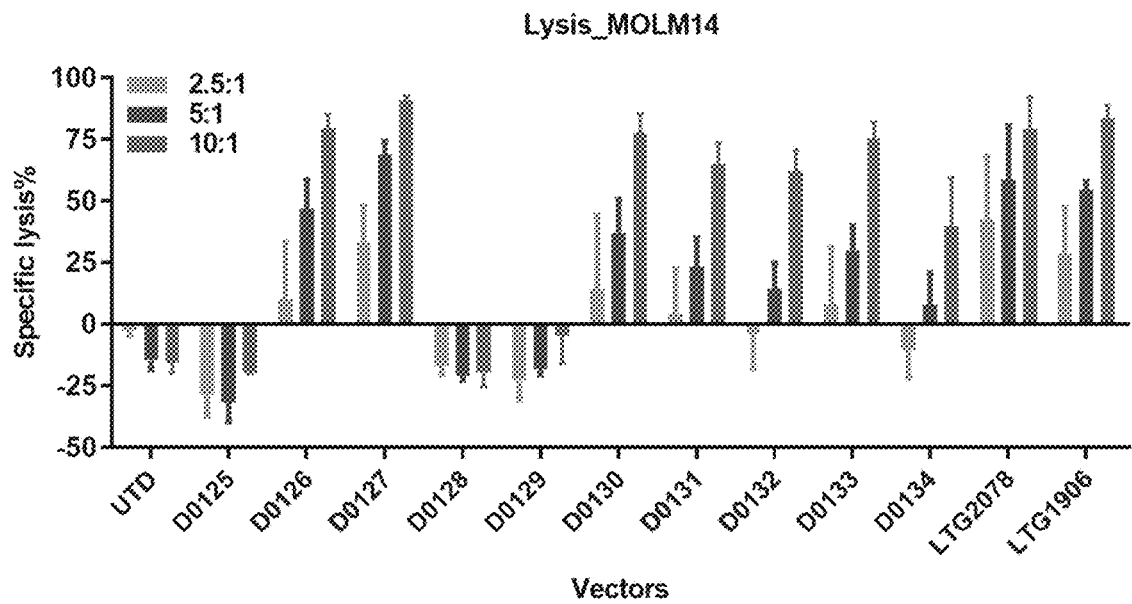
FIGS. 3A-3C depict the analysis of tumor cell lysis induced by CAR123 constructs in vitro. Luciferase-based cytotoxicity assays were performed using MOL14 (FIG. 3A), KG1a (FIG. 3B) and 293T (FIG. 3C) target cell lines stably expression firefly luciferase. CAR T cells and tumor cells were co-incubated overnight at the indicated effector to target (E:T) ratios: 2.5:1, 5:1, or 10:1. Percentage specific target lysis was assessed by luminometry.
Figure 3B:
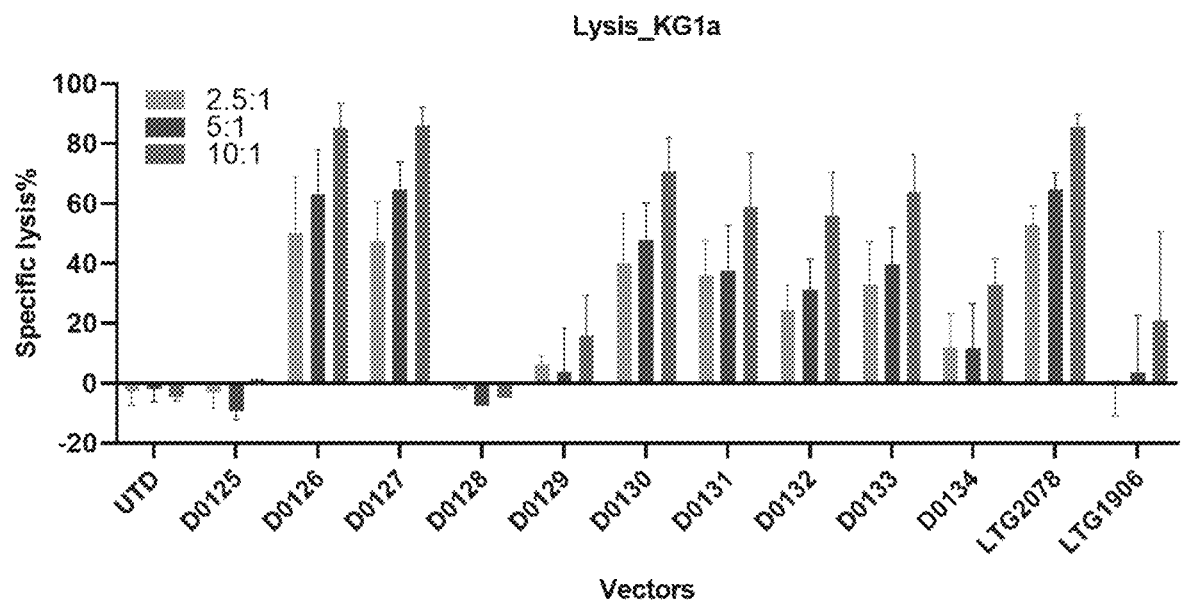
Figure 3C:
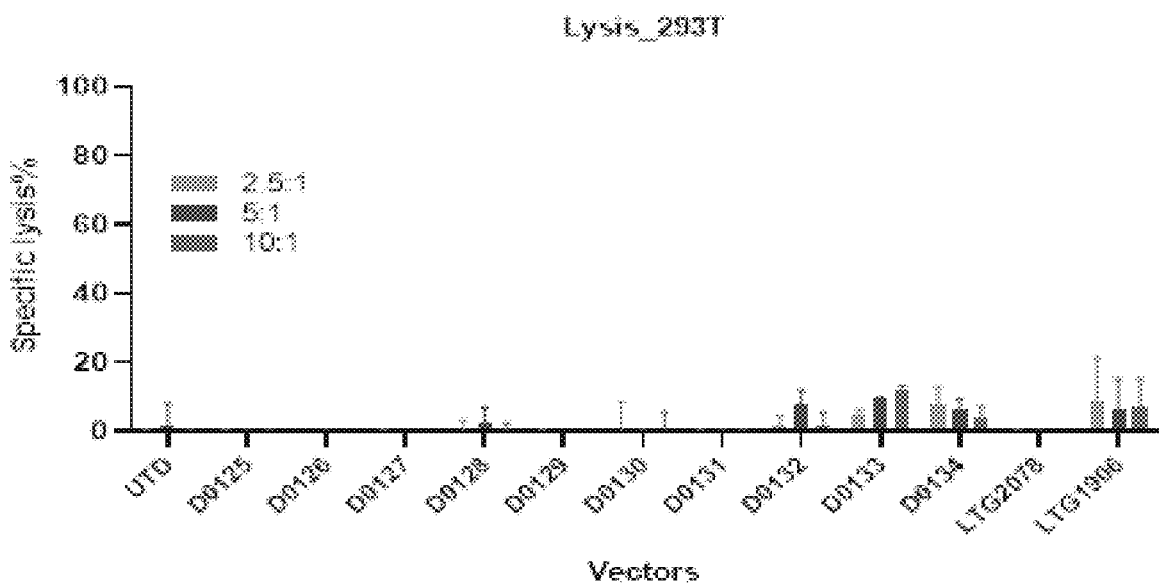

Target-specific cytotoxicity of CD123 CARs in vitro, was evaluated against CD123-positive leukemic lines (MOLM14, KG1a, RS4;11) and CD123-negative non-leukemic lines (293T and A431). CAR-T cells were co-incubated with MOLM14, KG-1a or 293T cell lines at effector to target ratios 2.5:1; 5:1 and 10:1. After overnight co-incubation, cultures were analyzed in luminescence based in vitro killing assays. Most CAR123 constructs-expressing primary T cell lines lysed MOL14-CD123+, while three CD123 CAR lines, D0125, D0128 and D0129, lacked target lytic capability (FIG. 3A). Similarly, KG-1a-CD123+ target cells were killed by most CAR T constructs, except for D0125, D0128 and D0129 (FIG. 3B). The control CD33 CAR LTG1906 exhibited high cytotoxicity toward MOLM14 (CD33$^{High}$) and low lytic potency towards KG1a (CD33$^{Low}$), in agreement with the CD123 expression levels. Furthermore, no killing above background of CD123 negative 293T cell line (FIG. 3C) was observed, demonstrating the robust target-specific cytotoxic function of all CD123 CAR constructs, except for CAR D0125, D0128, and D0129.

Figure 4A:
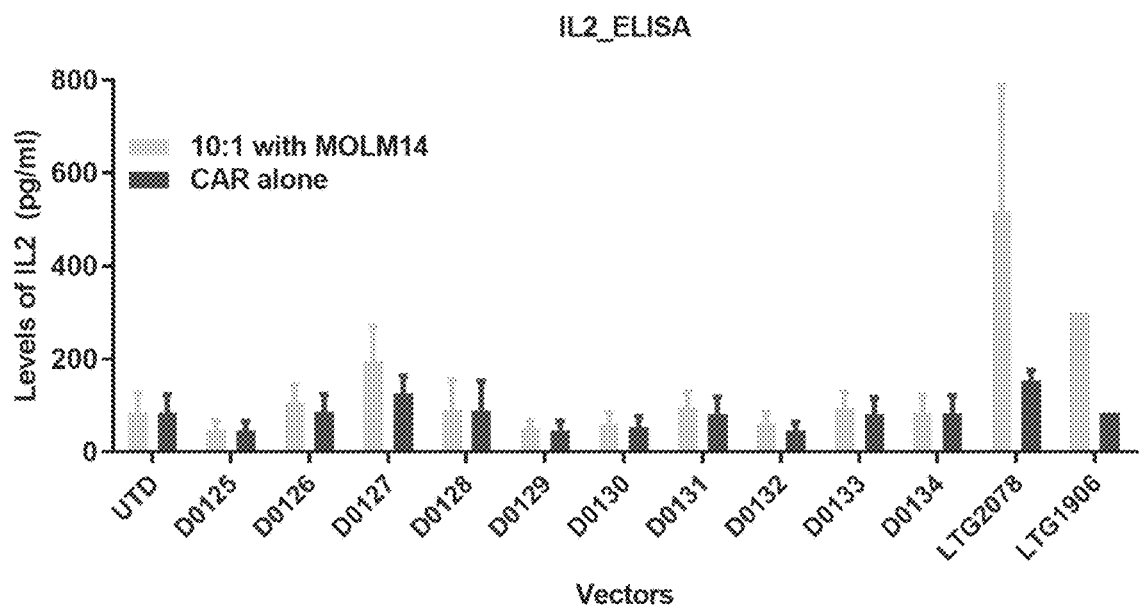
FIGS. 4A-4C depict CAR T cytokine release in response to leukemia cell lines. Cytokine production by CAR T cells, listed on the x-axis, upon overnight co-culture with the MOLM14 leukemia line at the E:T ratio of 10:1, was measured by ELISA. Bars represent mean+SD of replicate samples. Data are representative of three independent experiments performed with CAR T cells from three separate donors.
Figure 4B:
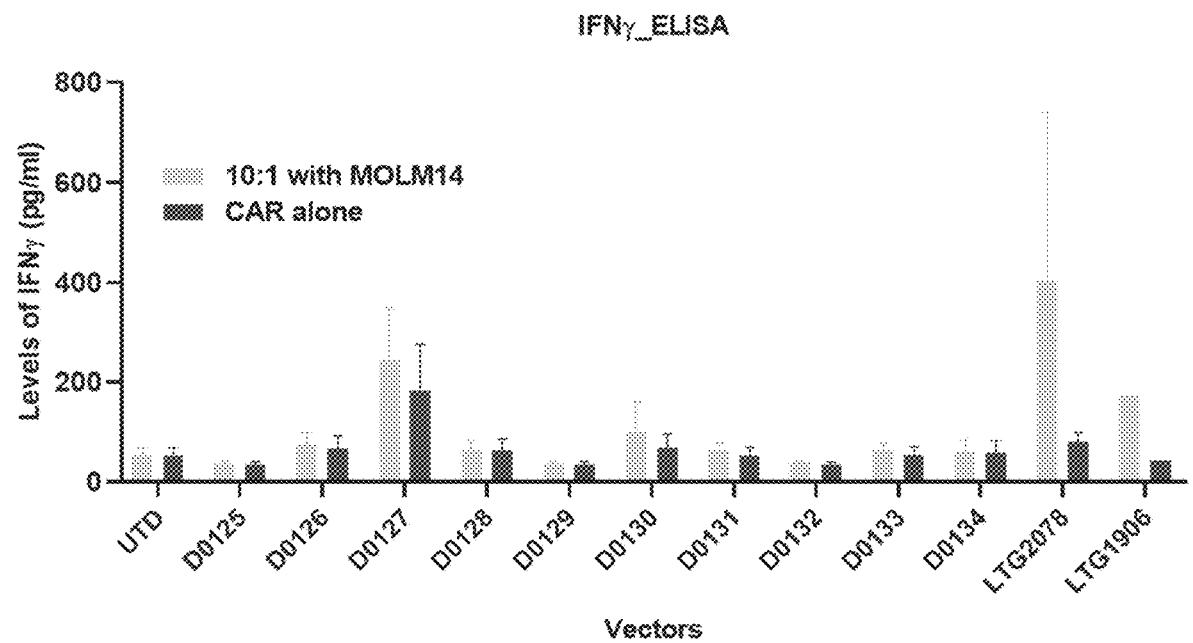
Figure 4C:
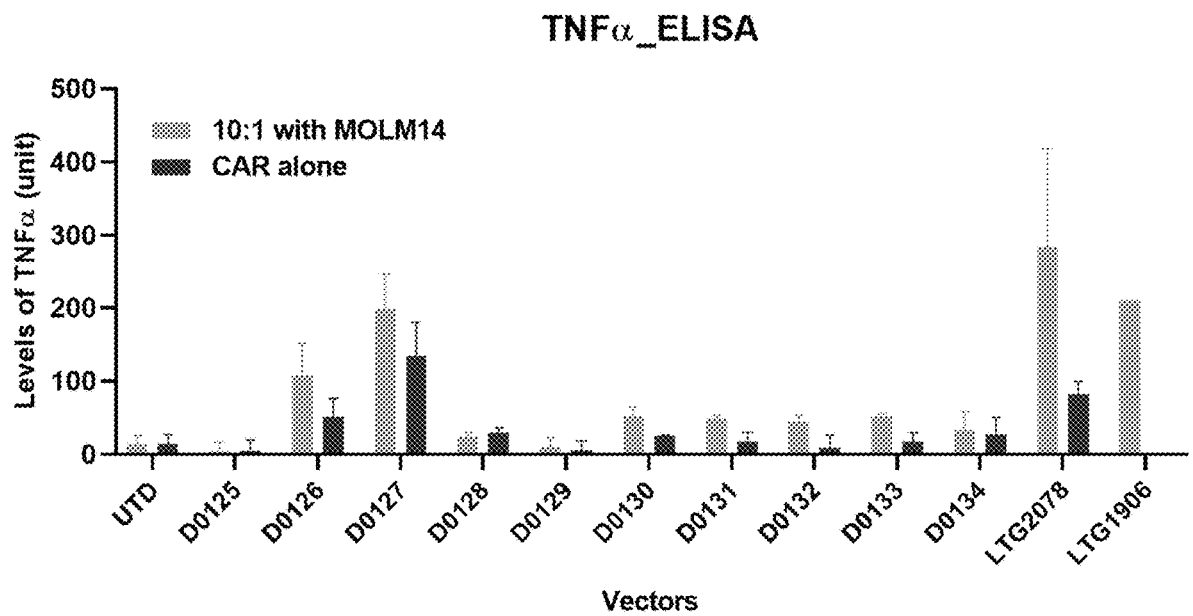

Production of the T cell homeostatic and pro-inflammatory cytokines IL-2, IFNγ, and TNFα by the CD123 CARs, and control constructs CAR LTG2078 and CD33 CAR LTG1906, was examined by ELISA in culture supernatants after overnight co-incubation of CAR T cells with MOLM14 target line at an E:T ratio of 10 (FIG. 4A-4C). Specific target induced cytokine release was detected by comparison of each CAR T group incubated with target cells to the respective CAR T alone experimental group, and also comparing the target co-incubated CAR T groups to the previously characterized CAR123 control LTG2078. While CAR123 control LTG2078 and CAR33 control LTG1906 elaborated cytokines after co-incubation with MOLM14 target cells, most test CD123 CAR T constructs have not produced significant increases in IFNγ, TNFα, or IL-2 cytokines after overnight co-culture with MOLM14 cells. One exception was CAR123 D0127, which elaborated IFNγ, and TNFα levels even in the absence of target cells (T cells alone group), indicating tumor-independent cytokine response. This effect could not be anticipated form previous experiments, and it demonstrates the non-obviousness of the present invention. Excluding CAR123 D0127, cytokine response of the CD123 CAR constructs evaluated herein was comparable to the non-transduced T cells (UTD) control, suggesting low risk of inducing cytokine-mediated adverse effects, such as cytokine release syndrome (CRS) and immune effector cell-associated neurotoxicity syndrome (ICANS).

Figure 5A:
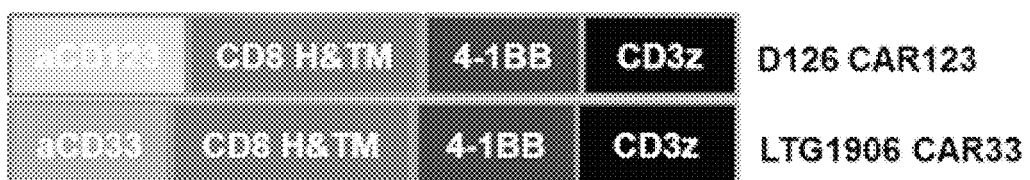
FIGS. 5A AND 5B depict the CAR constructs tested in the two in vivo studies.
Figure 5B:

NSG (NOD.Cg-Prkdc$^{scid}$ Il2rgtm1Wjl/SzJ) mouse MOLM14 xenograft AML model was used to further explore the in vivo tumor rejection functionality of the two top CAR123 candidates D0126 and D0131. Two animal studies using CAR T cells derived from separate healthy donors were performed, one focusing on CAR D0126 (FIG. 5A) and the other comparing between CAR123 constructs D0126 and D0131 (FIG. 5B). The previously characterized CAR LTG1906, targeting the CD33 antigen on MOLM14 tumor cells, was included as a comparative control.

Figure 6A:
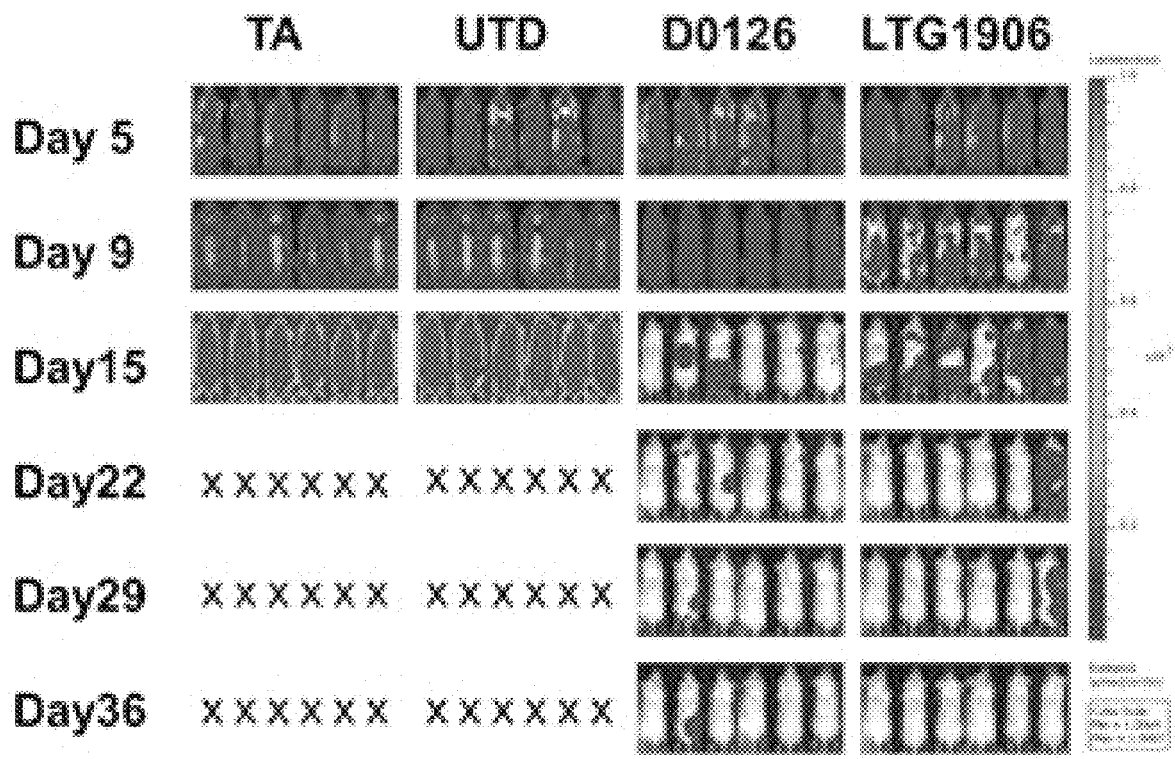
FIGS. 6A-6D depict the in vivo activity of CAR T constructs in the first animal study. NSG mice were injected i.v. with MOLM14-luciferase cells on Day 0, and treated with 5×10⁶/mouse T cells or UTD on day seven. Six mice per CAR T treatment group and control group were studied.
Figure 6B:
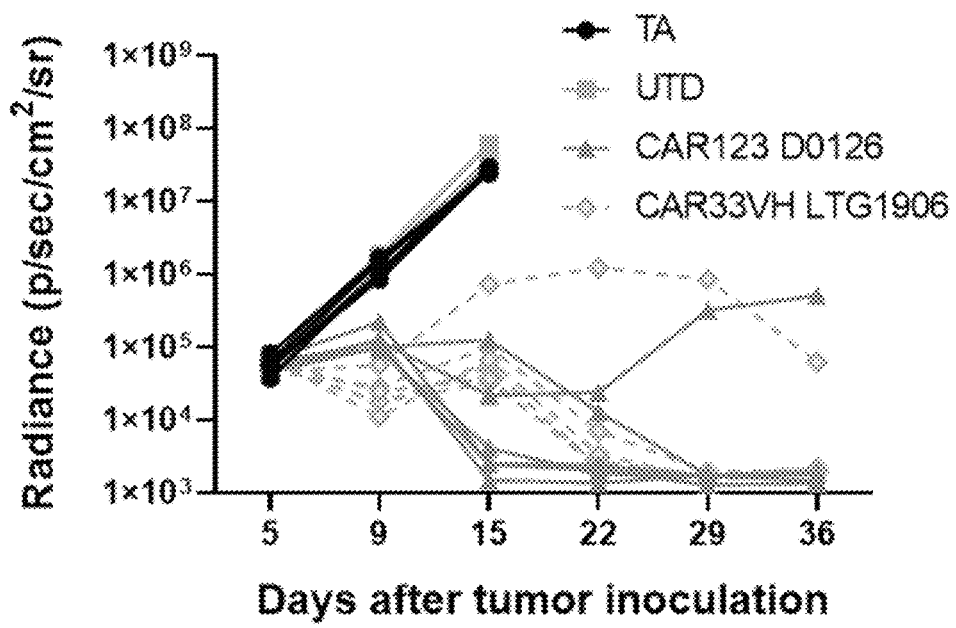
Figure 6C:
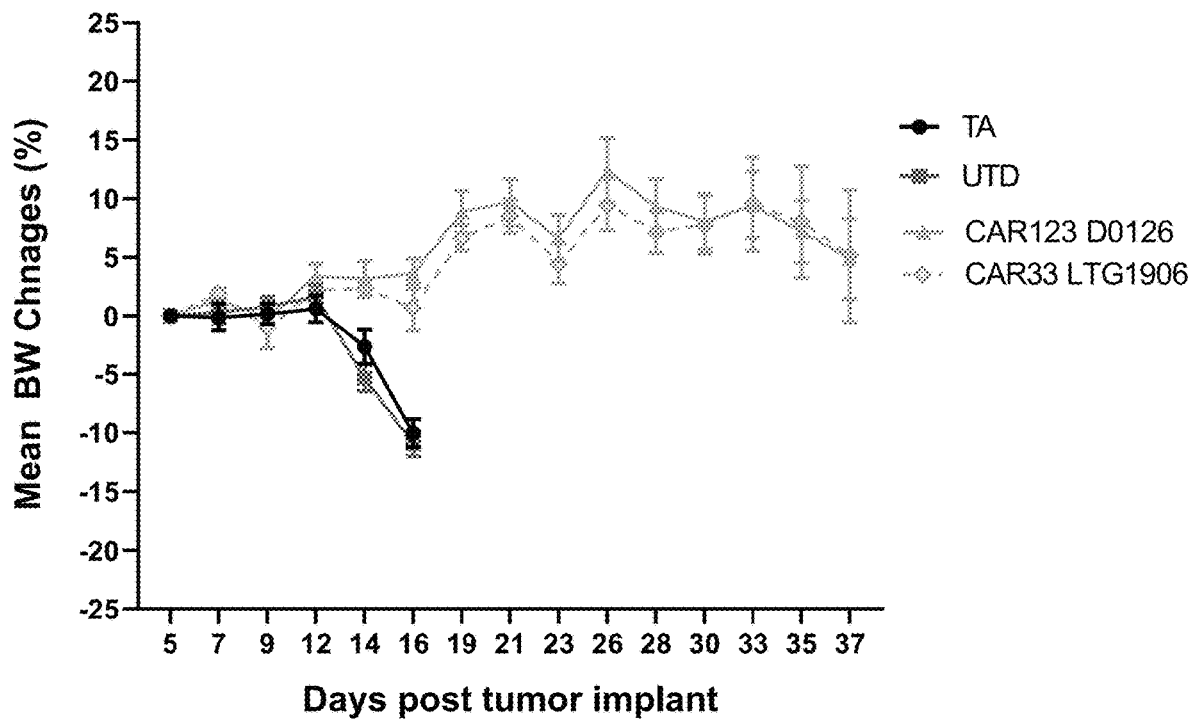
Figure 6D:
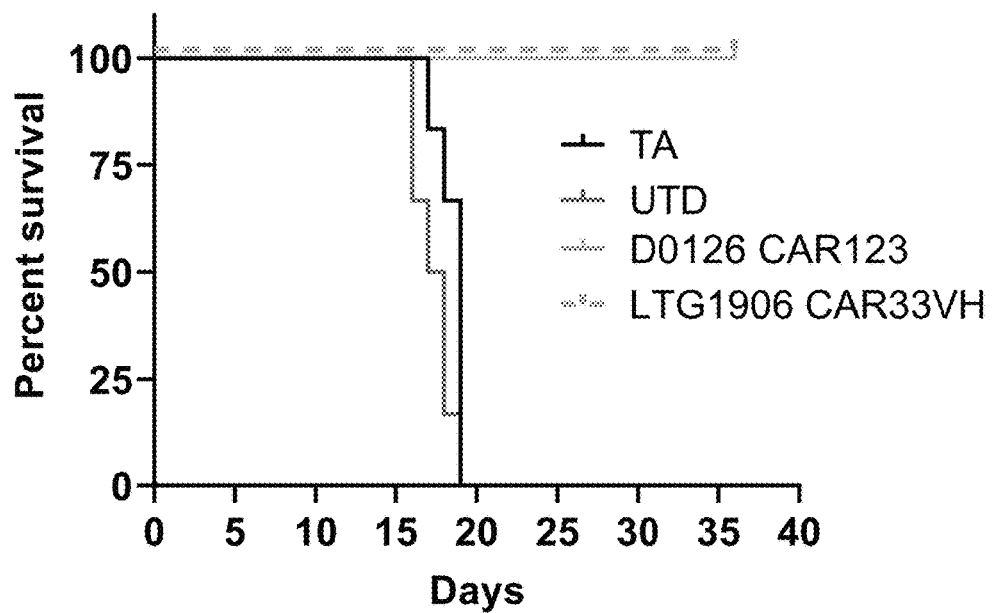
Figure 7A:
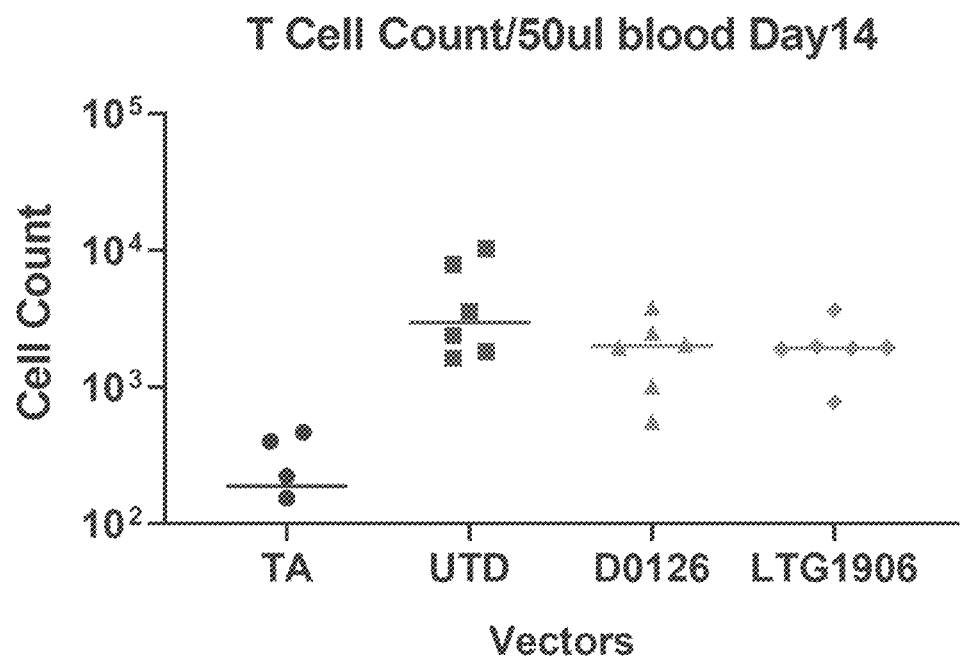
FIGS. 7A-7C depict human T cells detected in mouse blood during the first in vivo study. Total human T cells in mouse peripheral blood were measured at: day 14 (FIG. 7A), day 22 (FIG. 7B) and day 33 (FIG. 7C) by volumetric flow cytometry, and normalized using CountBright beads. All surviving mice are depicted. Results are shown as scatter dot plots. Lines indicate group means.
Figure 7B:
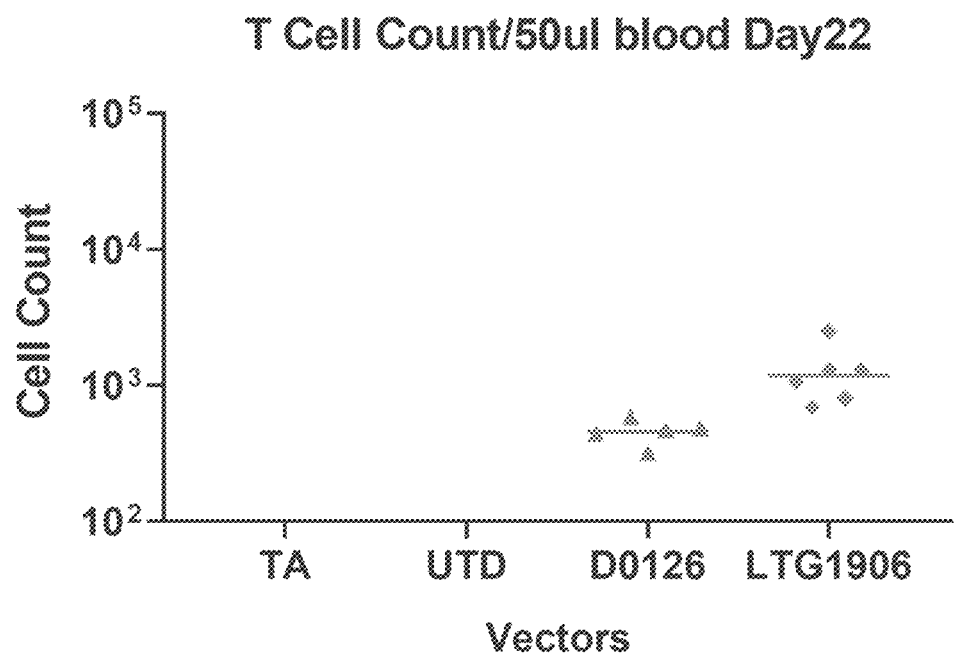
Figure 7C:
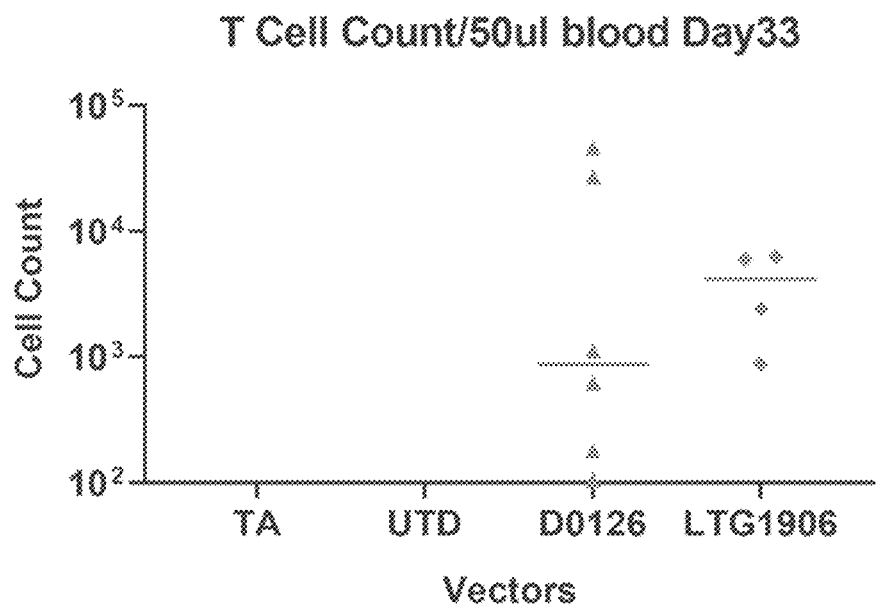

In the first in vivo study, CD123 CAR D0126 was compared with the previously characterized CD33 CAR-T construct LTG1906, and control experimental groups tumor alone (TA) and untransduced T cells (UTD) were also included. Tumor growth kinetics was monitored by in vivo imaging system (IVIS) overtime (FIGS. 6A and 6B). As MOLM14 tumors express both CD123 and CD33 antigens, treatment groups dosed with CAR D0126, targeting the CD123 antigen, as well as the comparator group dosed with the CAR LTG1906, targeting the CD33 antigen, showed robust tumor rejection compared to tumor alone (TA) and UTD control groups. Five of six mice in each group demonstrated complete tumor rejection, and only one mouse per group had residual tumor cells at study conclusion (FIG. 6B). Notably, both CAR D0126 and CAR LTG1906-treated groups showed no body weight loss (FIG. 6C), thus no CAR-related toxicity was detected in this model. CARs D0126 and LTG1906 both mediated complete survival to study termination at day 36 (6 out of 6 mice survived), while the tumor alone (TA), and UTD control groups succumbed to high-burden disseminated disease by day 15 (FIG. 6D). Mouse peripheral blood was sampled at days 14, 22 and 33. Human T cells were detected in all groups (FIG. 7A, 7B, 7C). Moreover, CAR D0126 and LTG1906 T cells were detected in the peripheral blood of mice at the end of the study, demonstrating high persistence of the CD123 CAR candidate D0126, and the comparative control CAR33 LTG1906 T cells.

Figure 8A:
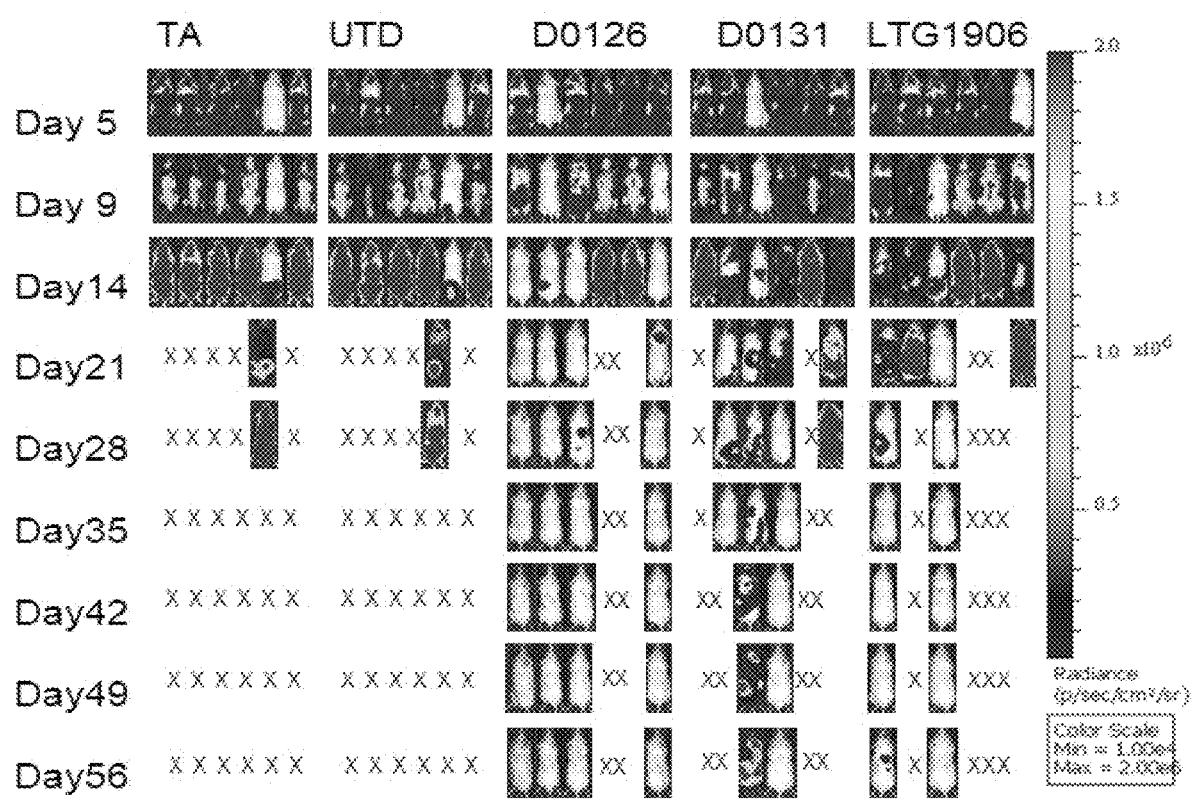
FIGS. 8A-8D depict the in vivo activity of CAR T constructs in the second in vivo study. NSG mice were injected i.v. with MOLM14-luciferase cells on Day 0, and administrated with 5×10⁶/mouse T cells on day seven.
Figure 8B:
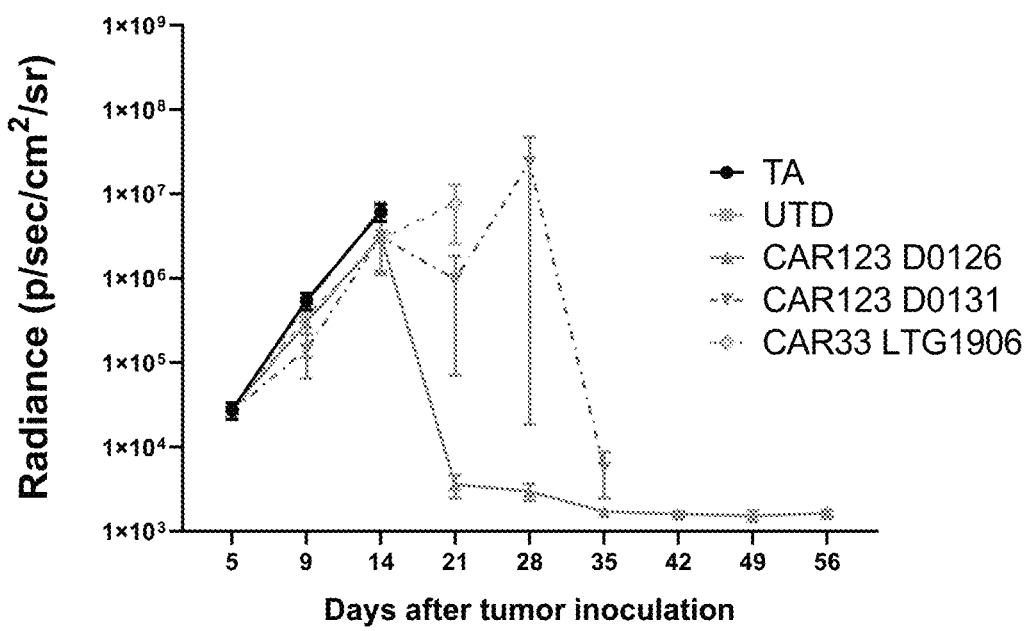
Figure 8C:
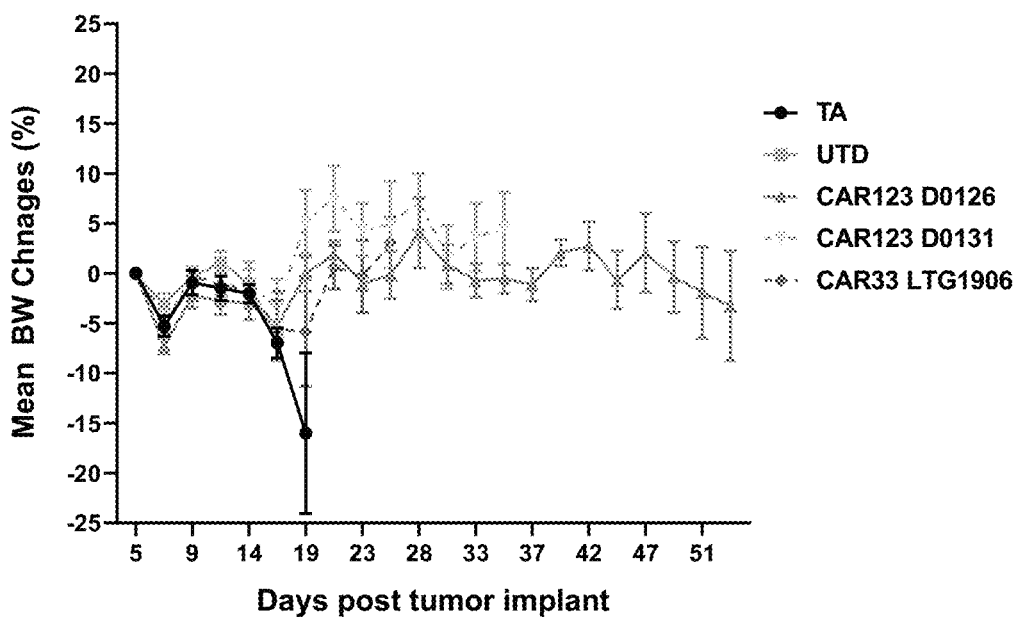
Figure 8D:
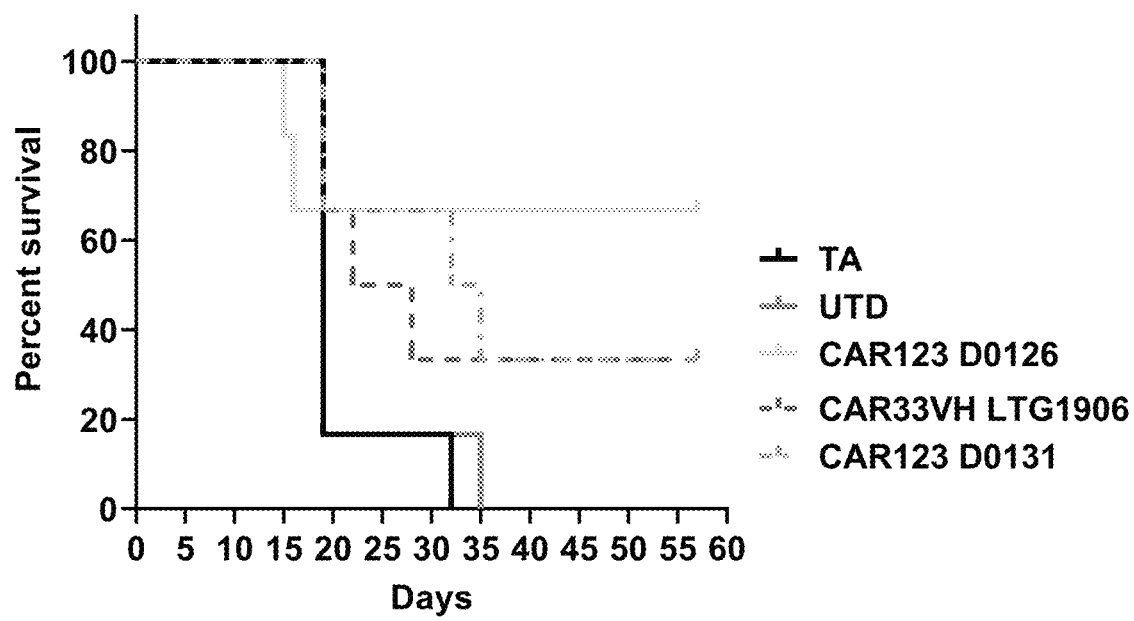
Figure 9A:
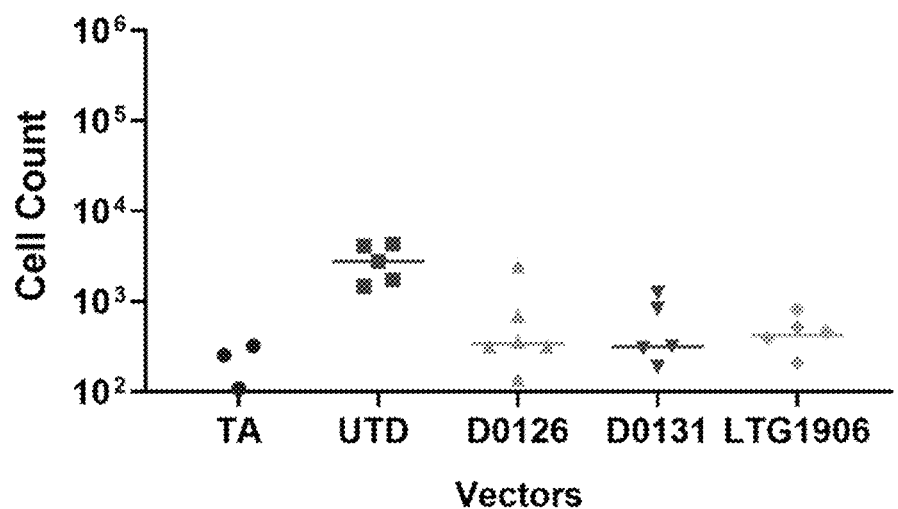
FIGS. 9A-9E depict human T cell detected in mouse peripheral blood throughout the second animal study. The total human T cells numbers were measured by flow cytometry at: day 2 (FIG. 9A), day 14 (FIG. 9B), day 21 (FIG. 9C), day 28 (FIG. 9D) and day 42 (FIG. 9E), and quantified with CountBright beads. Results are presented as scatter dot plots. Lines indicate group means.
Figure 9B:
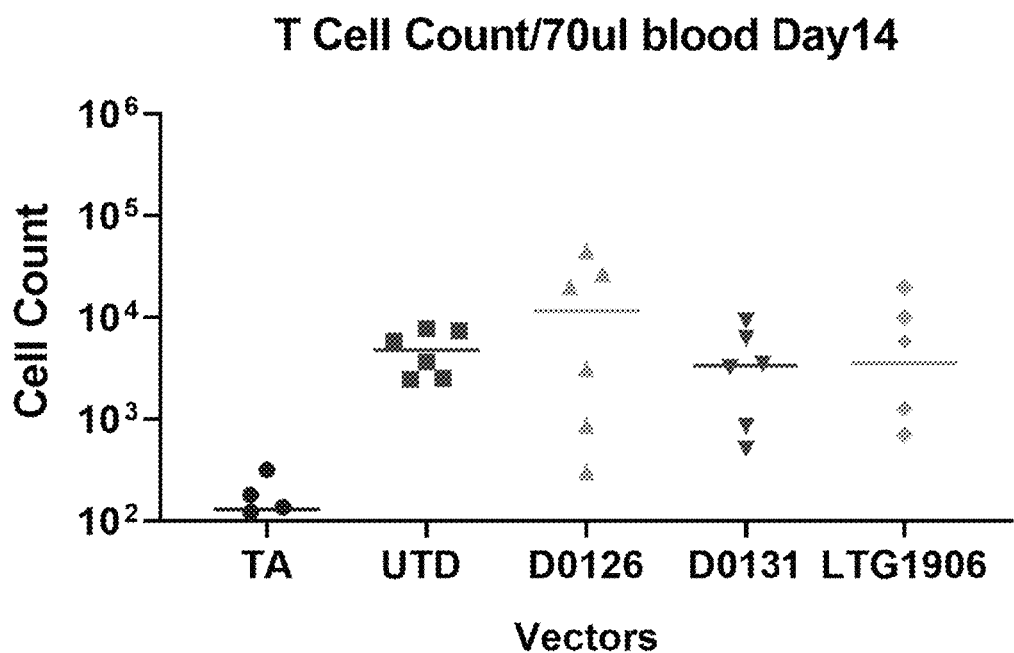
Figure 9C:
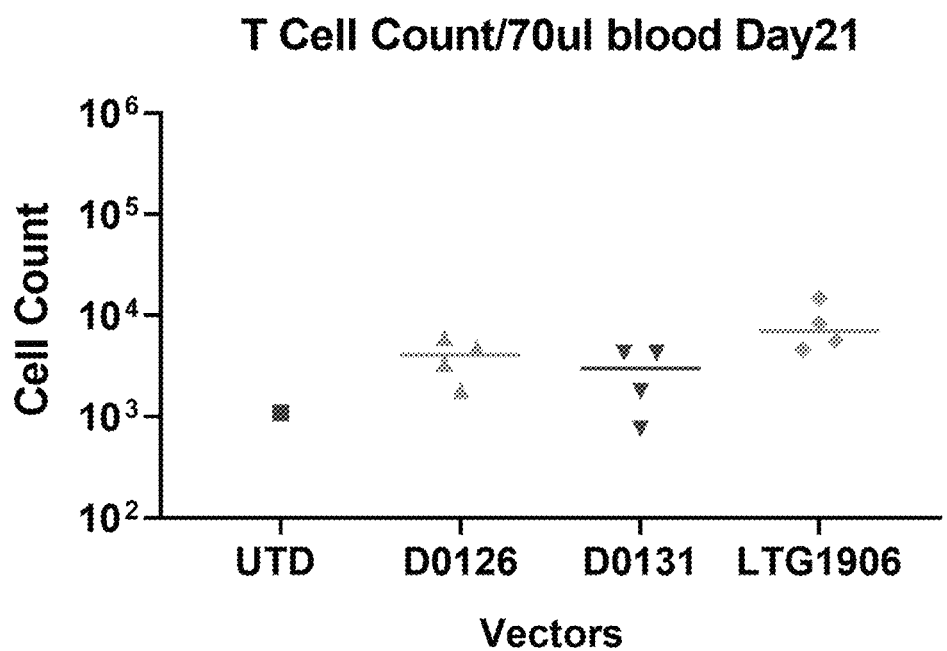
Figure 9D:
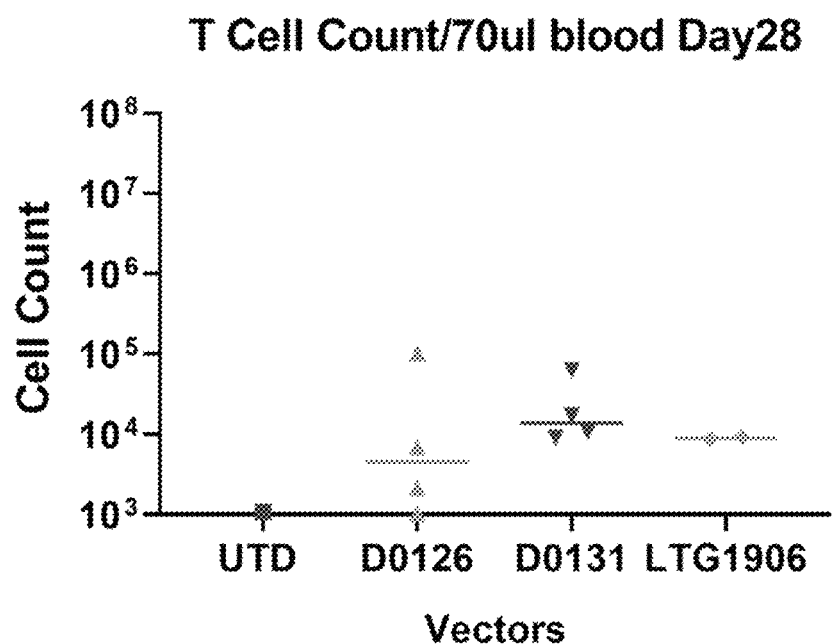
Figure 9E:
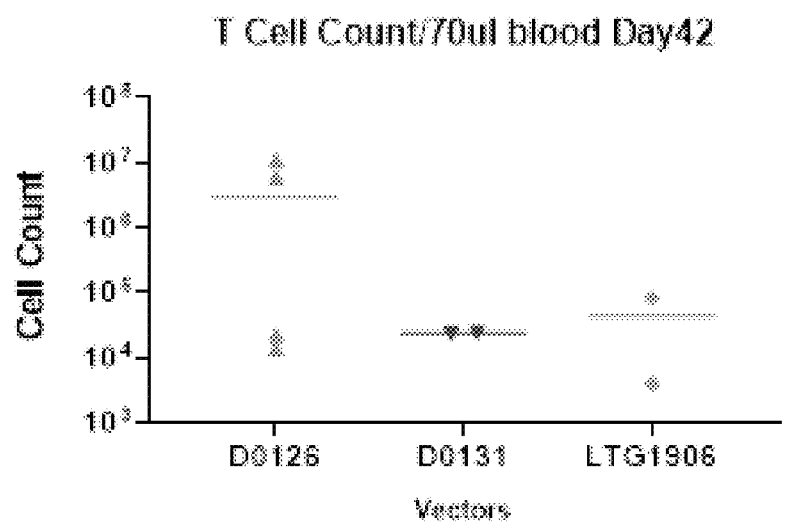

In the second animal study, CD123 CAR D0131 was included in addition to CAR D0126. Tumor progression is shown in FIG. 8A. Similarly to the first animal study, CAR D0126 demonstrated strong anti-tumor potency, and tumors were rejected in four out of six mice. CAR123 D0131 manifested weaker anti-tumor activity as compared with CAR123 D0126 (FIGS. 8A and 8B). The best survival effect was detected in the CAR D0126-treated group, with four of the six mice surviving to the extended study termination day, day 56, and remaining completely tumor-free (FIG. 8D). The total T cells in the peripheral blood were monitored in this study. As expected, human T cells were detected in the mice' peripheral blood two days after CAR T cell or UTD administration in all groups except the TA negative control (FIG. 9A). The T cell amounts increased in all CAR T cell groups overtime, suggesting T cell expansion (FIG. 9B), and persistence throughout days 21, 28 and 42 (FIG. 9C, 9D, 9E). On study day 42, the CAR123 D0126 group had the highest number of T cells (FIG. 9E), indicating the greatest T cell expansion and persistence among CAR constructs tested in this experiment.

In summary, the CD123 CAR T cell candidate D0126 efficiently eliminated tumors in NSG mice engrafted with MOLM-14 cells in two in vivo studies utilizing T cells from different human donors, and demonstrated efficient tumor clearance, CAR T persistence and prolonged survival in the MOLM14 AML xenograft mouse model (FIG. 9A).

Figure 10A:
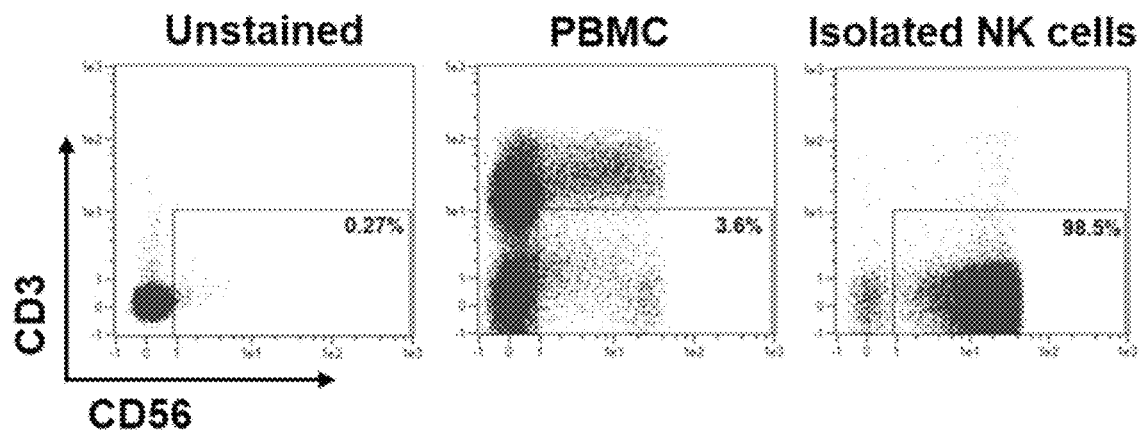
FIGS. 10A-10B depict NK cell isolation and generation of target cells for CD123-CAR.
Figure 10B:
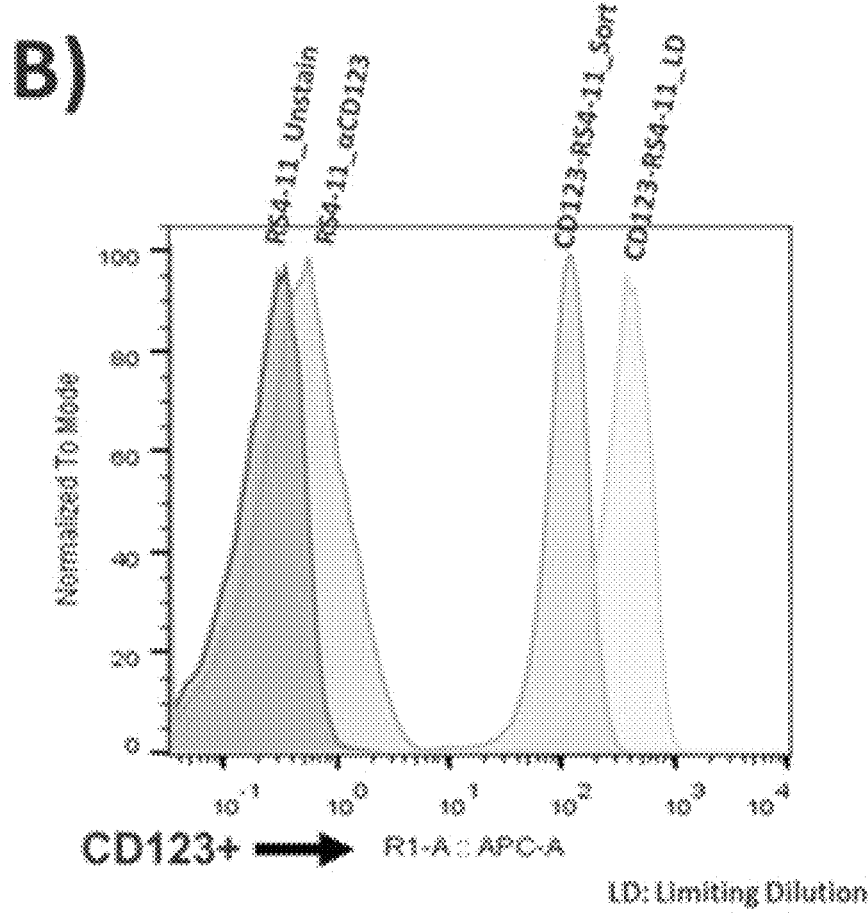

CAR NK cells targeting CD123 (Example 5, infra) were generated by transfection of primary NK cells from healthy donors using lentiviral vectors pseudotyped with Baboon envelope protein (BaEV-LV). Primary NK cells were isolated from PBMCs by magnetic separation resulting in pure cell populations (FIG. 10A). NK-resistant RS4-11 target cell line stably transduced with CD123 protein was used to test CD123-CAR functionality (FIG. 10B).

Figure 11:
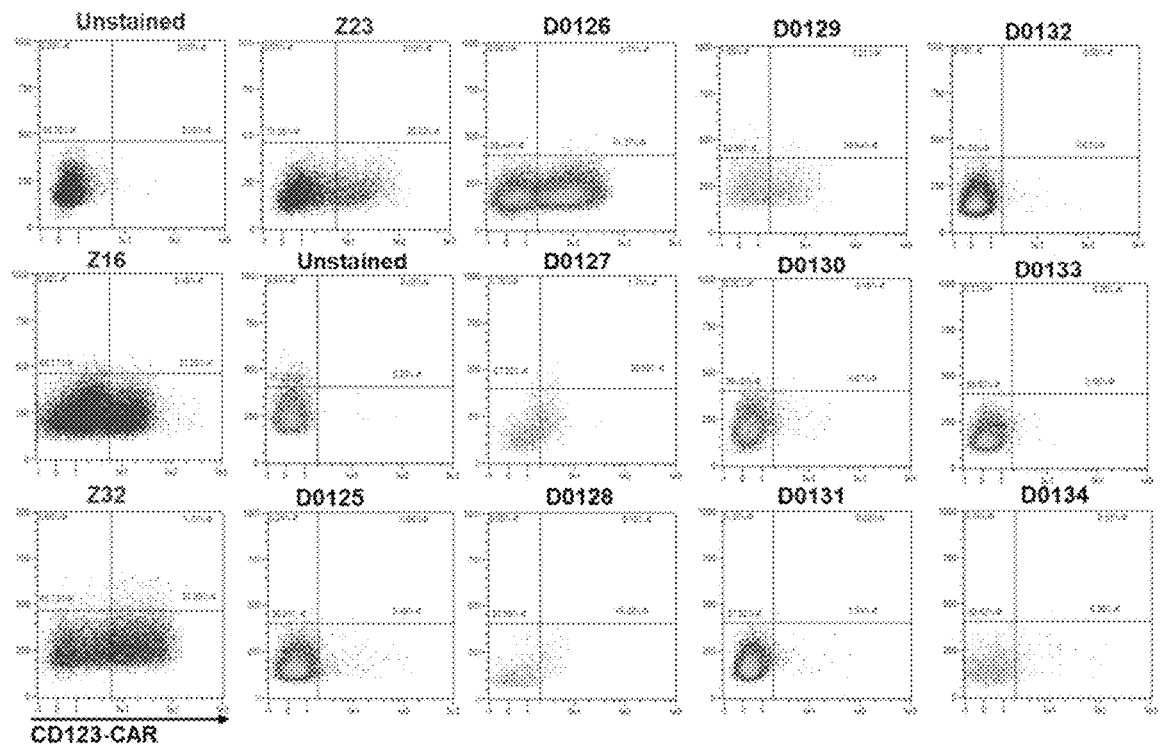
FIG. 11 depicts CD123-CAR binders expressed on transduced primary NK cells. Primary NK cells were isolated and cultured in a medium with IL-2, IL-15, and IL-10 for two days. On Day 3, activated NK cells were separately transduced with 13 different lentiviral vectors containing different CD123-CAR. CD123-CAR expressions on NK cells were detected on day 8 after transduction.

NK cells were activated by cultivation in NK MACS medium containing IL-2/IL-15/IL-1β for two days, followed by transduction with BaEV pseudotyped lentiviral vectors (BaEV-LV), resulting in efficient transduction of primary NK cells. Transduction of NK cells with lentiviral vectors containing different CD123-CAR constructs resulted in differential expression of CD123-CAR at the surface of NK cells (FIG. 11). Among the thirteen CD123-CARs, Z32 and D0126 CAR constructs were the best for transducing NK cells, and yielded transduction efficiency of 51.55% and 61.37%, respectively. Based on these expression results, we have selected CAR constructs Z32 and D0126 for further analysis.

Figure 12A:
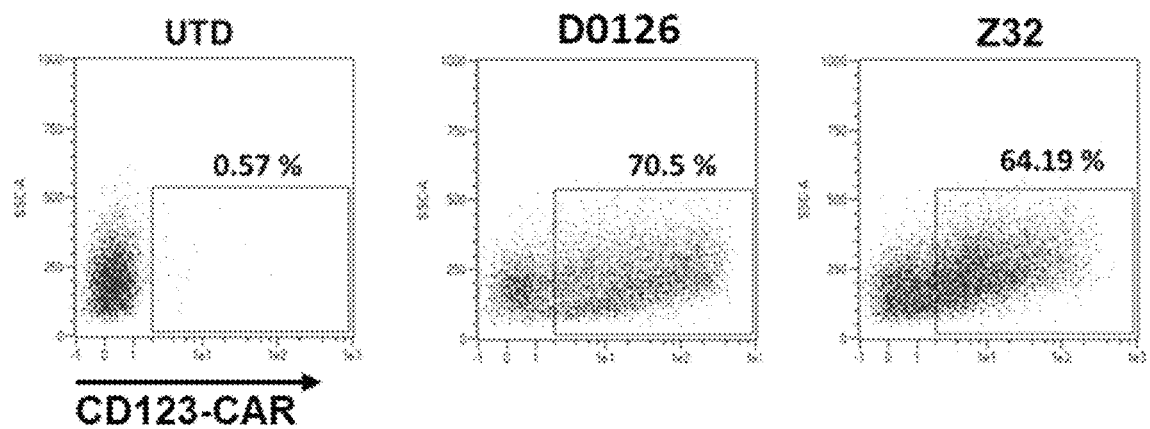
FIGS. 12A-12B depict the expression and cytotoxicity of CD123-CAR.
Figure 12B:
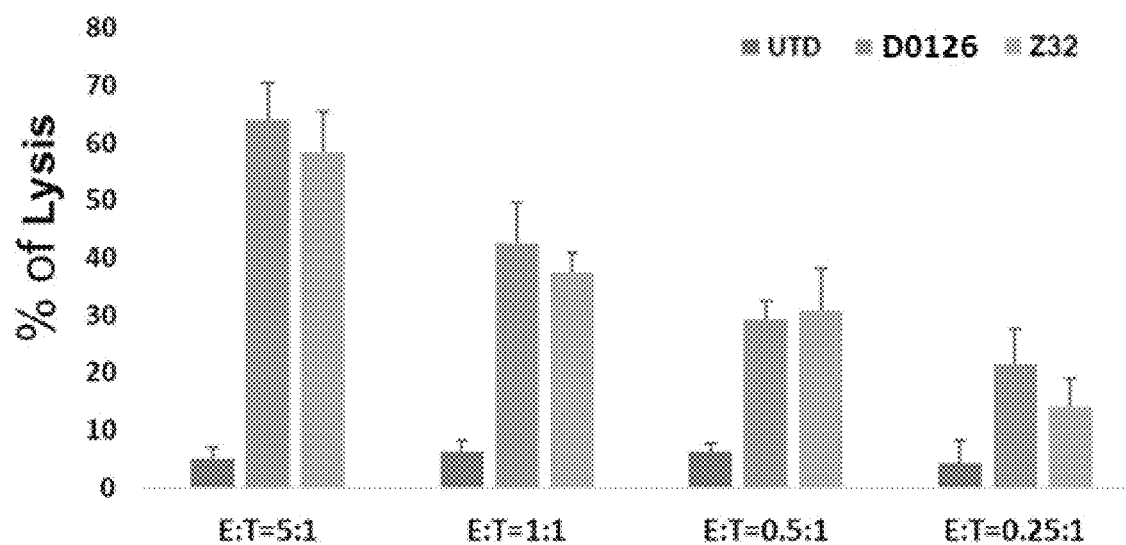

Activated NK cells were transduced with BaEV pseudotyped lentiviral vector containing CD123-CAR Z32 (Z32-BaEV-LV) and D0126 (D0126-BaEV-LV). CD123-CAR expression for Z32 and D0126 was 70.5% and 64.19%, respectively (FIG. 12A). In addition, the cytotoxicity of the CD123-CAR-expressing NK cells was tested against target cells RS4-11-CD123. RS4;11 cells expressing CD123 (FIG. 10B) are insensitive to NK cell natural cytotoxicity. Consequently, non-transduced NK cells could not kill RS4;11-CD123 cells, whereas both CD123-CAR (Z32 and D0126) NK cells killed RS4;11-CD123 very efficiently, demonstrating the high functionality and specificity of the generated CD123-CAR NK cells (FIG. 12B).

Figure 13A:
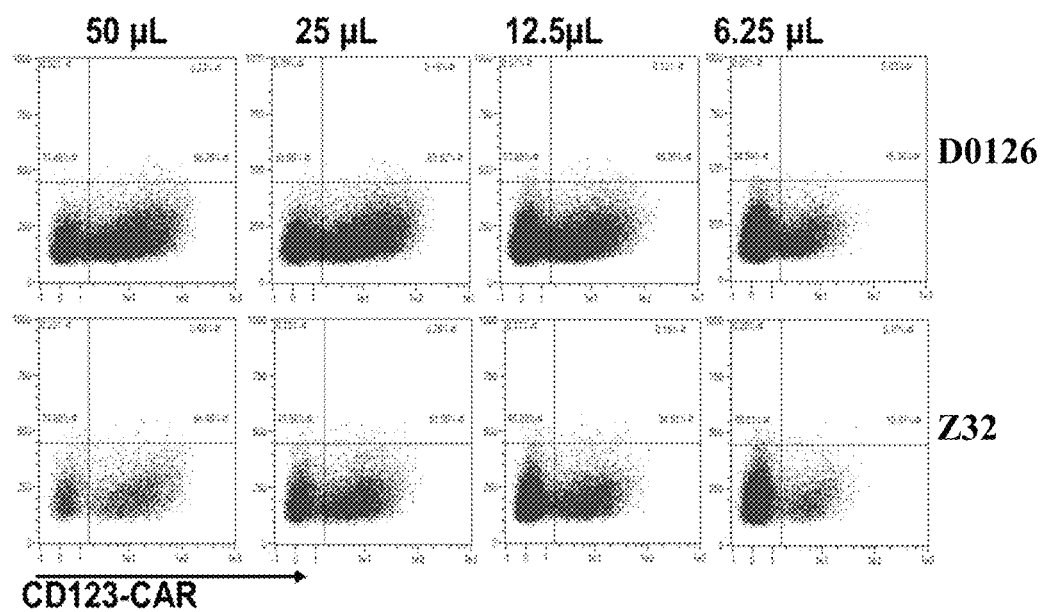
FIGS. 13A-13B depict the specific killing of CD123-CAR NK cells towards target cells expressing CD123.
Figure 13B:
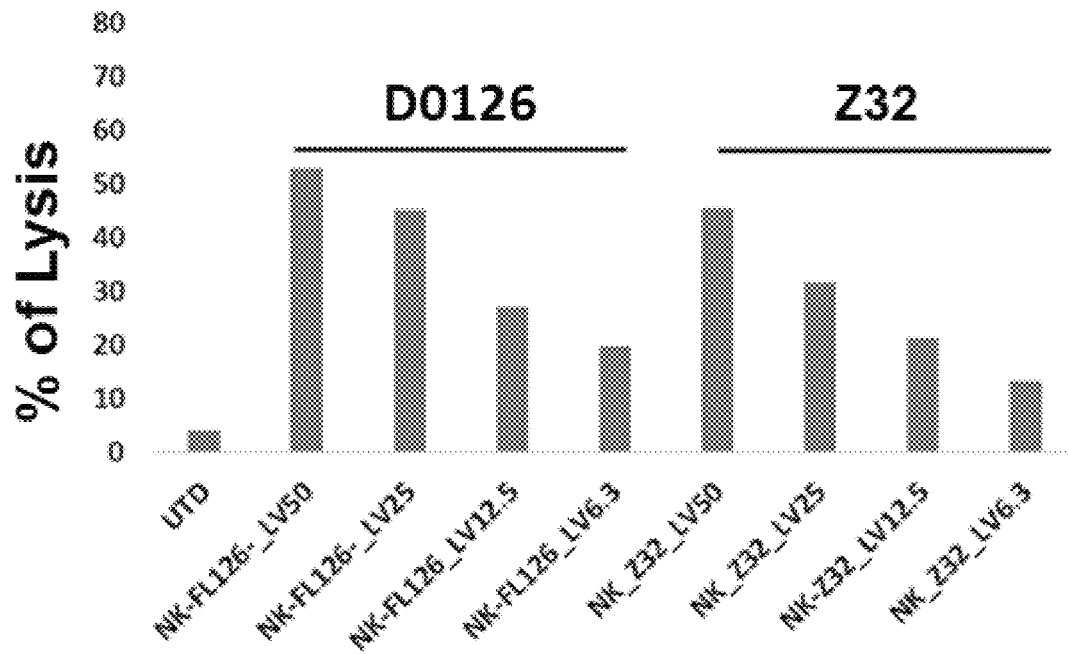
Figure 14A:
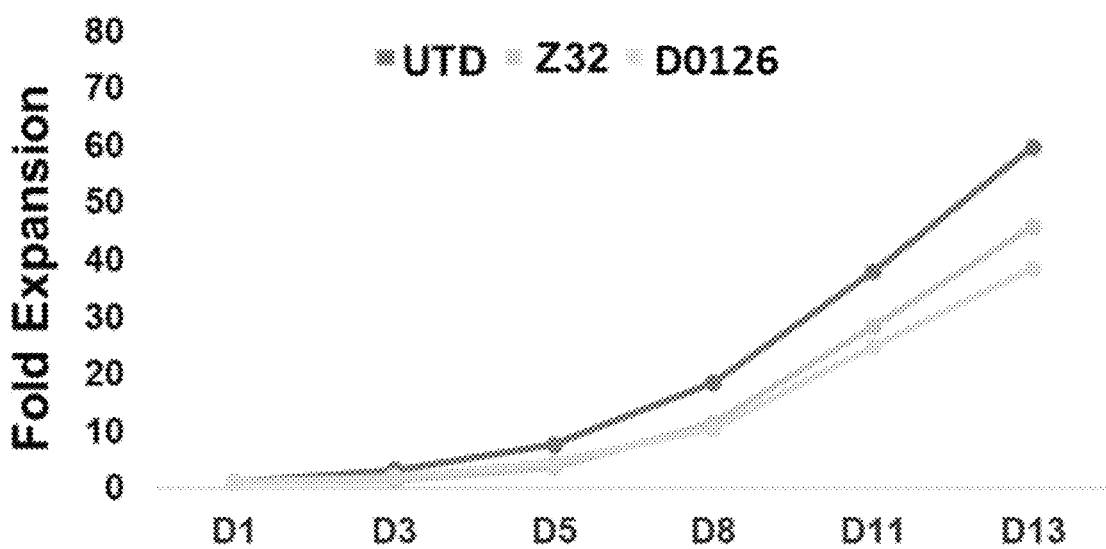
FIGS. 14A-14B depict impact of CD123-CAR on NK cell expansion and viability.
Figure 14B:
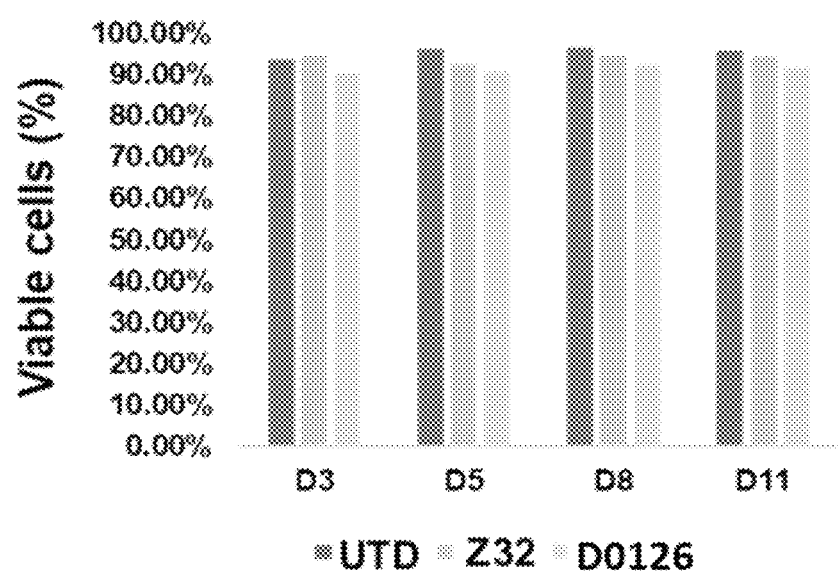

Next, the specificity of CD123-CAR toward CD123 antigen was confirmed by serial dilution. NK cells were transduced with different amounts of lentiviral vectors containing CD123-CAR. As expected, the higher quantity of CD123-CAR-LV showed higher expression of CD123-CAR (FIG. 13A). Finally, the cytotoxicity of differentially expressing CD123-CAR NK cells was tested against RS4-11-CD123 cells at the same effector-target ratio (FIG. 13B). The highest expressing CD123-CAR-NK cells showed the highest killing, and the lowest expressing CD123-CAR-NK cells showed the lowest killing confirmed the specificity of CD123-CAR toward CD123 antigen. Finally, expression of CD123-CAR has no adverse effect on NK expansion and viability. Primary NK cells were isolated, activated, and transduced with Z32 and D0126, followed by expansion for 13 days. Untransduced NK cells were used as control. The expansion of untransduced, Z32 transduced, and D0126 transduced NK cells was 61 fold, 49 fold, and 42 fold, respectively (FIG. 14A). There were no significant differences in cell viability among untransduced, Z32-transduced, and D0126-transduced NK cells (FIG. 14B), suggesting that the CD123-CARs have no adverse effect on NK cell viability.

Taken together, these results demonstrate successful generation of CAR-T and CAR-NK cells targeting the CD123 antigen for the treatment of cancer.

Without being intended to limit to any particular mechanism of action, it is believed that possible reasons for the enhanced therapeutic function associated with the exemplary CARs of the invention include, for example, and not by way of limitation, a) improved lateral movement within the plasma membrane allowing for more efficient signal transduction, b) superior location within plasma membrane microdomains, such as lipid rafts, and greater ability to interact with transmembrane signaling cascades associated with T cell activation, c) superior location within the plasma membrane by preferential movement away from dampening or down-modulatory interactions, such as less proximity to or interaction with phosphatases such as CD45, and d) superior assembly into T cell receptor signaling complexes (i.e. the immune synapse), or any combination thereof.

While the disclosure has been illustrated with an exemplary extracellular CD123 variable heavy chain only and ScFv antigen binding domains, other nucleotide and/or amino acid variants within the CD123 variable heavy chain only and ScFv antigen binding domains may be used to derive the CD123 antigen binding domains for use in the CARs described herein.

Depending on the desired antigen to be targeted, the CAR can be additionally engineered to include the appropriate antigen binding domain that is specific to the desired antigen target. For example, if CD19 is the desired antigen that is to be targeted, an antibody for CD19 can be used as the antigen bind domain incorporation into the CAR.

In one exemplary embodiment, the antigen binding domain portion of the CAR additionally targets CD19. Preferably, the antigen binding domain in the CAR is anti-CD19 ScFv, wherein the nucleic acid sequence of the anti-CD19 ScFv comprises the sequence set forth in SEQ ID NO: 37. In one embodiment, the anti-CD19 ScFv comprises the nucleic acid sequence that encodes the amino acid sequence of SEQ ID NO: 37. In another embodiment, the anti-CD19 ScFv portion of the CAR comprises the amino acid sequence set forth in SEQ ID NO: 38.

In one aspect of the present invention, there is provided a CAR capable of binding to a non-TSA or non-TAA including, for example and not by way of limitation, an antigen derived from Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus, or any combination thereof.

In another aspect of the present invention, there is provided a CAR capable of binding to an antigen derived from a bacterial strain of Staphylococci, *Streptococcus*, *Escherichia coli*, *Pseudomonas*, or *Salmonella*. Particularly, there is provided a CAR capable of binding to an antigen derived from an infectious bacterium, for example, *Helicobacter pyloris*, *Legionella pneumophilia*, a bacterial strain of Mycobacteria sps. (e.g. *M. tuberculosis, M. avium, M.*

*intracellulare, M. kansaii,* or *M. gordonea*), *Staphylococcus aureus, Neisseria gonorrhoeae, Neisseria meningitides, Listeria monocytogenes, Streptococcus pyogenes,* Group A *Streptococcus,* Group B *Streptococcus* (*Streptococcus agalactiae*), *Streptococcus pneumoniae,* or *Clostridium tetani,* or a combination thereof.

2. Transmembrane Domain

With respect to the transmembrane domain, the CAR comprises one or more transmembrane domains fused to the extracellular CD33 antigen binding domain of the CAR.

The transmembrane domain may be derived either from a natural or from a synthetic source. Where the source is natural, the domain may be derived from any membrane-bound or transmembrane protein.

Transmembrane regions of particular use in the CARs described herein may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, mesothelin, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain that naturally is associated with one of the domains in the CAR is used in addition to the transmembrane domains described supra.

In some instances, the transmembrane domain can be selected by amino acid substitution to avoid binding of such domains to the transmembrane domains of the same or different surface membrane proteins to minimize interactions with other members of the receptor complex.

In one embodiment, the transmembrane domain in the CAR of the invention is the CD8 transmembrane domain. In one embodiment, the CD8 transmembrane domain comprises the nucleic acid sequence of SEQ ID NO: 27. In one embodiment, the CD8 transmembrane domain comprises the nucleic acid sequence that encodes the amino acid sequence of SEQ ID NO: 28. In another embodiment, the CD8 transmembrane domain comprises the amino acid sequence of SEQ ID NO: 28.

In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO:28, or a sequence with 95-99% identity to an amino acid sequence of SEQ ID NO:28.

In some instances, the transmembrane domain of the CAR comprises the CD8.alpha.hinge domain. In one embodiment, the CD8 hinge domain comprises the nucleic acid sequence of SEQ ID NO: 29. In one embodiment, the CD8 hinge domain comprises the nucleic acid sequence that encodes the amino acid sequence of SEQ ID NO: 30. In another embodiment, the CD8 hinge domain comprises the amino acid sequence of SEQ ID NO: 30, or a sequence with 95-99% identify thereof.

In one embodiment, an isolated nucleic acid molecule is provided wherein the encoded linker domain is derived from the extracellular domain of CD8, and is linked to the transmembrane CD8 domain, the transmembrane CD28 domain, or a combination thereof.

In one embodiment, the transmembrane domain in the CAR of the invention is the TNFRSF19 transmembrane domain. In one embodiment, the TNFRSF19 transmembrane domain comprises the nucleic acid sequence of SEQ ID NO: 51. In one embodiment, the TNFRSF19 transmembrane domain comprises the nucleic acid sequence that encodes the amino acid sequence of SEQ ID NO: 52. In another embodiment, the TNFRSF19 transmembrane domain comprises the amino acid sequence of SEQ ID NO: 52.

In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO: 52, or a sequence with 95-99% identity to an amino acid sequence of SEQ ID NO: 52.

3. Spacer Domain

In the CAR, a spacer domain, also termed hinge domain, can be arranged between the extracellular domain and the transmembrane domain, or between the intracellular domain and the transmembrane domain. The spacer domain means any oligopeptide or polypeptide that serves to link the transmembrane domain with the extracellular domain and/or the transmembrane domain with the intracellular domain. The spacer domain comprises up to 300 amino acids, preferably 10 to 100 amino acids, and most preferably 25 to 50 amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,5667, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

The spacer domain preferably has a sequence that promotes binding of a CAR with an antigen and enhances signaling into a cell. Examples of an amino acid that is expected to promote the binding include cysteine, a charged amino acid, and serine and threonine in a potential glycosylation site, and these amino acids can be used as an amino acid constituting the spacer domain.

As the spacer domain, the entire or a part of amino acid numbers 118 to 178 (SEQ ID NO: 31) which is a hinge region of CD8.alpha. (NCBI RefSeq: NP.sub.--001759.3), amino acid numbers 135 to 195 of CD8.beta. (GenBank: AAA35664.1), amino acid numbers 315 to 396 of CD4 (NCBI RefSeq: NP.sub.--000607.1), or amino acid numbers 137 to 152 of CD28 (NCBI RefSeq: NP.sub.--006130.1) can be used. Also, as the spacer domain, a part of a constant region of an antibody H chain or L chain (CH1 region or CL region, for example, a peptide having an amino acid sequence shown in SEQ ID NO: 32) can be used. Further, the spacer domain may be an artificially synthesized sequence.

In addition, an entire or a part of amino acids comprising the constant region of a human IgG4 (UniProt ID: P01861), including CH1, (amino acid numbers 1-98), hinge, SEQ ID NO: 80, and the corresponding nucleotide SEQ ID NO:79, (amino acid numbers 99-110), CH2, amino acid SEQ ID NO: 82 and corresponding nucleotide SEQ ID NO: 81, (amino acid numbers 111-220) and CH3, SEQ ID NO:84 and corresponding nucleotide SEQ ID NO: 83, (amino acid numbers 221-327) or a combination thereof, such as IgG4 Hinge CH2 CH3 domain, SEQ ID NO: 86, and the corresponding nucleotide SEQ ID NO: 85, can be used.

In one embodiment, the spacer domain of the CAR comprises the TNFRSF19 hinge domain which comprises the nucleic acid sequence of SEQ ID NO: 53. In one embodiment, the TNFRSF19 hinge domain comprises the nucleic acid sequence that encodes the amino acid sequence of SEQ ID NO: 54. In another embodiment, the TNFRSF19 hinge domain comprises the amino acid sequence of SEQ ID NO: 54, or a sequence with 95-99% identify thereof.

In one embodiment, the spacer domain of the CAR comprises the TNFRSF19 truncated hinge domain comprises the nucleic acid sequence of SEQ ID NO: 55. In one embodiment, the TNFRSF19 truncated hinge domain comprises the nucleic acid sequence that encodes the amino acid sequence of SEQ ID NO: 56. In another embodiment, the TNFRSF19 truncated hinge domain comprises the amino acid sequence of SEQ ID NO: 56, or a sequence with 95-99% identify thereof.

In one embodiment, the TNFRSF19 hinge and transmembrane domains comprise the nucleic acid sequence of SEQ ID NO: 49. In one embodiment, the TNFRSF19 hinge and transmembrane domains comprise the nucleic acid sequence that encodes the amino acid sequence of SEQ ID NO: 50. In another embodiment, the TNFRSF19 hinge and transmembrane domains comprise the amino acid sequence of SEQ ID NO: 50, or a sequence with 95-99% identify thereof.

In one embodiment, a CD8a hinge domain is fused to a TNFRSF19 transmembrane domain comprising the nucleic acid sequence of SEQ ID NO: 57. In one embodiment, the CD8a hinge domain is fused to a TNFRSF19 transmembrane domain comprises the nucleic acid sequence that encodes the amino acid sequence of SEQ ID NO: 58. In another embodiment, the CD8a hinge domain is fused to a TNFRSF19 transmembrane domain comprises the amino acid sequence of SEQ ID NO: 58, or a sequence with 95-99% identify thereof.

Further, in the CAR, a signal peptide sequence, also termed leader peptide, can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the CAR. In one embodiment, the signal peptide comprises the amino acid sequence shown in SEQ ID NO: 14).

In one embodiment, the CD8 alpha leader peptide, is comprising the nucleic acid sequence of SEQ ID NO: 43. In one embodiment, CD8 alpha leader peptide comprises the nucleic acid sequence that encodes the amino acid sequence of SEQ ID NO: 44. In another embodiment, the CD8a hinge domain is fused to a TNFRSF19 transmembrane domain comprises the amino acid sequence of SEQ ID NO: 44, or a sequence with 95-99% identify thereof.

In another embodiment, the GMCSF leader peptide, is comprising the nucleic acid sequence of SEQ ID NO: 39. In one embodiment, the GMCSF leader peptide, comprises the nucleic acid sequence that encodes the amino acid sequence of SEQ ID NO: 40. In another embodiment, the CD8a hinge domain is fused to a TNFRSF19 transmembrane domain comprises the amino acid sequence of SEQ ID NO: 40, or a sequence with 95-99% identify thereof.

In another embodiment, the TNFRSF19 leader peptide is comprising the nucleic acid sequence of SEQ ID NO: 41. In one embodiment, TNFRSF19 leader peptide, and CD8 alpha leader peptide comprises the nucleic acid sequence that encodes the amino acid sequence of SEQ ID NO: 42. In another embodiment, the CD8a hinge domain is fused to a TNFRSF19 transmembrane domain comprises the amino acid sequence of SEQ ID NO: 42, or a sequence with 95-99% identify thereof.

In one embodiment, a tag sequence encoding a truncated sequence of epidermal growth factor receptor (tEGFR) is comprising the nucleic acid sequence of SEQ ID NO: 67. In one embodiment, tEGFR comprises the nucleic acid sequence that encodes the amino acid sequence of SEQ ID NO: 68. In another embodiment, the tEGFR tag comprises the amino acid sequence of SEQ ID NO: 68, or a sequence with 95-99% identify thereof.

In one embodiment, a furin recognition site and downstream T2A self-cleaving peptide sequence, designed for simultaneous bicistronic expression of the tag sequence and the CAR sequence, is comprising the nucleic acid sequence of SEQ ID NO: 65. In one embodiment, furin and T2A sequence comprises the nucleic acid sequence that encodes the amino acid sequence of SEQ ID NO: 66. In another embodiment, the tEGFR tag comprises the amino acid sequence of SEQ ID NO: 66 or a sequence with 95-99% identify thereof.

In one embodiment, an upstream furin recognition site and T2A self-cleaving peptide sequence and a furin recognition downstream site, designed for simultaneous bicistronic expression of the tag sequence and the CAR sequence, is comprising the nucleic acid sequence of SEQ ID NO: 67. In one embodiment, furin and T2A sequence comprises the nucleic acid sequence that encodes the amino acid sequence of SEQ ID NO: 68. In another embodiment, the tEGFR tag comprises the amino acid sequence of SEQ ID NO: 68 or a sequence with 95-99% identify thereof.

In one embodiment, the targeting domain of the CAR is expressed separately in the form of monoclonal antibody, ScFv Fab, Fab'2 and is containing at binding tag or epitope, whereas the effector-cell expressed component of the CAR contains a binding domain specifically directed to bind the tag or epitope expressed on the soluble CAR module, such as specific binding on the soluble component of the CAR to the cell bound component forms the full functional CAR structure.

4. Intracellular Domain

The cytoplasmic domain or otherwise the intracellular signaling domain of the CAR is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the CARs disclosed herein include those derived from TCR zeta (CD3 Zeta), FcR gamma, FcR beta, CD3 gamma, CD3 delta, CD3 epsilon, CD5, CD22, CD79a, CD79b, and CD66d. Specific, non-limiting examples, of the ITAM include peptides having sequences of amino acid numbers 51 to 164 of CD3.zeta. (NCBI RefSeq: NP.sub.--932170.1), amino acid numbers 45 to 86 of Fc.epsilon.RI.gamma. (NCBI RefSeq: NP.sub.--004097.1), amino acid numbers 201 to 244 of Fc.epsilon.RI.beta. (NCBI RefSeq: NP.sub.--000130.1), amino acid numbers 139 to 182 of CD3.gamma. (NCBI RefSeq: NP.sub.--000064.1), amino acid numbers 128 to 171 of CD3 delta. (NCBI RefSeq: NP.sub.--000723.1), amino acid numbers 153 to 207 of CD3.epsilon. (NCBI RefSeq: NP.sub.--000724.1), amino acid numbers 402 to 495 of CD5 (NCBI RefSeq: NP.sub.--055022.2), amino acid numbers 707 to 847 of 0022 (NCBI RefSeq: NP.sub.--001762.2), amino acid numbers 166 to 226 of CD79a (NCBI RefSeq: NP.sub.--001774.1), amino acid numbers 182 to 229 of CD79b (NCBI RefSeq: NP.sub.--000617.1), and amino acid numbers 177 to 252 of CD66d (NCBI RefSeq: NP.sub.--001806.2), and their variants having the same function as these peptides have. The amino acid number based on amino acid sequence information of NCBI RefSeq ID or GenBank described herein is numbered based on the full length of the precursor (comprising a signal peptide sequence etc.) of each protein. In one embodiment, the cytoplasmic signaling molecule in the CAR comprises a cytoplasmic signaling sequence derived from CD3 zeta.

In a preferred embodiment, the intracellular domain of the CAR can be designed to comprise the CD3-zeta signaling domain by itself or combined with any other desired cytoplasmic domain(s) useful in the context of the CAR. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such costimulatory molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Specific, non-limiting examples, of such costimulatory molecules include peptides having sequences of amino acid numbers 236 to 351 of CD2 (NCBI RefSeq: NP.sub.--001758.2), amino acid numbers 421 to 458 of CD4 (NCBI RefSeq: NP.sub.--000607.1), amino acid numbers 402 to 495 of CD5 (NCBI RefSeq: NP.sub.--055022.2), amino acid numbers 207 to 235 of CD8.alpha. (NCBI RefSeq: NP.sub.--001759.3), amino acid numbers 196 to 210 of CD83 (GenBank: AAA35664.1), amino acid numbers 181 to 220 of CD28 (NCBI RefSeq: NP.sub.--006130.1), amino acid numbers 214 to 255 of CD137 (4-1BB, NCBI RefSeq: NP.sub.--001552.2), amino acid numbers 241 to 277 of CD134 (OX40, NCBI RefSeq: NP.sub.--003318.1), and amino acid numbers 166 to 199 of ICOS (NCBI RefSeq: NP.sub.--036224.1), and their variants having the same function as these peptides have. Thus, while the disclosure herein is exemplified primarily with 4-1BB as the co-stimulatory signaling element, other costimulatory elements are within the scope of the disclosure.

The cytoplasmic signaling sequences within the cytoplasmic signaling portion of the CAR may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB. In yet another embodiment, the intracellular domain is designed to comprise the signaling domain of CD3-zeta and the signaling domain of CD28 and 4-1BB.

In one embodiment, the intracellular domain in the CAR is designed to comprise the signaling domain of 4-1BB and the signaling domain of CD3-zeta, wherein the signaling domain of 4-1BB comprises the nucleic acid sequence set forth in SEQ ID NO: 33 or SEQ ID NO: 73 and the signaling domain of CD3-zeta comprises the nucleic acid sequence set forth in SEQ ID NO: 35, SEQ ID NO: 47, SEQ ID NO: 61, or SEQ ID NO: 75.

In one embodiment, the intracellular domain in the CAR is designed to comprise the signaling domain of 4-1BB and the signaling domain of CD3-zeta, wherein the signaling domain of 4-1BB comprises the nucleic acid sequence that encodes the amino acid sequence of SEQ ID NO: 34, or SEQ ID NO: 74, respectively and the signaling domain of CD3-zeta comprises the nucleic acid sequence that encodes the amino acid sequence of SEQ ID NO: 36, or SEQ ID NO: 48, SEQ ID NO: 62, or SEQ ID NO 76.

In one embodiment, the intracellular domain in the CAR is designed to comprise the signaling domain of 4-1BB and the signaling domain of CD3-zeta, wherein the signaling domain of 4-1BB comprises the amino acid sequence set forth in SEQ ID NO: 34, or SEQ ID NO: 74, respectively and the signaling domain of CD3-zeta comprises the amino acid sequence set forth in SEQ ID NO: 36, SEQ ID NO: 48, SEQ ID NO: 62, or SEQ ID NO: 76, respectively.

In one embodiment, the intracellular domain in the CAR is designed to comprise the signaling domain of CD28 and the signaling domain of CD3-zeta, wherein the signaling domain of CD28 comprises the nucleic acid sequence set forth in SEQ ID NO: 45, or SEQ ID NO: 59, respectively, and the signaling domain of CD3-zeta comprises the nucleic acid sequence set forth in SEQ ID NO: 35, SEQ ID NO: 47, or SEQ ID NO: 61, respectively.

In one embodiment, the intracellular domain in the CAR is designed to comprise the signaling domain of CD28 and the signaling domain of CD3-zeta, wherein the signaling domain of CD28 comprises the nucleic acid sequence that encodes the amino acid sequence of SEQ ID NO: 46, or SEQ ID NO: 60, respectively and the signaling domain of CD3-zeta comprises the nucleic acid sequence that encodes the amino acid sequence of SEQ ID NO: 36, or SEQ ID NO: 48, or SEQ ID NO: 62.

In one embodiment, the intracellular domain in the CAR is designed to comprise the signaling domain of CD28 and the signaling domain of CD3-zeta, wherein the signaling domain of CD28 comprises the amino acid sequence set forth in SEQ ID NO: 46, or SEQ ID NO: 60, respectively and the signaling domain of CD3-zeta comprises the amino acid sequence set forth in SEQ ID NO: 36, SEQ ID NO: 48, or SEQ ID NO: 62, respectively.

5. Additional Description of CARs

Also expressly included within the scope of the invention are functional portions of the CARs disclosed herein. The term "functional portion" when used in reference to a CAR refers to any part or fragment of one or more of the CARs disclosed herein, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the disclosure are functional variants of the CARs disclosed herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, He, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., He, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs (including functional portions and functional variants) can be of any length, i.e., can comprise any number of amino acids, provided that the CARS (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, -amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, -aminocyclopentane carboxylic acid, a-aminocyclohexane carboxylic acid, a-aminocycloheptane carboxylic acid, a-(2-amino-2-norbornane)-carboxylic acid, γ-diaminobutyric acid, β-diaminopropionic acid, homophenylalanine, and a-tert-butylglycine.

The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, N Y, 1994. Further, some of the CARs (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies. In this respect, the CARs can be synthetic, recombinant, isolated, and/or purified.

A. Antibodies and Antigen Binding Fragments

One embodiment further provides a CAR, a T cell expressing a CAR, an antibody, or antigen binding domain or portion thereof, which specifically binds to one or more of the antigens disclosed herein. As used herein, a "T cell expressing a CAR," or a "CAR T cell" means a T cell expressing a CAR, and has antigen specificity determined by, for example, the antibody-derived targeting domain of the CAR.

As used herein, and "antigen binding domain" can include an antibody and antigen binding fragments thereof. The term "antibody" is used herein in the broadest sense and encompasses various antibody structures, including but not limited to monoclonal antibodies, polyclonal antibodies, multi-specific antibodies (e.g., bispecific antibodies), and antigen binding fragments thereof, so long as they exhibit the desired antigen-binding activity. Non-limiting examples of antibodies include, for example, intact immunoglobulins and variants and fragments thereof known in the art that retain binding affinity for the antigen.

A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. In some examples, a monoclonal antibody is an antibody produced by a single clone of B lymphocytes or by a cell into which nucleic acid encoding the light and heavy variable regions of the antibody of a single antibody (or an antigen binding fragment thereof) have been transfected, or a progeny thereof. In some examples monoclonal antibodies are isolated from a subject. Monoclonal antibodies can have conservative amino acid substitutions which have substantially no effect on antigen binding or other immunoglobulin functions. Exemplary methods of production of monoclonal antibodies are known, for example, see Harlow & Lane, Antibodies, A Laboratory Manual, 2nd ed. Cold Spring Harbor Publications, New York (2013).

Typically, an immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, $6^{th}$ ed., W.H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). References to "VH" or "VH" refer to the variable region of an antibody heavy chain, including that of an antigen binding fragment, such as Fv, ScFv, dsFv or Fab. References to "VL" or "VL" refer to the variable domain of an antibody light chain, including that of an Fv, ScFv, dsFv or Fab.

Light and heavy chain variable regions contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," $5^{th}$ Ed. Public Health Service, National Institutes of Health, Bethesda, Md., 1991; "Kabat" numbering scheme), Al-Lazikani et al., (JMB 273,927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a VH CDR3 is the CDR3 from the variable domain of the heavy chain of the antibody in which it is found, whereas a VL CDR1 is the CDR1 from the variable domain of the light chain of the antibody in which it is found. Light chain CDRs are sometimes referred to as LCDR1, LCDR2, and LCDR3. Heavy chain CDRs are sometimes referred to as HCDR1, HCDR2, and HCDR3.

An "antigen binding fragment" is a portion of a full length antibody that retains the ability to specifically recognize the cognate antigen, as well as various combinations of such portions. Non-limiting examples of antigen binding fragments include Fv, Fab, Fab', Fab'-SH, F(ab')2; diabodies; linear antibodies; single-chain antibody molecules (e.g. ScFv); and multi-specific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2nd Ed., Springer Press, 2010).

A single-chain antibody (ScFv) is a genetically engineered molecule containing the VH and VL domains of one or more antibody(ies) linked by a suitable polypeptide linker as a genetically fused single chain molecule (see, for example, Bird et al., Science, 242:423 426, 1988; Huston et al., Proc. Natl. Acad. Sci., 85:5879 5883, 1988; Ahmad et al., Clin. Dev. Immunol., 2012, doi:10.1155/2012/980250; Marbry, IDrugs, 13:543-549, 2010). The intramolecular orientation of the VH-domain and the VL-domain in a ScFv, is typically not decisive for ScFvs. Thus, ScFvs with both possible arrangements (VH-domain-linker domain-VL-domain; VL-domain-linker domain-VH-domain) may be used.

In a dsFv, the heavy and light chain variable chains have been mutated to introduce a disulfide bond to stabilize the association of the chains. Diabodies also are included, which are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., Proc. Natl. Acad. Sci., 90:6444 6448, 1993; Poljak et al., Structure, 2:1121 1123, 1994).

Antibodies also include genetically engineered forms such as chimeric antibodies (such as humanized murine antibodies) and heteroconjugate antibodies (such as bispecific antibodies). See also, Pierce Catalog and Handbook, 1994-1995 (Pierce Chemical Co., Rockford, Ill.); Kuby, J., Immunology, 3rd Ed., W.H. Freeman & Co., New York, 1997.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. Phage display: A Laboratory Manuel. 1st Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Methods of testing antibodies for the ability to bind to any functional portion of the CAR are known in the art and include any antibody-antigen binding assay, such as, for example, radioimmunoassay (RIA), ELISA, Western blot, immunoprecipitation, and competitive inhibition assays (see, e.g., Janeway et al., infra, U.S. Patent Application Publication No. 2002/0197266 A1, and U.S. Pat. No. 7,338, 929).

Also, a CAR, a T cell expressing a CAR, an antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

B. Conjugates

A CAR, a T cell expressing a CAR, or monoclonal antibodies, or antigen binding fragments thereof, specific for one or more of the antigens disclosed herein, can be conjugated to an agent, such as an effector molecule or detectable marker, using any number of means known to those of skill in the art. Both covalent and noncovalent attachment means may be used. Conjugates include, but are not limited to, molecules in which there is a covalent linkage of an effector molecule or a detectable marker to an antibody or antigen binding fragment that specifically binds one or more of the antigens disclosed herein. One of skill in the art will appreciate that various effector molecules and detectable markers can be used, including (but not limited to) chemotherapeutic agents, anti-angiogenic agents, toxins, radioactive agents such as $^{125}$I, $^{32}$P, $^{14}$C, $^{3}$H and $^{35}$S and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a tumor cell).

The procedure for attaching an effector molecule or detectable marker to an antibody or antigen binding fragment varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,5667, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15 amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

In several embodiments, conjugates of a CAR, a T cell expressing a CAR, an antibody, or antigen binding portion thereof, and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are well known in the art, and can be isolated from natural sources according to known methods, produced using genetic engineering techniques (see Yu et al. (2002) PNAS 99:7968-7973), or maytansinol and maytansinol analogues prepared synthetically according to known methods. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference.

Additional toxins can be employed with a CAR, a T cell expressing a CAR, an antibody, or antigen binding portion thereof. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.). Contemplated toxins also include variants of the toxins (see, for example, see, U.S. Pat. Nos. 5,079,163 and 4,689,401).

Saporin is a toxin derived from *Saponaria officinalis* that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. Nos. 5,792,458 and 5,208,021.

Ricin is the lectin RCA60 from *Ricinus communis* (Castor bean). For examples of ricin, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87, 1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

A CAR, a T cell expressing a CAR, monoclonal antibodies, antigen binding fragments thereof, specific for one or more of the antigens disclosed herein, can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). A CAR, a T cell expressing a CAR, an antibody, or antigen binding portion thereof, can also be conjugated with enzymes that are useful for detection, such as horseradish peroxidase, β-galactosidase, luciferase, alkaline phosphatase, glucose oxidase and the like. When a CAR, a T cell expressing a CAR, an antibody, or antigen binding portion thereof, is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. A CAR, a T cell expressing a CAR, an antibody, or antigen binding portion thereof, may also be conjugated with biotin, and detected through indirect measurement of avidin or streptavidin binding. It should be noted that the avidin itself can be conjugated with an enzyme or a fluorescent label.

A CAR, a T cell expressing a CAR, an antibody, or antigen binding portion thereof, may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

A CAR, a T cell expressing a CAR, an antibody, or antigen binding portion thereof, can also be conjugated with a radiolabeled amino acid. The radiolabel may be used for both diagnostic and therapeutic purposes. For instance, the radiolabel may be used to detect one or more of the antigens disclosed herein and antigen expressing cells by x-ray, emission spectra, or other diagnostic techniques. Further, the radiolabel may be used therapeutically as a toxin for treatment of tumors in a subject, for example for treatment of a neuroblastoma. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

C. Nucleotides, Expression, Vectors, and Host Cells

Further provided by an embodiment of the invention is a nucleic acid comprising a nucleotide sequence encoding any of the CARs, an antibody, or antigen binding portion thereof, described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In some embodiments, the nucleotide sequence may be codon-modified. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-modified nucleotide sequence that encodes the antigen binding domain of the inventive CAR. In another embodiment of the invention, the nucleic acid may comprise a codon-modified nucleotide sequence that encodes any of the CARs described herein (including functional portions and functional variants thereof).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Integrated DNA Technologies (Coralville, Iowa, USA).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

Also provided is a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids can be incorporated into a recombinant expression vector. In this regard, an embodiment provides recombinant expression vectors comprising any of the nucleic acids. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors are not naturally-occurring as a whole.

However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.).

Bacteriophage vectors, such as λŭTIO, λŭTI 1, λZapII (Stratagene), EMBL4, and λNMI 149, also can be used. Examples of plant expression vectors include pBIO1, pBI101.2, pBHO1.3, pBI121 and pBIN19 (Clontech). Examples of animal expression vectors include pEUK-Cl, pMAM, and pMAMneo (Clontech). The recombinant expression vector may be a viral vector, e.g., a retroviral vector or a lentiviral vector. A lentiviral vector is a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include, for example, and not by way of limitation, the LENTIVECTOR® gene delivery technology from Oxford BioMedica plc, the LENTIMAX™ vector system from Lentigen and the like. Nonclinical types of lentiviral vectors are also available and would be known to one skilled in the art.

A number of transfection techniques are generally known in the art (see, e.g., Graham et al., Virology, 52: 456-467 (1973); Sambrook et al., supra; Davis et al., Basic Methods in Molecular Biology, Elsevier (1986); and Chu et al, Gene, 13: 97 (1981).

Transfection methods include calcium phosphate co-precipitation (see, e.g., Graham et al., supra), direct micro injection into cultured cells (see, e.g., Capecchi, Cell, 22: 479-488 (1980)), electroporation (see, e.g., Shigekawa et al., BioTechniques, 6: 742-751 (1988)), liposome mediated gene transfer (see, e.g., Mannino et al., BioTechniques, 6: 682-690 (1988)), lipid mediated transduction (see, e.g., Feigner et al., Proc. Natl. Acad. Sci. USA, 84: 7413-7417 (1987)), and nucleic acid delivery using high velocity microprojectiles (see, e.g., Klein et al, Nature, 327: 70-73 (1987)).

In an embodiment, the recombinant expression vectors can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

An embodiment further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a E. coli cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4$^+$/CD8$^+$ double positive T cells, CD4$^+$ helper T cells, e.g., Th1 and Th2 cells, CD8$^+$ T cells (e.g., cytotoxic T cells), tumor infiltrating cells, memory T cells, memory stem cells, i.e. Tscm, naive T cells, and the like. The T cell may be a CD8$^+$ T cell or a CD4$^+$ T cell.

In an embodiment, the CARs as described herein can be used in suitable non-T cells. Such cells are those with an immune-effector function, such as, for example, NK cells, and T-like cells generated from pluripotent stem cells.

Also provided by an embodiment is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs (including functional portions and variants thereof), nucleic acids, recombinant expression vectors, host cells (including populations thereof), and antibodies (including antigen binding portions thereof), can be isolated and/or purified. For example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

D. Methods of Treatment

It is contemplated that the CARs disclosed herein can be used in methods of treating or preventing a disease in a mammal. In this regard, an embodiment provides a method of treating or preventing cancer in a mammal, comprising administering to the mammal the CARS, the nucleic acids, the recombinant expression vectors, the host cells, the population of cells, the antibodies and/or the antigen binding portions thereof, and/or the pharmaceutical compositions in an amount effective to treat or prevent cancer in the mammal.

An embodiment further comprises lymphodepleting the mammal prior to administering the CARs disclosed herein. Examples of lymphodepletion include, but may not be limited to, nonmyeloablative lymphodepleting chemotherapy, myeloablative lymphodepleting chemotherapy, total body irradiation, etc.

For purposes of the methods, wherein host cells or populations of cells are administered, the cells can be cells that are allogeneic or autologous to the mammal. Preferably, the cells are autologous to the mammal. As used herein, allogeneic means any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically. As used herein, "autologous" means any material derived from the same individual to whom it is later to be re-introduced into the individual.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods can provide any amount or any level of treatment or prevention of cancer in a mammal.

Furthermore, the treatment or prevention provided by the method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment provides a method of detecting the presence of cancer in a mammal, comprising: (a) contacting a sample comprising one or more cells from the mammal with the CARs, the nucleic acids, the recombinant expression vectors, the host cells, the population of cells, the antibodies, and/or the antigen binding portions thereof, or the pharmaceutical compositions, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the method of detecting the presence of a proliferative disorder, e.g., cancer, in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

The contacting can take place in vitro or in vivo with respect to the mammal. Preferably, the contacting is in vitro.

Also, detection of the complex can occur through any number of ways known in the art. For instance, the CARs disclosed herein, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles) as disclosed supra.

Methods of testing a CAR for the ability to recognize target cells and for antigen specificity are known in the art. For instance, Clay et al., J. Immunol, 163: 507-513 (1999), teaches methods of measuring the release of cytokines (e.g., interferon-γ, granulocyte/monocyte colony stimulating factor (GM-CSF), tumor necrosis factor a (TNF-a) or interleukin 2 (IL-2)). In addition, CAR function can be evaluated by measurement of cellular cytotoxicity, as described in Zhao et al, J. Immunol, 174: 4415-4423 (2005).

Another embodiment provides for the use of the CARs, nucleic acids, recombinant expression vectors, host cells, populations of cells, antibodies, or antigen binding portions thereof, and/or pharmaceutical compositions of the invention, for the treatment or prevention of a proliferative disorder, e.g., cancer, in a mammal. The cancer may be any of the cancers described herein.

Any method of administration can be used for the disclosed therapeutic agents, including local and systemic administration. For example topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, a chemotherapeutic agent may be administered orally and an antibody or antigen binding fragment or conjugate or composition may be administered intravenously. Methods of administration include injection for which the CAR, CAR T Cell, conjugates, antibodies, antigen binding fragments, or compositions are provided in a nontoxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody or antigen binding fragment to a region of tissue from which a tumor has been removed, or a region suspected of being prone to tumor development. In some embodiments, sustained intra-tumoral (or near-tumoral) release of the pharmaceutical preparation that includes a therapeutically effective amount of the antibody or antigen binding fragment may be beneficial. In other examples, the conjugate is applied as an eye drop topically to the cornea, or intravitreally into the eye.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies or conjugates can range from about 0.01 to about 30 mg/kg, such as from about 0.1 to about 10 mg/kg.

In particular examples, the subject is administered a therapeutic composition that includes one or more of the conjugates, antibodies, compositions, CARs, CAR T cells or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, the disclosed methods include providing surgery, radiation therapy, and/or chemotherapeutics to the subject in combination with a disclosed antibody, antigen binding fragment, conjugate, CAR or T cell expressing a CAR (for example, sequentially, substantially simultaneously, or simultaneously). Methods and therapeutic dosages of such agents and treatments are known to those skilled in the art, and can be determined by a skilled clinician. Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

In some embodiments, the combination therapy can include administration of a therapeutically effective amount of an additional cancer inhibitor to a subject. Non-limiting examples of additional therapeutic agents that can be used with the combination therapy include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the CARS, CAR-T cells, antibodies, antigen binding fragment, or conjugates disclosed herein. Methods and therapeutic dosages of such agents are known to those skilled in the art, and can be determined by a skilled clinician.

Additional chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masoprocol, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

In one embodiment, an effective amount of an antibody or antigen binding fragment that specifically binds to one or more of the antigens disclosed herein or a conjugate thereof is administered to a subject having a tumor following anti-cancer treatment. After a sufficient amount of time has elapsed to allow for the administered antibody or antigen binding fragment or conjugate to form an immune complex with the antigen expressed on the respective cancer cell, the immune complex is detected. The presence (or absence) of the immune complex indicates the effectiveness of the treatment. For example, an increase in the immune complex compared to a control taken prior to the treatment indicates that the treatment is not effective, whereas a decrease in the immune complex compared to a control taken prior to the treatment indicates that the treatment is effective.

E. Biopharmaceutical Compositions

Biopharmaceutical or biologics compositions (hereinafter, "compositions") are provided herein for use in gene therapy, immunotherapy and/or cell therapy that include one or more of the disclosed CARs, or T cells expressing a CAR, antibodies, antigen binding fragments, conjugates, CARs, or T cells expressing a CAR that specifically bind to one or more antigens disclosed herein, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenous) or local (such as intra-tumor) administration. In one example, a disclosed CARs, or T cells expressing a CAR, antibody, antigen binding fragment, conjugate, is formulated for parenteral administration, such as intravenous administration. Compositions including a CAR, or T cell expressing a CAR, a conjugate, antibody or antigen binding fragment as disclosed herein are of use, for example, for the treatment and detection of a tumor, for example, and not by way of limitation, a neuroblastoma. In some examples, the compositions are useful for the treatment or detection of a carcinoma. The compositions including a CAR, or T cell expressing a CAR, a conjugate, antibody or antigen binding fragment as disclosed herein are also of use, for example, for the detection of pathological angiogenesis.

The compositions for administration can include a solution of the CAR, or T cell expressing a CAR, conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents, adjuvant agents, and the like, for example, sodium acetate, sodium chloride, potassium chloride, calcium chloride, sodium lactate and the like. The concentration of a CAR, or T cell expressing a CAR, antibody or antigen binding fragment or conjugate in these formulations can vary widely, and will be selected primarily based on fluid volumes, viscosities, body weight and the like in accordance with the particular mode of administration selected and the subject's needs. Actual methods of preparing such dosage forms for use in in gene therapy, immunotherapy and/or cell therapy are known, or will be apparent, to those skilled in the art.

A typical composition for intravenous administration includes about 0.01 to about 30 mg/kg of antibody or antigen binding fragment or conjugate per subject per day (or the corresponding dose of a CAR, or T cell expressing a CAR, conjugate including the antibody or antigen binding fragment). Actual methods for preparing administrable compositions will be known or apparent to those skilled in the art and are described in more detail in such publications as *Remington's Pharmaceutical Science*, 19th ed., Mack Publishing Company, Easton, Pa. (1995).

A CAR, or T cell expressing a CAR, antibodies, antigen binding fragments, or conjugates may be provided in lyophilized form and rehydrated with sterile water before administration, although they are also provided in sterile solutions of known concentration. The CARs, or T cells expressing a CAR, antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. A CAR, or T cell expressing a CAR, antibodies, antigen binding fragments and conjugates thereof can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres, the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the CARs, or T cells expressing a CAR, antibody or antigen binding fragment or conjugate compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

F. Kits

In one aspect, kits employing the CARs disclosed herein are also provided. For example, kits for treating a tumor in a subject, or making a CAR T cell that expresses one or more of the CARs disclosed herein. The kits will typically include a disclosed antibody, antigen binding fragment, conjugate, nucleic acid molecule, CAR or T cell expressing a CAR as disclosed herein. More than one of the disclosed antibodies, antigen binding fragments, conjugates, nucleic acid molecules, CARs or T cells expressing a CAR can be included in the kit.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, CARs or T cells expressing a CAR. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed antibodies, antigen binding fragments, conjugates, nucleic acid molecules, CARs or T cells expressing a CAR, for example, in a method of treating or preventing a tumor or of making a CAR T cell. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Isolation of Human CD123-Specific Antibodies from a Fully Human Yeast Display scFv Library This example describes the derivation of fully human binding sequences targeting the CD123 antigen from a yeast display library.

Materials and Methods:

A large yeast display human naive single chain variable fragment (scFv) antibody library was used to isolate anti-human CD123 antibodies described herein. The library was constructed using a collection of human antibody gene repertoires from more than 60 individuals. Three rounds of magnetic-activated cell sorting (MACS) were performed to enrich human scFv binders to the recombinant human CD123-Fc. For the first round of yeast library panning, the yeast display scFv library ($5\times10^{10}$ cells) was incubated with 5 μg/mL CD123-Fc in 15 ml PBSA (consisting of 0.1% Bovine Serum Albumin (BSA) in Dulbecco's phosphate-buffered saline (PBS) buffer), at room temperature on a rotator for 1.5 hours. After two times washing with 25 ml PBSA, the yeast library mix was incubated with 100 μL Protein G microbeads (Miltenyi Biotec) at room temperature on a rotator for 30 minutes. After one time washing, the library mix was resuspended in 50 ml of PBSA and loaded onto the MACS cell separation column (LS column). After three times washing with 10 ml PBSA. The yeast displayed scFv binders to the column were then eluted two times with 2 ml PBSA. These eluted yeast cells were combined and then resuspended into 50 ml SDCAA medium (20 g D-glucose, 6.7 g BD Difco™ Yeast Nitrogen Base without Amino Acids, 5 g Bacto™ Casamino Acids, 5.4 g Na2.HPO4, and 8.56 g $NaH_2PO_4.H_2O$ in 1 L water) and amplified with shaking at 225 rpm at 30° C. for 20 hours. The amplified pool was then induced in SGCAA medium (consisting of the same composition of SDCAA medium, but containing galactose instead of glucose), with shaking at 225 rpm at 30° C. for another 16 hours and used for next round of panning. The same process was repeated two more times to enrich the CD123-Fc specific binders.

To further enrich the binders with higher affinity and better specificity, FACS based sorting was employed to isolate the strongest binders from the pool. The induced pool was incubated with 1 μg/ml of CD123-Fc at room temperature for 1 hour and then stained with Anti-c-Myc-Alexa 488 and Goat anti-Hu-Fc PE conjugates, the top 1% of the pool with the highest PE versus FITC signal was gated and sorted. The sorted pool was amplified in SDCAA medium and yeast plasmid DNA was extracted and transformed into bacterial for single clone DNA sequencing. Two unique sequences were identified and designated as MT-16 and MT-32, cloned into CAR constructs for expression in CAR-T or CAR-NK format constructs for expression in CAR-T or CAR-NK format, for further function characterizations.

Example 2

Isolation of Human CD123-Specific Antibodies from a Fully Human Phage Display InfinityOne scFv Library This example describes the derivation of fully human binding sequences targeting the CD123 antigen from a phage display library.

Materials and Methods:

Production of Human Phage-Displayed ScFv CD123-Specific Antibodies

A naïve human scFv (recombinant single chain fragment variable of immunoglobulin) phage display library (approximate diversity, $7\times10^{10}$ unique specificities), constructed from peripheral blood B cells of 121 healthy donors (F. Tomszak, unpublished data) was used for selection of scFvs specific for recombinant human CD123. Amplified libraries of $10^{12}$ phage-displayed ScFv were incubated with 1 μg of coated CD123 in 100 μl volume in one well of a 96-well plate for 2 h at room temperature during the first, second and third rounds of biopanning, respectively. After each round of incubation, the wells were washed 10 times for the first round, 20 times for the second round and 30 times for the third round with phosphate-buffered saline containing 0.05% Tween 20 (PBST) to remove nonspecifically bound phage. Antigen binding phage were eluted with 100 μl 10 μg/ml Trypsin diluted in PBS and mixed with TG1 competent cells for 1 hour at 37° C., and the phage was amplified from the infected cells and used in the next round of biopanning. After the third round of biopanning, 376 clones were randomly picked from the infected TG1 cells and each inoculated into 150 μl 2YT medium containing 100 μg/ml ampicillin and 200 mM glucose in 96-well plates by using the automated colony picking system (Molecular Devices, QPix 460) and were incubated at 37° C. overnight in a shaker at 300 rpm. Next day 10 μl of the bacterial cultures were used to inoculate 150 μl 2YT medium containing 100 μg/ml ampicillin and 50 μM isopropyl-β-d-thiogalactopyranoside in 96-well plates and the plates were further incubated at 30° C. overnight in a shaker at 300 rpm. The scFv supernatants were mixed with 2% BSA in PBST containing 1:2500 diluted horseradish peroxidase-conjugated recombinant monoclonal mouse anti-c-myc antibody at a 1:1 volume ratio and used for enzyme-linked immunosorbent assay (ELISA) to identify clones of phage displaying scFvs with high CD123 binding affinity. The supernatants were incubated for 1 h at room temperature with recombinant human CD123 coated at 30 ng per well in 384-well plates and washed three times with PBST, (after overnight incubation at 4° C. it was blocked with 2% BSA in PBS containing 0.05% Tween 20 and washed three times with PBS containing 0.05% Tween 20.) After incubation the 3,3,'5,5'-tetramethylbenzidine (TMB) substrate was added, and solution absorbance at 450 nm (A450) measured. Clones that bound to CD123 with a signal to noise ratio of >5 were selected for further characterization.

Flow Cytometry-Based Binding Assay.

Identified binders from ELISA were tested on CD123-positive the cell line MOLM-13. The CD123-negative cell line Jeko-1 CD20KO eGFP served as negative control. For positive control staining REAL270 (alpha CD123) and REAL116 (alpha CD123) antibodies were used, respectively. Soluble scFvs were expressed as described above. The bacterial pellets were disrupted by incubation with 0.3 mL TE buffer (10 mM Tris-HCl containing 1 mM EDTA, pH 8.0 at 37° C.)/well at 37° C., 250 rpm for 18 hours. Cultures were centrifuged at 4000×g, RT for 20 minutes and the supernatant was transferred to a fresh microtiter plate.

For cell staining cell number and viability were determined at MACSQuantX. A cell suspension containing needed cell number were centrifuged at 300×g, 4° C. for 10 minutes and supernatant was discarded. Cells are resuspended by addition of PEB buffer (1×PBS+2 mM EDTA, 0.5% BSA pH 7.4 at RT) to a concentration of 1E+06 cells/mL. One hundred thousand cells per cell line were added to each well of 96-well V-bottom plate and the plate were centrifuged at 1300×g, 4° C. for 2 minutes. The supernatant was discarded, cells were resuspended in 100 µL of supernatant from periplasmatic preparation and cells were incubated for 10 minutes on ice. Cells were washed by addition of 100 µL PEB followed by centrifugation (1300×g, 4° C. for 2 minutes), twice. Fifty microliter of secondary (Anti-His-APC conjugated antibody) or REAL antibody (diluted 1:50 in PEB buffer) per well were added and the plate is incubated for 10 minutes in the dark at 4° C. Cells were washed by addition of 100 µL PEB followed by centrifugation (1300×g, 4° C. for 2 minutes), twice. Propidium iodide was diluted 1:100 in Fixing solution (1×PBS+2 mM EDTA+1% PFA+0.3% MeOH+3% NaAzide) and washed cells were resuspended in 50 µL of the mixture. Signals are measured at MACSQuantX. Signals were analyzed using FlowLogic software. Statistical analysis was performed with VORTEX software.

Results:

Based upon the results of the ELISA binding assay, ten unique scFv clones specific for recombinant human CD123 and MOLM13 cells were identified (Table 1). The corresponding scFv sequences were incorporated as binder domains into CAR constructs for further analysis in CAR-T and CAR-NK format.

TABLE 1

| | ScFv designation |
|---|---|
| 1 | MB31-A01 |
| 2 | MB31-O01 |

TABLE 1-continued

| | ScFv designation |
|---|---|
| 3 | MB35-E02 |
| 4 | MB36-A05 |
| 5 | MB40-F08 |
| 6 | MB40-H08 |
| 7 | MB42-D03 |
| 8 | MB42-E02 |
| 9 | MB42-E12 |
| 10 | MB44-H01 |

Example 3

Development of CD123-Targeting CAR T Cell Constructs

Few treatment options exist for AML, and treatment-associated toxicities and post-treatment disease relapse are common. Moreover, immunotherapies employing non-human sequences, such as mouse-derived antibodies, may result in therapy rejection or adverse reactions in patients. In order to develop a new CAR T treatment for AML, fifteen CD123-targeting CAR T constructs incorporating fully human ScFv targeting domains were designed and evaluated for anti-tumor activity.

Materials and Methods:

Cell Lines Used to Demonstrate CAR Activity

Acute myeloid leukemia cell line MOLM-14 was purchased from the German Collection of Microorganisms and Cell Lines (DSMZ, Braunschweig Germany). Other cell lines, myelogenous leukemia line KG-1a, acute lymphocytic leukemia line RS4;11, epidermoid carcinoma line A431 and 293T cell line were purchased from American Tissue Culture Collection (ATCC, Manassas, Va.). The MOLM14 cell line was cultured in RPMI-1640 Medium (ATCC) supplemented with 20% heat-inactivated fetal bovine serum (FBS). The KG-1a line was cultured in IMDM Medium supplemented with 20% FBS. The A431 line was cultured in DMEM Medium (ATCC) supplemented with 10% heat inactivated FBS. The 293T cells were cultured in Dynamis™ medium (Thermo Fisher Scientific, Grand Island, N.Y.) with 4 mM L-Glutamine (Lonza, Morristown, N.J.). Each cell line was prepared as a single-cell clone of luciferase-expressing cell line by stably transducing wild-type tumor lines with lentiviral vector encoding firefly luciferase (Lentigen Technology, Inc., Gaithersburg, Md.).

Generation of CAR Constructs and Lentiviral Vector Production

The human anti-CD123 chimeric antigen receptor (CAR) constructs were generated from various single chain variable fragment (ScFv) sequences targeting the extracellular domain of human CD123/IL-3 receptor α. Each scFv sequence was linked in frame to CD8 hinge, 4-1BB costimulatory domain, and CD3-ζ activating domain sequences. The comparator CD33-targeting CAR sequence was generated in a similar manner, except that a heavy chain only variable domain (VH_4) was used as a targeting domain instead of an scFv. The VH_4 sequence was linked in frame to CD8 hinge, 4-1BB costimulatory domain, and CD3-ζ activating domain sequences (Schneider, Dina et al. "A Unique Human Immunoglobulin Heavy Chain Variable Domain-Only CD33 CAR for the Treatment of Acute Myeloid Leukemia." Frontiers in Oncology vol. 8 539. 22 Nov. 2018, doi:10.3389/fonc.2018.00539). Leader peptide derived from the human GMCSFR1 was included in all CAR constructs to facilitate trafficking to T cell membrane. CAR sequences were cloned into a Lentiviral Vector (LV) expression cassette under the control of the human EF-1α promoter (Lentigen Technology Inc., Gaithersburg, Md.). Lentiviral particles were generated by transient transfection of HEK 293T cells, pelleted by centrifugation and stored at −80° C. until transduction.

Primary T Cell Preparation and Transduction

Healthy donor primary T cells were isolated either from leukapheresis collections (AllCells, Alameda, Calif.) or from processed buffy coats (Oklahoma Blood Institute, Tulsa, Okla.), obtained with donors' written consent. The CD4-positive and CD8-positive human T cells were purified via positive selection using a 1:1 mixture of CD4 and CD8 Microbeads (Miltenyi Biotec, Bergisch Gladbach, Germany) according to manufacturer's protocol. Purified T cells were cultured in serum free TexMACS medium supplemented with either 30 IU/ml IL-2 at a density of $1\times10^6$ cells/ml, and activated with CD3/CD28 MACS® GMP T Cell TransAct reagent (Miltenyi Biotec). Further, activated T cells were transduced on day 1 with lentiviral vector particles encoding CAR constructs. On day 3, and every 2-3 days thereafter, cultures were supplemented with fresh TexMACS medium containing 30 IU/ml IL-2, until harvest on day 8-10. Where noted, TexMACS medium supplemented with 970 IU/ml IL-7 and 90 IU/ml IL-15 was used.

CD123 Surface Expression on Tumor Cell Lines

CD123 surface expression was determine in an array of tumor lines by flow cytometry using anti-CD123 antibody clone AC145 (Miltenyi Biotec, Bergisch Gladbach, Germany), and negative gating was based on the cognate isotype control. The CD123 surface expression density on target cell lines was evaluated by QuantiBRITE Phycoerythrin (PE) beads (BD Biosciences, San Jose, Calif.) based on the antibodies bound per cell (ABC) method as per manufacturer's protocol. Briefly, beads conjugated to the PE fluorophore at four different densities served to generate a standard curve, and tumor cells stained with anti CD123 antibodies conjugated to PE were acquired under identical settings. The ABC value was extrapolated for each tumor cell line based on the standard curve.

Flow Cytometric Analysis of CAR Surface Expression

Half million CAR T cells were washed two times in cold AutoMACS buffer supplemented with 0.5% bovine serum albumin (Miltenyi Biotec, Bergisch Gladbach, Germany) and stained with 2.5 ug/ml CD123-Fc peptide (Novoprotein, Summit, N.J.), followed by anti Fc-AF647 conjugate (Jackson ImmunoResearch, West Grove, Pa.). The 7-Aminoactinomycin D staining (7-AAD, BD Biosciences, San Jose, Calif.) was added to exclude dead cells. Non-transduced cells (UTD) were used as a negative control. Cells were washed twice with AutoMACS buffer supplemented with 0.5% bovine serum albumin, resuspended in 200 ul staining buffer and acquired by flow cytometry. Flow cytometric analysis was performed on a MACSQuant® 10 Analyzer (Miltenyi Biotec), and data plots were generated using FlowJo software (Ashland, Oreg.).

CAR T Cell Cytotoxicity and Cytokine Assay

To assess CAR T cell mediated cytotoxicity, $5\times10^3$ tumor target cells stably transduced with firefly luciferase were combined with CAR T cells at the indicated effector to target ratios and incubated overnight at 37° C. with 5% $CO_2$. SteadyGlo reagent (Promega, Madison Wis.) was added to each well and the resulting luminescence quantified as counts per second (sample CPS). Target only wells (max CPS) and target only wells plus 1% Tween-20 (min CPS) were used to determine assay range. Percent specific lysis was calculated as: (1−(sample CPS−min CPS)/(max CPS−min CPS)). For cytokine release analysis, $5\times10^4$ effectors and $5\times10^3$ targets were co-cultured overnight, and supernatants from co-cultures were removed and analyzed by ELISA (eBioscience, San Diego, Calif.) for IFNγ, TNFα and IL-2 concentration. Three technical replicates were performed for each condition, and each experiment was repeated using CAR T cells generated from at least three healthy donors.

Results

Example 3 data describes the generation and in vitro evaluation of CAR T cells targeting the CD123 antigen for the treatment of AML.

Schematic representations of the tandem CAR constructs targeting the CD123 antigen are shown in FIG. 1A. CAR 123 is comprised of a fully human binder (InfinityOne), linked in frame to CD8 hinge and transmembrane domain, 4-1BB co-stimulatory domain and CD3ζ activation domain. Ten scFv sequences were selected for evaluation in the CAR format based on flow cytometric binding analysis of the cognate soluble binders to target lines with and without CD123 expression. CAR variants D0125-D0134 were constructed (TABLE 2). CAR sequences were further incorporated into a third-generation lentiviral vectors and transduced into human primary T cells at saturation, to generate the CD123 CAR T cells under the control of the mammalian EF-1α promoter. Previously evaluated CAR control constructs, targeting CD123 (LTG2078) and CD33 (LTG1906) were also included (TABLE 3). Un-transduced T cells derived from same donor as the CAR-expressing cells (UTD) were used as a negative control.

TABLE 2

CD123 CAR constructs

| Construct Number | ScFv | Construct designation |
|---|---|---|
| D0125 | CD123 (MB31-A01) | EF-1a-CD123 MB31-A01CD8 BBz |
| D0126 | CD123 (MB31-O01) | EF-1a-CD123 MB31-C01CD8 BBz |
| D0127 | CD123 (MB35-E02) | EF-1a-CD123 MB35-E02 CD8 BBz |
| D0128 | CD123 (MB36-A05) | EF-1a-CD123 MB36-A05 CD8 BBz |
| D0129 | CD123 (MB40-F08) | EF-1a-CD123 MB40-F08 CD8 BBz |
| D0130 | CD123 (MB40-H08) | EF-1a-CD123 MB40-H08 CD8 BBz |
| D0131 | CD123 (MB42-D03) | EF-1a-CD123 MB42-D03 CD8 BBz |
| D0132 | CD123 (MB42-E02) | EF-1a-CD123 MB42-E02 CD8 BBz |
| D0133 | CD123 (MB42-E12) | EF-1a-CD123 MB42-E12 CD8 BBz |
| D0134 | CD123 (MB44-H01) | EF-1a-CD123 MB44 -H01CD8 BBz |

TABLE 3

Single-targeting CAR controls

| Construct Number | scFv | Construct designation |
|---|---|---|
| LTG2078 | M12306 | EF-1α CD123 CD8 BBz |
| LTG1906 | CD33_4 | EF-1α CD33 CD8 BBz |

Lentiviral vectors encoding the CD123 CAR constructs were used for CAR transduction into human primary T cells at multiplicity of infection (MOI) of 40. CAR surface expression of transduced T cells by flow cytometry using recombinant IL3R-alpha Fc-tagged, followed by staining with anti-Fc Alexa Flour 647. Different CD123 CAR construct exhibited different level of expression ranging from 0-80% (n=4 donors), FIG. 1B. CAR D0126, D0127, D0131, D0132, D0133 and D0134 exhibited similar or higher surface expression than positive CAR 123 control LTG2078; while CAR D0130 had slightly lower surface expression, followed by D0129 and D0128, while D0125 had lowest expression in multiple donors. Cell viability was examined at day 3 and day 7 after T cell activation, as showed in FIG. 1C. All the CD123 CAR T cells showed improved or equivalent viability compared with control CAR LTG2078.

Figure 2:
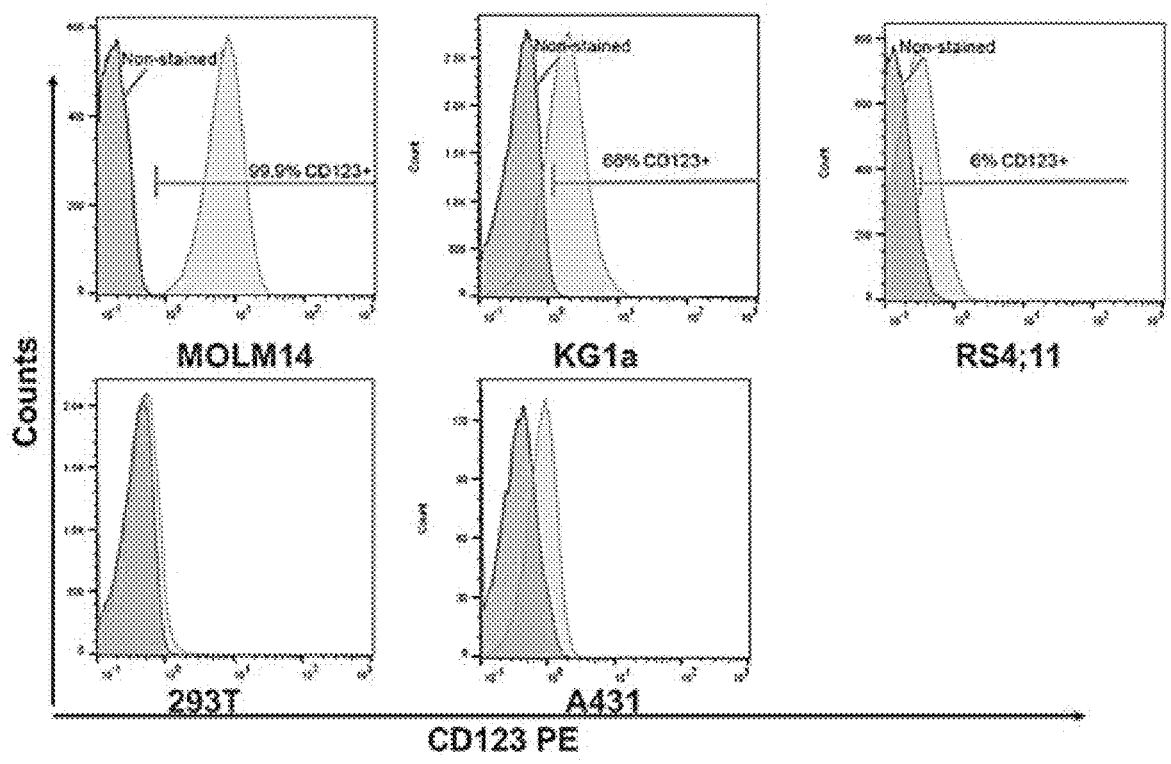
FIG. 2 depicts CD123 surface expression level on MOLM14, KG-1a, RS4;11, 293T and A431 tumor cell lines. Representative flow histograms are shown.

To evaluate the target specific cytotoxicity of CD123 CARs in vitro, leukemic lines (MOLM14, KG1a, RS4;11) and non-leukemic lines (293T and A431) were evaluated for surface CD123 expression by flow cytometry with CD123 specific antibodies. As shown in FIG. 2, 99% MOLM14, and 66% KG-1a human AML tumor cell lines express CD123, whereas the human B-ALL line RS4;11 has only limited CD123 expression. By contrast, 293T and A431 have no CD123 expression. Therefore, lines MOLM14 and KG-1a were selected as target cell lines, and 293T as negative control cell line for CAR T cells functional evaluation.

Human primary T cells were transduced with lentiviral vectors encoding CAR constructs and expanded in culture to day 8. CAR-T cells were co-incubated with MOLM14, KG-1a or 293T cell lines at effector to target ratios 2.5:1; 5:1 and 10:1. After overnight co-incubation, cultures were analyzed in a luminescence based in vitro killing assays. Most CAR123 constructs-expressing primary T cell lines lysed MOL14-CD123+ with varied potency, while three CD123 CAR lines, D0125, D0128 and D0129, lacked target lytic capability (FIG. 3A). Similarly, KG-1a-CD123+ target cells were killed by most CAR T constructs, except for D0125, D0128 and D0129 (FIG. 3B). The CD33 CAR LTG1906 exhibited high cytotoxicity toward MOLM14 (CD33$^{High}$) and low lytic potency towards KG1a (CD33$^{Low}$), in agreement with the CD123 expression levels. Furthermore, no killing above background of CD123 negative 293T cell line (FIG. 3C) was observed, demonstrating the robust target-specific cytotoxic function of all CD123 CAR constructs, except for CAR D0125, D0128, and D0129.

Production of the T cell homeostatic and pro-inflammatory cytokines IL-2, IFNγ, and TNFα by the CD123 CARs, and control constructs CAR LTG2078 and CD33 CAR LTG1906, was examined by ELISA in culture supernatants after overnight co-incubation of CAR T cells with MOLM14 target line at an E:T ratio of 10 (FIG. 4A-4C). Specific target induced cytokine release was detected by comparison of each CAR T group incubated with target cells to the respective CAR T alone experimental group, and also comparing the target co-incubated CAR T groups to the previously characterized CAR123 control LTG2078. While CAR123 control LTG2078 and CAR33 control LTG1906 elaborated cytokines after co-incubation with MOLM14 target cells, most test CD123 CAR T constructs have not produced significant increases in IFNγ, TNFα, or IL-2 cytokines after overnight co-culture with MOLM14 cells. One exception was CAR123 D0127, which elaborated IFNγ, and TNFα levels even in the absence of target cells (T cells alone group), indicating tumor-independent cytokine response. This effect could not be anticipated form previous experiments, and it demonstrates the non-obviousness of the present invention. Excluding CAR123 D0127, cytokine response of the CD123 CAR constructs evaluated herein was comparable to the non-transduced T cells (UTD) control, suggesting low risk of inducing cytokine-mediated adverse effects, such as cytokine release syndrome (CRS) and immune effector cell-associated neurotoxicity syndrome (ICANS).

Among all CAR123 constructs, D0126 showed the highest transduction efficiency and viability as well as best cytotoxic function against CD123+ tumor cells among this set of CAR constructs. Another CAR123 construct, D0131, also demonstrated high CAR transduction efficiency and viability, but moderate target cell killing activity in vitro. Therefore, CAR123 constructs D0126 and D0131 were selected for further evaluation in vivo.

Example 4

Evaluation of the Anti-Tumor Function of CD123-Targeting CAR T Cells in a Mouse MOLM14 Xenograft Model This example describes the evaluation of the CD123-targeting CAR T cells incorporating scFv sequences derived from the InfinityOne library in vivo.

Materials and Methods:

Cell Lines

Acute myeloid leukemia cell line MOLM-14 was purchased from the German Collection of Microorganisms and Cell Lines (DSMZ, Braunschweig Germany). The MOLM14 cell line was stably transduced with firefly luciferase gene and cultured in RPMI-1640 Medium (ATCC) supplemented with 20% heat-inactivated fetal bovine serum (FBS).

In Vivo Analysis of CAR T Function

Animal experiments were performed in compliance with the applicable laws, regulations and guidelines of the National Institutes of Health (NIH) and with the approval of MI Bioresearch (Ann Arbor, Mich.) Animal Care and Use Committee. In this study, the function of CD123-targeting CAR T cells was assessed in NSG (NOD.Cg-Prkdc$^{cid}$Il2rg$^{tm1Wjl}$/SzJ) mice in vivo. Six to eight week old female NSG mice, 6 per group, were injected with $1.0 \times 10^6$ MOLM-14 CD123$^+$ AML cells into the tail vein on day 0. Tumor burden was determined by IVIS bioluminescent imaging on day 4, and mice were then randomized to groups with equal mean tumor burden, and $5.0 \times 10^6$ CAR T$^+$ cells/mouse (normalized for transduction efficiency) were administered on study day 5. Tumor regression was determined by bioluminescent imaging on days 14, 21, 28, 35, 42, 49 using a Xenogen IVIS-200 instrument (Perkin Elmer, Shelton, Conn.). Images were analyzed using Living Image, version 4.1, software (Perkin Elmer) and the bioluminescent signal flux for each mouse was expressed as average radiance (photons per second per cm$^2$ per steradian). Survival was recorded and analyzed at the end of the study. To determine the presence of CAR T and tumor cells, peripheral blood was collected from all animals on study day 14, 21, 28 and 42. The absolute numbers of blood CAR T cell and MOLM-14 tumor cells were determined by flow cytometry.

Flow Cytometric Analysis of CAR T and Tumor Cells in Mouse Blood

Seventy microliters of mouse blood was collected on study day 14, 21, 28 and 42, and analyzed for CAR T and MOLM-14 tumor cell number by flow cytometry. Red Blood Cells were then lysed with Red Blood Cell Lysis Solution (BD BioScience, San Jose, Calif.) as per manufacturer's instructions, the remaining lymphocytes were stained with anti-human CD45, anti-human CD3 (Miltenyi Biotec), anti-human CD8 (Miltenyi Biotec), anti-human CD123 (Miltenyi Biotec), and 7-AAD (BD Biosciences, San Jose, Calif.) and then analyzed by flow cytometry. Dead cells were excluded from analysis by 7-AAD staining. To obtain direct counts of human T cell and MOLM-14 in blood, the MACSQuant 10 volumetric function was utilized, and CountBright Absolute Counting Beads (ThermoFischer Scientific, Waltham, Mass.) were used to account for sample loss during processing, as per manufacturer's protocol.

Results:

NSG MOLM14 xenograft AML model was used to further explore the in vivo tumor rejection functionality of the two top CAR123 candidates D0126 and D0131. Two animal studies using CAR T cells derived from separate healthy donors were performed, one focusing on CAR D0126 (FIG. 5A) and the other comparing between CAR123 constructs D0126 and D0131 (FIG. 5B). The previously characterized CAR LTG1906, targeting the CD33 antigen on MOLM14 tumor cells, was included as a comparative control.

In the first in vivo study, CD123 CAR D0126 was compared with the previously characterized CD33 CAR-T construct LTG1906, and control experimental groups tumor alone (TA) and untransduced T cells (UTD) were also included. CAR-T cells were generated by transduction with lentiviral vectors encoding CAR D0126 and CAR LTG1906 and subsequent culture expansion in TexMACS medium supplemented with 30 IU/ml IL2. MOLM14-Luc cells were used as target line. MOLM14-Luc cells, $1 \times 10^6$, were injected intravenously (i.v.) into each NSG mouse. Tumor growth was evaluated by IVIS imaging on day 6, and then mice were randomized into experimental groups. On day seven, $5 \times 10^6$ human CAR+ T cells or UTD cells per mouse were administrated by tail vein injection. Tumor growth kinetics was monitored by in vivo imaging system (IVIS) overtime (FIGS. 6A and 6B). As MOLM14 tumors express both CD123 and CD33 antigens, treatment groups dosed with CAR D0126, targeting the CD123 antigen, as well as the comparator group dosed with the CAR LTG1906, targeting the CD33 antigen, showed robust tumor rejection compared to tumor alone (TA) and UTD control groups. Five of six mice in each group demonstrated complete tumor rejection, and only one mouse per group had residual tumor cells at study conclusion (FIG. 6B). Notably, both CAR D0126 and CAR LTG1906-treated groups showed no body weight loss (FIG. 6C), thus no CAR-related toxicity was detected in this model. CARs D0126 and LTG1906 both mediated complete survival to study termination at day 36 (6 out of 6 mice survived), while the tumor alone (TA), and UTD control groups succumbed to high-burden disseminated disease by day 15 (FIG. 6D). Mouse peripheral blood was sampled at days 14, 22 and 33. Human T cells were detected in all groups (FIG. 7A, 7B, 7C). Moreover, CAR D0126 and LTG1906 T cells were detected in the peripheral blood of mice at the end of the study, demonstrating high persistence of the CD123 CAR candidate D0126, and the comparative control CAR33 LTG1906 T cells.

In the second animal study, CD123 CAR D0131 was included in addition to CAR D0126. CAR T cells in this study were generated from peripheral blood T cells of a different donor from the one used in the first in vivo study. T cells were transduced and expanded with TexMACS medium supplemented with 970 IU/ml IL-7 and 90 IU/ml IL-15. Tumor progression in each group is shown in FIG. 8A. Similarly to the first animal study, CAR D0126 demonstrated strong anti-tumor potency, and tumors were rejected in four out of six mice. CAR123 D0131 manifested weaker anti-tumor activity as compared with CAR123 D0126 (FIGS. 8A and 8B). Although no significant body weight loss was observed in the CAR T treated groups (FIG. 8C), mice death was observed in all groups. The best survival effect was detected in the CAR D0126-treated group, with four of the six mice surviving to the extended study termination day, day 56, and remaining completely tumor-free (FIG. 8D). The total T cells in the peripheral blood were monitored in this study. As expected, human T cells were detected in the mice' peripheral blood two days after CAR T cell or UTD administration in all groups except the TA negative control (FIG. 9A). The T cell amounts increased in all CAR T groups overtime, suggesting T cell expansion (FIG. 9B), and persistence throughout days 21, 28 and 42 (FIG. 9C, 9D, 9E). On study day 42, the CAR123 D0126 group had the highest number of T cells (FIG. 9E), indicating the greatest T cell expansion and persistence among CAR constructs tested in this experiment.

In summary, the CD123 CAR candidate D0126 efficiently eliminated tumors in NSG mice engrafted with MOLM-14 cells in two in vivo studies utilizing T cells from different human donors, and demonstrated efficient tumor clearance, CAR T persistence and prolonged survival in the MOLM14 AML xenograft mouse model (FIG. 9A). Therefore, CAR123 D0126 was identified as lead candidate for the development of CD123-targeting CAR T therapy for the treatment of CD123-positive malignancies.

Example 5

Development of CD123-Targeting CAR NK Cells

This example describes the generation of CAR NK cells by lentiviral transduction.

Materials and Methods:

Lentiviral Vector Constructs and Production

Each CD123-CAR was comprised of CD123 scFv binder, CD8 hinge and transmembrane domains, a 4-1BB transactivation domain and a CD3 zeta signaling domain. Constructs were cloned into a third-generation lentiviral plasmid backbone (Lentigen) under the control of a human EF-1α promoter. Lentiviral vector (LV) containing supernatants were generated by transient transfection of HEK 293T cells, as previously described (Kuroda H et al., J Virol Methods. (2009) 157:113-21). For pseudotyping the lentiviral vectors, a modified BaEV envelope glycoprotein was used as described previously (Girard-Gagnepain A et al., Blood. (2014) 124:1221-31). LV containing supernatants were stored at −80° C. and titers were determined on NK-92 cells.

Primary NK Cell Separation

For isolation of NK cells from buffy coats, peripheral blood mononuclear cell (PBMC) preparation was performed by standard density-gradient centrifugation using Ficoll-Paque PLUS (GE Healthcare). Resting NK cells were enriched from PBMCs by depleting the non-NK cell population using the NK cell isolation kit for human cells (Miltenyi Biotec).

Cell Culture and Transduction

NK cells were cultured at $10^6$ cells/mL in NK MACS medium with 5% human AB serum, 500 U/mL IL-2 (Miltenyi Biotec), 10 ng/mL IL-15 (Miltenyi Biotec), and 10 ng/mL IL-1β (Miltenyi Biotec). After 2 days of culture, NK cells were transduced as previously described (Ban R, Granzin M, et al., Front Immunol. (2019) 10:2001).

Briefly, NK cells were suspended at $5 \times 10^5$ cells/mL in 200 µL serum-free culture medium containing 10 µg/mL Vectofusin-1 and up to 50 µL LV supernatant for transduction. After spinoculation at 400 g for 2 h, the cells were cultured with the LV for 24 h in cell culture incubator. The cell culture medium was then exchanged with fresh complete cell culture medium containing 5% human AB serum, 500 U/mL IL-2, and 10 ng/mL IL-15. Transduction efficiency was determined by flow cytometry from day 3 post-transduction onwards. The transduced NK cells were spun down every 3 days, counted, and the cell number adjusted to 0.5 million cells/ml in fresh complete NK cell culture medium (5% human AB serum, 500 U/mL IL-2, and 10 ng/mL IL-15) for long-term culture.

Results:

Primary NK Cells were Efficiently Transduced with CD123-CAR Using Baboon Envelope Glycoprotein-Pseudotyped Lentiviral Vector.

We have generated thirteen CD123-CAR constructs containing CD123 binders, CD8 hinge and transmembrane domains, a 4-1BB transactivation domain, and a CD3 zeta signaling domain (TABLE 4). These CD123-CAR constructs were cloned into a third-generation lentiviral plasmid backbone (Lentigen) under the control of a human EF-1α promoter. We have shown in our earlier publication that a modified baboon envelope glycoprotein-pseudotyped lentiviral vector (BaEV) can efficiently transduce NK cells (Bari R et al., Front Immunol. (2019) 10:2001). All of the listed 13 lentiviral vectors (LV) containing CD123-CAR were pseudotyped with BaEV, and viral vectors were generated by transient transfection of HEK 293T cells.

TABLE 4

List of CD123 CARs and binders

| Construct Number | ScFv | Construct designation | SsFv source library |
|---|---|---|---|
| Z16 | CD123 (Z16) | EF-1a-CD123 Z16-CD8 BBz | yeast |
| LTG2078, control | CD123 (Z23) | EF-1a-CD123 Z23-CD8 BBz | yeast |
| Z32 | CD123 (Z32) | EF-1a-CD123 Z32-CD8 BBz | yeast |
| D0125 | CD123 (MB31-A01) | EF-1a-CD123 MB31-A01CD8 BBz | phage |
| D0126 | CD123 (MB31-001) | EF-1a-CD123 MB31-C01CD8 BBz | phage |
| D0127 | CD123 (MB35-E02) | EF-1a-CD123 MB35-E02 CD8 BBz | phage |
| D0128 | CD123 (MB36-A05) | EF-1a-CD123 MB36-A05 CD8 BBz | phage |
| D0129 | CD123 (MB40-F08) | EF-1a-CD123 MB40-F08 CD8 BBz | phage |
| D0130 | CD123 (MB40-H08) | EF-1a-CD123 MB40-H08 CD8 BBz | phage |
| D0131 | CD123 (MB42-D03) | EF-1a-CD123 MB42-D03 CD8 BBz | phage |
| D0132 | CD123 (MB42-E02) | EF-1a-CD123 MB42-E02 CD8 BBz | phage |
| D0133 | CD123 (MB42-E12) | EF-1a-CD123 MB42-E12 CD8 BBz | phage |
| D0134 | CD123 (MB44-H01) | EF-1a-CD123 MB44 -H01CD8 BBz | phage |

Primary NK cells were isolated from PBMCs by magnetic separation resulting in pure cell populations (FIG. 10A). Most of the cell lines, specifically acute myeloid leukemia (AML) cells, are sensitive to the natural cytotoxicity of NK cells, thus not suitable for testing the cytotoxicity of CAR-NK cells. However, RS4-11 cell lines are known to insensitive to NK cell natural cytotoxicity. Therefore, many NK cell research laboratories, including ours, routinely use RS4-11 as target cells to test CAR-NK cell functionality. To use the RS4-11 as a target cells to test CD123-CAR functionality, a daughter RS4-11 cell line stably expressing CD123 was generated (FIG. 10B).

NK cells were activated by cultivation in NK MACS medium containing IL-2/IL-15/IL-1β for two days, followed by transduction with BaEV pseudotyped lentiviral vectors (BaEV-LV), resulting in efficient efficiency transduction of primary NK cells. Transduction of NK cells with lentiviral vectors containing different CD123-CAR constructs resulted in differential expression of CD123-CAR at the surface of NK cells (FIG. 11). Among the thirteen CD123-CARs, Z32 and D0126 binders were the best for transducing NK cells, and yielded transduction efficiency of 51.55% and 61.37%, respectively. Based on these expression results, we have selected CAR constructs Z32 and D0126 for further analysis.

CD123-CAR NK Cells Efficiently and Specifically Kill Target Cells Expressing CD123.

Activated NK cells were transduced with BaEV pseudotyped lentiviral vector containing CD123-CAR Z32 (Z32-BaEV-LV) and D0126 (D0126-BaEV-LV). CD123-CAR expression for Z32 and D0126 was 70.5% and 64.19%, respectively (FIG. 12A). In addition, the cytotoxicity of the CD123-CAR-expressing NK cells was tested against target cells RS4-11-CD123. RS4;11 cells expressing CD123 (FIG. 10B) are insensitive to NK cell natural cytotoxicity. Consequently, non-transduced NK cells could not kill RS4;11-CD123 cells, whereas both CD123-CAR (Z32 and D0126) NK cells killed RS4;11-CD123 very efficiently, demonstrating the high functionality and specificity of the generated CD123-CAR NK cells (FIG. 12B).

Next, the specificity of CD123-CAR toward CD123 antigen was confirmed by serial dilution. NK cells were transduced with different amounts of lentiviral vectors containing CD123-CAR. As expected, the higher quantity of CD123-CAR-LV showed higher expression of CD123-CAR (FIG. 13A). Finally, the cytotoxicity of differentially expressing CD123-CAR NK cells was tested against RS4-11-CD123 cells at the same effector-target ratio (FIG. 13B). The highest expressing CD123-CAR-NK cells showed the highest killing, and the lowest expressing CD123-CAR-NK cells showed the lowest killing confirmed the specificity of CD123-CAR toward CD123 antigen.

Expression of CD123-CAR has No Adverse Effect on NK Expansion and Viability.

Primary NK cells were isolated, activated, and transduced with Z32 and D0126, followed by expansion for 13 days. Untransduced NK cells were used as control. The expansion of untransduced, Z32 transduced, and D0126 transduced NK cells was 61 fold, 49 fold, and 42 fold, respectively (FIG. 14A). The experiment was started with equal NK cell number for each condition. Some of the NK cells lost during the transduction process may explain the differences in cell expansion between untransduced and transduced cells. However, the expansion difference between NK cells transduced with lentiviral vectors encoding the Z32 and D0126-CARs was negligible. The viability of NK cells on day 3, day 5, day 8, and Day 11 (FIG. 5B) was checked as well. There were no significant differences in cell viability among untransduced, Z32-transduced, and D0126-transduced NK cells (FIG. 14B), suggesting that the CD123-CARs have no adverse effect on NK cell viability.

Reference to the Sequence Listing

This application contains a Sequence Listing electronically submitted to the United States Patent and Trademark Office via a PDF file entitled "Sequence Listing". The Sequence Listing is incorporated by reference.

Sequences of the Disclosure

The nucleic and amino acid sequences listed below are shown using standard letter abbreviations for nucleotide bases, and either single-letter or three-letter code for amino acids, as defined in 37 C.F.R. 1.822. Only one strand of each nucleic acid sequence is shown, but the complementary strand is understood as included by any reference to the displayed strand. In the accompanying sequence listing:

```
SEQ ID NO: 1 nucleotide sequence of CAR D0125 CD123 MB31-A01 CD8 BBz
ATGCTCTTGCTCGTGACTTCTTTGCTTTTGTGCGAACTTCCGCACCCAGCCTTCCTT

TTGATACCTCAGATACAATTGGTACAGTCTGGAGCCGAGGTTAAGAAGCCGGGAT

CTTCCGTCAAAGTGTCCTGTAAAGCCTCTGGGGGCACCTTCTCTTCCTACGCAATT

AGTTGGGTGAGACAAGCTCCAGGTCAGGGTTTGGAGTGGATGGGAGGGATAATC

CCGATATTCGGGACAGCAAACTACGCCCAGAAATTTCAAGGGCGCGTAACGATA

ACAGCTGACGAGTCCACATCTACGGCATACATGGAGTTGAGTTCTCTGAGGAGTG

AGGACACAGCTGTATATTACTGCGCGCGGGGAAGCGGAGAACTTCTCTACGCAA

GTTATTATTATTACTACATGGATGTCTGGGGTAAGGGCACTACCGTAACAGTTTC

AAGTGGAGGTGGTGGTTCTGGTGGGGGAGGTAGCGGCGGCGGGGGTTCCCAATC

CGCACTCACGCAGCCTGCCTCTGTTTCAGGATCACCGGGACAGTCTATAACAATC

AGTTGTACTGGCACCAGTTCAGATGTCGGGGGGTATAACTACGTTTCATGGTACC

AACAACACCCAGGAAAGGCACCAGAACTCATGATATATGACGTGTCAAACCGAC

CGTCTGGCGTATCTAACCGATTTAGTGGCTCCAAGTCTGGTAATACCGCGTCACT

GACAATCAGCGGGTTGCAGGCTGAGGATGAAGCTGACTACTATTGTAGTTCCTAC

ACCAGCTCTAGTACTCCTGTTGTCTTCGGCGGGGCACTAAGCTCACAGTATTGG

CGGCCGCAACGACCACTCCTGCACCCCGCCCTCCGACTCCGGCCCCAACCATTGC

CAGCCAGCCCCTGTCCCTGCGGCCGGAAGCCTGCAGACCGGCTGCCGGCGGAGC

CGTCCATACCCGGGGACTGGATTTCGCCTGCGATATCTATATCTGGGCACCACTC

GCCGGAACCTGTGGAGTGCTGCTGCTGTCCCTTGTGATCACCCTGTACTGCAAGC

GCGGACGGAAGAAACTCTTGTACATCTTCAAGCAGCCGTTCATGCGCCCTGTGCA

AACCACCCAAGAAGAGGACGGGTGCTCCTGCCGGTTCCCGGAAGAGGAAGAGGG

CGGCTGCGAACTGCGCGTGAAGTTTTCCCGGTCCGCCGACGCTCCGGCGTACCAG

CAGGGGCAAAACCAGCTGTACAACGAACTTAACCTCGGTCGCCGGGAAGAATAT

GACGTGCTGGACAAGCGGCGGGGAAGAGATCCCGAGATGGGTGGAAAGCCGCG

GCGGAAGAACCCTCAGGAGGGCTTGTACAACGAGCTGCAAAAGGACAAAATGGC

CGAAGCCTACTCCGAGATTGGCATGAAGGGAGAGCGCAGACGCGGGAAGGGAC

ACGATGGACTGTACCAGGGACTGTCAACCGCGACTAAGGACACTTACGACGCCC

TGCACATGCAGGCCCTGCCCCCGCGCTAA

SEQ ID NO: 2 amino acid sequence of CAR D0125 CD123 MB31-A01 CD8 BBz
MLLLVTSLLLCELPHPAFLLIPQIQLVQSGAEVKKPGSSVKVSCKASGGTFSSYAISWV

RQAPGQGLEWMGGIIPIFGTANYAQKFQGRVTITADESTSTAYMELSSLRSEDTAVY

YCARGSGELLYASYYYYYMDVWGKGTTVTVSSGGGGSGGGGSGGGGSQSALTQPA

SVSGSPGQSITISCTGTSSDVGGYNYVSWYQQHPGKAPELMIYDVSNRPSGVSNRFSG

SKSGNTASLTISGLQAEDEADYYCSSYTSSSTPVVFGGGTKLTVLAAATTTPAPRPPTP

APTIASQPLSLRPEACRPAAGGAVHTRGLDFACDIYIWAPLAGTCGVLLLSLVITLYC

KRGRKKLLYIFKQPFMRPVQTTQEEDGCSCRFPEEEEGGCELRVKFSRSADAPAYQQ
```

GQNQLYNELNLGRREEYDVLDKRRGRDPEMGGKPRRKNPQEGLYNELQKDKMAEA

YSEIGMKGERRRGKGHDGLYQGLSTATKDTYDALHMQALPPR

SEQ ID NO: 3 nucleotide sequence of CAR D0126 CD123 MB31-C01 CD8 BBz
ATGCTCTTGCTCGTGACTTCTTTGCTTTTGTGCGAACTTCCGCACCCAGCCTTCCTT

TTGATACCTGAAGTACAGCTCCTCGAATCTGGCGGTGGTCTCGTTAAGCCTGGTGG

GTCCCTTAGACTCTCTTGTGCAGCGAGCGGTTTCACCTTCAGCAACGCTTGGATGA

GTTGGGTCCGCCAGGCGCCTGGAAAGGGCCTCGAATGGGTTGGTCGGATAAAAAG

CAAGACGGATGGAGGGACCACAGATTACGCGGCGCCGGTGAAAGGTCGGTTCACA

ATTTCAAGGGATGACTCAAAAAATACTTTGTATCTGCAAATGAATTCCCTCAAGAC

GGAAGATACTGCAGTCTATTATTGCACAACCGGTTTGCTCTGGTTTGGCACTCGCA

ATTATTACTATGGCATGGATGTATGGGGCCAAGGAACGACCGTCACTGTTTCAAGT

GGAGGTGGCGGGAGCGGAGGAGGGGGCTCCGGAGGTGGCGGTTCTCAATCAGCA

CTTACTCAGCCAGCTTCAGTCAGTGGTTCCCCGGGCCAATCCATCACCATTTCATG

CACCGGCACATCAAGTGATGTTGGTGGCTACAATTACGTGAGTTGGTATCAGCAAC

ATCCAGGAAAGGCTCCTAAGCTTGTAATTTATGATGTATCCAATCGGCCTTCTGGG

CTTAGCAATCGCTTTTCCGGATCTAAATCAGGCAATACTGCGTCCCTTACCATAAG

CGGGCTTCAAGCCGAAGATGAAGCAGATTACTATTGTAACTCCTACGCTGGGAGC

GGTTCATGGGTATTTGGAGGCGGTACGAAGTTGACTGTCTTGGCGGCCGCAACGA

CCACTCCTGCACCCCGCCCTCCGACTCCGGCCCCAACCATTGCCAGCCAGCCCCTG

TCCCTGCGGCCGGAAGCCTGCAGACCGGCTGCCGGCGGAGCCGTCCATACCCGGG

GACTGGATTTCGCCTGCGATATCTATATCTGGGCACCACTCGCCGGAACCTGTGGA

GTGCTGCTGCTGTCCCTTGTGATCACCCTGTACTGCAAGCGCGGACGGAAGAAACT

CTTGTACATCTTCAAGCAGCCGTTCATGCGCCCTGTGCAAACCACCCAAGAAGAGG

ACGGGTGCTCCTGCCGGTTCCCGGAAGAGGAAGAGGGCGGCTGCGAACTGCGCGT

GAAGTTTTCCCGGTCCGCCGACGCTCCGGCGTACCAGCAGGGGCAAAACCAGCTG

TACAACGAACTTAACCTCGGTCGCCGGGAAGAATATGACGTGCTGGACAAGCGGC

GGGGAAGAGATCCCGAGATGGGTGGAAAGCCGCGGCGGAAGAACCCTCAGGAGG

GCTTGTACAACGAGCTGCAAAAGGACAAAATGGCCGAAGCCTACTCCGAGATTGG

CATGAAGGGAGAGCGCAGACGCGGGAAGGGACACGATGGACTGTACCAGGGACT

GTCAACCGCGACTAAGGACACTTACGACGCCCTGCACATGCAGGCCCTGCCCCCG

CGCTAA

SEQ ID NO: 4 amino acid sequence of CAR D0126 CD123 MB31-C01 CD8 BBz
MLLLVTSLLLCELPHPAFLLIPEVQLLESGGGLVKPGGSLRLSCAASGFTFSNAWMSW

VRQAPGKGLEWVGRIKSKTDGGTTDYAAPVKGRFTISRDDSKNTLYLQMNSLKTED

TAVYYCTTGLLWFGTRNYYYGMDVWGQGTTVTVSSGGGGSGGGGSGGGGSQSAL

TQPASVSGSPGQSITISCTGTSSDVGGYNYVSWYQQHPGKAPKLVIYDVSNRPSGLSN

RFSGSKSGNTASLTISGLQAEDEADYYCNSYAGSGSWVFGGGTKLTVLAAATTTPAP

RPPTPAPTIASQPLSLRPEACRPAAGGAVHTRGLDFACDIYIWAPLAGTCGVLLLSLVI

TLYCKRGRKKLLYIFKQPFMRPVQTTQEEDGCSCRFPEEEEGGCELRVKFSRSADAPA

YQQGQNQLYNELNLGRREEYDVLDKRRGRDPEMGGKPRRKNPQEGLYNELQKDK

MAEAYSEIGMKGERRRGKGFIDGLYQGLSTATKDTYDALHMQALPPR

SEQ ID NO: 5 nucleotide sequence of CAR D0127 CD123 MB35-E02 CD8 BBz
ATGCTCTTGCTCGTGACTTCTTTGCTTTTGTGCGAACTTCCGCACCCAGCCTT

CCTTTTGATACCTCAAGTTCAGCTGGTCCAGAGCGGCGCCGAGGTAAAAAA

GCCAGGCTCTTCTGTAAAGGTGTCCTGTAAGGCCAGTGGAGGCACTTTTTC

CTCCTACGCAATCTCATGGGTCCGACAAGCACCTGGTCAAGGACTGGAATG

GATGGGCGGTATCATCCCGATCTTTGGTACTGCTAACTATGCGCAGAAGTT

CCAGGGTAGGGTGACCATAACCGCAGATGAGAGTACATCCACTGCCTATAT

GGAGCTCAGTAGCCTGAGGTCTGAGGATACTGCCGTTTACTATTGTGCACG

CCACGGCGGGATGGCAACAATGCTCCCTTACGGAGCATTTGACATCTGGGG

TCAAGGTACAATGGTAACTGTATCATCTGGCGGTGGCGGTAGTGGTGGGGG

AGGCAGCGGAGGTGGGGGCAGTGATATACGACTGACGCAATCTCCCTCTA

GCCTGAGTGCCAGTGTCGGAGATCGGGTCACAATCACATGCCGGGCTAGTC

AGGGTATCAGTAGCTATCTTAATTGGTACCAACAAAAACCAGGAAAAGCA

CCGAAACTGCTCATTTATGCAGCTTCTCGGTTGCAATCTGGAGTCCCAAGCC

GGTTTAGTGGAAGTGGCAGTGGGACGGACTTTACCTTGACTATATCCTCAT

TGCAACCTGAGGATTTCGCTACTTATTACTGCCAACAATCTTACTCCACGAG

TCTTACGTTCGGTGGGGGCACGAAAGTGGAGATCAAAGCGGCCGCAACGA

CCACTCCTGCACCCCGCCCTCCGACTCCGGCCCCAACCATTGCCAGCCAGC

CCCTGTCCCTGCGGCCGGAAGCCTGCAGACCGGCTGCCGGCGGAGCCGTCC

ATACCCGGGGACTGGATTTCGCCTGCGATATCTATATCTGGGCACCACTCG

CCGGAACCTGTGGAGTGCTGCTGCTGTCCCTTGTGATCACCCTGTACTGCAA

GCGCGGACGGAAGAAACTCTTGTACATCTTCAAGCAGCCGTTCATGCGCCC

TGTGCAAACCACCCAAGAAGAGGACGGGTGCTCCTGCCGGTTCCCGGAAG

AGGAAGAGGGCGGCTGCGAACTGCGCGTGAAGTTTTCCCGGTCCGCCGAC

GCTCCGGCGTACCAGCAGGGGCAAAACCAGCTGTACAACGAACTTAACCTC

GGTCGCCGGGAAGAATATGACGTGCTGGACAAGCGGCGGGGAAGAGATCC

CGAGATGGGTGGAAAGCCGCGGCGGAAGAACCCTCAGGAGGGCTTGTACA

ACGAGCTGCAAAAGGACAAAATGGCCGAAGCCTACTCCGAGATTGGCATG

AAGGGAGAGCGCAGACGCGGGAAGGGACACGATGGACTGTACCAGGGACT

GTCAACCGCGACTAAGGACACTTACGACGCCCTGCACATGCAGGCCCTGCC

CCCGCGCTAA

SEQ ID NO: 6 amino acid sequence of CAR D0127 CD123 MB35-E02 CD8 BBz
MLLLVTSLLLCELPHPAFLLIPQVQLVQSGAEVKKPGSSVKVSCKASGGTFSSYAISW

VRQAPGQGLEWMGGIIPIFGTANYAQKFQGRVTITADESTSTAYMELSSLRSEDTAV

YYCARHGGMATMLPYGAFDIWGQGTMVTVSSGGGGSGGGGSGGGGSDIRLTQSPSS

LSASVGDRVTITCRASQGISSYLNWYQQKPGKAPKLLIYAASRLQSGVPSRFSGSGSG

TDFTLTISSLQPEDFATYYCQQSYSTSLTFGGGTKVEIKAAATTTPAPRPPTPAPTIASQ

PLSLRPEACRPAAGGAVHTRGLDFACDIYIWAPLAGTCGVLLLSLVITLYCKRGRKKL

LYIFKQPFMRPVQTTQEEDGCSCRFPEEEEGGCELRVKFSRSADAPAYQQGQNQLYN

ELNLGRREEYDVLDKRRGRDPEMGGKPRRKNPQEGLYNELQKDKMAEAYSEIGMK

GERRRGKGHDGLYQGLSTATKDTYDALHMQALPPR

SEQ ID NO: 7 nucleotide sequence of CAR D0128 CD123 MB36-A05 CD8 BBz
ATGCTCTTGCTCGTGACTTCTTTGCTTTTGTGCGAACTTCCGCACCCAGCCTTCCTT

TTGATACCTCAAGTCCAGCTCGTTCAGAGTGGTGCAGAGGTGAAGAAGCCCGGCT

CATCTGTGAAAGTGTCATGCAAAGCAAGCGGCGGGACCTTCAGCAGTTACGCGAT

CTCCTGGGTACGACAAGCCCCCGGCCAGGGCCTGGAATGGATGGGAGGGATCATT

CCGATTTTCGGTACAGCAAACTATGCACAAAAATTTCAGGGGAGAGTTACGATAA

CTGCAGACAAGAGCACTTCAACGGCATACATGGAGCTTTCATCATTGCGCTCCGAG

GACACGGCTGTTTACTACTGCGCTCGAGGGGGACGGAACTCTTACTATTATTACTA

CATGGACGTGTGGGGCAAAGGGACAACGGTGACGGTAAGTAGTGGGGGAGGCGG

AAGCGGTGGTGGGGGAAGTGGAGGCGGTGGGTCACAGTCAGCCCTCACACAACCG

GCCTCTGTCTCAGGGAGTCCAGGACAGAGTATTACTATAAGCTGCACTGGGACATC

CTCAGACGTCGGCGGTTATAATTATGTTTCCTGGTACCAACAACATCCCGGGAAGG

CTCCCAAGCTGATGATATACGAAGTGAGTAATCGACCCTCTGGCGTGAGCAATCG

ATTCTCTGGGAGTAAGAGTGGCAACACTGCGAGTCTTACGATTTCTGGCCTGCAGG

CGGAAGACGAAGCCGATTATTACTGTAGCAGCTACACTTCAAGCTCCCCTGTTGTT

TTCGGTGGCGGCACTAAACTTACCGTGCTTGCGGCCGCAACGACCACTCCTGCACC

CCGCCCTCCGACTCCGGCCCCAACCATTGCCAGCCAGCCCCTGTCCCTGCGGCCGG

AAGCCTGCAGACCGGCTGCCGGCGGAGCCGTCCATACCCGGGGACTGGATTTCGC

CTGCGATATCTATATCTGGGCACCACTCGCCGGAACCTGTGGAGTGCTGCTGCTGT

CCCTTGTGATCACCCTGTACTGCAAGCGCGGACGAAGAAACTCTTGTACATCTTC

AAGCAGCCGTTCATGCGCCCTGTGCAAACCACCCAAGAAGAGGACGGGTGCTCCT

GCCGGTTCCCGGAAGAGGAAGAGGGCGGCTGCGAACTGCGCGTGAAGTTTTCCG

GTCCGCCGACGCTCCGGCGTACCAGCAGGGCAAAACCAGCTGTACAACGAACTT

AACCTCGGTCGCCGGGAAGAATATGACGTGCTGGACAAGCGGCGGGGAAGAGAT

CCCGAGATGGGTGGAAAGCCGCGGCGGAAGAACCCTCAGGAGGGCTTGTACAAC

GAGCTGCAAAAGGACAAAATGGCCGAAGCCTACTCCGAGATTGGCATGAAGGGA

GAGCGCAGACGCGGGAAGGGACACGATGGACTGTACCAGGGACTGTCAACCGCG

ACTAAGGACACTTACGACGCCCTGCACATGCAGGCCCTGCCCCCGCGCTAA

SEQ ID NO: 8 amino acid sequence of CAR D0128 CD123 MB36-A05 CD8 BBz
MLLLVTSLLLCELPHPAFLLIPQVQLVQSGAEVKKPGSSVKVSCKASGGTFSSYAISW

VRQAPGQGLEWMGGIIPIFGTANYAQKFQGRVTITADKSTSTAYMELSSLRSEDTAV

YYCARGGRNSYYYYYMDVWGKGTTVTVSSGGGGSGGGGSGGGGSQSALTQPASVS

GSPGQSITISCTGTSSDVGGYNYVSWYQQHPGKAPKLMIYEVSNRPSGVSNRFSGSKS

GNTASLTISGLQAEDEADYYCSSYTSSSPVVFGGGTKLTVLAAATTTPAPRPPTPAPTI

ASQPLSLRPEACRPAAGGAVHTRGLDFACDIYIWAPLAGTCGVLLLSLVITLYCKRGR

KKLLYIFKQPFMRPVQTTQEEDGCSCRFPEEEEGGCELRVKFSRSADAPAYQQGQNQ

LYNELNLGRREEYDVLDKRRGRDPEMGGKPRRKNPQEGLYNELQKDKMAEAYSEI

GMKGERRRGKGHDGLYQGLSTATKDTYDALHMQALPPR

SEQ ID NO: 9 nucleotide sequence of CAR D0129 CD123 MB40-F08 CD8 BBz
ATGCTCTTGCTCGTGACTTCTTTGCTTTTGTGCGAACTTCCGCACCCAGCCTTCCTT

TTGATACCTCAGGTTCAGCTCGTTCAAAGCGGAGCTGAAGTTAAAAAACCTGGGTC

TTCTGTCAAGGTAAGTTGCAAAGCATCCGGAGGCACGTTTTCTTCCTATGCAATAA

-continued

```
GTTGGGTCCGGCAAGCACCTGGTCAGGGATTGGAATGGATGGGTGGTATTATACC

AATATTCGGAACGGCGAACTACGCACAGAAGTTTCAAGGCAGGGTAACTATTACC

GCGGACGAGTCTACCTCAACAGCGTATATGGAACTGAGCAGTCTCAGATCAGAAG

ATACCGCAGTTTATTACTGCGCTCGGGGTCTGGAGAGCTTCTCTATGCATCCTAC

TACTACTATTATATGGACGTATGGGGCAAGGGTACCACCGTTACCGTGTCTTCTGG

AGGTGGCGGATCTGGAGGTGGAGGATCCGGTGGGGGAGGCAGCCAATCTGCACTG

ACTCAACCCGCGTCCGTGAGCGGATCCCCTGGGCAATCAATAACAATCTCTTGCAC

GGGGACCTCATCTGATGTTGGTGGATATAATTACGTCAGCTGGTACCAACAACACC

CCGGTAAGGCTCCGAAGCTGATGATTTACGAAGTGAGTAATCGCCCAAGTGGTGT

AAGCAACAGATTCTCAGGCTCAAAGAGTGGGAACACTGCGTCCCTGACTATCTCA

GGCCTCCAGGCTGAGGACGAAGCAGATTATTACTGTTCTTCATACACCAGTAGTAG

TCCTTTGGTCTTCGGCACCGGCACCAAGGTAACTGTACTGGCGGCCGCAACGACCA

CTCCTGCACCCCGCCCTCCGACTCCGGCCCCAACCATTGCCAGCCAGCCCCTGTCC

CTGCGGCCGGAAGCCTGCAGACCGGCTGCCGGCGGAGCGTCCATACCCGGGGAC

TGGATTTCGCCTGCGATATCTATATCTGGGCACCACTCGCCGGAACCTGTGGAGTG

CTGCTGCTGTCCCTTGTGATCACCCTGTACTGCAAGCGCGGACGGAAGAAACTCTT

GTACATCTTCAAGCAGCCGTTCATGCGCCCTGTGCAAACCACCCAAGAAGAGGAC

GGGTGCTCCTGCCGGTTCCCGGAAGAGGAAGAGGGCGGCTGCGAACTGCGCGTGA

AGTTTTCCCGGTCCGCCGACGCTCCGGCGTACCAGCAGGGGCAAAACCAGCTGTA

CAACGAACTTAACCTCGGTCGCCGGGAAGAATATGACGTGCTGGACAAGCGGCGG

GGAAGAGATCCCGAGATGGGTGGAAAGCCGCGGCGGAAGAACCCTCAGGAGGGC

TTGTACAACGAGCTGCAAAAGGACAAAATGGCCGAAGCCTACTCCGAGATTGGCA

TGAAGGGAGAGCGCAGACGCGGGAAGGGACACGATGGACTGTACCAGGGACTGT

CAACCGCGACTAAGGACACTTACGACGCCCTGCACATGCAGGCCCTGCCCCCGCG

CTAA

SEQ ID NO: 10 amino acid sequence of CAR D0129 CD123 MB40-F08 CD8 BBz
MLLLVTSLLLCELPHPAFLLIPQVQLVQSGAEVKKPGSSVKVSCKASGGTFSSYAISW

VRQAPGQGLEWMGGIIPIFGTANYAQKFQGRVTITADESTSTAYMELSSLRSEDTAV

YYCARGSGELLYASYYYYYMDVWGKGTTVTVSSGGGGSGGGGSGGGGSQSALTQP

ASVSGSPGQSITISCTGTSSDVGGYNYVSWYQQHPGKAPKLMIYEVSNRPSGVSNRFS

GSKSGNTASLTISGLQAEDEADYYCSSYTSSSPLVFGTGTKVTVLAAATTTPAPRPPTP

APTIASQPLSLRPEACRPAAGGAVHTRGLDFACDIYIWAPLAGTCGVLLLSLVITLYC

KRGRKKLLYIFKQPFMRPVQTTQEEDGCSCRFPEEEEGGCELRVKFSRSADAPAYQQ

GQNQLYNELNLGRREEYDVLDKRRGRDPEMGGKPRRKNPQEGLYNELQKDKMAEA

YSEIGMKGERRRGKGHDGLYQGLSTATKDTYDALHMQALPPR

SEQ ID NO: 11 nucleotide sequence of CAR D0130 CD123 MB40-H08 CD8 BBz
ATGCTCTTGCTCGTGACTTCTTTGCTTTTGTGCGAACTTCCGCACCCAGCCTT

CCTTTTGATACCTCAGGTTCAGCTGGTACAGTCCGGCGCAGAGGTTAAAAA

GCCAGGAAGCTCCGTGAAGGTTTCATGCAAGGCATCCGGTGGTACATTCTC

ATCATATGCGATCAGTTGGGTCCGGCAGGCTCCCGGCCAGGGATTGGAGTG

GATGGGAGGGATAATCCCCATATTTGGCACAGCAAATTACGCTCAAAAATT
```

-continued

```
TCAAGGTAGAGTAACGATAACTGCGGATGAATCTACTAGCACGGCGTATAT

GGAACTGAGTAGTCTCCGGAGCGAGGATACAGCGGTTTACTACTGCGCTAG

GAATGAATGGTACTCCTATTATTACTACTACATGGGTGTGTGGGGTAAAGG

AACTACTGTTACGGTGTCCAGTGGAGGAGGAGGTAGCGGAGGTGGAGGAT

CAGGCGGTGGGGGCTCCCAAAGTGCGCTTACACAACCTGCAAGCGTATCAG

GTTCCCCAGGGCAATCAATTACAATAAGCTGCACGGGTACCTCCAGTGATG

TCGGAGGTTACAACTACGTGTCATGGTACCAGCAACATCCAGGCAAGGCAC

CAAAACTTATGATCTACGAAGTCAGCAACAGACCCAGCGGTGTAAGCAAT

AGGTTTAGCGGATCTAAGTCCGGTAATACTGCTTCTCTGACAATCTCAGGA

CTCCAAGCCGAGGACGAAGCTGATTACTACTGCTCATCATACACCAGTAGC

TCTACACTGGTGGTGTTCGGAGGGGGAACGAAGCTTACCGTACTGGCGGCC

GCAACGACCACTCCTGCACCCCGCCCTCCGACTCCGGCCCCAACCATTGCC

AGCCAGCCCCTGTCCCTGCGGCCGGAAGCCTGCAGACCGGCTGCCGGCGGA

GCCGTCCATACCCGGGGACTGGATTTCGCCTGCGATATCTATATCTGGGCA

CCACTCGCCGGAACCTGTGGAGTGCTGCTGCTGTCCCTTGTGATCACCCTGT

ACTGCAAGCGCGGACGGAAGAAACTCTTGTACATCTTCAAGCAGCCGTTCA

TGCGCCCTGTGCAAACCACCCAAGAAGAGGACGGGTGCTCCTGCCGGTTCC

CGGAAGAGGAAGAGGGCGGCTGCGAACTGCGCGTGAAGTTTTCCCGGTCC

GCCGACGCTCCGGCGTACCAGCAGGGGCAAAACCAGCTGTACAACGAACT

TAACCTCGGTCGCCGGGAAGAATATGACGTGCTGGACAAGCGGCGGGGAA

GAGATCCCGAGATGGGTGGAAAGCCGCGGCGGAAGAACCCTCAGGAGGGC

TTGTACAACGAGCTGCAAAAGGACAAAATGGCCGAAGCCTACTCCGAGAT

TGGCATGAAGGGAGAGCGCAGACGCGGGAAGGGACACGATGGACTGTACC

AGGGACTGTCAACCGCGACTAAGGACACTTACGACGCCCTGCACATGCAG

GCCCTGCCCCCGCGCTAA

SEQ ID NO: 12 amino acid sequence of CAR D0130 CDAR123 MB40-H08 CD8 BBz
MLLLVTSLLLCELPHPAFLLIPQVQLVQSGAEVKKPGSSVKVSCKASGGTFSSY

AISWVRQAPGQGLEWMGGIIPIFGTANYAQKFQGRVTITADESTSTAYMELSSL

RSEDTAVYYCARNEWYSYYYYYMGVWGKGTTVTVSSGGGGSGGGGSGGGG

SQSALTQPASVSGSPGQSITISCTGTSSDVGGYNYVSWYQQHPGKAPKLMIYEV

SNRPSGVSNRFSGSKSGNTASLTISGLQAEDEADYYCSSYTSSSTLVVFGGGTK

LTVLAAATTTPAPRPPTPAPTIASQPLSLRPEACRPAAGGAVHTRGLDFACDIYI

WAPLAGTCGVLLLSLVITLYCKRGRKKLLYIFKQPFMRPVQTTQEEDGCSCRFP

EEEEGGCELRVKFSRSADAPAYQQGQNQLYNELNLGRREEYDVLDKRRGRDP

EMGGKPRRKNPQEGLYNELQKDKMAEAYSEIGMKGERRRGKGHDGLYQGLS

TATKDTYDALHMQALPPR

SEQ ID NO: 13 nucleotide sequence of leader/signal peptide sequence
atgctgctgctggtgaccagcctgctgctgtgcgaactgccgcatccggcgtttctgctgattccg SEQ ID NO: 14 amino acid sequence of leader/signal peptide sequence
MLLLVTSLLLCELPHPAFLLIP SEQ ID NO: 15 nucleotide sequence of CAR D0131 CD123 MB42-D03 CD8 BBz
ATGCTCTTGCTCGTGACTTCTTTGCTTTTGTGCGAACTTCCGCACCCAGCCTT

CCTTTTGATACCTCAAGTTCAACTTGTACAATCCGGAGCAGAAGTAAAAAA
```

```
ACCCGGGGCCAGCGTAAAAGTTTCCTGTAAAGCTAGCGGCTACACATTCAC

TAGCTACGGCATCTCCTGGGTACGCCAAGCGCCAGGACAAGGCCTCGAATG

GATGGGATGGATTAGCGCTTACAACGGTAATACCAATTATGCACAAAAGCT

GCAAGGACGGGTTACGATGACAACAGACACGAGCACGAGTACGGCCTATA

TGGAGCTGAGAAGTCTTCGAAGTGATGACACTGCAGTATATTACTGTGCCC

GCGGAGCGTACTACGATTTTTGGAGCAGTTACAGCTGGTTTGATCCCTGGG

GGCAGGGGACCCTGGTTACTGTTAGCTCAGGTGGGGGGGGCTCAGGAGGT

GGAGGAAGCGGGGGTGGAGGATCTAGTTATGTTCTTACCCAGCCGCCTTCT

GTCAGTGTGGCCCCTGGTAAGACAGCCAGGATAACCTGTGGTGGGAATTCA

ATTGGCAGCAAATCAGTACAGTGGTACCAACAAAAACCCGGACAAGCCCC

CGTTTTGGTCATATATGATGATAGCGATAGGCCTTCTGGAATCCCGGAGAG

GTTTTCAGGATCAAATAGCGGGAACACCGCCACATTGACCATAAGTCGAGT

CGAGGCGGGCGACGAAGCTGACTATTATTGTCAAGTGTGGGATAGCTCTAG

TGATGTGGTATTCGGTGGGGGGACCAAATTGACAGTCTTGGCGGCCGCAAC

GACCACTCCTGCACCCCGCCCTCCGACTCCGGCCCCAACCATTGCCAGCCA

GCCCCTGTCCCTGCGGCCGGAAGCCTGCAGACCGGCTGCCGGCGGAGCCGT

CCATACCCGGGGACTGGATTTCGCCTGCGATATCTATATCTGGGCACCACT

CGCCGGAACCTGTGGAGTGCTGCTGCTGTCCCTTGTGATCACCCTGTACTGC

AAGCGCGGACGGAAGAAACTCTTGTACATCTTCAAGCAGCCGTTCATGCGC

CCTGTGCAAACCACCCAAGAAGAGGACGGGTGCTCCTGCCGGTTCCCGGAA

GAGGAAGAGGGCGGCTGCGAACTGCGCGTGAAGTTTTCCCGGTCCGCCGA

CGCTCCGGCGTACCAGCAGGGCAAAACCAGCTGTACAACGAACTTAACCT

CGGTCGCCGGGAAGAATATGACGTGCTGGACAAGCGGCGGGGAAGAGATC

CCGAGATGGGTGGAAAGCCGCGGCGGAAGAACCCTCAGGAGGGCTTGTAC

AACGAGCTGCAAAAGGACAAAATGGCCGAAGCCTACTCCGAGATTGGCAT

GAAGGGAGAGCGCAGACGCGGGAAGGGACACGATGGACTGTACCAGGGA

CTGTCAACCGCGACTAAGGACACTTACGACGCCCTGCACATGCAGGCCCTG

CCCCCGCGCTAA

SEQ ID NO: 16 amino acid sequence of CAR D0131 CD123 MB42-D03 CD8 BBz
MLLLVTSLLLCELPHPAFLLIPQVQLVQSGAEVKKPGASVKVSCKASGYTFTSY

GISWVRQAPGQGLEWMGWISAYNGNTNYAQKLQGRVTMTTDTSTSTAYMEL

RSLRSDDTAVYYCARGAYYDFWSSYSWFDPWGQGTLVTVSSGGGGSGGGGS

GGGGSSYVLTQPPSVSVAPGKTARITCGGNSIGSKSVQWYQQKPGQAPVLVIY

DDSDRPSGIPERFSGSNSGNTATLTISRVEAGDEADYYCQVWDSSSDVVFGGG

TKLTVLAAATTTPAPRPPTPAPTIASQPLSLRPEACRPAAGGAVHTRGLDFACDI

YIWAPLAGTCGVLLLSLVITLYCKRGRKKLLYIFKQPFMRPVQTTQEEDGCSCR

FPEEEEGGCELRVKFSRSADAPAYQQGQNQLYNELNLGRREEYDVLDKRRGR

DPEMGGKPRRKNPQEGLYNELQKDKMAEAYSEIGMKGERRRGKGFIDGLYQG

LSTATKDTYDALHMQALPPR
```

SEQ ID NO: 17 nucleotide sequence of CAR D0132 CD123 MB42-E02 CD8 BBz
ATGCTCTTGCTCGTGACTTCTTTGCTTTTGTGCGAACTTCCGCACCCAGCCTT

CCTTTTGATACCTCAGGTACAACTTGTCCAATCCGGTGCCGAAGTCAAGAA

ACCTGGAGCATCCGTAAAGGTCAGCTGCAAAGCCAGCGGGTATACCTTCAC

GAGTTATGGAATCTCTTGGGTCAGACAAGCGCCAGGCCAAGGGCTGGAAT

GGATGGGATGGATAAGCGCATACAATGGCAACACAAATTATGCTCAGAAA

CTGCAAGGTCGCGTTACCATGACCACCGACACATCAACGTCCACCGCCTAT

ATGGAGCTTAGAAGCTTGCGAAGTGACGACACAGCCGTGTATTATTGCGCT

CGGGGTGCTTATTATGACTTCTGGTCTGGTTACTCTTGGTTTGATCCTTGGG

GTCAAGGCACGCTTGTGACGGTATCCTCAGGAGGCGGCGGAAGTGGAGGG

GGTGGATCAGGTGGTGGTGGAAGCCAATCAGTACTCACTCAGCCACCAAGT

GTATCAGTGGCTCCAGGTCAGACCGCGCGGATACCGTGTGGAGGAAACAA

CATCGGGTCAAAGGGCGTACATTGGTACCAGCAGAAGTCTGGACAAGCTCC

CGTTATGGTGGTGTACGATGACTCAGACAGGCCATCCGGCATCCCTGAGCG

GTTCAGCGGTTCTAATTCAGGAAATACAGCAACATTGACCATCAGCAGGGT

CGAAGCCGGTGACGAGGCGGACTATTATTGTCAGGTCTGGGATTCAAGCGG

CGACCTTGTTTTGTTTGGGGGTGGAACTAAACTGACCGTACTGGCGGCCGC

AACGACCACTCCTGCACCCCGCCCTCCGACTCCGGCCCCAACCATTGCCAG

CCAGCCCCTGTCCCTGCGGCCGGAAGCCTGCAGACCGGCTGCCGGCGGAGC

CGTCCATACCCGGGGACTGGATTTCGCCTGCGATATCTATATCTGGGCACC

ACTCGCCGGAACCTGTGGAGTGCTGCTGCTGTCCCTTGTGATCACCCTGTAC

TGCAAGCGCGGACGGAAGAAACTCTTGTACATCTTCAAGCAGCCGTTCATG

CGCCCTGTGCAAACCACCCAAGAAGAGGACGGGTGCTCCTGCCGGTTCCCG

GAAGAGGAAGAGGGCGGCTGCGAACTGCGCGTGAAGTTTTCCCGGTCCGC

CGACGCTCCGGCGTACCAGCAGGGGCAAAACCAGCTGTACAACGAACTTA

ACCTCGGTCGCCGGGAAGAATATGACGTGCTGGACAAGCGGCGGGGAAGA

GATCCCGAGATGGGTGGAAAGCCGCGGCGGAAGAACCCTCAGGAGGGCTT

GTACAACGAGCTGCAAAAGGACAAAATGGCCGAAGCCTACTCCGAGATTG

GCATGAAGGGAGAGCGCAGACGCGGGAAGGGACACGATGGACTGTACCAG

GGACTGTCAACCGCGACTAAGGACACTTACGACGCCCTGCACATGCAGGCC

CTGCCCCCGCGCTAA

SEQ ID NO: 18 amino acid sequence of CAR D0132 CD123 MB42-E02 CD8 BBz
MLLLVTSLLLCELPHPAFLLIPQVQLVQSGAEVKKPGASVKVSCKASGYTFTSY

GISWVRQAPGQGLEWMGWISAYNGNTNYAQKLQGRVTMTTDTSTSTAYMEL

RSLRSDDTAVYYCARGAYYDFWSGYSWFDPWGQGTLVTVSSGGGGSGGGGS

GGGGSQSVLTQPPSVSVAPGQTARIPCGGNNIGSKGVHWYQQKSGQAPVMVV

YDDSDRPSGIPERFSGSNSGNTATLTISRVEAGDEADYYCQVVVDSSGDLVLFG

GGTKLTVLAAATTTPAPRPPTPAPTIASQPLSLRPEACRPAAGGAVHTRGLDFA

CDIYIWAPLAGTCGVLLLSLVITLYCKRGRKKLLYIFKQPFMRPVQTTQEEDGC

SCRFPEEEEGGCELRVKFSRSADAPAYQQGQNQLYNELNLGRREEYDVLDKR

RGRDPEMGGKPRRKNPQEGLYNELQKDKMAEAYSEIGMKGERRRGKGHDGL

YQGLSTATKDTYDALHMQALPPR

SEQ ID NO: 19 nucleotide sequence of CAR D0133 CD123 MB42-E12 CD8 BBz
ATGCTCTTGCTCGTGACTTCTTTGCTTTTGTGCGAACTTCCGCACCCAGCCTT

CCTTTTGATACCTCAGGTGCAACTGGTTCAATCTGGCGCCGAAGTAAAAAA

ACCGGGCGCCAGCGTTAAAGTATCCTGTAAAGCGAGCGGCTACACATTTAC

CAGCTATGGCATCTCATGGGTGAGACAAGCGCCCGGCCAAGGACTGGAAT

GGATGGGGTGGATCAGCGCCTACAATGGGAACACTAACTACGCACAGAAG

CTGCAAGGCCGGGTTACCATGACGACCGATACGAGTACCTCAACAGCGTAC

ATGGAACTTCGAAGTCTGCGCAGTGACGACACCGCAGTATACTACTGCGCC

CGAGGAGCGTACTACGACTTCTGGTCCAGCTACTCTTGGTTTGACCCGTGG

GGCCAAGGAACACTCGTAACAGTATCCAGTGGAGGAGGCGGGTCAGGTGG

CGGTGGTTCAGGCGGTGGCGGGTCATCTTATGTTCTCACTCAGCCCCCATCC

GTGTCCGTAGCGCCAGGGAAAACAGCCCGGATTACGTGCGGGGGAAATAA

TATAGGCAGCAAGAGCGTTCATTGGTATCAACAAAAGCCAGGGCAGGCAC

CGGTCTTGGTGGTCTACGACGACAGTGATCGGCCCTCAGGAATTCCTGAAA

GATTCTCAGGGTCAAATTCTGGCAACACGGCGACGCTTACAATAAGCAGGG

TCGAGGCAGGAGACGAAGCCGATTATTACTGCCAGGTATGGGATTCCTCTT

CTGACCATGTGGTGTTTGGCGGTGGCACAAAGCTCACGGTCTTGGCGGCCG

CAACGACCACTCCTGCACCCCGCCCTCCGACTCCGGCCCCAACCATTGCCA

GCCAGCCCCTGTCCCTGCGGCCGGAAGCCTGCAGACCGGCTGCCGGCGGAG

CCGTCCATACCCGGGGACTGGATTTCGCCTGCGATATCTATATCTGGGCAC

CACTCGCCGGAACCTGTGGAGTGCTGCTGCTGTCCCTTGTGATCACCCTGTA

CTGCAAGCGCGGACGGAAGAAACTCTTGTACATCTTCAAGCAGCCGTTCAT

GCGCCCTGTGCAAACCACCCAAGAAGAGGACGGGTGCTCCTGCCGGTTCCC

GGAAGAGGAAGAGGGCGGCTGCGAACTGCGCGTGAAGTTTTCCCGGTCCG

CCGACGCTCCGGCGTACCAGCAGGGGCAAAACCAGCTGTACAACGAACTT

AACCTCGGTCGCCGGGAAGAATATGACGTGCTGGACAAGCGGCGGGGAAG

AGATCCCGAGATGGGTGGAAAGCCGCGGCGGAAGAACCCTCAGGAGGGCT

TGTACAACGAGCTGCAAAAGGACAAAATGGCCGAAGCCTACTCCGAGATT

GGCATGAAGGGAGAGCGCAGACGCGGGAAGGGACACGATGGACTGTACCA

GGGACTGTCAACCGCGACTAAGGACACTTACGACGCCCTGCACATGCAGGC

CCTGCCCCCGCGCTAA

SEQ ID NO: 20 amino acid sequence of CAR D0133 CD123 MB42-E12 CD8 BBz
MLLLVTSLLLCELPHPAFLLIPQVQLVQSGAEVKKPGASVKVSCKASGYTFTSY

GISWVRQAPGQGLEWMGWISAYNGNTNYAQKLQGRVTMTTDTSTSTAYMEL

RSLRSDDTAVYYCARGAYYDFWSSYSWFDPWGQGTLVTVSSGGGGSGGGGS

GGGGSSYVLTQPPSVSVAPGKTARITCGGNNIGSKSVHWYQQKPGQAPVLVV

YDDSDRPSGIPERFSGSNSGNTATLTISRVEAGDEADYYCQVVVDSSSDHVVFG

GGTKLTVLAAATTTPAPRPPTPAPTIASQPLSLRPEACRPAAGGAVHTRGLDFA

-continued

CDIYIWAPLAGTCGVLLLSLVITLYCKRGRKKLLYIFKQPFMRPVQTTQEEDGC

SCRFPEEEEGGCELRVKFSRSADAPAYQQGQNQLYNELNLGRREEYDVLDKR

RGRDPEMGGKPRRKNPQEGLYNELQKDKMAEAYSEIGMKGERRRGKGHDGL

YQGLSTATKDTYDALHMQALPPR

SEQ ID NO: 21 nucleotide sequence of CAR D0134 CD123 MB44-H01 CD8 BBz
ATGCTCTTGCTCGTGACTTCTTTGCTTTTGTGCGAACTTCCGCACCCAGCCTT

CCTTTTGATACCTCAGGTTCAACTCGTTCAAAGCGGGGCTGAAGTTAAAAA

GCCGGGGTCTAGCGTTAAGGTTTCCTGTAAAGCGTCTGGAGGAACTTTTTC

CTCCTACGCCATTAGCTGGGTACGACAAGCTCCAGGACAGGGTCTCGAGTG

GATGGGTGGGATAATTCCGATCTTTGGAACTGCGAATTACGCCCAGCGATT

CCAAGGCCGAGTTACGATTACTGCTGACGAGAGTACGTCTACCGCATACAT

GGAATTGAGTTCTCTTCGGTCAGAAGATACAGCGGTATACTACTGCGCTAG

GGGCCTCGGCACTAGTTACTACTATTACTATATGGATGTATGGGGCAAGGG

CACAACTGTGACTGTTTCTAGCGGTGGCGGCGGGTCCGGTGGTGGTGGAAG

CGGTGGCGGAGGGTCACAGTCAGTACTCACTCAGCCACCGAGTGCGTCTGG

CTCACCAGGACAATCTGTAACCATTAGTTGCACAGGCACTAGCTCTGATGT

TGGGGGCTACAATTATGTCTCCTGGTACCAACAACACCCCGGAAAAGCGCC

GAAGCTGATGATCTACGAGGTGAGTAATAGACCTAGTGGTGTTAGTAACAG

GTTCTCAGGCTCTAAGTCCGGTAACACCGCGTCTCTCACTATATCTGGCCTT

CAAGCTGAGGACGAGGCAGACTATTATTGCAGCTCATACACCTCAAGCAGT

ACCCCCGTTGTGTTTGGTGGCGGTACCAAATTGACTGTGCTGGCGGCCGCA

ACGACCACTCCTGCACCCCGCCCTCCGACTCCGGCCCCAACCATTGCCAGC

CAGCCCCTGTCCCTGCGGCCGGAAGCCTGCAGACCGGCTGCCGGCGGAGCC

GTCCATACCCGGGGACTGGATTTCGCCTGCGATATCTATATCTGGGCACCA

CTCGCCGGAACCTGTGGAGTGCTGCTGCTGTCCCTTGTGATCACCCTGTACT

GCAAGCGCGGACGGAAGAAACTCTTGTACATCTTCAAGCAGCCGTTCATGC

GCCCTGTGCAAACCACCCAAGAAGAGGACGGGTGCTCCTGCCGGTTCCCGG

AAGAGGAAGAGGGCGGCTGCGAACTGCGCGTGAAGTTTTCCCGGTCCGCC

GACGCTCCGGCGTACCAGCAGGGGCAAAACCAGCTGTACAACGAACTTAA

CCTCGGTCGCCGGGAAGAATATGACGTGCTGGACAAGCGGCGGGGAAGAG

ATCCCGAGATGGGTGGAAAGCCGCGGCGGAAGAACCCTCAGGAGGGCTTG

TACAACGAGCTGCAAAAGGACAAAATGGCCGAAGCCTACTCCGAGATTGG

CATGAAGGGAGAGCGCAGACGCGGGAAGGGACACGATGGACTGTACCAGG

GACTGTCAACCGCGACTAAGGACACTTACGACGCCCTGCACATGCAGGCCC

TGCCCCCGCGCTAA

SEQ ID NO: 22 amino acid sequence of CAR D0134 CD123 MB44-H01 CD8 BBz
MLLLVTSLLLCELPHPAFLLIPQVQLVQSGAEVKKPGSSVKVSCKASGGTFSSY

AISWVRQAPGQGLEWMGGIIPIFGTANYAQRFQGRVTITADESTSTAYMELSSL

RSEDTAVYYCARGLGTSYYYYMDVWGKGTTVTVSSGGGGSGGGGSGGGGS

QSVLTQPPSASGSPGQSVTISCTGTSSDVGGYNYVSWYQQHPGKAPKLMIYEV

SNRPSGVSNRFSGSKSGNTASLTISGLQAEDEADYYCSSYTSSSTPVVFGGGTKL

TVLAAATTTPAPRPPTPAPTIASQPLSLRPEACRPAAGGAVHTRGLDFACDIYIW

-continued

APLAGTCGVLLLSLVITLYCKRGRKKLLYIFKQPFMRPVQTTQEEDGCSCRFPE

EEEGGCELRVKFSRSADAPAYQQGQNQLYNELNLGRREEYDVLDKRRGRDPE

MGGKPRRKNPQEGLYNELQKDKMAEAYSEIGMKGERRRGKGHDGLYQGLST

ATKDTYDALHMQALPPR

SEQ ID NO: 23 nucleotide sequence of CAR LTG2078 CD123 M12306 CD8 BBz
ATGCTGCTGCTGGTGACCAGCCTGCTGCTGTGCGAACTGCCGCATCCGGCG

TTTCTGCTGATTCCGGAAGTCCAATTGGTGCAGAGCGGATCCGAACTTAAG

AAACCTGGCGCGAGCGTGAAAGTGTCCTGCAAGGCCTCCGGAGGGACTTTC

TCGTCGTACGCCATTAGCTGGGTCCGCCAAGCTCCTGGCCAAGGCCTGGAG

TGGATGGGCGGGATTATCCCCATCTTCGGGACTGCGAACTACGCCCAGAAG

TTTCAGGGCCGGGTCACTATCACCGCCGACGAATCAACCTCGACCGCCTAC

ATGGAACTGTCCTCGCTTCGGTCCGAGGATACTGCCGTGTACTATTGTGCCT

CAACGGCCAGACGCGGATGGGACACCGCTGGTCCGCTCGATTACTGGGGCC

AGGGAACCCTCGTGACCGTCAGCTCCGGAGGAGGAGGCTCCGGTGGTGGA

GGATCCGGGGGTGGTGGATCCGACATCCAAATGACCCAGTCCCCCTCGTCC

CTGAGCGCCTCTGTGGGCGACAGAGTGACAATTGCATGCAGGGCCTCACAG

ACTATCTCCCGCTACCTGAACTGGTACCAGCAGAAGCCAGGAAAGGCCCCT

AAGCTGCTCATCTACGCTGCGTCCTCGCTCCAATCCGGGGTGTCCTCACGGT

TTTCCGGATCGGGTTCCGGCACCGAGTTCACCCTGACCATCAGCAGCCTGC

AGCCCGAGGACTTCGCAACCTACTTCTGCCAGCAAACCTACTCCCCGCCGA

TTACGTTCGGACAGGGGACTCGGCTGGAAATCAAGGCGGCCGCAACTACC

ACCCCTGCCCCTCGGCCGCCGACTCCGGCCCCAACCATCGCAAGCCAACCC

CTCTCCTTGCGCCCCGAAGCTTGCCGCCCGGCCGCGGGTGGAGCCGTGCAT

ACCCGGGGGCTGGACTTTGCCTGCGATATCTACATTTGGGCCCCGCTGGCC

GGCACTTGCGGCGTGCTCCTGCTGTCGCTGGTCATCACCCTTTACTGCAAGA

GGGGCCGGAAGAAGCTGCTTTACATCTTCAAGCAGCCGTTCATGCGGCCCG

TGCAGACGACTCAGGAAGAGGACGGATGCTCGTGCAGATTCCCTGAGGAG

GAAGAGGGGGGATGCGAACTGCGCGTCAAGTTCTCACGGTCCGCCGACGC

CCCCGCATATCAACAGGGCCAGAATCAGCTCTACAACGAGCTGAACCTGGG

AAGGAGAGAGGAGTACGACGTGCTGGACAAGCGACGCGGACGCGACCCGG

AGATGGGGGGGAAACCACGGCGGAAAAACCCTCAGGAAGGACTGTACAAC

GAACTCCAGAAAGACAAGATGGCGGAAGCCTACTCAGAAATCGGGATGAA

GGGAGAGCGGAGGAGGGGAAAGGGTCACGACGGGCTGTACCAGGGACTG

AGCACCGCCACTAAGGATACCTACGATGCCTTGCATATGCAAGCACTCCCA

CCCCGGTAG

SEQ ID NO: 24 amino acid sequence of CAR LTG2078 CD123 M12306 CD8 BBz
MLLLVTSLLLCELPHPAFLLIPEVQLVQSGSELKKPGASVKVSCKASGGTFSSY

AISWVRQAPGQGLEWMGGIIPIFGTANYAQKFQGRVTITADESTSTAYMELSSL

RSEDTAVYYCASTARRGWDTAGPLDYVVGQGTLVTVSSGGGGSGGGGSGGGG

SDIQMTQSPSSLSASVGDRVTIACRASQTISRYLNWYQQKPGKAPKLLIYAASS

LQSGVSSRFSGSGSGTEFTLTISSLQPEDFATYFCQQTYSPPITFGQGTRLEIKAA

-continued

ATTTPAPRPPTPAPTIASQPLSLRPEACRPAAGGAVHTRGLDFACDIYIWAPLAG

TCGVLLLSLVITLYCKRGRKKLLYIFKQPFMRPVQTTQEEDGCSCRFPEEEEGG

CELRVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATKDT

YDALHMQALPPR

SEQ ID NO: 25 nucleotide sequence of CAR LTG1906 CD33_4 CD8 BBz
ATGCTGCTGCTGGTGACCAGCCTGCTGCTGTGCGAACTGCCGCATCCGGCG

TTTCTGCTGATTCCGGAGGTGCAGCTGGTGGAGTCTGGGGGAGGCTTGGTA

CAGCCTGGAGGGTCCCTGAGACTCTCCTGTGCAGCCTCTGGATTCACCTTCA

GTAGCTATGGCATGAGCTGGGTCCGCCAGGCTCCAAGACAAGGGCTTGAGT

GGGTGGCCAACATAAAGCAAGATGGAAGTGAGAAATACTATGCGGACTCA

GTGAAGGGCCGATTCACCATCTCCAGAGACAATTCCAAGAACACGCTGTAT

CTGCAAATGAACAGCCTGAGAGCCGAGGACACAGCCACGTATTACTGTGC

GAAAGAAAATGTGGACTGGGGCCAGGGCACCCTGGTCACCGTCTCCTCAGC

GGCCGCAACTACCACCCCTGCCCCTCGGCCGCCGACTCCGGCCCCAACCAT

CGCAAGCCAACCCCTCTCCTTGCGCCCCGAAGCTTGCCGCCCGGCCGCGGG

TGGAGCCGTGCATACCCGGGGGCTGGACTTTGCCTGCGATATCTACATTTG

GGCCCCGCTGGCCGGCACTTGCGGCGTGCTCCTGCTGTCGCTGGTCATCAC

CCTTTACTGCAAGAGGGGCCGGAAGAAGCTGCTTTACATCTTCAAGCAGCC

GTTCATGCGGCCCGTGCAGACGACTCAGGAAGAGGACGGATGCTCGTGCA

GATTCCCTGAGGAGGAAGAGGGGGGATGCGAACTGCGCGTCAAGTTCTCA

CGGTCCGCCGACGCCCCCGCATATCAACAGGGCCAGAATCAGCTCTACAAC

GAGCTGAACCTGGGAAGGAGAGAGGAGTACGACGTGCTGGACAAGCGACG

CGGACGCGACCCGGAGATGGGGGGGAAACCACGGCGGAAAAACCCTCAGG

AAGGACTGTACAACGAACTCCAGAAAGACAAGATGGCGGAAGCCTACTCA

GAAATCGGGATGAAGGGAGAGCGGAGGAGGGGAAAGGGTCACGACGGGC

TGTACCAGGGACTGAGCACCGCCACTAAGGATACCTACGATGCCTTGCATA

TGCAAGCACTCCCACCCCGGTAG

SEQ ID NO: 26 amino acid sequence of CAR LTG1906 CD33_4 CD8 BBz
MLLLVTSLLLCELPHPAFLLIPEVQLVESGGGLVQPGGSLRLSCAASGFTFSSYG

MSWVRQAPRQGLEWVANIKQDGSEKYYADSVKGRFTISRDNSKNTLYLQMNS

LRAEDTATYYCAKENVDWGQGTLVTVSSAAATTTPAPRPPTPAPTIASQPLSLR

PEACRPAAGGAVHTRGLDFACDIYIWAPLAGTCGVLLLSLVITLYCKRGRKKL

LYIFKQPFMRPVQTTQEEDGCSCRFPEEEEGGCELRVKFSRSADAPAYQQGQN

QLYNELNLGRREEYDVLDKRRGRDPEMGGKPRRKNPQEGLYNELQKDKMAE

AYSEIGMKGERRRGKGHDGLYQGLSTATKDTYDALHMQALPPR

SEQ ID NO: 27 nucleotide sequence of DNA CD8 transmembrane domain
atctacatct gggcgccctt ggccgggact tgtggggtcc ttctcctgtc actggttatc acccttact gc SEQ ID NO: 28 amino acid sequence of CD8 transmembrane domain
Ile Trp Ala Pro Leu Ala Gly Thr Cys Gly Val Leu Leu Leu Ser Leu Val Ile Thr Leu Tyr Cys -continued SEQ ID NO: 29 nucleotide sequence of DNA CD8 hinge domain
accacgacgc cagcgccgcg accaccaaca ccggcgccca ccatcgcgtc gcagcccctg tccctgcgcc cagaggcgtg ccggccagcg gcgggggggcg cagtgcacac gagggggctg gacttcgcct gtgat SEQ ID NO: 30 amino acid sequence of CD8 hinge domain
Thr Thr Thr Pro Ala Pro Arg Pro Pro Thr Pro Ala Pro Thr Ile Ala Ser Gln Pro Leu Ser Leu Arg Pro Glu Ala Cys Arg Pro Ala Ala Gly Gly Ala Val His Thr Arg Gly Leu Asp Phe Ala Cys Asp Ile Tyr SEQ ID NO: 31 amino acid sequence of amino acid numbers 118 to 178
hinge region of CD8.alpha. (NCBI RefSeq: NP.sub.--001759.3)
Lys Arg Gly Arg Lys Lys Leu Leu Tyr Ile Phe Lys Gln Pro Phe Met Arg Pro Val Gln Thr Thr Gln Glu Glu Asp Gly Cys Ser Cys ArgP he Pro Glu Glu Glu Glu Gly Gly Cys Glu Leu SEQ ID NO: 32 amino acid sequence of Human IgG CLs equence
Gly Gln Pro Lys Ala Ala Pro Ser Val Thr Leu Phe Pro Pro Ser Ser Glu Glu Leu Gln Ala Asn Lys Ala Thr Leu Val Cys Leu Ile Ser Asp Phe Tyr Pro Gly Ala Val Thr Val Ala Trp Lys Ala Asp Ser Ser Pro Val Lys Ala Gly Val Glu Thr Thr Thr Pro Ser Lys Gln Ser Asn Asn Lys Tyr Ala Ala Ser Ser Tyr Leu Ser Leu Thr Pro Glu Gln Trp Lys Ser His Arg Ser Tyr Ser Cys Gln Val Thr His Glu Gly Ser Thr Val Glu Lys Thr Val Ala Pro Thr Glu Cys Ser SEQ ID NO: 33 nucleotide sequence of DNA signaling domain of 4-1BB
aaacgggggca gaaagaaact cctgtatata ttcaaacaac catttatgag accagtacaa actactcaag aggaagatgg ctgtagctgc cgatttccag aagaagaaga aggaggatgt gaactg SEQ ID NO: 34 amino acid sequence of signaling domain of 4-1BB
Lys Arg Gly Arg Lys Lys Leu Leu Tyr Ile Phe Lys Gln Pro Phe Met Arg Pro Val Gln Thr Thr Gln Glu Glu Asp Gly Cys Ser Cys Arg Phe Pro Glu Glu Glu Glu Gly Gly Cys Glu Leu SEQ ID NO: 35 nucleotide sequence of DNA signaling domain of CD3-zeta
agagtgaagt tcagcaggag cgcagacgcc cccgcgtaca agcagggcca gaaccagctc tataacgagc tcaatctagg acgaagagag gagtacgatg ttttggacaa gagacgtggc cgggaccctg agatgggggg aaagccgaga aggaagaacc ctcaggaagg cctgtacaat gaactgcaga agataagat ggcggaggcc tacagtgaga ttgggatgaa aggcgagcgc cggaggggca aggggcacga tggcctttac cagggtctca gtacagccac caaggacacc tacgacgccc ttcacatgca ggccctgccc cctcgc SEQ ID NO: 36 amino acid sequence of CD3zeta
Arg Val Lys Phe Ser Arg Ser Ala Asp Ala Pro Ala Tyr Lys Gln Gly Gln Asn Gln Leu Tyr Asn Glu Leu Asn Leu Gly Arg Arg Glu Glu Tyr Asp Val Leu Asp Lys Arg Arg Gly Arg Asp Pro Glu Met Gly Gly Lys Pro Arg Arg Lys Asn Pro Gln Glu Gly Leu Tyr Asn Glu Leu Gln Lys Asp Lys Met Ala Glu Ala Tyr Ser Glu Ile Gly Met Lys Gly Glu Arg Arg Arg Gly Lys Gly His Asp Gly Leu Tyr Gln Gly Leu Ser Thr Ala Thr Lys Asp Thr Tyr Asp Ala Leu His Met Gln Ala Leu Pro Pro Arg SEQ ID NO: 37 nucleotide sequence of ScFv CD 19
gacatccaga tgacacagac tacatcctcc ctgtctgcct ctctgggaga cagagtcacc atcagttgca gggcaagtca ggacattagt aaatatttaa attggtatca gcagaaacca gatggaactg ttaaactcct gatctaccat acatcaagat tacactcagg agtcccatca aggttcagtg gcagtgggtc tggaacagat tattctctca ccattagcaa cctggagcaa gaagatattg ccacttactt ttgccaacag gtaatacgc ttccgtacac gttcggaggg gggaccaagc tggagatcac aggtggcggt ggctcgggcg gtggtgggtc gggtggcggc ggatctgagg tgaaactgca ggagtcagga cctggcctgg tggcgccctc acagagcctg tccgtcacat gcactgtctc aggggtctca ttcccgact atggtgtaag ctggattcgc cagcctccac gaaagggtct ggagtggctg ggagtaatat ggggtagtga aaccacatac tataattcag ctctcaaatc cagactgacc atcatcaagg acaactccaa gagccaagtt ttcttaaaaa tgaacagtct gcaaactgat gacacagcca tttactactg tgccaaacat tattactacg gtggtagcta tgctatggac tactggggcca aggaacctc agtcaccgtc tcctca SEQ ID NO: 38 amino acid sequence of ScFv CD 19
Asp Ile Gln Met Thr Gln Thr Thr Ser Ser Leu Ser Ala Ser Leu Gly Asp Arg Val Thr Ile Ser Cys Arg Ala Ser Gln Asp Ile Ser Lys Tyr Leu Asn Trp Tyr Gln Gln Lys Pro Asp Gly Thr Val Lys Leu Leu Ile Tyr His Thr Ser Arg Leu His Ser Gly Val Pro Ser Arg Phe Ser Gly Ser Gly Ser Gly Thr Asp Tyr Ser Leu Thr Ile Ser Asn Leu Glu Gln Glu Asp Ile Ala Thr Tyr Phe Cys Gln Gln Gly Asn Thr Leu Pro Tyr Thr Phe Gly Gly Gly Thr Lys Leu Glu Ile Thr Gly Gly Gly Gly Ser Gly Gly Gly Ser Gly Gly Gly Ser Glu Val Lys Leu Gln Glu Ser Gly Pro Gly Leu Val Ala Pro Ser Gln Ser Leu Ser Val Thr Cys Thr Val Ser Gly Val Ser Leu Pro Asp Tyr Gly Val Ser Trp Ile Arg Gln Pro Pro Arg Lys Gly Leu Glu Trp Leu Gly Val Ile Trp Gly Ser Glu Thr Thr Tyr Tyr Asn Ser Ala Leu Lys Ser Arg Leu Thr Ile Ile Lys Asp Asn Ser Lys Ser Gln Val Phe Leu Lys Met Asn Ser Leu Gln Thr Asp Asp Thr Ala Ile Tyr Tyr Cys Ala Lys His Tyr Tyr Tyr Gly Gly Ser Tyr Ala Met Asp Tyr Trp Gly Gln Gly Thr Ser Val Thr Val Ser Ser SEQ ID NO: 39 nucleotide sequence of GMCSF leader peptide
ATGCTGCTGCTGGTGACCAGCCTGCTGCTGTGCGAACTGCCGCATCCGGCG

TTTCTGCTGATTCCG

SEQ ID NO: 40 amino acid sequence of GMCSF leader peptide
MLLLVTSLLLCELPHPAFLLIP SEQ ID NO: 41 nucleotide sequence of TNFRSF19 leader peptide
GGCTCTGAAAGTGCTGTTGGAACAAGAAAAGACCTTCTTCACCTTGCTCGT

GTTGCTGGGGTACCTGTCCTGCAAAGTCACCTGT

SEQ ID NO: 42 amino acid sequence of TNFRSF19 leader peptide
MALKVLLEQEKTFFTLLVLLGYLSCKVTC SEQ ID NO: 43 nucleotide sequence of CD8 alpha leader peptide
atggcgctgccggtgaccgcgctgctgctgccgctggcgctgctgctgcatgcggcgcgc ccg SEQ ID NO: 44 amino acid sequence of CD8 alpha leader peptide
MALPVTALLLPLALLLHAARP SEQ ID NO: 45 nucleotide sequence of CD28 co-stimulatory domain
CGGTCGAAGAGGTCCAGACTCTTGCACTCCGACTACATGAACATGACTCCT

AGAAGGCCCGGACCCACTAGAAAGCACTACCAGCCGTACGCCCCTCCTCGG

GATTTCGCCGCATACCGGTCC

SEQ ID NO: 46 amino acid sequence of CD28 co-stimulatory domain
RSKRSRLLHSDYMNMTPRRPGPTRKHYQPYAPPRDFAAYRS -continued SEQ ID NO: 47 nucleotide sequence of CD3 zeta activation domain
AGAGTGAAGTTCAGCCGCTCAGCCGATGCACCGGCCTACCAGCAGGGACA

GAACCAGCTCTACAACGAGCTCAACCTGGGTCGGCGGGAAGAATATGACGT

GCTGGACAAACGGCGCGGCAGAGATCCGGAGATGGGGGGAAAGCCGAGGA

GGAAGAACCCTCAAGAGGGCCTGTACAACGAACTGCAGAAGGACAAGATG

GCGGAAGCCTACTCCGAGATCGGCATGAAGGGAGAACGCCGGAGAGGGAA

GGGTCATGACGGACTGTACCAGGGCCTGTCAACTGCCACTAAGGACACTTA

CGATGCGCTCCATATGCAAGCTTTGCCCCCGCGG

SEQ ID NO: 48 amino acid sequence of CD3 zeta activation domain
RVKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTYD

ALHMQALPPR

SEQ ID NO: 49 nucleotide sequence of TNFRSF19 hinge and transmembrane domain
(transmembrane domain underlined)
GCGGCCGCGGTCGGATTCCAAGACATGGAATGCGTGCCCTGCGGCGACCCG

CCACCTCCTTACGAGCCGCACTGCGCATCGAAGGTCAACCTCGTGAAGATC

GCGAGCACCGCGTCCTCACCCCGGGATACTGCTCTG<u>GCCGCCGTGATTTGTT</u>

<u>CCGCCTTGGCCACCGTGCTTCTGGCCCTGCTGATCCTCTGTGTGATC</u>

SEQ ID NO: 50 amino acid sequence of TNFRSF19 hinge and transmembrane domain
(transmembrane domain underlined)
A A A V G F Q D M E C V P C G D P P P P Y E P H C A S K V N L V K I A S T A S S P R D T A <u>L A A V I C S A L A T V L L A L L I L C V I</u>

SEQ ID NO: 51 nucleotide sequence of TNFRSF19 transmembrane domain
GCCGCCGTGATTTGTTCCGCCTTGGCCACCGTGCTTCTGGCCCTGCTGATCC

TCTGTGTGATC

SEQ ID NO: 52 amino acid sequence of TNFRSF19 transmembrane domain
A A V I C S A L A T V L L A L L I L C V I SEQ ID NO: 53 nucleotide sequence of TNFRSF19 hinge domain
GCGGCCGCGGTCGGATTCCAAGACATGGAATGCGTGCCCTGCGGCGACCCG

CCACCTCCTTACGAGCCGCACTGCGCATCGAAGGTCAACCTCGTGAAGATC

GCGAGCACCGCGTCCTCACCCCGGGATACTGCTCTG

SEQ ID NO: 54 amino acid sequence of TNFRSF19 hinge domain
A A A V G F Q D M E C V P C G D P P P P Y E P H C A S K V N L

V K I A S T A S S P R D T A L

SEQ ID NO: 55 nucleotide sequence of truncated TNFRSF19 hinge domain
TACGAGCCTCACTGCGCCAGCAAAGTCAACTTGGTGAAGATCGCGAGCACT

GCCTCGTCCCCTCGGGACACTGCTCTGGC

SEQ ID NO: 56 amino acid sequence of truncated TNFRSF19 hinge domain
Y E P H C A S K V N L V K I A S T A S S P R D T A L SEQ ID NO: 57 nucleotide sequence of CD8a hinge domain fused to TNFRSF19
transmembrane domain(transmembrane sequence underlined)
GCGGCCGCGCCCGCCCCTCGGCCCCCGACTCCTGCCCCGACGATCGCTTCCC

AACCTCTCTCGCTGCGCCCGGAAGCATGCCGGCCCGCCGCCGGTGGCGCTG

TCCACACTCGCGGACTGGACTTTGATACCGCACTGGCG<u>GCCGTGATCTGTA</u>

<u>GCGCCCTGGCCACCGTGCTGCTGGCGCTGCTCATCCTTTGCGTGATCTACTG</u>

<u>CAAGCGGCAGCCTAGG</u>

-continued

SEQ ID NO: 58 amino acid sequence of CD8a hinge domain fused to TNFRSF19
transmembrane domain(transmembrane sequence underlined)
A A A P A P R P P T P A P T I A S Q P L S R P E A C R P A A G G A V H T R G L D F D T A L <u>A A V I C S A L A T V L L A L L I L C V I Y C K R Q P R</u>

SEQ ID NO: 59 nucleotide sequence of CD28 co-stimulatory domain
CGGTCGAAGAGGTCCAGACTCTTGCACTCCGACTACATGAACATGACTCCT

AGAAGGCCCGGACCCACTAGAAAGCACTACCAGCCGTACGCCCCTCCTCGG

GATTTCGCCGCATACCGGTCC

SEQ ID NO: 60 amino acid sequence of CD28 co-stimulatory domain
RSKRSRLLHSDYMNMTPRRPGPTRKHYQPYAPPRDFAAYRS SEQ ID NO: 61 nucleotide sequence of CD3 zeta version 2
cgcgtgaaatttagccgcagcgcggatgcgccggcgtatcagcagggccagaaccagctg tataacgaactgaacctgggccgccgcgaagaatatgatgtgctggataaacgccgcggc cgcgatccggaaatgggcggcaaaccgcgccgcaaaaacccgcaggaaggcctgtataac gaactgcagaaagataaaatggcggaagcgtatagcgaaattggcatgaaaggcgaacgc cgccgcggcaaaggccatgatggcctgtatcagggcctgagcaccgcgaccaaagatacc tatgatgcgctgcatatgcaggcgctgccgccgcgc SEQ ID NO: 62 amino acid sequence of CD3 zeta version 2
R V K F S R S A D A P A Y Q Q G Q N Q L Y N E L N L G R R E

E Y D V L D K R R G R D P E M G G K P R R K N P Q E G L Y N

E L Q K D K M A E A Y S E I G M K G E R R R G K G H D G L Y

Q G L S T A T K D T Y D A L H M Q A L P P R

SEQ ID NO: 63 nucleotide sequence of Furin P2A Furin
CGCGCGAAACGCAGCGGCAGCGGCGCGACCAACTTTAGCCTGCTGAAACA

GGCGGGCGATGTGGAAGAAAACCCGGGCCCGCGAGCAAAGAGG

SEQ ID NO: 64 amino acid sequence of Furin P2A Furin
(furin sequence underlined)
<u>RAKR</u>SGSGATNFSLLKQAGDVEENPGP<u>RAKR</u>

SEQ ID NO: 65 nucleotide sequence of Furin T2A
AGAGCTAAACGCTCTGGGTCTGGTGAAGGACGAGGTAGCCTTCTTACGTGC

GGAGACGTGGAGGAAAACCCAGGACCC

SEQ ID NO: 66 amino acid sequence of Furin T2A
(furin sequence underlined)
<u>RAKR</u>SGSGEGRGSLLTCGDVEENPGP SEQ ID NO: 67 nucleotide sequence of truncated EGFR (tEGFR) tag
AGGAAGGTTTGCAATGGAATCGGTATAGGGGAGTTTAAGGATTCACTTAGC

ATAAACGCTACTAATATTAAACACTTCAAAAACTGTACGAGTATAAGTGGA

GATCTTCACATTTTGCCGGTTGCATTCCGAGGCGATTCATTCACCCACACGC

CACCGCTTGACCCACAAGAATTGGATATTCTTAAAACCGTTAAAGAAATAA

CGGGGTTTTTGCTCATTCAAGCGTGGCCAGAAAATCGCACTGACCTCCATG

CTTTCGAGAACCTGGAGATTATAAGAGGACGAACTAAGCAGCATGGTCAAT

TCTCCCTTGCTGTGGTCAGCCTGAACATCACCAGTCTTGGTTTGCGGTCCCT

CAAGGAAATTTCAGATGGAGATGTCATCATAAGCGGCAACAAGAATTTGTG

CTATGCAAATACCATAAACTGGAAAAAACTGTTTGGCACTTCCGGCCAGAA

AACCAAGATTATTTCAAATCGGGGTGAGAACAGCTGCAAAGCCACCGGCCA

GGTTTGTCATGCCTTGTGCTCTCCGGAAGGCTGTTGGGGCCAGAACCCAG

GGACTGCGTCAGTTGCAGAAACGTCTCAAGAGGCCGCGAATGCGTTGACAA

```
GTGTAACCTCCTTGAGGGTGAGCCACGAGAGTTTGTTGAGAACAGCGAGTG

TATACAATGTCACCCTGAATGTTTGCCCCAGGCTATGAATATAACCTGCACA

GGCCGCGGGCCTGATAACTGCATCCAGTGTGCTCATTACATAGATGGACCT

CACTGTGTGAAAACCTGCCCGGCCGGAGTTATGGGAGAAAACAACACTCTG

GTGTGGAAATACGCTGATGCAGGCCACGTGTGCCACCTTTGTCACCCGAAT

TGTACATATGGGTGTACCGGTCCTGGACTTGAAGGTTGCCCTACCAATGGC

CCTAAAATACCCAGTATCGCAACTGGCATGGTAGGCGCTCTTCTCTTGCTCT

TGGTAGTTGCTCTCGGCATAGGTCTTTTTATG
```

SEQ ID NO: 68 amino acid sequence of truncated EGFR (tEGFR) tag
```
RKVCNGIGIGEFKDSLSINATNIKHFKNCTSISGDLHILPVAFRGDSFTHTPPLDP

QELDILKTVKEITGFLLIQAWPENRTDLHAFENLEIIRGRTKQHGQFSLAVVSLN

ITSLGLRSLKEISDGDVIISGNKNLCYANTINWKKLFGTSGQKTKIISNRGENSCK

ATGQVCHALCSPEGCWGPEPRDCVSCRNVSRGRECVDKCNLLEGEPREFVENS

ECIQCHPECLPQAMNITCTGRGPDNCIQCAHYIDGPHCVKTCPAGVMGENNTL

VVVKYADAGHVCHLCHPNCTYGCTGPGLEGCPTNGPKIPSIATGMVGALLLLL

VVALGIGLFM
```

SEQ ID NO: 69 nucleotide sequence of CD123 binder MT-16
```
CAGGTCCAGCTGGTGCAGTCTGGGGCTGAGGTGAAGAAGCCTGGGTCCTCGGTG

AAGGTCTCCTGCAAGGCTTCTGGAGGCACCTTCAGCAGCTATGCTATCAGCTGGG

TGCGACAGGCCCCTGGACAAGGGCTTGAGTGGATGGGAGGGATCATCCCTATCTT

TGGTACAGCAAACTACGCACAGAAGTTCCAGGGCAGAGTCACGATTACCGCGGA

CGAATCCACGAGCACAGCCTACACGGAGCTGAGCAGCCTGAGATCTGAGGACAC

GGCCGTGTATTACTGTGCGAGAGCCCGGTTGGGAGGAGCTTTTGATATCTGGGGC

CAAGGGACAATGGTCACCGTCTCTTCAGGAGGTGGCGGGTCTGGTGGAGGCGGT

AGCGGTGGTGGCGGATCCCAGTCTGTGCTGACGCAGCCGCCCTCAGTGTCTGCGG

CCCCAGGACAGAAGGTCACCATCTCCTGCTCTGGAGGCAGCTCCAACATTGGCAA

TCATTATGTGTCCTGGTATCAGCAGCTCCCAGGAGCAGCCCCCAAACTCCTCATTT

ATGACGATAATAAGCGACCCTCAGGGATTCCTGACCGATTCTCTGGCTCCAGGTC

TGGCACGTCAGCCACCCTGGGCATCACCGGACTCCAGAGTGGGGACGAGGCCGA

TTATTACTGCGGAGCATGGGATAGTAGTCTTGCTGCTCATGTCTTCGGAACTGGG

ACCAAGGTCACCGTCCTAGGT
```

SEQ ID NO: 70 amino acid sequence of CD123 binder MT-16
```
QVQLVQSGAEVKKPGSSVKVSCKASGGTFSSYAISWVRQAPGQGLEWMGGIIP

IFGTANYAQKFQGRVTITADESTSTAYTELSSLRSEDTAVYYCARARLGGAFDI

WGQGTMVTVSSGGGGSGGGGSGGGGSQSVLTQPPSVSAAPGQKVTISCSGGSS

NIGNHYVSWYQQLPGAAPKLLIYDDNKRPSGIPDRFSGSRSGTSATLGITGLQS

GDEADYYCGAWDSSLAAHVFGTGTKVTVLG
```

SEQ ID NO: 71 nucleotide sequence of CD123 binder MT-32
```
CAGGTACAGCTGCAGCAGTCAGGTCCAGGACTGGTGAAGCCCTCGCAGACC

CTCTCACTCACCTGTGCCATCTCCGGGGACAGTGTCTCTAGCAACAGTGCTG

CTTGGAACTGGATCAGGCAGTCCCCATCGAGAGGCCTTGAGTGGCTGGGAA

GGACATACTACAGGTCCAAGTGGTATAATGATTATGCAGTATCTGTGAAAA
```

```
                                          -continued
GTCGAATAACCATCAACCCAGACACATCCAAGAACCAGTTCTCCCTGCAGC

TGAACTCTGTGACTCCCGAGGACATGGCTGTGTATTACTGTGCAAGAGGCG

TTGATAGTAGCTTTGACTACTGGGGCCAGGGAACCCTGGTCACCGTCTCCTC

AGGAGGTGGCGGGTCTGGTGGAGGCGGTAGCGGTGGTGGCGGATCCCAGT

CTGTCGTGACGCAGCCGCCCTCAGTGTCTGCGGCCCCAGGACAGAGCGTCA

CCATCTCCTGTTCTGGAAGCAGTTCCACCGTTGGCGATAATTATGTGTCCTG

GTACCAGCAACTCCCAGGAACAGCCCCCAAACTCCTCATTTTTGACGATTAT

AAACGACCCTCAGGGGTTCCTGACCGATTCTCTGGCTCCCAGTCTGGCACCT

CAGCCTCCCTGGTCATCACTGGTCTCCAGGCAGAAGATGAGGCTGATTATT

ACTGCCAGTCTTATGACAGCAGCCTGAGTGGTTATGTCTTCGGGCCTGGGA

CCAAGGTCACCGTCCTAGGT

SEQ ID NO: 72 amino acid sequence of CD123 binder MT-32
QVQLQQSGPGLVKPSQTLSLTCAISGDSVSSNSAAWNWIRQSPSRGLEWLGRT

YYRSKWYNDYAVSVKSRITINPDTSKNQFSLQLNSVTPEDMAVYYCARGVDSS

FDYWGQGTLVTVSSGGGGSGGGGSGGGGSQSVVTQPPSVSAAPGQSVTISCSG

SSSTVGDNYVSWYQQLPGTAPKLLIFDDYKRPSGVPDRFSGSQSGTSASLVITG

LQAEDEADYYCQSYDSSLSGYVFGPGTKVTVLG

SEQ ID NO: 73 nucleotide sequence of DNA signaling domain of 4-1BB
AAGCGCGGACGGAAGAAACTCTTGTACATCTTCAAGCAGCCGTTCATGCGC

CCTGTGCAAACCACCCAAGAAGAGGACGGGTGCTCCTGCCGGTTCCCGGAA

GAGGAAGAGGGCGGCTGCGAACTG

SEQ ID NO: 74 amino acid sequence of DNA signaling domain of 4-1BB
KRGRKKLLYIFKQPFMRPVQTTQEEDGCSCRFPEEEEGGCEL SEQ ID NO: 75 nucleotide sequence of DNA signaling domain of CD3z
CGCGTGAAGTTTTCCCGGTCCGCCGACGCTCCGGCGTACCAGCAGGGGCAA

AACCAGCTGTACAACGAACTTAACCTCGGTCGCCGGGAAGAATATGACGTG

CTGGACAAGCGGCGGGGAAGAGATCCCGAGATGGGTGGAAAGCCGCGGCG

GAAGAACCCTCAGGAGGGCTTGTACAACGAGCTGCAAAAGGACAAAATGG

CCGAAGCCTACTCCGAGATTGGCATGAAGGGAGAGCGCAGACGCGGGAAG

GGACACGATGGACTGTACCAGGGACTGTCAACCGCGACTAAGGACACTTAC

GACGCCCTGCACATGCAGGCCCTGCCCCCGCGC

SEQ ID NO: 76 amino acid sequence of DNA signaling domain of CD3z
RVKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTYD

ALHMQALPPR

SEQ ID NO: 77 nucleotide sequence of CAR123 Z16
ATGCTCTTGCTCGTGACTTCTTTGCTTTTGTGCGAACTTCCGCACCCAGCCTT

CCTTTTGATACCTCAGGTCCAGCTGGTGCAGTCTGGGGCTGAGGTGAAGAA

GCCTGGGTCCTCGGTGAAGGTCTCCTGCAAGGCTTCTGGAGGCACCTTCAG

CAGCTATGCTATCAGCTGGGTGCGACAGGCCCCTGGACAAGGGCTTGAGTG

GATGGGAGGGATCATCCCTATCTTTGGTACAGCAAACTACGCACAGAAGTT

CCAGGGCAGAGTCACGATTACCGCGGACGAATCCACGAGCACAGCCTACA

CGGAGCTGAGCAGCCTGAGATCTGAGGACACGGCCGTGTATTACTGTGCGA

GAGCCCGGTTGGGAGGAGCTTTTGATATCTGGGGCCAAGGGACAATGGTCA
```

```
CCGTCTCTTCAGGAGGTGGCGGGTCTGGTGGAGGCGGTAGCGGTGGTGGCG

GATCCCAGTCTGTGCTGACGCAGCCGCCCTCAGTGTCTGCGGCCCCAGGAC

AGAAGGTCACCATCTCCTGCTCTGGAGGCAGCTCCAACATTGGCAATCATT

ATGTGTCCTGGTATCAGCAGCTCCCAGGAGCAGCCCCCAAACTCCTCATTTA

TGACGATAATAAGCGACCCTCAGGGATTCCTGACCGATTCTCTGGCTCCAG

GTCTGGCACGTCAGCCACCCTGGGCATCACCGGACTCCAGAGTGGGGACGA

GGCCGATTATTACTGCGGAGCATGGGATAGTAGTCTTGCTGCTCATGTCTTC

GGAACTGGGACCAAGGTCACCGTCCTgGGTGCGGCCGCAACGACCACTCCT

GCACCCCGCCCTCCGACTCCGGCCCCAACCATTGCCAGCCAGCCCCTGTCCC

TGCGGCCGGAAGCCTGCAGACCGGCTGCCGGCGGAGCCGTCCATACCCGGG

GACTGGATTTCGCCTGCGATATCTATATCTGGGCACCACTCGCCGGAACCTG

TGGAGTGCTGCTGCTGTCCCTTGTGATCACCCTGTACTGCAAGCGCGGACG

GAAGAAACTCTTGTACATCTTCAAGCAGCCGTTCATGCGCCCTGTGCAAAC

CACCCAAGAAGAGGACGGGTGCTCCTGCCGGTTCCCGGAAGAGGAAGAGG

GCGGCTGCGAACTGCGCGTGAAGTTTTCCCGGTCCGCCGACGCTCCGGCGT

ACCAGCAGGGGCAAAACCAGCTGTACAACGAACTTAACCTCGGTCGCCGG

GAAGAATATGACGTGCTGGACAAGCGGCGGGGAAGAGATCCCGAGATGGG

TGGAAAGCCGCGGCGGAAGAACCCTCAGGAGGGCTTGTACAACGAGCTGC

AAAAGGACAAAATGGCCGAAGCCTACTCCGAGATTGGCATGAAGGGAGAG

CGCAGACGCGGGAAGGGACACGATGGACTGTACCAGGGACTGTCAACCGC

GACTAAGGACACTTACGACGCCCTGCACATGCAGGCCCTGCCCCCGCGC

SEQ ID NO: 78 amino acid sequence of CAR123 Z16
MLLLVTSLLLCELPHPAFLLIPQVQLVQSGAEVKKPGSSVKVSCKASGGTFSSY

AISWVRQAPGQGLEWMGGIIPIFGTANYAQKFQGRVTITADESTSTAYTELSSL

RSEDTAVYYCARARLGGAFDIWGQGTMVTVSSGGGGSGGGGSGGGGSQSVLT

QPPSVSAAPGQKVTISCSGGSSNIGNHYVSWYQQLPGAAPKLLIYDDNKRPSGI

PDRFSGSRSGTSATLGITGLQSGDEADYYCGAWDSSLAAHVFGTGTKVTVLGA

AATTTPAPRPPTPAPTIASQPLSLRPEACRPAAGGAVHTRGLDFACDIYIWAPLA

GTCGVLLLSLVITLYCKRGRKKLLYIFKQPFMRPVQTTQEEDGCSCRFPEEEEG

GCELRVKFSRSADAPAYQQGQNQLYNELNLGRREEYDVLDKRRGRDPEMGG

KPRRKNPQEGLYNELQKDKMAEAYSEIGMKGERRRGKGHDGLYQGLSTATK

DTYDALHMQALPPR

SEQ ID NO: 79 nucleotide sequence of human IgG4 hinge
GAGAGCAAATACGGGCCGCCATGTCCCCCGTGTCCG SEQ ID NO: 80 amino acid sequence of human IgG4 hinge
ESKYGPPCPPCP SEQ ID NO: 81 nucleotide sequence of human IgG4 CH2 domain
GCACCACCAGTTGCTGGCCCTAGTGTCTTCTTGTTCCCTCCCAAGCCCAAAG

ACACCTTGATGATTTCCAGAACTCCTGAGGTTACCTGCGTTGTCGTAGATGT

TTCTCAGGAGGACCCAGAGGTCCAATTTAACTGGTACGTTGATGGGGTGGA

AGTTCACAATGCGAAGACAAAGCCGCGGGAAGAACAATTTCAGTCCACTTA

CCGGGTTGTCAGCGTTCTGACGGTATTGCATCAAGACTGGCTTAATGGAAA
```

```
GGAATATAAGTGTAAGGTGTCCAACAAAGGTTTGCCGAGCAGTATTGAGAA

GACCATATCAAAGGCGAAG
```

SEQ ID NO: 82 amino acid sequence of human IgG4 CH2 domain
```
APPVAGPSVFLFPPKPKDTLMISRTPEVTCVVVDVSQEDPEVQFNWYV

DGVEVHNAKTKPREEQFQSTYRVVSVLTVLHQDWLNGKEYKCKVSNKGLPSS

IEKTISKA K
```

SEQ ID NO: 83 nucleotide sequence of human IgG4 CH3 domain
```
GGGCAGCCGCGCGAGCCACAAGTTTACACTTTGCCGCCATCTCAAGAGGAA

ATGACTAAAAACCAGGTATCCTTGACATGCCTCGTAAAAGGATTTTATCCA

TCTGATATTGCTGTGGAATGGGAGTCTAACGGGCAGCCGGAAAATAATTAC

AAAACTACACCACCTGTGCTCGATTCAGATGGAAGTTTCTTCCTTTACAGTA

GACTTACGGTGGACAAATCTAGGTGGCAGGAAGGGAATGTGTTTAGTTGTA

GTGTAATGCACGAGGCACTTCATAACCACTATACACAGAAGTCACTGAGTT

TGAGTCTTGGCAAA
```

SEQ ID NO: 84 amino acid sequence of human IgG4 CH3 domain
```
GQPREPQVYTLPPSQEEMTKNQVSLTCLVKGFYPSDIAVEWESNGQPENNYKT

TPPVLDSDGSFFLYSRLTVDKSRWQEGNVFSCSVMHEALHNHYTQKSLSLSLG

K
```

SEQ ID NO: 85 nucleotide sequence of human IgG4 hinge CH2 CH3 domain
```
GAGAGCAAATACGGGCCGCCATGTCCCCCGTGTCCGGCACCACCAGTTGCTGGCC

CTAGTGTCTTCTTGTTCCCTCCCAAGCCCAAAGACACCTTGATGATTTCCAGAACTC

CTGAGGTTACCTGCGTTGTCGTAGATGTTTCTCAGGAGGACCCAGAGGTCCAATTT

AACTGGTACGTTGATGGGGTGGAAGTTCACAATGCGAAGACAAAGCCGCGGGAAG

AACAATTTCAGTCCACTTACCGGGTTGTCAGCGTTCTGACGGTATTGCATCAAGAC

TGGCTTAATGGAAAGGAATATAAGTGTAAGGTGTCCAACAAAGGTTTGCCGAGCA

GTATTGAGAAGACCATATCAAAGGCGAAGGGGCAGCCGCGCGAGCCACAAGTTTA

CACTTTGCCGCCATCTCAAGAGGAAATGACTAAAAACCAGGTATCCTTGACATGCC

TCGTAAAAGGATTTTATCCATCTGATATTGCTGTGGAATGGGAGTCTAACGGGCAG

CCGGAAAATAATTACAAAACTACACCACCTGTGCTCGATTCAGATGGAAGTITCTT

CCTTTACAGTAGACTTACGGTGGACAAATCTAGGTGGCAGGAAGGGAATGTGTTT

AGTTGTAGTGTAATGCACGAGGCACTTCATAACCACTATACACAGAAGTCACTGA

GTTTGAGTCTTGGCAAA
```

SEQ ID NO: 86 amino acid sequence of human IgG4 hinge CH2 CH3 domain
```
ESKYGPPCPPCPAPPVAGPSVFLFPPKPKDTLMISRTPEVTCVVVDVSQEDPEVQFNWY

VDGVEVHNAKTKPREEQFQSTYRVVSVLTVLHQDWLNGKEYKCKVSNKGLPSSIEKT

ISKAKGQPREPQVYTLPPSQEEMTKNQVSLTCLVKGFYPSDIAVEWESNGQPENNYKT

TPPVLDSDGSFFLYSRLTVDKSRWQEGNVFSCSVMHEALHNHYTQKSLSLSLGK
```

SEQ ID NO: 87 nucleotide sequence of CAR123 Z32
```
ATGCTCTTGCTCGTGACTTCTTTGCTTTTGTGCGAACTTCCGCACCCAGCCTTCCTT

TTGATACCTCAGGTACAGCTGCAGCAGTCAGGTCCAGGACTGGTGAAGCCCTCGC

AGACCCTCTCACTCACCTGTGCCATCTCCGGGGACAGTGTCTCTAGCAACAGTGCT

GCTTGGAACTGGATCAGGCAGTCCCCATCGAGAGGCCTTGAGTGGCTGGGAAGGA

CATACTACAGGTCCAAGTGGTATAATGATTATGCAGTATCTGTGAAAAGTCGAATA

ACCATCAACCCAGACACATCCAAGAACCAGTTCTCCCTGCAGCTGAACTCTGTGAC
```

-continued

TCCCGAGGACATGGCTGTGTATTACTGTGCAAGAGGCGTTGATAGTAGCTTTGACT

ACTGGGGCCAGGGAACCCTGGTCACCGTCTCCTCAGGAGGTGGCGGGTCTGGTGG

AGGCGGTAGCGGTGGTGGCGGATCCCAGTCTGTCGTGACGCAGCCGCCCTCAGTG

TCTGCGGCCCCAGGACAGAGCGTCACCATCTCCTGTTCTGGAAGCAGTTCCACCGT

TGGCGATAATTATGTGTCCTGGTACCAGCAACTCCCAGGAACAGCCCCCAAACTCC

TCATTTTTGACGATTATAAACGACCCTCAGGGGTTCCTGACCGATTCTCTGGCTCCC

AGTCTGGCACCTCAGCCTCCCTGGTCATCACTGGTCTCCAGGCAGAAGATGAGGCT

GATTATTACTGCCAGTCTTATGACAGCAGCCTGAGTGGTTATGTCTTCGGGCCTGG

GACCAAGGTCACCGTCCTGGGTGCGGCCGCAACGACCACTCCTGCACCCCGCCCTC

CGACTCCGGCCCCAACCATTGCCAGCCAGCCCCTGTCCCTGCGGCCGGAAGCCTGC

AGACCGGCTGCCGGCGGAGCCGTCCATACCCGGGGACTGGATTTCGCCTGCGATA

TCTATATCTGGGCACCACTCGCCGGAACCTGTGGAGTGCTGCTGCTGTCCCTTGTG

ATCACCCTGTACTGCAAGCGCGGACGGAAGAAACTCTTGTACATCTTCAAGCAGC

CGTTCATGCGCCCTGTGCAAACCACCCAAGAAGAGGACGGGTGCTCCTGCCGGTT

CCCGGAAGAGGAAGAGGGCGGCTGCGAACTGCGCGTGAAGTTTTCCCGGTCCGCC

GACGCTCCGGCGTACCAGCAGGGGCAAAACCAGCTGTACAACGAACTTAACCTCG

GTCGCCGGGAAGAATATGACGTGCTGGACAAGCGGCGGGGAAGAGATCCCGAGA

TGGGTGGAAAGCCGCGGCGGAAGAACCCTCAGGAGGGCTTGTACAACGAGCTGCA

AAAGGACAAAATGGCCGAAGCCTACTCCGAGATTGGCATGAAGGGAGAGCGCAG

ACGCGGGAAGGGACACGATGGACTGTACCAGGGACTGTCAACCGCGACTAAGGA

CACTTACGACGCCCTGCACATGCAGGCCCTGCCCCCGCGC

SEQ ID NO: 88 amino acid sequence of sequence of CAR123 Z32
MLLLVTSLLLCELPHPAFLLIPQVQLQQSGPGLVKPSQTLSLTCAISGDSVSSNS

AAWNWIRQSPSRGLEWLGRTYYRSKWYNDYAVSVKSRITINPDTSKNQFSLQL

NSVTPEDMAVYYCARGVDSSFDYWGQGTLVTVSSGGGGSGGGGSGGGGSQS

VVTQPPSVSAAPGQSVTISCSGSSSTVGDNYVSWYQQLPGTAPKLLIFDDYKRP

SGVPDRFSGSQSGTSASLVITGLQAEDEADYYCQSYDSSLSGYVFGPGTKVTVL

GAAATTTPAPRPPTPAPTIASQPLSLRPEACRPAAGGAVHTRGLDFACDIYIWAP

LAGTCGVLLLSLVITLYCKRGRKKLLYIFKQPFMRPVQTTQEEDGCSCRFPEEE

EGGCELRVKFSRSADAPAYQQGQNQLYNELNLGRREEYDVLDKRRGRDPEMG

GKPRRKNPQEGLYNELQKDKMAEAYSEIGMKGERRRGKGHDGLYQGLSTAT

KDTYDALHMQALPPR

---

What is claimed is:

1. An isolated nucleic acid molecule encoding a chimeric antigen receptor (CAR) comprising amino acid residues 23 to 274 of the amino acid sequence of SEQ ID NO: 4.

2. A chimeric antigen receptor (CAR) encoded by the isolated nucleic acid molecule of claim 1.

3. A pharmaceutical composition comprising an anti-tumor effective amount of a population of human T cells, wherein the T cells comprise a nucleic acid sequence that encodes the chimeric antigen receptor (CAR) of claim 2, and wherein the T cells are T cells of a human having a cancer.

4. A vector comprising a nucleic acid molecule of claim 1.

5. The vector of claim 4, wherein the vector is selected from the group consisting of a DNA vector, an RNA vector, a plasmid vector, a cosmid vector, a herpes virus vector, a measles virus vector, a lentivirus vector, an adenoviral vector, and a retrovirus vector.

6. A cell comprising the vector of claim 4.

7. The isolated nucleic acid molecule of claim 1, wherein the CAR comprises the amino acid sequence of SEQ ID NO: 4.

8. A method of treating cancer in a subject in need thereof, the method comprising administering to the subject a pharmaceutical composition comprising an anti-tumor effective amount of a population of T cells, wherein the T cells comprise a nucleic acid sequence that encodes a chimeric antigen receptor (CAR), wherein the CAR comprises at least one extracellular antigen binding domain comprising a CD123 antigen binding domain comprising amino acid residues 23 to 274 of the amino acid sequence of SEQ ID NO: 4, at least one linker or spacer domain, at least one transmembrane domain, at least one intracellular signaling domain, wherein the T cells are T cells of the subject having cancer.

9. The method of claim 8, wherein the at least one transmembrane domain comprises a transmembrane domain of a protein selected from the group consisting of: the alpha chain of a T-cell receptor, the beta chain of the T-cell receptor, the zeta chain of the T-cell receptor, CD8, CD28, CD3 epsilon, CD45, CD4, CD5, CD9, CD16, CD22, CD33, CD37, CD64, CD80, CD86, CD134, CD137 and CD154.

10. The method of claim 8, wherein the at least one extracellular antigen binding domain, the at least one intracellular signaling domain, or both are connected to the at least one transmembrane domain by a linker or spacer domain.

11. The method of claim 10, wherein the at least one linker or spacer domain is obtained from the extracellular domain of CD8, TNFRSF19, IgG4, or CD28, and is linked to the at least one transmembrane domain.

12. The method of claim 8, wherein the nucleic acid sequence encoding the extracellular antigen binding domain comprises a nucleic acid sequence comprising a sequence with 85%, 90%, 95%, 96%, 97%, 98%, or 99% identity to amino acid residues 23 to 274 of the amino acid sequence of SEQ ID NO: 4.

13. The method of claim 8, wherein the CAR comprises the amino acid sequence of SEQ ID NO: 4.

14. The method of claim 8, wherein the at least one intracellular signaling domain further comprises a CD3 zeta intracellular domain.

15. The method of claim 8, wherein the at least one intracellular signaling domain comprises a costimulatory domain, a primary signaling domain, or any combination thereof.

16. The method of claim 15, wherein the at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), or any combination thereof.

17. The method of claim 8, wherein the cancer is a hematological cancer.

18. The method of claim 17, wherein the hematological cancer is leukemia, lymphoma, or multiple myeloma.

19. The method of claim 18, wherein the leukemia is acute myeloid leukemia (AML), blastic plasmacytoid dendritic cell neoplasm (BPDCN), chronic myelogenous leukemia (CML), chronic lymphocytic leukemia (CLL), acute lymphoblastic T cell leukemia (T-ALL), or acute lymphoblastic B cell leukemia (B-ALL).

20. The method of claim 18, wherein the lymphoma is mantle cell lymphoma, non-Hodgkin's lymphoma or Hodgkin's lymphoma.

* * * * *

SEQUENCE LISTING

<160> NUMBER OF SEQ ID NOS: 88

<210> SEQ ID NO 1
<211> LENGTH: 1503
<212> TYPE: DNA
<213> ORGANISM: Artificial
<220> FEATURE:
<223> OTHER INFORMATION: nucleotide sequence of CAR D0125 CD123 MB31-A01
      CD8 BBz

<400> SEQUENCE: 1

```
atgctcttgc tcgtgacttc tttgcttttg tgcgaacttc cgcacccagc cttccttttg    60
atacctcaga tacaattggt acagtctgga gccgaggtta agaagccggg atcttccgtc   120
aaagtgtcct gtaaagcctc tggggcacc ttctcttcct acgcaattag ttgggtgaga   180
caagctccag gtcagggttt ggagtggatg gagggataa tcccgatatt cgggacagca   240
aactacgccc agaaatttca agggcgcgta acgataacag ctgacgagtc cacatctacg   300
gcatacatgg agttgagttc tctgaggagt gaggacacag ctgtatatta ctgcgcgcgg   360
ggaagcggag aacttctcta cgcaagttat tattattact acatggatgt ctggggtaag   420
ggcactaccg taacagtttc aagtggaggt ggtggttctg gtggggagg tagcggcggc   480
ggggttccc aatccgcact cacgcagcct gcctctgttt caggatcacc gggacagtct   540
ataacaatca gttgtactgg caccagttca gatgtcgggg gtataacta cgtttcatgg   600
taccaacaac acccaggaaa ggcaccagaa ctcatgatat atgacgtgtc aaaccgaccg   660
tctggcgtat ctaaccgatt tagtggctcc aagtctggta ataccgcgtc actgacaatc   720
agcgggttgc aggctgagga tgaagctgac tactattgta gttcctacac cagctctagt   780
actcctgttg tcttcggcgg gggcactaag ctcacagtat tggcggccgc aacgaccact   840
cctgcacccc gccctccgac tccggcccca accattgcca gccagcccct gtccctgcgg   900
ccggaagcct gcagaccggc tgccggcgga gccgtccata cccggggact ggatttcgcc   960
tgcgatatct atatctgggc accactcgcc ggaacctgtg agtgctgct gctgtccctt  1020
gtgatcaccc tgtactgcaa gcgcggacgg aagaaactct tgtacatctt caagcagccg  1080
ttcatgcgcc ctgtgcaaac cacccaagaa gaggacgggt gctcctgccg gttcccggaa  1140
gaggaagagg gcggctgcga actgcgcgtg aagttttccc ggtccgccga cgctccggcg  1200
taccagcagg ggcaaaacca gctgtacaac gaacttaacc tcggtcgccg ggaagaatat  1260
gacgtgctgg acaagcggcg gggaagagat cccgagatgg gtggaaagcc gcggcggaag  1320
aaccctcagg agggcttgta caacgagctg caaaaggaca aaatggccga agcctactcc  1380
gagattggca tgaagggaga gcgcagacgc gggaagggac acgatggact gtaccaggga  1440
ctgtcaaccg cgactaagga cacttacgac gccctgcaca tgcaggccct gccccgcgc  1500
taa                                                                1503
```

<210> SEQ ID NO 2
<211> LENGTH: 500
<212> TYPE: PRT
<213> ORGANISM: Artificial
<220> FEATURE:
<223> OTHER INFORMATION: amino acid sequence of CAR D0125 CD123 MB31-A01
      CD8 BBz

<400> SEQUENCE: 2

```
Met Leu Leu Leu Val Thr Ser Leu Leu Cys Glu Leu Pro His Pro
1               5                   10                  15

Ala Phe Leu Leu Ile Pro Gln Ile Gln Leu Val Gln Ser Gly Ala Glu
                20                  25                  30

Val Lys Lys Pro Gly Ser Ser Val Lys Val Ser Cys Lys Ala Ser Gly
            35                  40                  45

Gly Thr Phe Ser Ser Tyr Ala Ile Ser Trp Val Arg Gln Ala Pro Gly
        50                  55                  60

Gln Gly Leu Glu Trp Met Gly Gly Ile Ile Pro Ile Phe Gly Thr Ala
65                  70                  75                  80
```

```
Asn Tyr Ala Gln Lys Phe Gln Gly Arg Val Thr Ile Thr Ala Asp Glu
                85                  90                  95

Ser Thr Ser Thr Ala Tyr Met Glu Leu Ser Ser Leu Arg Ser Glu Asp
            100                 105                 110

Thr Ala Val Tyr Tyr Cys Ala Arg Gly Ser Gly Glu Leu Leu Tyr Ala
        115                 120                 125

Ser Tyr Tyr Tyr Tyr Met Asp Val Trp Gly Lys Gly Thr Thr Val
130                 135                 140

Thr Val Ser Ser Gly Gly Gly Ser Gly Gly Gly Ser Gly Gly
145                 150                 155                 160

Gly Gly Ser Gln Ser Ala Leu Thr Gln Pro Ala Ser Val Ser Gly Ser
            165                 170                 175

Pro Gly Gln Ser Ile Thr Ile Ser Cys Thr Gly Thr Ser Ser Asp Val
            180                 185                 190

Gly Gly Tyr Asn Tyr Val Ser Trp Tyr Gln Gln His Pro Gly Lys Ala
            195                 200                 205

Pro Glu Leu Met Ile Tyr Asp Val Ser Asn Arg Pro Ser Gly Val Ser
    210                 215                 220

Asn Arg Phe Ser Gly Ser Lys Ser Gly Asn Thr Ala Ser Leu Thr Ile
225                 230                 235                 240

Ser Gly Leu Gln Ala Glu Asp Glu Ala Asp Tyr Tyr Cys Ser Ser Tyr
            245                 250                 255

Thr Ser Ser Ser Thr Pro Val Val Phe Gly Gly Gly Thr Lys Leu Thr
            260                 265                 270

Val Leu Ala Ala Ala Thr Thr Thr Pro Ala Pro Arg Pro Pro Thr Pro
            275                 280                 285

Ala Pro Thr Ile Ala Ser Gln Pro Leu Ser Leu Arg Pro Glu Ala Cys
    290                 295                 300

Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
            325                 330                 335

Leu Leu Ser Leu Val Ile Thr Leu Tyr Cys Lys Arg Gly Arg Lys Lys
            340                 345                 350

Leu Leu Tyr Ile Phe Lys Gln Pro Phe Met Arg Pro Val Gln Thr Thr
            355                 360                 365

Gln Glu Glu Asp Gly Cys Ser Cys Arg Phe Pro Glu Glu Glu Glu Gly
    370                 375                 380

Gly Cys Glu Leu Arg Val Lys Phe Ser Arg Ser Ala Asp Ala Pro Ala
385                 390                 395                 400

Tyr Gln Gln Gly Gln Asn Gln Leu Tyr Asn Glu Leu Asn Leu Gly Arg
            405                 410                 415

Arg Glu Glu Tyr Asp Val Leu Asp Lys Arg Gly Arg Asp Pro Glu
            420                 425                 430

Met Gly Gly Lys Pro Arg Arg Lys Asn Pro Gln Glu Gly Leu Tyr Asn
            435                 440                 445

Glu Leu Gln Lys Asp Lys Met Ala Glu Ala Tyr Ser Glu Ile Gly Met
    450                 455                 460

Lys Gly Glu Arg Arg Arg Gly Lys Gly His Asp Gly Leu Tyr Gln Gly
465                 470                 475                 480

Leu Ser Thr Ala Thr Lys Asp Thr Tyr Asp Ala Leu His Met Gln Ala
            485                 490                 495

Leu Pro Pro Arg
```

<210> SEQ ID NO 3
<211> LENGTH: 1503
<212> TYPE: DNA
<213> ORGANISM: Artificial
<220> FEATURE:
<223> OTHER INFORMATION: nucleotide sequence of CAR D0126 CD123 MB31-C01 CD8 BBz

<400> SEQUENCE: 3

```
atgctcttgc tcgtgacttc tttgcttttg tgcgaacttc cgcacccagc cttccttttg      60
ataccctgaag tacagctcct cgaatctggc ggtggtctcg ttaagcctgg tgggtccctt     120
agactctctt gtgcagcgag cggtttcacc ttcagcaacg cttggatgag ttgggtccgc     180
caggcgcctg gaaagggcct cgaatgggtt ggtcggataa aaagcaagac ggatggaggg     240
accacagatt acgcggcgcc ggtgaaaggt cggttcacaa tttcaaggga tgactcaaaa     300
aatactttgt atctgcaaat gaattccctc aagacggaag atactgcagt ctattattgc     360
acaaccggtt tgctctggtt tggcactcgc aattattact atggcatgga tgtatggggc     420
caaggaacga ccgtcactgt ttcaagtgga ggtggcggga gcggaggagg gggctccgga     480
ggtggcggtt ctcaatcagc acttactcag ccagcttcag tcagtggttc cccgggccaa     540
tccatcacca tttcatgcac cggcacatca agtgatgttg gtggctacaa ttacgtgagt     600
tggtatcagc aacatccagg aaaggctcct aagcttgtaa tttatgatgt atccaatcgg     660
ccttctgggc ttagcaatcg cttttccgga tctaaatcag gcaatactgc gtcccttacc     720
ataagcgggc ttcaagccga agatgaagca gattactatt gtaactccta cgctgggagc     780
ggttcatggg tatttggagg cggtacgaag ttgactgtct tggcggccgc aacgaccact     840
cctgcacccc gccctccgac tccggcccca accattgcca gccagcccct gtccctgcgg     900
ccggaagcct gcagaccggc tgccggcgga gccgtccata cccggggact ggatttcgcc     960
tgcgatatct atatctgggc accactcgcc ggaacctgtg gagtgctgct gctgtccctt    1020
gtgatcaccc tgtactgcaa gcgcggacgg aagaaactct tgtacatctt caagcagccg    1080
ttcatgcgcc ctgtgcaaac cacccaagaa gaggacgggt gctcctgccg gttcccggaa    1140
gaggaagagg gcggctgcga actgcgcgtg aagttttccc ggtccgccga cgctccggcg    1200
taccagcagg ggcaaaacca gctgtacaac gaacttaacc tcggtcgccg gaagaatat    1260
gacgtgctgg acaagcggcg gggaagagat cccgagatgg gtggaaagcc gcggcggaag    1320
aaccctcagg agggcttgta caacgagctg caaaaggaca aaatggccga agcctactcc    1380
gagattggca tgaagggaga gcgcagacgc gggaagggac acgatggact gtaccaggga    1440
ctgtcaaccg cgactaagga cacttacgac gccctgcaca tgcaggccct gccccgcgc    1500
taa                                                                  1503
```

<210> SEQ ID NO 4
<211> LENGTH: 500
<212> TYPE: PRT
<213> ORGANISM: Artificial
<220> FEATURE:
<223> OTHER INFORMATION: amino acid sequence of CAR D0126 CD123 MB31-C01 CD8 BBz

<400> SEQUENCE: 4

Met Leu Leu Leu Val Thr Ser Leu Leu Leu Cys Glu Leu Pro His Pro
1               5                   10                  15

-continued

```
Ala Phe Leu Leu Ile Pro Glu Val Gln Leu Glu Ser Gly Gly
            20              25              30

Leu Val Lys Pro Gly Gly Ser Leu Arg Leu Ser Cys Ala Ala Ser Gly
            35              40              45

Phe Thr Phe Ser Asn Ala Trp Met Ser Trp Val Arg Gln Ala Pro Gly
        50              55              60

Lys Gly Leu Glu Trp Val Gly Arg Ile Lys Ser Lys Thr Asp Gly Gly
65              70              75              80

Thr Thr Asp Tyr Ala Ala Pro Val Lys Gly Arg Phe Thr Ile Ser Arg
                85              90              95

Asp Asp Ser Lys Asn Thr Leu Tyr Leu Gln Met Asn Ser Leu Lys Thr
            100             105             110

Glu Asp Thr Ala Val Tyr Tyr Cys Thr Thr Gly Leu Leu Trp Phe Gly
            115             120             125

Thr Arg Asn Tyr Tyr Tyr Gly Met Asp Val Trp Gly Gln Gly Thr Thr
    130             135             140

Val Thr Val Ser Ser Gly Gly Gly Gly Ser Gly Gly Gly Gly Ser Gly
145             150             155             160

Gly Gly Gly Ser Gln Ser Ala Leu Thr Gln Pro Ala Ser Val Ser Gly
            165             170             175

Ser Pro Gly Gln Ser Ile Thr Ile Ser Cys Thr Gly Thr Ser Ser Asp
            180             185             190

Val Gly Gly Tyr Asn Tyr Val Ser Trp Tyr Gln Gln His Pro Gly Lys
            195             200             205

Ala Pro Lys Leu Val Ile Tyr Asp Val Ser Asn Arg Pro Ser Gly Leu
210             215             220

Ser Asn Arg Phe Ser Gly Ser Lys Ser Gly Asn Thr Ala Ser Leu Thr
225             230             235             240

Ile Ser Gly Leu Gln Ala Glu Asp Glu Ala Asp Tyr Tyr Cys Asn Ser
            245             250             255

Tyr Ala Gly Ser Gly Ser Trp Val Phe Gly Gly Gly Thr Lys Leu Thr
            260             265             270

Val Leu Ala Ala Ala Thr Thr Thr Pro Ala Pro Arg Pro Pro Thr Pro
        275             280             285

Ala Pro Thr Ile Ala Ser Gln Pro Leu Ser Leu Arg Pro Glu Ala Cys
    290             295             300

Arg Pro Ala Ala Gly Gly Ala Val His Thr Arg Gly Leu Asp Phe Ala
305             310             315             320

Cys Asp Ile Tyr Ile Trp Ala Pro Leu Ala Gly Thr Cys Gly Val Leu
                325             330             335

Leu Leu Ser Leu Val Ile Thr Leu Tyr Cys Lys Arg Gly Arg Lys Lys
            340             345             350

Leu Leu Tyr Ile Phe Lys Gln Pro Phe Met Arg Pro Val Gln Thr Thr
            355             360             365

Gln Glu Glu Asp Gly Cys Ser Cys Arg Phe Pro Glu Glu Glu Glu Gly
    370             375             380

Gly Cys Glu Leu Arg Val Lys Phe Ser Arg Ser Ala Asp Ala Pro Ala
385             390             395             400

Tyr Gln Gln Gly Gln Asn Gln Leu Tyr Asn Glu Leu Asn Leu Gly Arg
            405             410             415

Arg Glu Glu Tyr Asp Val Leu Asp Lys Arg Arg Gly Arg Asp Pro Glu
            420             425             430

Met Gly Gly Lys Pro Arg Arg Lys Asn Pro Gln Glu Gly Leu Tyr Asn
```

```
            435                 440                 445
Glu Leu Gln Lys Asp Lys Met Ala Glu Ala Tyr Ser Glu Ile Gly Met
        450                 455                 460
Lys Gly Glu Arg Arg Arg Gly Lys Gly His Asp Gly Leu Tyr Gln Gly
465                 470                 475                 480
Leu Ser Thr Ala Thr Lys Asp Thr Tyr Asp Ala Leu His Met Gln Ala
                485                 490                 495
Leu Pro Pro Arg
            500

<210> SEQ ID NO 5
<211> LENGTH: 1485
<212> TYPE: DNA
<213> ORGANISM: Artificial
<220> FEATURE:
<223> OTHER INFORMATION: nucleotide sequence of CAR D0127 CD123 MB35-E02
      CD8 BBz

<400> SEQUENCE: 5
atgctcttgc tcgtgacttc tttgcttttg tgcgaacttc cgcacccagc cttccttttg      60
atacctcaag ttcagctggt ccagagcggc gccgaggtaa aaaagccagg ctcttctgta     120
aaggtgtcct gtaaggccag tggaggcact ttttcctcct acgcaatctc atgggtccga     180
caagcacctg gtcaaggact ggaatggatg ggcggtatca tcccgatctt tggtactgct     240
aactatgcgc agaagttcca gggtagggtg accataaccg cagatgagag tacatccact     300
gcctatatgg agctcagtag cctgaggtct gaggatactg ccgtttacta ttgtgcacgc     360
cacggcggga tggcaacaat gctcccttac ggagcatttg acatctgggg tcaaggtaca     420
atggtaactg tatcatctgg cggtggcggt agtggtgggg gaggcagcgg aggtggggc      480 agtgatatac gactgacgca atctccctct agcctgagtg ccagtgtcgg agatcgggtc     540
acaatcacat gccgggctag tcagggtatc agtagctatc ttaattggta ccaacaaaaa     600
ccaggaaaag caccgaaact gctcatttat gcagcttctc ggttgcaatc tggagtccca     660
agccggttta gtggaagtgg cagtgggacg gactttacct tgactatatc ctcattgcaa     720
cctgaggatt tcgctactta ttactgccaa caatcttact ccacgagtct tacgttcggt     780 ggggcacga agtgtgagat caaagcggcc gcaacgacca ctcctgcacc ccgccctccg     840
actccggccc caaccattgc cagccagccc tgtccctgc ggccggaagc tgcagaccg     900 gctgccggcg gagccgtcca tacccgggga ctggatttcg cctgcgatat ctatatctgg     960
gcaccactcg ccggaacctg tggagtgctg ctgctgtccc ttgtgatcac cctgtactgc    1020
aagcgcggac ggaagaaact cttgtacatc ttcaagcagc cgttcatgcg ccctgtgcaa    1080
accacccaag aagaggacgg tgctcctgc cggttcccgg aagaggaaga gggcggctgc    1140
gaactgcgcg tgaagttttc ccggtccgcc gacgctccgg cgtaccagca ggggcaaaac    1200
cagctgtaca cgaacttaa cctcggtcgc gggaagaat atgacgtgct ggacaagcgg    1260
cggggaagag atcccgagat gggtggaaag ccgcggcgga agaaccctca ggagggcttg    1320
tacaacgagc tgcaaaagga caaaatggcc gaagcctact ccgagattgg catgaaggga    1380
gagcgcagac gcgggaaggg acacgatgga ctgtaccagg actgtcaac cgcgactaag    1440 gacacttacg acgccctgca catgcaggcc ctgccccgc gctaa                    1485

<210> SEQ ID NO 6
<211> LENGTH: 494
<212> TYPE: PRT
```

<213> ORGANISM: Artificial
<220> FEATURE:
<223> OTHER INFORMATION: amino acid sequence of CAR D0127 CD123 MB35-E02 CD8 BBz

<400> SEQUENCE: 6

```
Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Gly Thr Phe Ser Ser Tyr Ala Ile Ser Trp Val Arg Gln Ala Pro Gly
    50                  55                  60

Gln Gly Leu Glu Trp Met Gly Gly Ile Ile Pro Ile Phe Gly Thr Ala
65                  70                  75                  80

Asn Tyr Ala Gln Lys Phe Gln Gly Arg Val Thr Ile Thr Ala Asp Glu
                85                  90                  95

Ser Thr Ser Thr Ala Tyr Met Glu Leu Ser Ser Leu Arg Ser Glu Asp
            100                 105                 110

Thr Ala Val Tyr Tyr Cys Ala Arg His Gly Gly Met Ala Thr Met Leu
        115                 120                 125

Pro Tyr Gly Ala Phe Asp Ile Trp Gly Gln Gly Thr Met Val Thr Val
    130                 135                 140

Ser Ser Gly Gly Gly Gly Ser Gly Gly Gly Gly Ser Gly Gly Gly Gly
145                 150                 155                 160

Ser Asp Ile Arg Leu Thr Gln Ser Pro Ser Ser Leu Ser Ala Ser Val
                165                 170                 175

Gly Asp Arg Val Thr Ile Thr Cys Arg Ala Ser Gln Gly Ile Ser Ser
            180                 185                 190

Tyr Leu Asn Trp Tyr Gln Gln Lys Pro Gly Lys Ala Pro Lys Leu Leu
        195                 200                 205

Ile Tyr Ala Ala Ser Arg Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Ser Tyr Ser Thr Ser
                245                 250                 255

Leu Thr Phe Gly Gly Gly Thr Lys Val Glu Ile Lys Ala Ala Ala Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380
```

```
Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
            405                 410                 415

Leu Asp Lys Arg Arg Gly Arg Asp Pro Glu Met Gly Gly Lys Pro Arg
        420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465             470                 475                 480

Asp Thr Tyr Asp Ala Leu His Met Gln Ala Leu Pro Pro Arg
                485                 490

<210> SEQ ID NO 7
<211> LENGTH: 1488
<212> TYPE: DNA
<213> ORGANISM: Artificial
<220> FEATURE:
<223> OTHER INFORMATION: nucleotide sequence of CAR D0128 CD123 MB36-A05
      CD8 BBz

<400> SEQUENCE: 7
atgctcttgc tcgtgacttc tttgcttttg tgcgaacttc cgcacccagc cttccttttg      60
atacctcaag tccagctcgt tcagagtggt gcagaggtga agaagcccgg ctcatctgtg     120
aaagtgtcat gcaaagcaag cggcgggacc ttcagcagtt acgcgatctc ctgggtacga     180
caagcccccg ccagggcct  ggaatggatg ggagggatca ttccgatttt cggtacagca     240
aactatgcac aaaaatttca ggggagagtt acgataactg cagacaagag cacttcaacg     300
gcatacatgg agctttcatc attgcgctcc gaggacacgg ctgtttacta ctgcgctcga     360
gggggacgga actcttacta ttattactac atggacgtgt ggggcaaagg acaacggtg      420 acggtaagta gtgggggagg cggaagcggt ggtggggaa  gtggaggcgg tgggtcacag     480
tcagccctca cacaccggc  ctctgtctca gggagtccag acagagtat  tactataagc     540 tgcactggga catcctcaga cgtcggcggt tataattatg tttcctggta ccaacaacat     600
cccgggaagg ctcccaagct gatgatatac gaagtgagta atcgaccctc tggcgtgagc     660
aatcgattct ctgggagtaa gagtggcaac actgcgagtc ttacgatttc tggcctgcag     720
gcggaagacg aagccgatta ttactgtagc agctacactt caagctcccc tgttgttttc     780
ggtggcggca ctaaacttac cgtgcttgcg ccgcaacga  ccactcctgc accccgccct     840
ccgactccgg ccccaaccat tgccagccag cccctgtccc tgcggccgga agcctgcaga     900
ccggctgccg gcggagccgt ccatacccgg gactggatt  tcgcctgcga tatctatatc     960
tgggcaccac tcgccggaac ctgtggagtg ctgctgctgt cccttgtgat cacccctgtac    1020 tgcaagcgcg gacggaagaa actcttgtac atcttcaagc agccgttcat gcgccctgtg    1080
caaaccaccc aagaagagga cgggtgctcc tgccggttcc cggaagagga agagggcggc    1140
tgcgaactgc gcgtgaagtt tccccggtcc gccgacgctc cggcgtacca gcaggggcaa    1200
aaccagctgt acaacgaact taacctcggt cgccgggaag aatatgacgt gctggacaag    1260
cggcggggaa gagatcccga gatgggtgga aagccgcggc ggaagaaccc tcaggagggc    1320
ttgtacaacg agctgcaaaa ggacaaaatg gccgaagcct actccgagat tggcatgaag    1380
ggagagcgca gacgcgggaa gggacacgat ggactgtacc agggactgtc aaccgcgact    1440
```
aaggacactt acgacgccct gcacatgcag gccctgcccc cgcgctaa          1488

<210> SEQ ID NO 8
<211> LENGTH: 495
<212> TYPE: PRT
<213> ORGANISM: Artificial
<220> FEATURE:
<223> OTHER INFORMATION: amino acid sequence of CAR D0128 CD123 MB36-A05
    CD8 BBz

<400> SEQUENCE: 8

```
Met Leu Leu Leu Val Thr Ser Leu Leu Cys Glu Leu Pro His Pro
1               5                   10                  15

Ala Phe Leu Leu Ile Pro Gln Val Gln Leu Val Gln Ser Gly Ala Glu
            20                  25                  30

Val Lys Lys Pro Gly Ser Ser Val Lys Val Ser Cys Lys Ala Ser Gly
            35                  40                  45

Gly Thr Phe Ser Ser Tyr Ala Ile Ser Trp Val Arg Gln Ala Pro Gly
50                  55                  60

Gln Gly Leu Glu Trp Met Gly Gly Ile Ile Pro Ile Phe Gly Thr Ala
65                  70                  75                  80

Asn Tyr Ala Gln Lys Phe Gln Gly Arg Val Thr Ile Thr Ala Asp Lys
            85                  90                  95

Ser Thr Ser Thr Ala Tyr Met Glu Leu Ser Ser Leu Arg Ser Glu Asp
            100                 105                 110

Thr Ala Val Tyr Tyr Cys Ala Arg Gly Gly Arg Asn Ser Tyr Tyr Tyr
            115                 120                 125

Tyr Tyr Met Asp Val Trp Gly Lys Gly Thr Thr Val Thr Val Ser Ser
            130                 135                 140

Gly Gly Gly Gly Ser Gly Gly Gly Ser Gly Gly Gly Gly Ser Gln
145                 150                 155                 160

Ser Ala Leu Thr Gln Pro Ala Ser Val Ser Gly Ser Pro Gly Gln Ser
            165                 170                 175

Ile Thr Ile Ser Cys Thr Gly Thr Ser Ser Asp Val Gly Gly Tyr Asn
            180                 185                 190

Tyr Val Ser Trp Tyr Gln Gln His Pro Gly Lys Ala Pro Lys Leu Met
            195                 200                 205

Ile Tyr Glu Val Ser Asn Arg Pro Ser Gly Val Ser Asn Arg Phe Ser
            210                 215                 220

Gly Ser Lys Ser Gly Asn Thr Ala Ser Leu Thr Ile Ser Gly Leu Gln
225                 230                 235                 240

Ala Glu Asp Glu Ala Asp Tyr Tyr Cys Ser Ser Tyr Thr Ser Ser Ser
            245                 250                 255

Pro Val Val Phe Gly Gly Gly Thr Lys Leu Thr Val Leu Ala Ala Ala
            260                 265                 270

Thr Thr Thr Pro Ala Pro Arg Pro Pro Thr Pro Ala Pro Thr Ile Ala
            275                 280                 285

Ser Gln Pro Leu Ser Leu Arg Pro Glu Ala Cys Arg Pro Ala Ala Gly
            290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
            325                 330                 335

Ile Thr Leu Tyr Cys Lys Arg Gly Arg Lys Lys Leu Leu Tyr Ile Phe
            340                 345                 350
```

```
Lys Gln Pro Phe Met Arg Pro Val Gln Thr Thr Gln Glu Glu Asp Gly
            355                 360                 365
Cys Ser Cys Arg Phe Pro Glu Glu Glu Gly Gly Cys Glu Leu Arg
        370                 375                 380
Val Lys Phe Ser Arg Ser Ala Asp Ala Pro Ala Tyr Gln Gln Gly Gln
385                 390                 395                 400
Asn Gln Leu Tyr Asn Glu Leu Asn Leu Gly Arg Arg Glu Glu Tyr Asp
                405                 410                 415
Val Leu Asp Lys Arg Arg Gly Arg Asp Pro Glu Met Gly Gly Lys Pro
            420                 425                 430
Arg Arg Lys Asn Pro Gln Glu Gly Leu Tyr Asn Glu Leu Gln Lys Asp
                435                 440                 445
Lys Met Ala Glu Ala Tyr Ser Glu Ile Gly Met Lys Gly Glu Arg Arg
        450                 455                 460
Arg Gly Lys Gly His Asp Gly Leu Tyr Gln Gly Leu Ser Thr Ala Thr
465                 470                 475                 480
Lys Asp Thr Tyr Asp Ala Leu His Met Gln Ala Leu Pro Pro Arg
                485                 490                 495

<210> SEQ ID NO 9
<211> LENGTH: 1500
<212> TYPE: DNA
<213> ORGANISM: Artificial
<220> FEATURE:
<223> OTHER INFORMATION: nucleotide sequence of CAR D0129 CD123 MB40-F08
      CD8 BBz

<400> SEQUENCE: 9
atgctcttgc tcgtgacttc tttgcttttg tgcgaacttc cgcacccagc cttccttttg      60
atacctcagg ttcagctcgt tcaaagcgga gctgaagtta aaaaacctgg gtcttctgtc     120
aaggtaagtt gcaaagcatc cggaggcacg ttttcttcct atgcaataag ttgggtccgg     180
caagcacctg gtcagggatt ggaatggatg gtggtatta ccaatatt cggaacggcg       240 aactacgcac agaagtttca aggcagggta actattaccg cggacgagtc tacctcaaca     300
gcgtatatgg aactgagcag tctcagatca aagataccg cagtttatta ctgcgctcgg     360
gggtctggag agcttctcta tgcatcctac tactactatt atatggacgt atggggcaag     420
ggtaccaccg ttaccgtgtc ttctggaggt ggcggatctg gaggtggagg atccggtggg     480
ggaggcagcc aatctgcact gactcaaccc gcgtccgtga gcggatcccc tgggcaatca     540
ataacaatct cttgcacggg gacctcatct gatgttggtg atataatta cgtcagctgg     600 taccaacaac accccggtaa ggctccgaag ctgatgattt acgaagtgag taatcgccca     660
agtggtgtaa gcaacagatt ctcaggctca aagagtggga acactgcgtc cctgactatc     720
tcaggcctcc aggctgagga cgaagcagat tattactgtt cttcatacac cagtagtagt     780
cctttggtct tcggcaccgg caccaaggta actgtactgg cggccgcaac gaccactcct     840
gcaccccgcc ctccgactcc ggccccaacc attgcagcc agccctgtc cctgcggccg      900 gaagcctgca gaccggctgc cggcggagcc gtccatacccc ggggactgga tttcgcctgc     960
gatatctata tctgggcacc actcgccgga acctgtggaa tgctgctgct gtcccttgtg    1020
atcaccctgt actgcaagcg cggacggaag aaactcttgt acatcttcaa gcagccgttc    1080
atgcgccctg tgcaaaccac caagaagag acgggtgct cctgccggtt ccgggaagag    1140
gaagagggcg gctgcgaact gcgcgtgaag ttttcccggt ccgccgacgc tccggcgtac    1200
```

```
cagcagggc  aaaaccagct  gtacaacgaa  cttaacctcg  gtcgccggga  agaatatgac    1260
gtgctggaca  gcggcgggg   aagagatccc  gagatgggtg  gaaagccgcg  gcggaagaac   1320
cctcaggagg  gcttgtacaa  cgagctgcaa  aaggacaaaa  tggccgaagc  ctactccgag   1380
attggcatga  aggagagcg   cagacgcggg  aagggacacg  atggactgta  ccagggactg   1440
tcaaccgcga  ctaaggacac  ttacgacgcc  ctgcacatgc  aggccctgcc  cccgcgctaa   1500
```

<210> SEQ ID NO 10
<211> LENGTH: 499
<212> TYPE: PRT
<213> ORGANISM: Artificial
<220> FEATURE:
<223> OTHER INFORMATION: amino acid sequence of CAR D0129 CD123 MB40-F08
      CD8 BBz

<400> SEQUENCE: 10

```
Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Gly Thr Phe Ser Ser Tyr Ala Ile Ser Trp Val Arg Gln Ala Pro Gly
    50                  55                  60

Gln Gly Leu Glu Trp Met Gly Gly Ile Ile Pro Ile Phe Gly Thr Ala
65                  70                  75                  80

Asn Tyr Ala Gln Lys Phe Gln Gly Arg Val Thr Ile Thr Ala Asp Glu
                85                  90                  95

Ser Thr Ser Thr Ala Tyr Met Glu Leu Ser Ser Leu Arg Ser Glu Asp
            100                 105                 110

Thr Ala Val Tyr Tyr Cys Ala Arg Gly Ser Gly Glu Leu Leu Tyr Ala
        115                 120                 125

Ser Tyr Tyr Tyr Tyr Met Asp Val Trp Gly Lys Gly Thr Thr Val
    130                 135                 140

Thr Val Ser Ser Gly Gly Gly Ser Gly Gly Gly Gly Ser Gly Gly
145                 150                 155                 160

Gly Gly Ser Gln Ser Ala Leu Thr Gln Pro Ala Ser Val Ser Gly Ser
                165                 170                 175

Pro Gly Gln Ser Ile Thr Ile Ser Cys Thr Gly Thr Ser Ser Asp Val
            180                 185                 190

Gly Gly Tyr Asn Tyr Val Ser Trp Tyr Gln Gln His Pro Gly Lys Ala
        195                 200                 205

Pro Lys Leu Met Ile Tyr Glu Val Ser Asn Arg Pro Ser Gly Val Ser
    210                 215                 220

Asn Arg Phe Ser Gly Ser Lys Ser Gly Asn Thr Ala Ser Leu Thr Ile
225                 230                 235                 240

Ser Gly Leu Gln Ala Glu Asp Glu Ala Asp Tyr Tyr Cys Ser Ser Tyr
                245                 250                 255

Thr Ser Ser Ser Pro Leu Val Phe Gly Thr Gly Thr Lys Val Thr Val
            260                 265                 270

Leu Ala Ala Ala Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
```

```
                305                 310                 315                 320
Asp Ile Tyr Ile Trp Ala Pro Leu Ala Gly Thr Cys Gly Val Leu Leu
                    325                 330                 335
Leu Ser Leu Val Ile Thr Leu Tyr Cys Lys Arg Gly Arg Lys Lys Leu
                    340                 345                 350
Leu Tyr Ile Phe Lys Gln Pro Phe Met Arg Pro Val Gln Thr Thr Gln
                    355                 360                 365
Glu Glu Asp Gly Cys Ser Cys Arg Phe Pro Glu Glu Glu Gly Gly
                370                 375                 380
Cys Glu Leu Arg Val Lys Phe Ser Arg Ser Ala Asp Ala Pro Ala Tyr
385                 390                 395                 400
Gln Gln Gly Gln Asn Gln Leu Tyr Asn Glu Leu Asn Leu Gly Arg Arg
                    405                 410                 415
Glu Glu Tyr Asp Val Leu Asp Lys Arg Arg Gly Arg Asp Pro Glu Met
                    420                 425                 430
Gly Gly Lys Pro Arg Arg Lys Asn Pro Gln Glu Gly Leu Tyr Asn Glu
                    435                 440                 445
Leu Gln Lys Asp Lys Met Ala Glu Ala Tyr Ser Glu Ile Gly Met Lys
                    450                 455                 460
Gly Glu Arg Arg Arg Gly Lys Gly His Asp Gly Leu Tyr Gln Gly Leu
465                 470                 475                 480
Ser Thr Ala Thr Lys Asp Thr Tyr Asp Ala Leu His Met Gln Ala Leu
                    485                 490                 495
Pro Pro Arg

<210> SEQ ID NO 11
<211> LENGTH: 1491
<212> TYPE: DNA
<213> ORGANISM: Artificial
<220> FEATURE:
<223> OTHER INFORMATION: nucleotide sequence of CAR D0130 CD123 MB40-H08
      CD8 BBz

<400> SEQUENCE: 11
atgctcttgc tcgtgacttc tttgcttttg tgcgaacttc cgcacccagc cttccttttg      60
atacctcagg ttcagctggt acagtccggc gcagaggtta aaaagccagg aagctccgtg     120
aaggtttcat gcaaggcatc cggtggtaca ttctcatcat atgcgatcag ttgggtccgg     180
caggctcccg gccagggatt ggagtggatg ggagggataa tccccatatt tggcacagca     240
aattacgctc aaaaatttca aggtagagta acgataactg cggatgaatc tactagcacg     300
gcgtatatgg aactgagtag tctccggagc gaggatacag cggtttacta ctgcgctagg     360
aatgaatggt actcctatta ttactactac atgggtgtgt ggggtaaagg aactactgtt     420
acggtgtcca gtggaggagg aggtagcgga ggtggaggat caggcggtgg gggctcccaa     480
agtgcgctta cacaacctgc aagcgtatca ggttccccag gcaatcaat  acaataagc     540
tgcacgggta cctccagtga tgtcggaggt tacaactacg tgtcatggta ccagcaacat     600
ccaggcaagg caccaaaact tatgatctac gaagtcagca acagacccag cggtgtaagc     660
aataggttta gcggatctaa gtccggtaat actgcttctc tgacaatctc aggactccaa     720
gccgaggacg aagctgatta ctactgctca tcatacacca gtagctctac actggtggtg     780
ttcggagggg gaacgaagct taccgtactg gcgccgcaa  cgaccactcc tgcaccccgc     840
cctccgactc cggccccaac cattgccagc cagcccctgt ccctgcggcc ggaagcctgc     900
agaccggctg ccggcggagc cgtccatacc cggggactgg atttcgcctg cgatatctat     960
```

-continued

```
atctgggcac cactcgccgg aacctgtgga gtgctgctgc tgtcccttgt gatcaccctg    1020
tactgcaagc gcggacggaa gaaactcttg tacatcttca agcagccgtt catgcgccct    1080
gtgcaaacca cccaagaaga ggacgggtgc tcctgccggt ccccggaaga ggaagagggc    1140
ggctgcgaac tgcgcgtgaa gttttcccgg tccgccgacg ctccggcgta ccagcagggg    1200
caaaaccagc tgtacaacga acttaacctc ggtcgccggg aagaatatga cgtgctggac    1260
aagcggcggg gaagagatcc cgagatgggt ggaaagccgc ggcggaagaa ccctcaggag    1320
ggcttgtaca cgagctgca aaaggacaaa atggccgaag cctactccga gattggcatg    1380
aagggagagc gcagacgcgg gaagggacac gatggactgt accagggact gtcaaccgcg    1440
actaaggaca cttacgacgc cctgcacatg caggccctgc ccccgcgcta a             1491
```

<210> SEQ ID NO 12
<211> LENGTH: 496
<212> TYPE: PRT
<213> ORGANISM: Artificial
<220> FEATURE:
<223> OTHER INFORMATION: amino acid sequence of CAR D0130 CDAR123
      MB40-H08 CD8 BBz

<400> SEQUENCE: 12

```
Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
                20                  25                  30

Val Lys Lys Pro Gly Ser Ser Val Lys Val Ser Cys Lys Ala Ser Gly
            35                  40                  45

Gly Thr Phe Ser Ser Tyr Ala Ile Ser Trp Val Arg Gln Ala Pro Gly
        50                  55                  60

Gln Gly Leu Glu Trp Met Gly Gly Ile Ile Pro Ile Phe Gly Thr Ala
65                  70                  75                  80

Asn Tyr Ala Gln Lys Phe Gln Gly Arg Val Thr Ile Thr Ala Asp Glu
                85                  90                  95

Ser Thr Ser Thr Ala Tyr Met Glu Leu Ser Ser Leu Arg Ser Glu Asp
            100                 105                 110

Thr Ala Val Tyr Tyr Cys Ala Arg Asn Glu Trp Tyr Ser Tyr Tyr Tyr
        115                 120                 125

Tyr Tyr Met Gly Val Trp Gly Lys Gly Thr Thr Val Thr Val Ser Ser
    130                 135                 140

Gly Gly Gly Gly Ser Gly Gly Gly Ser Gly Gly Gly Ser Gln
145                 150                 155                 160

Ser Ala Leu Thr Gln Pro Ala Ser Val Ser Gly Ser Pro Gly Gln Ser
                165                 170                 175

Ile Thr Ile Ser Cys Thr Gly Thr Ser Ser Asp Val Gly Gly Tyr Asn
            180                 185                 190

Tyr Val Ser Trp Tyr Gln Gln His Pro Gly Lys Ala Pro Lys Leu Met
        195                 200                 205

Ile Tyr Glu Val Ser Asn Arg Pro Ser Gly Val Ser Asn Arg Phe Ser
    210                 215                 220

Gly Ser Lys Ser Gly Asn Thr Ala Ser Leu Thr Ile Ser Gly Leu Gln
225                 230                 235                 240

Ala Glu Asp Glu Ala Asp Tyr Tyr Cys Ser Ser Tyr Thr Ser Ser Ser
                245                 250                 255

Thr Leu Val Val Phe Gly Gly Gly Thr Lys Leu Thr Val Leu Ala Ala
```

```
                260             265             270
Ala Thr Thr Thr Pro Ala Pro Arg Pro Pro Thr Pro Ala Pro Thr Ile
                275             280             285

Ala Ser Gln Pro Leu Ser Leu Arg Pro Glu Ala Cys Arg Pro Ala Ala
        290             295             300

Gly Gly Ala Val His Thr Arg Gly Leu Asp Phe Ala Cys Asp Ile Tyr
305             310             315             320

Ile Trp Ala Pro Leu Ala Gly Thr Cys Gly Val Leu Leu Ser Leu
                325             330             335

Val Ile Thr Leu Tyr Cys Lys Arg Gly Arg Lys Leu Leu Tyr Ile
        340             345             350

Phe Lys Gln Pro Phe Met Arg Pro Val Gln Thr Thr Gln Glu Glu Asp
        355             360             365

Gly Cys Ser Cys Arg Phe Pro Glu Glu Glu Gly Gly Cys Glu Leu
    370             375             380

Arg Val Lys Phe Ser Arg Ser Ala Asp Ala Pro Ala Tyr Gln Gln Gly
385             390             395             400

Gln Asn Gln Leu Tyr Asn Glu Leu Asn Leu Gly Arg Arg Glu Glu Tyr
                405             410             415

Asp Val Leu Asp Lys Arg Arg Gly Arg Asp Pro Glu Met Gly Gly Lys
                420             425             430

Pro Arg Arg Lys Asn Pro Gln Glu Gly Leu Tyr Asn Glu Leu Gln Lys
                435             440             445

Asp Lys Met Ala Glu Ala Tyr Ser Glu Ile Gly Met Lys Gly Glu Arg
        450             455             460

Arg Arg Gly Lys Gly His Asp Gly Leu Tyr Gln Gly Leu Ser Thr Ala
465             470             475             480

Thr Lys Asp Thr Tyr Asp Ala Leu His Met Gln Ala Leu Pro Pro Arg
                485             490             495

<210> SEQ ID NO 13
<211> LENGTH: 66
<212> TYPE: DNA
<213> ORGANISM: Artificial
<220> FEATURE:
<223> OTHER INFORMATION: nucleotide sequence of leader/signal peptide
      sequence

<400> SEQUENCE: 13
atgctgctgc tggtgaccag cctgctgctg tgcgaactgc cgcatccggc gtttctgctg    60
attccg                                                               66

<210> SEQ ID NO 14
<211> LENGTH: 22
<212> TYPE: PRT
<213> ORGANISM: Artificial
<220> FEATURE:
<223> OTHER INFORMATION: amino acid sequence of leader/signal peptide
      sequence

<400> SEQUENCE: 14

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 15
<211> LENGTH: 1485
```

<212> TYPE: DNA
<213> ORGANISM: Artificial
<220> FEATURE:
<223> OTHER INFORMATION: nucleotide sequence of CAR D0131 CD123 MB42-D03
      CD8 BBz

<400> SEQUENCE: 15

```
atgctcttgc tcgtgacttc tttgcttttg tgcgaacttc cgcacccagc cttccttttg        60
atacctcaag ttcaacttgt acaatccgga gcagaagtaa aaaaacccgg ggccagcgta       120
aaagtttcct gtaaagctag cggctacaca ttcactagct acggcatctc ctgggtacgc       180
caagcgccag acaaggcct cgaatggatg gatggattag cgcttacaa cggtaatacc        240
aattatgcac aaaagctgca aggacgggtt acgatgacaa cagacacgag cacgagtacg       300
gcctatatgg agctgagaag tcttcgaagt gatgacactg cagtatatta ctgtgcccgc       360
ggagcgtact acgattttg gagcagttac agctggtttg atccctgggg gcaggggacc       420
ctggttactg ttagctcagg tgggggggc tcaggaggtg aggaagcgg gggtggagga        480
tctagttatg ttcttacca gccgccttct gtcagtgtgg cccctggtaa gacagccagg       540
ataacctgtg gtgggaattc aattggcagc aaatcagtac agtggtacca acaaaaaccc       600
ggacaagccc ccgttttggt catatatgat gatagcgata ggccttctgg aatcccggag       660
aggttttcag gatcaaatag cgggaacacc gccacattga ccataagtcg agtcgaggcg       720
ggcgacgaag ctgactatta ttgtcaagtg tgggatagct ctagtgatgt ggtattcggt       780
ggggggacca aattgacagt cttggcggcc gcaacgacca ctcctgcacc cgccctccg       840
actccggccc caaccattgc cagcagccc tgtccctgc ggccggaagc tgcagaccg        900
gctgccggcg gagccgtcca tacccgggga ctggattcg cctgcgatat ctatatctgg       960
gcaccactcg ccggaacctg tggagtgctg ctgctgtccc ttgtgatcac cctgtactgc      1020
aagcgcggac ggaagaaact cttgtacatc ttcaagcagc cgttcatgcg ccctgtgcaa      1080
accacccaag aagaggacgg tgctcctgc cggttcccgg aagaggaaga gggcggctgc      1140
gaactgcgcg tgaagttttc ccggtccgcc gacgctccgg cgtaccagca ggggcaaaac      1200
cagctgtaca cgaacttaa cctcggtcgc cgggaagaat atgacgtgct ggacaagcgg      1260
cggggaagag atcccgagat gggtggaaag ccgcggcgga agaaccctca ggagggcttg      1320
tacaacgagc tgcaaaagga caaaatggcc gaagcctact ccgagattgg catgaaggga      1380
gagcgcagac gcgggaaggg cacgatggga ctgtaccagg actgtcaac cgcgactaag      1440
gacacttacg acgccctgca catgcaggcc ctgccccgc gctaa                      1485
```

<210> SEQ ID NO 16
<211> LENGTH: 494
<212> TYPE: PRT
<213> ORGANISM: Artificial
<220> FEATURE:
<223> OTHER INFORMATION: amino acid sequence of CAR D0131 CD123 MB42-D03
      CD8 BBz

<400> SEQUENCE: 16

```
Met Leu Leu Leu Val Thr Ser Leu Leu Cys Glu Leu Pro His Pro
1               5                   10                  15

Ala Phe Leu Leu Ile Pro Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Ser Tyr Gly Ile Ser Trp Val Arg Gln Ala Pro Gly
```

```
                 50                  55                  60
Gln Gly Leu Glu Trp Met Gly Trp Ile Ser Ala Tyr Asn Gly Asn Thr
 65                  70                  75                  80

Asn Tyr Ala Gln Lys Leu Gln Gly Arg Val Thr Met Thr Thr Asp Thr
                     85                  90                  95

Ser Thr Ser Thr Ala Tyr Met Glu Leu Arg Ser Leu Arg Ser Asp Asp
                100                 105                 110

Thr Ala Val Tyr Tyr Cys Ala Arg Gly Ala Tyr Asp Phe Trp Ser
                115                 120                 125

Ser Tyr Ser Trp Phe Asp Pro Trp Gly Gln Gly Thr Leu Val Thr Val
                130                 135                 140

Ser Ser Gly Gly Gly Gly Ser Gly Gly Gly Gly Ser Gly Gly Gly Gly
145                 150                 155                 160

Ser Ser Tyr Val Leu Thr Gln Pro Pro Ser Val Ser Val Ala Pro Gly
                165                 170                 175

Lys Thr Ala Arg Ile Thr Cys Gly Gly Asn Ser Ile Gly Ser Lys Ser
                180                 185                 190

Val Gln Trp Tyr Gln Gln Lys Pro Gly Gln Ala Pro Val Leu Val Ile
                195                 200                 205

Tyr Asp Asp Ser Asp Arg Pro Ser Gly Ile Pro Glu Arg Phe Ser Gly
210                 215                 220

Ser Asn Ser Gly Asn Thr Ala Thr Leu Thr Ile Ser Arg Val Glu Ala
225                 230                 235                 240

Gly Asp Glu Ala Asp Tyr Tyr Cys Gln Val Trp Asp Ser Ser Ser Asp
                245                 250                 255

Val Val Phe Gly Gly Gly Thr Lys Leu Thr Val Leu Ala Ala Ala Thr
                260                 265                 270

Thr Thr Pro Ala Pro Arg Pro Pro Thr Pro Ala Pro Thr Ile Ala Ser
                275                 280                 285

Gln Pro Leu Ser Leu Arg Pro Glu Ala Cys Arg Pro Ala Ala Gly Gly
                290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
                340                 345                 350

Gln Pro Phe Met Arg Pro Val Gln Thr Thr Gln Glu Glu Asp Gly Cys
                355                 360                 365

Ser Cys Arg Phe Pro Glu Glu Glu Glu Gly Gly Cys Glu Leu Arg Val
370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
                420                 425                 430

Arg Lys Asn Pro Gln Glu Gly Leu Tyr Asn Glu Leu Gln Lys Asp Lys
                435                 440                 445

Met Ala Glu Ala Tyr Ser Glu Ile Gly Met Lys Gly Glu Arg Arg Arg
                450                 455                 460

Gly Lys Gly His Asp Gly Leu Tyr Gln Gly Leu Ser Thr Ala Thr Lys
465                 470                 475                 480
```

Asp Thr Tyr Asp Ala Leu His Met Gln Ala Leu Pro Pro Arg
              485                 490

<210> SEQ ID NO 17
<211> LENGTH: 1488
<212> TYPE: DNA
<213> ORGANISM: Artificial
<220> FEATURE:
<223> OTHER INFORMATION: nucleotide sequence of CAR D0132 CD123 MB42-E02
      CD8 BBz

<400> SEQUENCE: 17

| | | |
|---|---|---|
| atgctcttgc tcgtgacttc tttgcttttg tgcgaacttc cgcacccagc cttccttttg | 60 |
| atacctcagg tacaacttgt ccaatccggt gccgaagtca agaaacctgg agcatccgta | 120 |
| aaggtcagct gcaaagccag cgggtatacc ttcacgagtt atggaatctc ttgggtcaga | 180 |
| caagcgccag gccaagggct ggaatggatg ggatggataa gcgcatacaa tggcaacaca | 240 |
| aattatgctc agaaactgca aggtcgcgtt accatgacca ccgacacatc aacgtccacc | 300 |
| gcctatatgg agcttagaag cttgcgaagt gacgacacag ccgtgtatta ttgcgctcgg | 360 |
| ggtgcttatt atgacttctg gtctggttac tcttggtttg atccttgggg tcaaggcacg | 420 |
| cttgtgacgg tatcctcagg aggcggcgga agtggagggg gtggatcagg tggtggtgga | 480 |
| agccaatcag tactcactca gccaccaagt gtatcagtgg ctccaggtca gaccgcgcgg | 540 |
| ataccgtgtg gaggaaacaa catcgggtca aagggcgtac attggtacca gcagaagtct | 600 |
| ggacaagctc ccgttatggt ggtgtacgat gactcagaca ggccatccgg catccctgag | 660 |
| cggttcagcg gttctaattc aggaaataca gcaacattga ccatcagcag ggtcgaagcc | 720 |
| ggtgacgagg cggactatta ttgtcaggtc tgggattcaa gcggcgacct tgttttgttt | 780 |
| gggggtggaa ctaaactgac cgtactggcg ccgcaacga ccactcctgc accccgccct | 840 |
| ccgactccgg ccccaaccat tgccagccag cccctgtccc tgcggccgga agcctgcaga | 900 |
| ccggctgccg gcggagccgt ccatacccgg ggactggatt tcgcctgcga tatctatatc | 960 |
| tgggcaccac tcgccggaac ctgtggagtc ctgctgctgt cccttgtgat caccctgtac | 1020 |
| tgcaagcgcg gacggaagaa actcttgtac atcttcaagc agccgttcat gcgccctgtg | 1080 |
| caaaccaccc aagaagagga cggggtgctcc tgccggttcc cggaagagga gagggcggc | 1140 |
| tgcgaactgc gcgtgaagtt ttcccggtcc gccgacgctc cggcgtacca gcaggggcaa | 1200 |
| aaccagctgt acaacgaact taacctcggt cgccgggaag aatatgacgt gctggacaag | 1260 |
| cggcggggaa gagatcccga gatgggtgga aagccgcggc ggaagaaccc tcaggagggc | 1320 |
| ttgtacaacg agctgcaaaa ggacaaaatg gccgaagcct actccgagat tggcatgaag | 1380 |
| ggagagcgca gacgcgggaa gggacacgat ggactgtacc agggactgtc aaccgcgact | 1440 |
| aaggacactt acgacgccct gcacatgcag gccctgcccc cgcgctaa | 1488 |

<210> SEQ ID NO 18
<211> LENGTH: 495
<212> TYPE: PRT
<213> ORGANISM: Artificial
<220> FEATURE:
<223> OTHER INFORMATION: amino acid sequence of CAR D0132 CD123 MB42-E02
      CD8 BBz

<400> SEQUENCE: 18

Met Leu Leu Leu Val Thr Ser Leu Leu Leu Cys Glu Leu Pro His Pro
1               5                   10                  15

-continued

```
Ala Phe Leu Leu Ile Pro Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Ser Tyr Gly Ile Ser Trp Val Arg Gln Ala Pro Gly
 50                  55                  60

Gln Gly Leu Glu Trp Met Gly Trp Ile Ser Ala Tyr Asn Gly Asn Thr
 65                  70                  75                  80

Asn Tyr Ala Gln Lys Leu Gln Gly Arg Val Thr Met Thr Thr Asp Thr
                85                  90                  95

Ser Thr Ser Thr Ala Tyr Met Glu Leu Arg Ser Leu Arg Ser Asp Asp
                100                 105                 110

Thr Ala Val Tyr Tyr Cys Ala Arg Gly Ala Tyr Tyr Asp Phe Trp Ser
            115                 120                 125

Gly Tyr Ser Trp Phe Asp Pro Trp Gly Gln Gly Thr Leu Val Thr Val
        130                 135                 140

Ser Ser Gly Gly Gly Ser Gly Gly Gly Ser Gly Gly Gly Gly
145                 150                 155                 160

Ser Gln Ser Val Leu Thr Gln Pro Pro Ser Val Ser Val Ala Pro Gly
        165                 170                 175

Gln Thr Ala Arg Ile Pro Cys Gly Gly Asn Asn Ile Gly Ser Lys Gly
            180                 185                 190

Val His Trp Tyr Gln Gln Lys Ser Gly Gln Ala Pro Val Met Val Val
        195                 200                 205

Tyr Asp Asp Ser Asp Arg Pro Ser Gly Ile Pro Glu Arg Phe Ser Gly
 210                 215                 220

Ser Asn Ser Gly Asn Thr Ala Thr Leu Thr Ile Ser Arg Val Glu Ala
225                 230                 235                 240

Gly Asp Glu Ala Asp Tyr Tyr Cys Gln Val Trp Asp Ser Ser Gly Asp
                245                 250                 255

Leu Val Leu Phe Gly Gly Gly Thr Lys Leu Thr Val Leu Ala Ala Ala
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
 290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
 370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
```

```
                435                 440                 445
Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 19
<211> LENGTH: 1488
<212> TYPE: DNA
<213> ORGANISM: Artificial
<220> FEATURE:
<223> OTHER INFORMATION: nucleotide sequence of CAR D0133 CD123 MB42-E12
      CD8 BBz

<400> SEQUENCE: 19
```

| | | | |
|---|---|---|---|
| atgctcttgc tcgtgacttc tttgcttttg tgcgaacttc cgcacccagc cttcctttg | | | 60 |
| atacctcagg tgcaactggt tcaatctggc gccgaagtaa aaaaaccggg cgccagcgtt | | | 120 |
| aaagtatcct gtaaagcgag cggctacaca tttaccagct atggcatctc atgggtgaga | | | 180 |
| caagcgcccg gccaaggact ggaatggatg ggtggatca gcgcctacaa tgggaacact | | | 240 |
| aactacgcac agaagctgca aggcggggtt accatgacga ccgatacgag tacctcaaca | | | 300 |
| gcgtacatgg aacttcgaag tctgcgcagt gacgacaccg cagtatacta ctgcgcccga | | | 360 |
| ggagcgtact acgacttctg gtccagctac tcttggtttg acccgtgggg ccaaggaaca | | | 420 |
| ctcgtaacag tatccagtgg aggaggcggg tcaggtggcg gtggttcagg cggtggcggg | | | 480 |
| tcatcttatg ttctcactca gcccccatcc gtgtccgtag cgccagggaa acagcccgg | | | 540 |
| attacgtgcg gggaaaataa taggcagc aagagcgttc attggtatca acaaaagcca | | | 600 |
| gggcaggcac cggtcttggt ggtctacgac gacagtgatc ggccctcagg aattcctgaa | | | 660 |
| agattctcag ggtcaaattc tggcaacacg gcgacgctta caataagcag ggtcgaggca | | | 720 |
| ggagacgaag ccgattatta ctgccaggta tgggattcct cttctgacca tgtggtgttt | | | 780 |
| ggcggtggca caaagctcac ggtcttggcg ccgcaacga ccactcctgc accccgccct | | | 840 |
| ccgactccgg ccccaaccat tgccagccag cccctgtccc tgcggccgga agcctgcaga | | | 900 |
| ccggctgccg gcggagccgt ccatacccgg ggactggatt tcgcctgcga tatctatatc | | | 960 |
| tgggcaccac tcgccggaac ctgtggagtg ctgctgctgt ccttgtgat caccctgtac | | | 1020 |
| tgcaagcgcg gacggaagaa actcttgtac atcttcaagc agccgttcat gcgccctgtg | | | 1080 |
| caaaccaccc aagaagagga cgggtgctcc tgccggttcc cggaagagga gagggcggc | | | 1140 |
| tgcgaactgc gcgtgaagtt tccccggtcc gccgacgctc cggcgtacca gcaggggcaa | | | 1200 |
| aaccagctgt acaacgaact taacctcggt cgccgggaag aatatgacgt gctggacaag | | | 1260 |
| cggcggggaa gagatcccga gatgggtgga aagccgcggc ggaagaaccc tcaggagggc | | | 1320 |
| ttgtacaacg agctgcaaaa ggacaaaatg gccgaagcct actccgagat tggcatgaag | | | 1380 |
| ggagagcgca gacgcgggaa gggacacgat ggactgtacc agggactgtc aaccgcgact | | | 1440 |
| aaggacactt acgacgccct gcacatgcag gccctgcccc cgcgctaa | | | 1488 |

```
<210> SEQ ID NO 20
<211> LENGTH: 495
<212> TYPE: PRT
<213> ORGANISM: Artificial
<220> FEATURE:
<223> OTHER INFORMATION: amino acid sequence of CAR D0133 CD123 MB42-E12
```

CD8 BBz

<400> SEQUENCE: 20

Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Ser Tyr Gly Ile Ser Trp Val Arg Gln Ala Pro Gly
    50                  55                  60

Gln Gly Leu Glu Trp Met Gly Trp Ile Ser Ala Tyr Asn Gly Asn Thr
65                  70                  75                  80

Asn Tyr Ala Gln Lys Leu Gln Gly Arg Val Thr Met Thr Thr Asp Thr
                85                  90                  95

Ser Thr Ser Thr Ala Tyr Met Glu Leu Arg Ser Leu Arg Ser Asp Asp
            100                 105                 110

Thr Ala Val Tyr Tyr Cys Ala Arg Gly Ala Tyr Tyr Asp Phe Trp Ser
        115                 120                 125

Ser Tyr Ser Trp Phe Asp Pro Trp Gly Gln Gly Thr Leu Val Thr Val
    130                 135                 140

Ser Ser Gly Gly Gly Gly Ser Gly Gly Gly Gly Ser Gly Gly Gly Gly
145                 150                 155                 160

Ser Ser Tyr Val Leu Thr Gln Pro Pro Ser Val Ser Val Ala Pro Gly
            165                 170                 175

Lys Thr Ala Arg Ile Thr Cys Gly Gly Asn Asn Ile Gly Ser Lys Ser
        180                 185                 190

Val His Trp Tyr Gln Gln Lys Pro Gly Gln Ala Pro Val Leu Val Val
    195                 200                 205

Tyr Asp Asp Ser Asp Arg Pro Ser Gly Ile Pro Glu Arg Phe Ser Gly
210                 215                 220

Ser Asn Ser Gly Asn Thr Ala Thr Leu Thr Ile Ser Arg Val Glu Ala
225                 230                 235                 240

Gly Asp Glu Ala Asp Tyr Tyr Cys Gln Val Trp Asp Ser Ser Ser Asp
            245                 250                 255

His Val Val Phe Gly Gly Gly Thr Lys Leu Thr Val Leu Ala Ala Ala
        260                 265                 270

Thr Thr Thr Pro Ala Pro Arg Pro Pro Thr Pro Ala Pro Thr Ile Ala
    275                 280                 285

Ser Gln Pro Leu Ser Leu Arg Pro Glu Ala Cys Arg Pro Ala Ala Gly
290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
            325                 330                 335

Ile Thr Leu Tyr Cys Lys Arg Gly Arg Lys Lys Leu Leu Tyr Ile Phe
        340                 345                 350

Lys Gln Pro Phe Met Arg Pro Val Gln Thr Thr Gln Glu Glu Asp Gly
    355                 360                 365

Cys Ser Cys Arg Phe Pro Glu Glu Glu Glu Gly Gly Cys Glu Leu Arg
370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
        420                 425                 430

Arg Arg Lys Asn Pro Gln Glu Gly Leu Tyr Asn Glu Leu Gln Lys Asp
    435                 440                 445

Lys Met Ala Glu Ala Tyr Ser Glu Ile Gly Met Lys Gly Glu Arg Arg
450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 21
<211> LENGTH: 1491
<212> TYPE: DNA
<213> ORGANISM: Artificial
<220> FEATURE:
<223> OTHER INFORMATION: nucleotide sequence of CAR D0134 CD123 MB44-H01
      CD8 BBz

<400> SEQUENCE: 21

| | | |
|---|---|---|
| atgctcttgc tcgtgacttc tttgcttttg tgcgaacttc cgcacccagc cttccttttg | 60 |
| atacctcagg ttcaactcgt tcaaagcggg gctgaagtta aaagccgggg tctagcgtt | 120 |
| aaggtttcct gtaaagcgtc tggaggaact ttttcctcct acgccattag ctgggtacga | 180 |
| caagctccag acagggtct cgagtggatg gtgggataa ttccgatctt tggaactgcg | 240 |
| aattacgccc agcgattcca aggccgagtt acgattactg ctgacgagag tacgtctacc | 300 |
| gcatacatgg aattgagttc tcttcggtca gaagatacag cggtatacta ctgcgctagg | 360 |
| ggcctcggca ctagttacta ctattactat atggatgtat ggggcaaggg cacaactgtg | 420 |
| actgtttcta gcggtggcgg cgggtccggt ggtggtggaa gcggtggcgg agggtcacag | 480 |
| tcagtactca ctcagccacc gagtgcgtct ggctcaccag acaatctgt aaccattagt | 540 |
| tgcacaggca ctagctctga tgttgggggc tacaattatg tctcctggta ccaacaacac | 600 |
| cccggaaaag cgccgaagct gatgatctac gaggtgagta atagacctag tggtgttagt | 660 |
| aacaggttct caggctctaa gtccggtaac accgcgtctc tcactatatc tggccttcaa | 720 |
| gctgaggacg aggcagacta ttattgcagc tcatacacct caagcagtac cccgttgtg | 780 |
| tttggtggcg gtaccaaatt gactgtgctg gcggccgcaa cgaccactcc tgcaccccgc | 840 |
| cctccgactc cggccccaac cattgccagc cagcccctgt ccctgcggcc ggaagcctgc | 900 |
| agaccggctg ccggcggagc cgtccatacc cggggactgg atttcgcctg cgatatctat | 960 |
| atctgggcac cactcgccgg aacctgtgga gtgctgctgc tgtcccttgt gatcaccctg | 1020 |
| tactgcaagc gcggacggaa gaaactcttg tacatcttca gcagccgtt catgcgccct | 1080 |
| gtgcaaacca cccaagaaga ggacgggtgc tcctgccggt tccggaagga ggagagggc | 1140 |
| ggctgcgaac tgcgcgtgaa gtttcccgg tccgccgacg ctccggcgta ccagcagggg | 1200 |
| caaaaccagc tgtacaacga acttaacctc ggtcgccggg aagaatatga cgtgctggac | 1260 |
| aagcggcggg gaagagatcc cgagatgggt ggaaagccgc ggcggaagaa ccctcaggag | 1320 |
| ggcttgtaca acgagctgca aaaggacaaa atggccgaag cctactccga gattggcatg | 1380 |
| aagggagagc gcagacgcgg gaagggacac gatggactgt accagggact gtcaaccgcg | 1440 |
| actaaggaca cttacgacgc cctgcacatg caggccctgc cccgcgcta a | 1491 |

<210> SEQ ID NO 22
<211> LENGTH: 496
<212> TYPE: PRT
<213> ORGANISM: Artificial
<220> FEATURE:
<223> OTHER INFORMATION: amino acid sequence of CAR D0134 CD123 MB44-H01 CD8 BBz

<400> SEQUENCE: 22

```
Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Gly Thr Phe Ser Ser Tyr Ala Ile Ser Trp Val Arg Gln Ala Pro Gly
    50                  55                  60

Gln Gly Leu Glu Trp Met Gly Gly Ile Ile Pro Ile Phe Gly Thr Ala
65                  70                  75                  80

Asn Tyr Ala Gln Arg Phe Gln Gly Arg Val Thr Ile Thr Ala Asp Glu
                85                  90                  95

Ser Thr Ser Thr Ala Tyr Met Glu Leu Ser Ser Leu Arg Ser Glu Asp
            100                 105                 110

Thr Ala Val Tyr Tyr Cys Ala Arg Gly Leu Gly Thr Ser Tyr Tyr Tyr
        115                 120                 125

Tyr Tyr Met Asp Val Trp Gly Lys Gly Thr Thr Val Thr Val Ser Ser
    130                 135                 140

Gly Gly Gly Gly Ser Gly Gly Gly Ser Gly Gly Gly Gly Ser Gln
145                 150                 155                 160

Ser Val Leu Thr Gln Pro Pro Ser Ala Ser Gly Ser Pro Gly Gln Ser
                165                 170                 175

Val Thr Ile Ser Cys Thr Gly Thr Ser Ser Asp Val Gly Gly Tyr Asn
            180                 185                 190

Tyr Val Ser Trp Tyr Gln Gln His Pro Gly Lys Ala Pro Lys Leu Met
        195                 200                 205

Ile Tyr Glu Val Ser Asn Arg Pro Ser Gly Val Ser Asn Arg Phe Ser
    210                 215                 220

Gly Ser Lys Ser Gly Asn Thr Ala Ser Leu Thr Ile Ser Gly Leu Gln
225                 230                 235                 240

Ala Glu Asp Glu Ala Asp Tyr Tyr Cys Ser Ser Tyr Thr Ser Ser Ser
                245                 250                 255

Thr Pro Val Val Phe Gly Gly Gly Thr Lys Leu Thr Val Leu Ala Ala
            260                 265                 270

Ala Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Lys Arg Gly Arg Lys Lys Leu Leu Tyr Ile
            340                 345                 350

Phe Lys Gln Pro Phe Met Arg Pro Val Gln Thr Thr Gln Glu Glu Asp
        355                 360                 365
```

```
Gly Cys Ser Cys Arg Phe Pro Glu Glu Glu Glu Gly Cys Glu Leu
        370                 375                 380
Arg Val Lys Phe Ser Arg Ser Ala Asp Ala Pro Ala Tyr Gln Gln Gly
385                 390                 395                 400
Gln Asn Gln Leu Tyr Asn Glu Leu Asn Leu Gly Arg Arg Glu Glu Tyr
            405                 410                 415
Asp Val Leu Asp Lys Arg Arg Gly Arg Asp Pro Glu Met Gly Gly Lys
        420                 425                 430
Pro Arg Arg Lys Asn Pro Gln Glu Gly Leu Tyr Asn Glu Leu Gln Lys
            435                 440                 445
Asp Lys Met Ala Glu Ala Tyr Ser Glu Ile Gly Met Lys Gly Glu Arg
        450                 455                 460
Arg Arg Gly Lys Gly His Asp Gly Leu Tyr Gln Gly Leu Ser Thr Ala
465                 470                 475                 480
Thr Lys Asp Thr Tyr Asp Ala Leu His Met Gln Ala Leu Pro Pro Arg
            485                 490                 495

<210> SEQ ID NO 23
<211> LENGTH: 1482
<212> TYPE: DNA
<213> ORGANISM: Artificial
<220> FEATURE:
<223> OTHER INFORMATION: nucleotide sequence of CAR LTG2078 CD123 M12306
      CD8 BBz

<400> SEQUENCE: 23
atgctgctgc tggtgaccag cctgctgctg tgcgaactgc cgcatccggc gtttctgctg      60
attccggaag tccaattggt gcagagcgga tccgaactta gaaacctggc gcgagcgtg     120 aaagtgtcct gcaaggcctc cggagggact ttctcgtcgt acgccattag ctgggtccgc    180
caagctcctg gccaaggcct ggagtggatg ggcgggatta tccccatctt cgggactgcg    240
aactacgccc agaagtttca gggccgggtc actatcaccg ccgacgaatc aacctcgacc    300
gcctacatgg aactgtcctc gcttcggtcc gaggatactg ccgtgtacta ttgtgcctca    360
acggccagac gcggatggga caccgctggt ccgctcgatt actggggcca gggaaccctc    420
gtgaccgtca gctccggagg aggaggctcc ggtggtggag gatccggggg tggtggatcc    480
gacatccaaa tgacccagtc cccctcgtcc ctgagcgcct ctgtgggcga cagagtgaca    540
attgcatgca gggcctcaca gactatctcc cgctacctga actggtacca gcagaagcca    600
ggaaaggccc ctaagctgct catctacgct cgtcctcgc tccaatccgg ggtgtcctca    660
cggttttccg gatcgggttc cggcaccgag ttcaccctga ccatcagcag cctgcagccc    720
gaggacttcg caacctactt ctgccagcaa acctactccc cgccgattac gttcggacag    780
gggactcggc tggaaatcaa gcggccgca actaccaccc ctgcccctcg ccgccgact    840 ccggccccaa ccatcgcaag ccaaccccctc tccttgcgcc ccgaagcttg ccgcccggcc    900
gcgggtggag ccgtgcatac ccgggggctg actttgcct cgatatcta catttgggcc    960 ccgctggccg gcacttgcgg cgtgctcctg ctgtcgctgg tcatcaccct ttactgcaag   1020
aggggccgga gaagctgct ttacatcttc aagcagccgt tcatgcggcc cgtgcagacg   1080
actcaggaag aggacggatg ctcgtgcaga ttccctgagg aggaagaggg gggatgcgaa   1140
ctgcgcgtca gttctcacg gtccgccgac gccccgcat atcaacaggg ccagaatcag   1200
ctctacaacg agctgaacct ggaaggaga gaggagtacg acgtgctgga caagcgacgc   1260
ggacgcgacc cggagatggg ggggaaacca cggcggaaaa accctcagga aggactgtac   1320
```

-continued

```
aacgaactcc agaaagacaa gatggcggaa gcctactcag aaatcgggat gaagggagag   1380
cggaggaggg gaaagggtca cgacgggctg taccaggac  tgagcaccgc cactaaggat   1440
acctacgatg ccttgcatat gcaagcactc ccaccccggt ag                     1482
```

<210> SEQ ID NO 24
<211> LENGTH: 493
<212> TYPE: PRT
<213> ORGANISM: Artificial
<220> FEATURE:
<223> OTHER INFORMATION: amino acid sequence of CAR LTG2078 CD123 M12306 CD8 BBz

<400> SEQUENCE: 24

```
Met Leu Leu Leu Val Thr Ser Leu Leu Cys Glu Leu Pro His Pro
1               5                   10                  15

Ala Phe Leu Leu Ile Pro Glu Val Gln Leu Val Gln Ser Gly Ser Glu
            20                  25                  30

Leu Lys Lys Pro Gly Ala Ser Val Lys Val Ser Cys Lys Ala Ser Gly
        35                  40                  45

Gly Thr Phe Ser Ser Tyr Ala Ile Ser Trp Val Arg Gln Ala Pro Gly
    50                  55                  60

Gln Gly Leu Glu Trp Met Gly Gly Ile Ile Pro Ile Phe Gly Thr Ala
65              70                  75                  80

Asn Tyr Ala Gln Lys Phe Gln Gly Arg Val Thr Ile Thr Ala Asp Glu
                85                  90                  95

Ser Thr Ser Thr Ala Tyr Met Glu Leu Ser Ser Leu Arg Ser Glu Asp
            100                 105                 110

Thr Ala Val Tyr Tyr Cys Ala Ser Thr Ala Arg Arg Gly Trp Asp Thr
        115                 120                 125

Ala Gly Pro Leu Asp Tyr Trp Gly Gln Gly Thr Leu Val Thr Val Ser
    130                 135                 140

Ser Gly Gly Gly Gly Ser Gly Gly Gly Ser Gly Gly Gly Gly Ser
145                 150                 155                 160

Asp Ile Gln Met Thr Gln Ser Pro Ser Ser Leu Ser Ala Ser Val Gly
                165                 170                 175

Asp Arg Val Thr Ile Ala Cys Arg Ala Ser Gln Thr Ile Ser Arg Tyr
            180                 185                 190

Leu Asn Trp Tyr Gln Gln Lys Pro Gly Lys Ala Pro Lys Leu Leu Ile
        195                 200                 205

Tyr Ala Ala Ser Ser Leu Gln Ser Gly Val Ser Ser Arg Phe Ser Gly
    210                 215                 220

Ser Gly Ser Gly Thr Glu Phe Thr Leu Thr Ile Ser Ser Leu Gln Pro
225                 230                 235                 240

Glu Asp Phe Ala Thr Tyr Phe Cys Gln Gln Thr Tyr Ser Pro Pro Ile
                245                 250                 255

Thr Phe Gly Gln Gly Thr Arg Leu Glu Ile Lys Ala Ala Ala Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
```

```
                    325                 330                 335
Leu Tyr Cys Lys Arg Gly Arg Lys Lys Leu Leu Tyr Ile Phe Lys Gln
                340                 345                 350

Pro Phe Met Arg Pro Val Gln Thr Thr Gln Glu Glu Asp Gly Cys Ser
            355                 360                 365

Cys Arg Phe Pro Glu Glu Glu Glu Gly Gly Cys Glu Leu Arg Val Lys
        370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 25
<211> LENGTH: 1086
<212> TYPE: DNA
<213> ORGANISM: Artificial
<220> FEATURE:
<223> OTHER INFORMATION: nucleotide sequence of CAR LTG1906 CD33_4 CD8
      BBz

<400> SEQUENCE: 25
atgctgctgc tggtgaccag cctgctgctg tgcgaactgc cgcatccggc gtttctgctg      60
attccggagg tgcagctggt ggagtctggg ggaggcttgg tacagcctgg agggtccctg     120
agactctcct gtgcagcctc tggattcacc ttcagtagct atggcatgag ctgggtccgc     180
caggctccaa gacaagggct tgagtgggtg gccaacataa agcaagatgg aagtgagaaa     240
tactatgcgg actcagtgaa gggccgattc accatctcca gagacaattc caagaacacg     300
ctgtatctgc aaatgaacag cctgagagcc gaggacacag ccacgtatta ctgtgcgaaa     360
gaaaatgtgg actggggcca gggcaccctg gtcaccgtct cctcagcggc cgcaactacc     420
acccctgccc ctcggccgcc gactccggcc caaccatcg caagccaacc cctctccttg     480
cgccccgaag cttgccgccc ggccgcgggt ggagccgtgc atacccgggg gctggacttt     540
gcctgcgata tctacatttg gccccgctg ccggcactt cggcgtgct cctgctgtcg     600 ctggtcatca cccttactg caagagggc cggaagaagc tgctttacat cttcaagcag     660
ccgttcatgc ggcccgtgca gacgactcag gaagaggacg gatgctcgtg cagattccct     720
gaggaggaag agggggggatg cgaactgcgc gtcaagttct cacggtccgc cgacgccccc     780
gcatatcaac agggccagaa tcagctctac aacgagctga acctgggaag gagagaggag     840
tacgacgtgc tggacaagcg acgcggacgc gacccggaga tggggggaaa accacggcgg     900
aaaaaccctc aggaaggact gtacaacgaa ctccagaaag acaagatggc ggaagcctac     960
tcagaaatcg gatgaagggg agagcggagg aggggaaagg gtcacgacgg gctgtaccag    1020
ggactgagca ccgccactaa ggatacctac gatgccttgc atatgcaagc actcccaccc    1080
```

```
cggtag                                                              1086
```

<210> SEQ ID NO 26
<211> LENGTH: 361
<212> TYPE: PRT
<213> ORGANISM: Artificial
<220> FEATURE:
<223> OTHER INFORMATION: amino acid sequence of CAR LTG1906 CD33_4 CD8
      BBz

<400> SEQUENCE: 26

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Gly Met Ser Trp Val Arg Gln Ala Pro Arg
    50                  55                  60

Gln Gly Leu Glu Trp Val Ala Asn Ile Lys Gln Asp Gly Ser Glu Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Thr Tyr Tyr Cys Ala Lys Glu Asn Val Asp Trp Gly Gln Gly
        115                 120                 125

Thr Leu Val Thr Val Ser Ser Ala Ala Thr Thr Thr Pro Ala Pro
    130                 135                 140

Arg Pro Pro Thr Pro Ala Pro Thr Ile Ala Ser Gln Pro Leu Ser Leu
145                 150                 155                 160

Arg Pro Glu Ala Cys Arg Pro Ala Ala Gly Gly Ala Val His Thr Arg
                165                 170                 175

Gly Leu Asp Phe Ala Cys Asp Ile Tyr Ile Trp Ala Pro Leu Ala Gly
            180                 185                 190

Thr Cys Gly Val Leu Leu Leu Ser Leu Val Ile Thr Leu Tyr Cys Lys
        195                 200                 205

Arg Gly Arg Lys Lys Leu Leu Tyr Ile Phe Lys Gln Pro Phe Met Arg
    210                 215                 220

Pro Val Gln Thr Thr Gln Glu Glu Asp Gly Cys Ser Cys Arg Phe Pro
225                 230                 235                 240

Glu Glu Glu Glu Gly Gly Cys Glu Leu Arg Val Lys Phe Ser Arg Ser
                245                 250                 255

Ala Asp Ala Pro Ala Tyr Gln Gln Gly Gln Asn Gln Leu Tyr Asn Glu
            260                 265                 270

Leu Asn Leu Gly Arg Arg Glu Glu Tyr Asp Val Leu Asp Lys Arg Arg
        275                 280                 285

Gly Arg Asp Pro Glu Met Gly Gly Lys Pro Arg Arg Lys Asn Pro Gln
    290                 295                 300

Glu Gly Leu Tyr Asn Glu Leu Gln Lys Asp Lys Met Ala Glu Ala Tyr
305                 310                 315                 320

Ser Glu Ile Gly Met Lys Gly Glu Arg Arg Arg Gly Lys Gly His Asp
                325                 330                 335

Gly Leu Tyr Gln Gly Leu Ser Thr Ala Thr Lys Asp Thr Tyr Asp Ala
            340                 345                 350
```

Leu His Met Gln Ala Leu Pro Pro Arg
         355                 360

<210> SEQ ID NO 27
<211> LENGTH: 72
<212> TYPE: DNA
<213> ORGANISM: Artificial
<220> FEATURE:
<223> OTHER INFORMATION: nucleotide sequence of DNA CD8 transmembrane
      domain

<400> SEQUENCE: 27
atctacatct gggcgccctt ggccgggact tgtggggtcc ttctcctgtc actggttatc    60
accctttact gc    72

<210> SEQ ID NO 28
<211> LENGTH: 22
<212> TYPE: PRT
<213> ORGANISM: Artificial
<220> FEATURE:
<223> OTHER INFORMATION: amino acid sequence of CD8 transmembrane domain

<400> SEQUENCE: 28

Ile Trp Ala Pro Leu Ala Gly Thr Cys Gly Val Leu Leu Leu Ser Leu
1               5                   10                  15

Val Ile Thr Leu Tyr Cys
            20

<210> SEQ ID NO 29
<211> LENGTH: 135
<212> TYPE: DNA
<213> ORGANISM: Artificial
<220> FEATURE:
<223> OTHER INFORMATION: nucleotide sequence of DNA CD8 hinge domain

<400> SEQUENCE: 29
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
gacttcgcct gtgat    135

<210> SEQ ID NO 30
<211> LENGTH: 47
<212> TYPE: PRT
<213> ORGANISM: Artificial
<220> FEATURE:
<223> OTHER INFORMATION: amino acid sequence of CD8 hinge domain

<400> SEQUENCE: 30

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45

<210> SEQ ID NO 31
<211> LENGTH: 42
<212> TYPE: PRT
<213> ORGANISM: Human

<400> SEQUENCE: 31

Lys Arg Gly Arg Lys Lys Leu Leu Tyr Ile Phe Lys Gln Pro Phe Met
1               5                   10                  15

```
Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 32
<211> LENGTH: 106
<212> TYPE: PRT
<213> ORGANISM: Human

<400> SEQUENCE: 32

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 33
<211> LENGTH: 126
<212> TYPE: DNA
<213> ORGANISM: Artificial
<220> FEATURE:
<223> OTHER INFORMATION: nucleotide sequence of DNA signaling domain of
      4-1BB

<400> SEQUENCE: 33
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126

<210> SEQ ID NO 34
<211> LENGTH: 42
<212> TYPE: PRT
<213> ORGANISM: Artificial
<220> FEATURE:
<223> OTHER INFORMATION: amino acid sequence of signaling domain of
      4-1BB

<400> SEQUENCE: 34

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 35
<211> LENGTH: 336
<212> TYPE: DNA
<213> ORGANISM: Artificial
<220> FEATURE:
```

<223> OTHER INFORMATION: nucleotide sequence of DNA signaling domain of
      CD3-zeta

<400> SEQUENCE: 35
agagtgaagt tcagcaggag cgcagacgcc cccgcgtaca agcagggcca gaaccagctc    60
tataacgagc tcaatctagg acgaagagag gagtacgatg ttttggacaa gagacgtggc   120
cgggaccctg agatggggg aaagccgaga aggaagaacc ctcaggaagg cctgtacaat    180
gaactgcaga aagataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgc                             336

<210> SEQ ID NO 36
<211> LENGTH: 112
<212> TYPE: PRT
<213> ORGANISM: Artificial
<220> FEATURE:
<223> OTHER INFORMATION: amino acid sequence of CD3zeta

<400> SEQUENCE: 36

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 37
<211> LENGTH: 726
<212> TYPE: DNA
<213> ORGANISM: Artificial
<220> FEATURE:
<223> OTHER INFORMATION: nucleotide sequence of ScFv CD 19

<400> SEQUENCE: 37
gacatccaga tgacacagac tacatcctcc ctgtctgcct ctctgggaga cagagtcacc    60
atcagttgca gggcaagtca ggacattagt aaatatttaa attggtatca gcagaaacca   120
gatggaactg ttaaactcct gatctaccat acatcaagat tacactcagg agtcccatca   180
aggttcagtg gcagtgggtc tggaacagat tattctctca ccattagcaa cctggagcaa   240
gaagatattg ccacttactt ttgccaacag gtaatacgc ttccgtacac gttcggaggg    300
gggaccaagc tggagatcac aggtggcggt ggctcgggcg gtggtgggtc gggtggcggc   360
ggatctgagg tgaaactgca ggagtcagga cctggcctgg tggcgccctc acagagcctg   420
tccgtcacat gcactgtctc aggggtctca ttacccgact atggtgtaag ctggattcgc   480
cagcctccac gaaagggtct ggagtggctg ggagtaatat ggggtagtga aaccacatac   540
tataattcag ctctcaaatc cagactgacc atcatcaagg acaactccaa gagccaagtt   600
ttcttaaaaa tgaacagtct gcaaactgat gacacagcca tttactactg tgccaaacat   660

```
tattactacg gtggtagcta tgctatggac tactggggcc aaggaacctc agtcaccgtc    720
tcctca                                                                726
```

<210> SEQ ID NO 38
<211> LENGTH: 242
<212> TYPE: PRT
<213> ORGANISM: Artificial
<220> FEATURE:
<223> OTHER INFORMATION: amino acid sequence of ScFv CD 19

<400> SEQUENCE: 38

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser
```

<210> SEQ ID NO 39
<211> LENGTH: 66
<212> TYPE: DNA
<213> ORGANISM: Artificial
<220> FEATURE:
<223> OTHER INFORMATION: nucleotide sequence of GMCSF leader peptide

<400> SEQUENCE: 39

```
atgctgctgc tggtgaccag cctgctgctg tgcgaactgc cgcatccggc gtttctgctg    60
attccg                                                                66
```

<210> SEQ ID NO 40
<211> LENGTH: 22

-continued

```
<212> TYPE: PRT
<213> ORGANISM: Artificial
<220> FEATURE:
<223> OTHER INFORMATION: amino acid sequence of GMCSF leader peptide

<400> SEQUENCE: 40

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 41
<211> LENGTH: 85
<212> TYPE: DNA
<213> ORGANISM: Artificial
<220> FEATURE:
<223> OTHER INFORMATION: nucleotide sequence of TNFRSF19 leader peptide

<400> SEQUENCE: 41
ggctctgaaa gtgctgttgg aacaagaaaa gaccttcttc accttgctcg tgttgctggg      60
gtacctgtcc tgcaaagtca cctgt                                           85

<210> SEQ ID NO 42
<211> LENGTH: 29
<212> TYPE: PRT
<213> ORGANISM: Artificial
<220> FEATURE:
<223> OTHER INFORMATION: amino acid sequence of TNFRSF19 leader peptide

<400> SEQUENCE: 42

Met Ala Leu Lys Val Leu Leu Glu Gln Glu Lys Thr Phe Phe Thr Leu
1               5                   10                  15

Leu Val Leu Leu Gly Tyr Leu Ser Cys Lys Val Thr Cys
            20                  25

<210> SEQ ID NO 43
<211> LENGTH: 63
<212> TYPE: DNA
<213> ORGANISM: Artificial
<220> FEATURE:
<223> OTHER INFORMATION: nucleotide sequence of CD8 alpha leader peptide

<400> SEQUENCE: 43
atggcgctgc cggtgaccgc gctgctgctg ccgctggcgc tgctgctgca tgcggcgcgc      60
ccg                                                                    63

<210> SEQ ID NO 44
<211> LENGTH: 21
<212> TYPE: PRT
<213> ORGANISM: Artificial
<220> FEATURE:
<223> OTHER INFORMATION: amino acid sequence of CD8 alpha leader peptide

<400> SEQUENCE: 44

Met Ala Leu Pro Val Thr Ala Leu Leu Leu Pro Leu Ala Leu Leu Leu
1               5                   10                  15

His Ala Ala Arg Pro
            20

<210> SEQ ID NO 45
<211> LENGTH: 123
<212> TYPE: DNA
<213> ORGANISM: Artificial
<220> FEATURE:
```

<223> OTHER INFORMATION: nucleotide sequence of CD28 co-stimulatory
      domain

<400> SEQUENCE: 45
cggtcgaaga ggtccagact cttgcactcc gactacatga acatgactcc tagaaggccc    60
ggacccacta gaaagcacta ccagccgtac gcccctcctc gggatttcgc cgcataccgg   120
tcc                                                                 123

<210> SEQ ID NO 46
<211> LENGTH: 41
<212> TYPE: PRT
<213> ORGANISM: Artificial
<220> FEATURE:
<223> OTHER INFORMATION: amino acid sequence of CD28 co-stimulatory
      domain

<400> SEQUENCE: 46

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 47
<211> LENGTH: 336
<212> TYPE: DNA
<213> ORGANISM: Artificial
<220> FEATURE:
<223> OTHER INFORMATION: nucleotide sequence of CD3 zeta activation
      domain

<400> SEQUENCE: 47
agagtgaagt tcagccgctc agccgatgca ccggcctacc agcagggaca gaaccagctc    60
tacaacgagc tcaacctggg tcggcgggaa gaatatgacg tgctggacaa acggcgcggc   120
agagatccgg agatgggggg aaagccgagg aggaagaacc ctcaagaggg cctgtacaac   180
gaactgcaga ggacaagat ggcggaagcc tactccgaga tcggcatgaa gggagaacgc   240
cggagaggga agggtcatga cggactgtac cagggcctgt caactgccac taaggacact   300
tacgatgcgc tccatatgca agctttgccc ccgcgg                             336

<210> SEQ ID NO 48
<211> LENGTH: 112
<212> TYPE: PRT
<213> ORGANISM: Artificial
<220> FEATURE:
<223> OTHER INFORMATION: amino acid sequence of CD3 zeta activation
      domain

<400> SEQUENCE: 48

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
            100                 105                 110

<210> SEQ ID NO 49
<211> LENGTH: 201
<212> TYPE: DNA
<213> ORGANISM: Artificial
<220> FEATURE:
<223> OTHER INFORMATION: nucleotide sequence of TNFRSF19 hinge and
      transmembrane domain

<400> SEQUENCE: 49
gcggccgcgg tcggattcca agacatggaa tgcgtgccct gcggcgaccc gccacctcct     60
tacgagccgc actgcgcatc gaaggtcaac ctcgtgaaga tcgcgagcac cgcgtcctca    120
ccccgggata ctgctctggc cgccgtgatt tgttccgcct ggccaccgt gcttctggcc    180 ctgctgatcc tctgtgtgat c                                              201

<210> SEQ ID NO 50
<211> LENGTH: 67
<212> TYPE: PRT
<213> ORGANISM: Artificial
<220> FEATURE:
<223> OTHER INFORMATION: amino acid sequence of TNFRSF19 hinge and
      transmembrane domain

<400> SEQUENCE: 50

Ala Ala Ala Val Gly Phe Gln Asp Met Glu Cys Val Pro Cys Gly Asp
1               5                   10                  15

Pro Pro Pro Pro Tyr Glu Pro His Cys Ala Ser Lys Val Asn Leu Val
            20                  25                  30

Lys Ile Ala Ser Thr Ala Ser Ser Pro Arg Asp Thr Ala Leu Ala Ala
        35                  40                  45

Val Ile Cys Ser Ala Leu Ala Thr Val Leu Leu Ala Leu Leu Ile Leu
    50                  55                  60

Cys Val Ile
65

<210> SEQ ID NO 51
<211> LENGTH: 63
<212> TYPE: DNA
<213> ORGANISM: Artificial
<220> FEATURE:
<223> OTHER INFORMATION: nucleotide sequence of TNFRSF19 transmembrane
      domain

<400> SEQUENCE: 51
gccgccgtga tttgttccgc cttggccacc gtgcttctgg ccctgctgat cctctgtgtg     60
atc                                                                   63

<210> SEQ ID NO 52
<211> LENGTH: 21
<212> TYPE: PRT
<213> ORGANISM: Artificial
<220> FEATURE:
<223> OTHER INFORMATION: amino acid sequence of TNFRSF19 transmembrane
      domain

<400> SEQUENCE: 52

Ala Ala Val Ile Cys Ser Ala Leu Ala Thr Val Leu Leu Ala Leu Leu

```
1               5                   10                  15
Ile Leu Cys Val Ile
            20
```

<210> SEQ ID NO 53
<211> LENGTH: 138
<212> TYPE: DNA
<213> ORGANISM: Artificial
<220> FEATURE:
<223> OTHER INFORMATION: nucleotide sequence of TNFRSF19 hinge domain

<400> SEQUENCE: 53

```
gcggccgcgg tcggattcca agacatggaa tgcgtgccct gcggcgaccc gccacctcct      60
tacgagccgc actgcgcatc gaaggtcaac ctcgtgaaga tcgcgagcac cgcgtcctca     120
ccccgggata ctgctctg                                                   138
```

<210> SEQ ID NO 54
<211> LENGTH: 46
<212> TYPE: PRT
<213> ORGANISM: Artificial
<220> FEATURE:
<223> OTHER INFORMATION: amino acid sequence of TNFRSF19 hinge domain

<400> SEQUENCE: 54

```
Ala Ala Ala Val Gly Phe Gln Asp Met Glu Cys Val Pro Cys Gly Asp
1               5                   10                  15

Pro Pro Pro Pro Tyr Glu Pro His Cys Ala Ser Lys Val Asn Leu Val
            20                  25                  30

Lys Ile Ala Ser Thr Ala Ser Ser Pro Arg Asp Thr Ala Leu
        35                  40                  45
```

<210> SEQ ID NO 55
<211> LENGTH: 80
<212> TYPE: DNA
<213> ORGANISM: Artificial
<220> FEATURE:
<223> OTHER INFORMATION: nucleotide sequence of truncated TNFRSF19
      hinge domain

<400> SEQUENCE: 55

```
tacgagcctc actgcgccag caaagtcaac ttggtgaaga tcgcgagcac tgcctcgtcc      60
cctcgggaca ctgctctggc                                                  80
```

<210> SEQ ID NO 56
<211> LENGTH: 26
<212> TYPE: PRT
<213> ORGANISM: Artificial
<220> FEATURE:
<223> OTHER INFORMATION: amino acid sequence of truncated TNFRSF19
      hinge domain

<400> SEQUENCE: 56

```
Tyr Glu Pro His Cys Ala Ser Lys Val Asn Leu Val Lys Ile Ala Ser
1               5                   10                  15

Thr Ala Ser Ser Pro Arg Asp Thr Ala Leu
            20                  25
```

<210> SEQ ID NO 57
<211> LENGTH: 222
<212> TYPE: DNA
<213> ORGANISM: Artificial
<220> FEATURE:
<223> OTHER INFORMATION: nucleotide sequence of CD8a hinge domain fused -continued to TNFRSF19 transmembrane domain

<400> SEQUENCE: 57
gcggccgcgc cgcccctcg gcccccgact cctgccccga cgatcgcttc ccaacctctc    60
tcgctgcgcc cggaagcatg ccggcccgcc gccggtggcg ctgtccacac tcgcggactg   120
gactttgata ccgcactggc ggccgtgatc tgtagcgccc tggccaccgt gctgctggcg   180
ctgctcatcc tttgcgtgat ctactgcaag cggcagccta gg                      222

<210> SEQ ID NO 58
<211> LENGTH: 74
<212> TYPE: PRT
<213> ORGANISM: Artificial
<220> FEATURE:
<223> OTHER INFORMATION: amino acid sequence of CD8a hinge domain fused
      to TNFRSF19 transmembrane domain

<400> SEQUENCE: 58

Ala Ala Ala Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Asp Thr Ala Leu Ala Ala
            35                  40                  45

Val Ile Cys Ser Ala Leu Ala Thr Val Leu Leu Ala Leu Leu Ile Leu
        50                  55                  60

Cys Val Ile Tyr Cys Lys Arg Gln Pro Arg
65                  70

<210> SEQ ID NO 59
<211> LENGTH: 123
<212> TYPE: DNA
<213> ORGANISM: Artificial
<220> FEATURE:
<223> OTHER INFORMATION: nucleotide sequence of CD28 co-stimulatory
      domain

<400> SEQUENCE: 59
cggtcgaaga ggtccagact cttgcactcc gactacatga acatgactcc tagaaggccc    60
ggacccacta gaaagcacta ccagccgtac gcccctcctc gggatttcgc cgcataccgg   120
tcc                                                                  123

<210> SEQ ID NO 60
<211> LENGTH: 41
<212> TYPE: PRT
<213> ORGANISM: Artificial
<220> FEATURE:
<223> OTHER INFORMATION: amino acid sequence of CD28 co-stimulatory
      domain

<400> SEQUENCE: 60

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40

<210> SEQ ID NO 61
<211> LENGTH: 336
<212> TYPE: DNA

-continued

```
<213> ORGANISM: Artificial
<220> FEATURE:
<223> OTHER INFORMATION: nucleotide sequence of CD3 zeta version 2

<400> SEQUENCE: 61
cgcgtgaaat ttagccgcag cgcggatgcg ccggcgtatc agcagggcca gaaccagctg      60
tataacgaac tgaacctggg ccgccgcgaa gaatatgatg tgctggataa acgccgcggc     120
cgcgatccgg aaatgggcgg caaaccgcgc cgcaaaaacc cgcaggaagg cctgtataac     180
gaactgcaga agataaaat ggcggaagcg tatagcgaaa ttggcatgaa aggcgaacgc      240
cgccgcggca aggccatga tggcctgtat cagggcctga gcaccgcgac caaagatacc     300
tatgatgcgc tgcatatgca ggcgctgccg ccgcgc                              336

<210> SEQ ID NO 62
<211> LENGTH: 112
<212> TYPE: PRT
<213> ORGANISM: Artificial
<220> FEATURE:
<223> OTHER INFORMATION: amino acid sequence of CD3 zeta version 2

<400> SEQUENCE: 62

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 63
<211> LENGTH: 93
<212> TYPE: DNA
<213> ORGANISM: Artificial
<220> FEATURE:
<223> OTHER INFORMATION: nucleotide sequence of Furin P2A Furin

<400> SEQUENCE: 63
cgcgcgaaac gcagcggcag cggcgcgacc aactttagcc tgctgaaaca ggcgggcgat      60
gtggaagaaa acccgggccc gcgagcaaag agg                                  93

<210> SEQ ID NO 64
<211> LENGTH: 31
<212> TYPE: PRT
<213> ORGANISM: Artificial
<220> FEATURE:
<223> OTHER INFORMATION: amino acid sequence of Furin P2A Furin

<400> SEQUENCE: 64

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro Arg Ala Lys Arg
            20                  25                  30
```

<210> SEQ ID NO 65
<211> LENGTH: 78
<212> TYPE: DNA
<213> ORGANISM: Artificial
<220> FEATURE:
<223> OTHER INFORMATION: nucleotide sequence of Furin T2A

<400> SEQUENCE: 65
agagctaaac gctctgggtc tggtgaagga cgaggtagcc ttcttacgtg cggagacgtg    60
gaggaaaacc caggaccc                                                  78

<210> SEQ ID NO 66
<211> LENGTH: 26
<212> TYPE: PRT
<213> ORGANISM: Artificial
<220> FEATURE:
<223> OTHER INFORMATION: amino acid sequence of Furin T2A

<400> SEQUENCE: 66

Arg Ala Lys Arg Ser Gly Ser Gly Glu Gly Arg Gly Ser Leu Leu Thr
1               5                   10                  15

Cys Gly Asp Val Glu Glu Asn Pro Gly Pro
            20                  25

<210> SEQ ID NO 67
<211> LENGTH: 1005
<212> TYPE: DNA
<213> ORGANISM: Artificial
<220> FEATURE:
<223> OTHER INFORMATION: nucleotide sequence of truncated EGFR (tEGFR)
      tag

<400> SEQUENCE: 67
aggaaggttt gcaatggaat cggtataggg gagtttaagg attcacttag cataaacgct    60
actaatatta aacacttcaa aaactgtacg agtataagtg gagatcttca cattttgccg   120
gttgcattcc gaggcgattc attcacccac acgccaccgc ttgacccaca agaattggat   180
attcttaaaa ccgttaaaga ataacggggt tttttgctca ttcaagcgtg gccagaaaat   240
cgcactgacc tccatgcttt cgagaacctg agagattaaa gaggacgaac taagcagcat   300
ggtcaattct cccttgctgt ggtcagcctg aacatcacca gtcttggttt gcggtccctc   360
aaggaaattt cagatggaga tgtcatcata agcggcaaca gaatttgtg ctatgcaaat   420 accataaact ggaaaaaact gtttggcact tccggccaga aaccaagat tatttcaaat   480 cggggtgaga cagctgcaa agccaccggc caggtttgtc atgccttgtg ctctccggaa   540
ggctgttggg ggccagaacc cagggactgc gtcagttgca gaaacgtctc aagaggccgc   600
gaatgcgttg acaagtgtaa cctccttgag ggtgagccac gagagtttgt tgagaacagc   660
gagtgtatac aatgtcaccc tgaatgtttg ccccaggcta tgaatataac ctgcacaggc   720
cgcgggcctg ataactgcat ccagtgtgct cattacatag atggacctca ctgtgtgaaa   780
acctgcccgg ccggagttat gggagaaaac aacactctgg tgtggaaata cgctgatgca   840
ggccacgtgt gccaccttg tcacccgaat tgtacatatg ggtgtaccgg tcctggactt   900
gaaggttgcc ctaccaatgg ccctaaaata cccagtatcg caactggcat ggtaggcgct   960
cttctcttgc tcttggtagt tgctctcggc ataggtcttt ttatg                  1005

<210> SEQ ID NO 68
<211> LENGTH: 335
<212> TYPE: PRT

<213> ORGANISM: Artificial
<220> FEATURE:
<223> OTHER INFORMATION: amino acid sequence of truncated EGFR (tEGFR) tag

<400> SEQUENCE: 68

```
Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335
```

<210> SEQ ID NO 69
<211> LENGTH: 732
<212> TYPE: DNA
<213> ORGANISM: Artificial
<220> FEATURE:
<223> OTHER INFORMATION: nucleotide sequence of CD123 binder MT-16

<400> SEQUENCE: 69

```
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcgacg aatccacgag cacagcctac      240
acggagctga gcagcctgag atctgaggac acggccgtgt attactgtgc gagagcccgg     300
ttgggaggag cttttgatat ctggggccaa gggacaatgg tcaccgtctc ttcaggaggt     360
ggcgggtctg gtggaggcgg tagcggtggt ggcggatccc agtctgtgct gacgcagccg     420
ccctcagtgt ctgcggcccc aggacagaag gtcaccatct cctgctctgg aagcagctcc     480
aacattggca atcattatgt gtcctggtat cagcagctcc caggagcagc ccccaaactc     540
ctcatttatg acgataataa gcgaccctca gggattcctg accgattctc tggctccagg     600
tctggcacgt cagccaccct gggcatcacc ggactccaga gtggggacga ggccgattat     660
tactgcggag catgggatag tagtcttgct gctcatgtct tcggaactgg gaccaaggtc     720
accgtcctag gt                                                          732
```

<210> SEQ ID NO 70
<211> LENGTH: 244
<212> TYPE: PRT
<213> ORGANISM: Artificial
<220> FEATURE:
<223> OTHER INFORMATION: amino acid sequence of CD123 binder MT-16

<400> SEQUENCE: 70

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Thr Glu Leu Ser Ser Leu Arg Ser Glu Asp Thr Ala Val Tyr Tyr Cys
                85                  90                  95

Ala Arg Ala Arg Leu Gly Gly Ala Phe Asp Ile Trp Gly Gln Gly Thr
            100                 105                 110

Met Val Thr Val Ser Ser Gly Gly Gly Ser Gly Gly Gly Gly Ser
        115                 120                 125

Gly Gly Gly Gly Ser Gln Ser Val Leu Thr Gln Pro Pro Ser Val Ser
    130                 135                 140

Ala Ala Pro Gly Gln Lys Val Thr Ile Ser Cys Ser Gly Ser Ser
145                 150                 155                 160

Asn Ile Gly Asn His Tyr Val Ser Trp Tyr Gln Gln Leu Pro Gly Ala
                165                 170                 175

Ala Pro Lys Leu Leu Ile Tyr Asp Asp Asn Lys Arg Pro Ser Gly Ile
            180                 185                 190

Pro Asp Arg Phe Ser Gly Ser Arg Ser Gly Thr Ser Ala Thr Leu Gly
        195                 200                 205

Ile Thr Gly Leu Gln Ser Gly Asp Glu Ala Asp Tyr Tyr Cys Gly Ala
    210                 215                 220
```

Trp Asp Ser Ser Leu Ala Ala His Val Phe Gly Thr Gly Thr Lys Val
225                 230                 235                 240

Thr Val Leu Gly

<210> SEQ ID NO 71
<211> LENGTH: 738
<212> TYPE: DNA
<213> ORGANISM: Artificial
<220> FEATURE:
<223> OTHER INFORMATION: nucleotide sequence of CD123 binder MT-32

<400> SEQUENCE: 71

| | | | | | |
|---|---|---|---|---|---|
| caggtacagc | tgcagcagtc | aggtccagga | ctggtgaagc | cctcgcagac | cctctcactc | 60 |
| acctgtgcca | tctccgggga | cagtgtctct | agcaacagtg | ctgcttggaa | ctggatcagg | 120 |
| cagtccccat | cgagaggcct | tgagtggctg | ggaaggacat | actacaggtc | caagtggtat | 180 |
| aatgattatg | cagtatctgt | gaaaagtcga | ataaccatca | acccagacac | atccaagaac | 240 |
| cagttctccc | tgcagctgaa | ctctgtgact | cccgaggaca | tggctgtgta | ttactgtgca | 300 |
| agaggcgttg | atagtagctt | tgactactgg | ggccagggaa | ccctggtcac | cgtctcctca | 360 |
| ggaggtggcg | gtctggtgg | aggcggtagc | ggtggtggcg | gatcccagtc | tgtcgtgacg | 420 |
| cagccgccct | cagtgtctgc | ggccccagga | cagagcgtca | ccatctcctg | ttctggaagc | 480 |
| agttccaccg | ttggcgataa | ttatgtgtcc | tggtaccagc | aactcccagg | aacagccccc | 540 |
| aaactcctca | tttttgacga | ttataaacga | ccctcagggg | ttcctgaccg | attctctggc | 600 |
| tcccagtctg | gcacctcagc | ctccctggtc | atcactggtc | tccaggcaga | agatgaggct | 660 |
| gattattact | gccagtctta | tgacagcagc | ctgagtggtt | atgtcttcgg | gcctgggacc | 720 |
| aaggtcaccg | tcctaggt | | | | | 738 |

<210> SEQ ID NO 72
<211> LENGTH: 246
<212> TYPE: PRT
<213> ORGANISM: Artificial
<220> FEATURE:
<223> OTHER INFORMATION: amino acid sequence of CD123 binder MT-32

<400> SEQUENCE: 72

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Met Ala Val
                85                  90                  95

Tyr Tyr Cys Ala Arg Gly Val Asp Ser Ser Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gln Ser Val Val Thr Gln Pro Pro Ser
    130                 135                 140

Val Ser Ala Ala Pro Gly Gln Ser Val Thr Ile Ser Cys Ser Gly Ser

```
                    145                 150                 155                 160
Ser Ser Thr Val Gly Asp Asn Tyr Val Ser Trp Tyr Gln Gln Leu Pro
                165                 170                 175

Gly Thr Ala Pro Lys Leu Leu Ile Phe Asp Asp Tyr Lys Arg Pro Ser
            180                 185                 190

Gly Val Pro Asp Arg Phe Ser Gly Ser Gln Ser Gly Thr Ser Ala Ser
        195                 200                 205

Leu Val Ile Thr Gly Leu Gln Ala Glu Asp Glu Ala Asp Tyr Tyr Cys
    210                 215                 220

Gln Ser Tyr Asp Ser Ser Leu Ser Gly Tyr Val Phe Gly Pro Gly Thr
225                 230                 235                 240

Lys Val Thr Val Leu Gly
                245

<210> SEQ ID NO 73
<211> LENGTH: 126
<212> TYPE: DNA
<213> ORGANISM: Artificial
<220> FEATURE:
<223> OTHER INFORMATION: nucleotide sequence of DNA signaling domain of
      4-1BB

<400> SEQUENCE: 73
aagcgcggac ggaagaaact cttgtacatc ttcaagcagc cgttcatgcg ccctgtgcaa    60
accacccaag aagaggacgg gtgctcctgc cggttcccgg aagaggaaga gggcggctgc   120
gaactg                                                              126

<210> SEQ ID NO 74
<211> LENGTH: 42
<212> TYPE: PRT
<213> ORGANISM: Artificial
<220> FEATURE:
<223> OTHER INFORMATION: amino acid sequence of DNA signaling domain of
      4-1BB

<400> SEQUENCE: 74

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 75
<211> LENGTH: 336
<212> TYPE: DNA
<213> ORGANISM: Artificial
<220> FEATURE:
<223> OTHER INFORMATION: nucleotide sequence of DNA signaling domain of
      CD3z

<400> SEQUENCE: 75
cgcgtgaagt tttcccggtc cgccgacgct ccggcgtacc agcaggggca aaaccagctg    60
tacaacgaac ttaacctcgg tcgccgggaa gaatatgacg tgctggacaa gcggcgggga   120
agagatcccg agatgggtgg aaagccgcgg cggaagaacc ctcaggaggg cttgtacaac   180
gagctgcaaa aggacaaaat ggccgaagcc tactccgaga ttggcatgaa gggagagcgc   240
agacgcggga agggacacga tggactgtac caggggactgt caaccgcgac taaggacact   300
tacgacgccc tgcacatgca ggccctgccc ccgcgc                             336
```

-continued

<210> SEQ ID NO 76
<211> LENGTH: 112
<212> TYPE: PRT
<213> ORGANISM: Artificial
<220> FEATURE:
<223> OTHER INFORMATION: amino acid sequence of DNA signaling domain of
      CD3z

<400> SEQUENCE: 76

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 77
<211> LENGTH: 1476
<212> TYPE: DNA
<213> ORGANISM: Artificial
<220> FEATURE:
<223> OTHER INFORMATION: nucleotide sequence of CAR123 Z16

<400> SEQUENCE: 77
atgctcttgc tcgtgacttc tttgcttttg tgcgaacttc cgcacccagc cttccttttg      60
atacctcagg tccagctggt gcagtctggg gctgaggtga agaagcctgg gtcctcggtg     120
aaggtctcct gcaaggcttc tggaggcacc ttcagcagct atgctatcag ctgggtgcga     180
caggcccctg gacaagggct tgagtggatg ggagggatca tccctatctt tggtacagca     240
aactacgcac agaagttcca gggcagagtc acgattaccg cggacgaatc cacgagcaca     300
gcctacatgg agctgagcag cctgagatct gaggacacgg ccgtgtatta ctgtgcgaga     360
gcccggttgg gaggagcttt tgatatctgg ggccaaggga caatggtcac cgtctcttca     420
ggaggtggcg gtctggtgg aggcggtagc ggtggtggcg gatcccagtc tgtgctgacg     480
cagccgccct cagtgtctgc ggccccagga cagaaggtca ccatctcctg ctctggaggc     540
agctccaaca ttggcaatca ttatgtgtcc tggtatcagc agctcccagg agcagccccc     600
aaactcctca tttatgacga taataagcga ccctcaggga ttcctgaccg attctctggc     660
tccaggtctg gcacgtcagc caccctgggc atcaccggac tccagagtgg gacgaggcc     720 gattattact gcggagcatg ggatagtagt cttgctgctc atgtcttcgg aactgggacc     780
aaggtcaccg tcctgggtgc ggccgcaacg accactcctg caccccgccc tccgactccg     840
gccccaacca ttgccagcca gccctgtccc tgcggccgg aagcctgcag accggctgcc     900
ggcggagccg tccatacccg gggactggat ttcgcctgcg atatctatat ctgggcacca     960
ctcgccggaa cctgtggagt gctgctgctc tcccttgtga tcaccctgta ctgcaagcgc    1020
ggacggaaga actcttgta catcttcaag cagccgttca tgcgccctgt gcaaaccacc    1080

```
caagaagagg acgggtgctc ctgccggttc ccggaagagg aagagggcgg ctgcgaactg    1140
cgcgtgaagt tttcccggtc cgccgacgct ccggcgtacc agcaggggca aaaccagctg    1200
tacaacgaac ttaacctcgg tcgccgggaa gaatatgacg tgctggacaa gcggcgggga    1260
agagatcccg agatgggtgg aaagccgcgg cggaagaacc ctcaggaggg cttgtacaac    1320
gagctgcaaa aggacaaaat ggccgaagcc tactccgaga ttggcatgaa gggagagcgc    1380
agacgcggga agggacacga tggactgtac cagggactgt caaccgcgac taaggacact    1440
tacgacgccc tgcacatgca ggccctgccc ccgcgc                              1476
```

<210> SEQ ID NO 78
<211> LENGTH: 492
<212> TYPE: PRT
<213> ORGANISM: Artificial
<220> FEATURE:
<223> OTHER INFORMATION: amino acid sequence of CAR123 Z16

<400> SEQUENCE: 78

```
Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Gly Thr Phe Ser Ser Tyr Ala Ile Ser Trp Val Arg Gln Ala Pro Gly
    50                  55                  60

Gln Gly Leu Glu Trp Met Gly Gly Ile Ile Pro Ile Phe Gly Thr Ala
65                  70                  75                  80

Asn Tyr Ala Gln Lys Phe Gln Gly Arg Val Thr Ile Thr Ala Asp Glu
                85                  90                  95

Ser Thr Ser Thr Ala Tyr Thr Glu Leu Ser Ser Leu Arg Ser Glu Asp
            100                 105                 110

Thr Ala Val Tyr Tyr Cys Ala Arg Ala Arg Leu Gly Gly Ala Phe Asp
        115                 120                 125

Ile Trp Gly Gln Gly Thr Met Val Thr Val Ser Ser Gly Gly Gly Gly
    130                 135                 140

Ser Gly Gly Gly Gly Ser Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Gly Ser Ser Asn Ile Gly Asn His Tyr Val Ser Trp Tyr
            180                 185                 190

Gln Gln Leu Pro Gly Ala Ala Pro Lys Leu Leu Ile Tyr Asp Asp Asn
        195                 200                 205

Lys Arg Pro Ser Gly Ile Pro Asp Arg Phe Ser Gly Ser Arg Ser Gly
    210                 215                 220

Thr Ser Ala Thr Leu Gly Ile Thr Gly Leu Gln Ser Gly Asp Glu Ala
225                 230                 235                 240

Asp Tyr Tyr Cys Gly Ala Trp Asp Ser Ser Leu Ala Ala His Val Phe
                245                 250                 255

Gly Thr Gly Thr Lys Val Thr Val Leu Gly Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
```

```
                290                 295                 300
His Thr Arg Gly Leu Asp Phe Ala Cys Asp Ile Tyr Ile Trp Ala Pro
305                 310                 315                 320

Leu Ala Gly Thr Cys Gly Val Leu Leu Ser Leu Val Ile Thr Leu
                325                 330                 335

Tyr Cys Lys Arg Gly Arg Lys Lys Leu Leu Tyr Ile Phe Lys Gln Pro
                340                 345                 350

Phe Met Arg Pro Val Gln Thr Thr Gln Glu Glu Asp Gly Cys Ser Cys
            355                 360                 365

Arg Phe Pro Glu Glu Glu Glu Gly Gly Cys Glu Leu Arg Val Lys Phe
370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
                435                 440                 445

Glu Ala Tyr Ser Glu Ile Gly Met Lys Gly Glu Arg Arg Arg Gly Lys
            450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 79
<211> LENGTH: 36
<212> TYPE: DNA
<213> ORGANISM: Human

<400> SEQUENCE: 79
gagagcaaat acgggccgcc atgtcccccg tgtccg                         36

<210> SEQ ID NO 80
<211> LENGTH: 12
<212> TYPE: PRT
<213> ORGANISM: Human

<400> SEQUENCE: 80

Glu Ser Lys Tyr Gly Pro Pro Cys Pro Pro Cys Pro
1               5                   10

<210> SEQ ID NO 81
<211> LENGTH: 327
<212> TYPE: DNA
<213> ORGANISM: Human

<400> SEQUENCE: 81
gcaccaccag ttgctggccc tagtgtcttc ttgttccctc ccaagcccaa agacaccttg    60
atgatttcca gaactcctga ggttacctgc gttgtcgtag atgtttctca ggaggaccca   120
gaggtccaat ttaactggta cgttgatggg gtggaagttc acaatgcgaa gacaaagccg   180
cgggaagaac aatttcagtc cacttaccgg gttgtcagcg ttctgacggt attgcatcaa   240
gactggctta tgaaaggaa atataagtgt aaggtgtcca acaaaggttt gccgagcagt   300
attgagaaga ccatatcaaa ggcgaag                                       327
```

<210> SEQ ID NO 82
<211> LENGTH: 109
<212> TYPE: PRT
<213> ORGANISM: Human

<400> SEQUENCE: 82

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser Gln Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Gln Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Gly
                85                  90                  95

Leu Pro Ser Ser Ile Glu Lys Thr Ile Ser Lys Ala Lys
            100                 105

<210> SEQ ID NO 83
<211> LENGTH: 321
<212> TYPE: DNA
<213> ORGANISM: Human

<400> SEQUENCE: 83
gggcagccgc gcgagccaca agtttacact ttgccgccat ctcaagagga aatgactaaa      60
aaccaggtat ccttgacatg cctcgtaaaa ggatttttatc catctgatat tgctgtggaa    120
tgggagtcta acgggcagcc ggaaaataat tacaaaacta caccacctgt gctcgattca    180
gatggaagtt tcttcccttta cagtagactt acggtggaca atctaggtg gcaggaaggg    240 aatgtgttta gttgtagtgt aatgcacgag gcacttcata accactatac acagaagtca    300
ctgagtttga gtcttggcaa a                                               321

<210> SEQ ID NO 84
<211> LENGTH: 107
<212> TYPE: PRT
<213> ORGANISM: Human

<400> SEQUENCE: 84

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

-continued

```
<210> SEQ ID NO 85
<211> LENGTH: 684
<212> TYPE: DNA
<213> ORGANISM: Artificial
<220> FEATURE:
<223> OTHER INFORMATION: human IgG4 hinge CH2 CH3 domain

<400> SEQUENCE: 85
gagagcaaat acgggccgcc atgtcccccg tgtccggcac caccagttgc tggccctagt    60
gtcttcttgt tccctcccaa gcccaaagac accttgatga tttccagaac tcctgaggtt   120
acctgcgttg tcgtagatgt ttctcaggag gacccagagg tccaatttaa ctggtacgtt   180
gatggggtgg aagttcacaa tgcgaagaca agccgcggg aagaacaatt tcagtccact    240
taccgggttg tcagcgttct gacggtattg catcaagact ggcttaatgg aaggaatat    300
aagtgtaagg tgtccaacaa aggtttgccg agcagtattg agaagaccat atcaaaggcg   360
aaggggcagc cgcgcgagcc acaagtttac actttgccgc catctcaaga ggaaatgact   420
aaaaaccagg tatccttgac atgcctcgta aaggatttt atccatctga tattgctgtg    480
gaatgggagt ctaacgggca gccggaaaat aattacaaaa ctacaccacc tgtgctcgat   540
tcagatggaa gtttcttcct ttacagtaga cttacggtgg acaaatctag gtggcaggaa   600
gggaatgtgt ttagttgtag tgtaatgcac gaggcacttc ataaccacta tacacagaag   660
tcactgagtt tgagtcttgg caaa                                          684

<210> SEQ ID NO 86
<211> LENGTH: 228
<212> TYPE: PRT
<213> ORGANISM: Artificial
<220> FEATURE:
<223> OTHER INFORMATION: human IgG4 hinge CH2 CH3 domain

<400> SEQUENCE: 86

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190
```

Val Asp Lys Ser Arg Trp Gln Glu Gly Asn Val Phe Ser Cys Ser Val
    195                 200                 205

Met His Glu Ala Leu His Asn His Tyr Thr Gln Lys Ser Leu Ser Leu
    210                 215                 220

Ser Leu Gly Lys
225

<210> SEQ ID NO 87
<211> LENGTH: 1482
<212> TYPE: DNA
<213> ORGANISM: Artificial
<220> FEATURE:
<223> OTHER INFORMATION: nucleotide sequence of CAR123 Z32

<400> SEQUENCE: 87

| | |
|---|---|
| atgctcttgc tcgtgacttc tttgcttttg tgcgaacttc cgcacccagc cttccttttg | 60 |
| atacctcagg tacagctgca gcagtcaggt ccaggactgg tgaagccctc gcagaccctc | 120 |
| tcactcacct gtgccatctc cggggacagt gtctctagca acagtgctgc ttggaactgg | 180 |
| atcaggcagt ccccatcgag aggccttgag tggctgggaa ggacatacta caggtccaag | 240 |
| tggtataatg attatgcagt atctgtgaaa agtcgaataa ccatcaaccc agacacatcc | 300 |
| aagaaccagt tctccctgca gctgaactct gtgactcccg aggacatggc tgtgtattac | 360 |
| tgtgcaagag gcgttgatag tagctttgac tactggggcc agggaaccct ggtcaccgtc | 420 |
| tcctcaggag gtggcgggtc tggtggaggc ggtagcggtg gtggcggatc ccagtctgtc | 480 |
| gtgacgcagc cgccctcagt gtctgcggcc ccaggacaga gcgtcaccat ctcctgttct | 540 |
| ggaagcagtt ccaccgttgg cgataattat gtgtcctggt accagcaact cccaggaaca | 600 |
| gcccccaaac tcctcatttt tgacgattat aaacgaccct caggggttcc tgaccgattc | 660 |
| tctggctccc agtctggcac ctcagcctcc ctggtcatca ctggtctcca ggcagaagat | 720 |
| gaggctgatt attactgcca gtcttatgac agcagcctga gtggttatgt cttcgggcct | 780 |
| gggaccaagg tcaccgtcct gggtgcggcc gcaacgacca ctcctgcacc ccgccctccg | 840 |
| actccggccc caaccattgc cagccagccc tgtccctgc ggccggaagc tgcagaccg | 900 |
| gctgccggcg gagccgtcca tacccgggga ctggatttcg cctgcgatat ctatatctgg | 960 |
| gcaccactcg ccggaacctg tggagtgctg ctgctgtccc ttgtgatcac cctgtactgc | 1020 |
| aagcgcggac ggaagaaact cttgtacatc ttcaagcagc cgttcatgcg ccctgtgcaa | 1080 |
| accacccaag aagaggacgg tgctcctgc cggttcccgg aagaggaaga gggcggctgc | 1140 |
| gaactgcgcg tgaagttttc ccggtccgcc gacgctccgg cgtaccagca ggggcaaaac | 1200 |
| cagctgtaca cgaacttaa cctcggtcgc cgggaagaat atgacgtgct ggacaagcgg | 1260 |
| cggggaagag atcccgagat gggtggaaag ccgcggcgga agaaccctca ggagggcttg | 1320 |
| tacaacgagc tgcaaaagga caaatggcc gaagcctact ccgagattgg catgaaggga | 1380 |
| gagcgcagac gcgggaaggg acacgatgga ctgtaccagg gactgtcaac cgcgactaag | 1440 |
| gacacttacg acgccctgca catgcaggcc ctgcccccgc gc | 1482 |

<210> SEQ ID NO 88
<211> LENGTH: 494
<212> TYPE: PRT
<213> ORGANISM: Artificial
<220> FEATURE:
<223> OTHER INFORMATION: amino acid sequence of sequence of CAR123 Z32

<400> SEQUENCE: 88

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
            35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Met Ala Val Tyr Tyr Cys Ala Arg Gly Val Asp Ser Ser
            115                 120                 125

Phe Asp Tyr Trp Gly Gln Gly Thr Leu Val Thr Val Ser Ser Gly Gly
            130                 135                 140

Gly Gly Ser Gly Gly Gly Ser Gly Gly Gly Ser Gln Ser Val
145                 150                 155                 160

Val Thr Gln Pro Pro Ser Val Ser Ala Ala Pro Gly Gln Ser Val Thr
                165                 170                 175

Ile Ser Cys Ser Gly Ser Ser Thr Val Gly Asp Asn Tyr Val Ser
                180                 185                 190

Trp Tyr Gln Gln Leu Pro Gly Thr Ala Pro Lys Leu Leu Ile Phe Asp
    195                 200                 205

Asp Tyr Lys Arg Pro Ser Gly Val Pro Asp Arg Phe Ser Gly Ser Gln
    210                 215                 220

Ser Gly Thr Ser Ala Ser Leu Val Ile Thr Gly Leu Gln Ala Glu Asp
225                 230                 235                 240

Glu Ala Asp Tyr Tyr Cys Gln Ser Tyr Asp Ser Ser Leu Ser Gly Tyr
                245                 250                 255

Val Phe Gly Pro Gly Thr Lys Val Thr Val Leu Gly Ala Ala Ala Thr
                260                 265                 270

Thr Thr Pro Ala Pro Arg Pro Pro Thr Pro Ala Pro Thr Ile Ala Ser
            275                 280                 285

Gln Pro Leu Ser Leu Arg Pro Glu Ala Cys Arg Pro Ala Ala Gly Gly
            290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
                340                 345                 350

Gln Pro Phe Met Arg Pro Val Gln Thr Thr Gln Glu Glu Asp Gly Cys
            355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
            405                 410                 415

Leu Asp Lys Arg Arg Gly Arg Asp Pro Glu Met Gly Gly Lys Pro Arg
```

-continued

```
            420                 425                 430
Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490
```